United States Patent
Wu et al.

(10) Patent No.: US 6,432,994 B1
(45) Date of Patent: Aug. 13, 2002

(54) SULFONAMIDES FOR TREATMENT OF ENDOTHELIN-MEDIATED DISORDERS

(75) Inventors: Chengde Wu; Natalie Blok, both of Houston, TX (US); Timothy Kogan, deceased, late of Escondido, CA (US), by Patricia Woodard, legal representative; Karin Keller, Houston, TX (US); Patricia Woodard, Escondido, CA (US)

(73) Assignee: Texas Biotechnology Corporation, Houston, TX (US)

( * ) Notice: Subject to any disclaimer, the term of this patent is extended or adjusted under 35 U.S.C. 154(b) by 0 days.

(21) Appl. No.: 09/403,599

(22) PCT Filed: Apr. 2, 1998

(86) PCT No.: PCT/US98/06680
§ 371 (c)(1),
(2), (4) Date: Mar. 27, 2000

(87) PCT Pub. No.: WO98/49162
PCT Pub. Date: Nov. 5, 1998

Related U.S. Application Data

(63) Continuation-in-part of application No. 08/938,444, filed on Sep. 26, 1997, now Pat. No. 6,248,767, which is a continuation-in-part of application No. 08/847,797, filed on Apr. 28, 1997, now Pat. No. 5,783,705.

(51) Int. Cl.[7] .................. A61K 31/42; C07D 413/00

(52) U.S. Cl. .................. 514/380; 548/245; 548/246; 548/247

(58) Field of Search .................. 514/380; 548/245, 548/246, 247

(56) References Cited

U.S. PATENT DOCUMENTS

| | | | |
|---|---|---|---|
| 2,888,455 A | 5/1959 | Kano et al. | 260/239.9 |
| 3,300,488 A | 1/1967 | Onoue et al. | 260/239.9 |
| 3,660,383 A | 5/1972 | Sumimoto et al. | 260/239.9 |
| 3,710,795 A | 1/1973 | Higuchi et al. | 128/260 |
| RE28,819 E | 5/1976 | Thompson | 424/243 |
| 4,044,126 A | 8/1977 | Cook et al. | 424/243 |
| 4,328,245 A | 5/1982 | Yu et al. | 424/305 |
| 4,358,603 A | 11/1982 | Yu | 560/2 |
| 4,364,923 A | 12/1982 | Cook et al. | 424/46 |
| 4,409,239 A | 10/1983 | Yu | 424/305 |
| 4,410,545 A | 10/1983 | Yu et al. | 424/305 |
| 4,414,209 A | 11/1983 | Cook et al. | 424/243 |
| 4,485,108 A | 11/1984 | Jozic | 424/267 |
| 4,522,811 A | 6/1985 | Eppstein et al. | 514/2 |
| 4,752,613 A | 6/1988 | Floyd et al. | 514/438 |
| 4,997,836 A | 3/1991 | Sugihara et al. | 514/253 |
| 5,082,838 A | 1/1992 | Naka et al. | 514/211 |
| 5,114,918 A | 5/1992 | Ishikawa et al. | 514/11 |
| 5,187,195 A | 2/1993 | Oohata et al. | 514/610 |
| 5,198,548 A | 3/1993 | Beylin et al. | 546/136 |
| 5,208,243 A | 5/1993 | Peglion et al. | 514/309 |
| 5,230,999 A | 7/1993 | Suzuki et al. | 435/71 |
| 5,240,910 A | 8/1993 | Lam et al. | 514/11 |
| 5,248,807 A | 9/1993 | Fujimoto et al. | 560/75 |
| 5,270,313 A | 12/1993 | Burri et al. | 514/256 |
| 5,292,740 A | 3/1994 | Burri et al. | 514/256 |
| 5,334,598 A | 8/1994 | Bagley et al. | 514/303 |
| 5,352,659 A | 10/1994 | Wakimasu et al. | 514/9 |
| 5,352,800 A | 10/1994 | Bills et al. | 548/539 |
| 5,378,715 A | 1/1995 | Stein et al. | 514/329 |
| 5,382,569 A | 1/1995 | Cody et al. | 514/17 |
| 5,389,620 A | 2/1995 | Ishikawa et al. | 514/80 |
| 5,389,633 A | 2/1995 | Miyake et al. | 514/233.2 |
| 5,407,941 A | 4/1995 | Carceller et al. | 514/290 |
| 5,420,123 A | 5/1995 | Murugesan | 514/220 |
| 5,420,129 A | 5/1995 | Breu et al. | 514/252 |
| 5,420,131 A | 5/1995 | Carceller et al. | 514/253 |
| 5,420,133 A | 5/1995 | Dhanoa et al. | 514/256 |
| 5,420,138 A | 5/1995 | Corbier et al. | 514/300 |
| 5,420,275 A | 5/1995 | Masuya et al. | 544/236 |
| 5,464,853 A | 11/1995 | Chan et al. | 514/378 |
| 5,514,691 A | 5/1996 | Chan et al. | 514/312 |
| 5,514,696 A | 5/1996 | Murugesan et al. | 514/380 |
| 5,543,521 A | 8/1996 | Chan et al. | 544/349 |
| 5,565,485 A | 10/1996 | Bagley et al. | 514/452 |
| 5,571,821 A | 11/1996 | Chan et al. | 514/312 |

(List continued on next page.)

FOREIGN PATENT DOCUMENTS

| | | |
|---|---|---|
| AU | 5461286 | 3/1985 |
| CA | 2067288 | 10/1992 |
| CA | 2071193 | 12/1992 |

(List continued on next page.)

OTHER PUBLICATIONS

Database Crossfire Beilstein Registry No. 1021364 and 1086426, citing Saito et al., *Yakugaku Zasshi* 88:1289, 1292 (1968).

Chemical Abstracts vol. 65, abstract No. 14649g, citing Uno et al., *Chem. Pharm. Bull.* 14:756–762 (1966).

Allen et al., The Cambridge crystallographic data centre: Computer–based search, retrieval, analysis and display of information, *Acta Crystallogr. B35*:2331–2339 (1979).

(List continued on next page.)

*Primary Examiner*—Amelia Owens
(74) *Attorney, Agent, or Firm*—Stephanie L. Seidman; Dale L. Rieger; Heller Ehrman White & McAuliffe LLP

(57) ABSTRACT

Thienyl-, furyl- and pyrrolyl-sulfonamides, pharmaceutically-acceptable salts of sulfonamides, formulations of salts and the sulfonamides, and methods for modulating or altering the activity of the endothelin family of peptides using the formulations and sulfonamides are provided. In particular, formulations of sodium salts of N-(isoxazolyl)thienylsulfonamides, N-(isoxazolyl) furylsulfonamides and N-(isoxazolyl)pyrrolylsulfonamides are provided. A process of preparing an alkali metal salt of a hydrophobic sulfonamide is provided. The process includes the step of dissolving a free sulfonamide in an organic solvent in the presence of a saturated alkali metal salt solution and recovering the formed sulfonamide salt from the organic phase.

18 Claims, No Drawings

U.S. PATENT DOCUMENTS

| | | | |
|---|---|---|---|
| 5,585,397 A | 12/1996 | Tung et al. ................. | 514/473 |
| 5,589,478 A | 12/1996 | Yamada et al. ............. | 514/269 |
| 5,591,728 A | 1/1997 | de Nanteuil et al. .......... | 514/80 |
| 5,591,761 A | 1/1997 | Chan et al. ................. | 514/380 |
| 5,594,021 A | 1/1997 | Chan et al. ................. | 514/378 |
| 5,599,811 A | 2/1997 | Berryman et al. ........ | 514/226.5 |
| 5,612,359 A | 3/1997 | Murugesan ................. | 514/365 |
| 5,641,793 A | 6/1997 | Bradbury .................... | 514/352 |
| 5,661,152 A | 8/1997 | Bishop et al. .............. | 514/254 |
| 5,668,137 A | 9/1997 | Phillips et al. .............. | 514/255 |
| 5,668,176 A | 9/1997 | Bagley et al. .............. | 514/569 |
| 5,726,194 A | 3/1998 | Osswald et al. ............ | 514/362 |
| 5,783,701 A | 7/1998 | Tung et al. ................. | 546/169 |
| 5,783,705 A | 7/1998 | Blok et al. .................. | 548/247 |
| 5,804,585 A | 9/1998 | Verner ........................ | 514/301 |
| 5,827,869 A | 10/1998 | Murugesan ................. | 514/374 |
| 5,846,990 A | 12/1998 | Murugesan et al. ........ | 514/374 |
| 5,958,905 A | 9/1999 | Chan et al. ................... | 514/92 |
| 5,962,490 A | 10/1999 | Chan et al. ................. | 514/380 |
| 5,962,691 A | 10/1999 | Schmidt et al. .......... | 546/269.7 |
| 5,977,157 A | 11/1999 | Chan et al. ................. | 514/256 |
| 6,013,655 A | 1/2000 | Verner ........................ | 514/301 |
| 6,017,916 A | 1/2000 | Berryman et al. ........ | 514/233.8 |
| 6,017,951 A | 1/2000 | Patt et al. ................... | 514/464 |
| 6,030,991 A | 2/2000 | Chan et al. ................. | 514/380 |
| 6,043,241 A | 3/2000 | Cheng et al. ............ | 514/233.8 |
| 6,043,265 A | 3/2000 | Murugesan et al. ........ | 514/374 |
| 6,060,475 A | 5/2000 | Bradbury et al. ........... | 514/255 |
| 6,063,911 A | 5/2000 | Vournakis et al. ............ | 536/20 |
| 6,083,955 A | 7/2000 | Harada et al. ............... | 514/269 |
| 6,107,320 A | 8/2000 | Murugesan et al. ........ | 514/379 |
| 6,133,263 A | 10/2000 | Cheng et al. ............ | 514/233.8 |
| 6,133,442 A | 10/2000 | Breu et al. .................. | 544/123 |

FOREIGN PATENT DOCUMENTS

| | | |
|---|---|---|
| EP | 0248399 | 12/1987 |
| EP | 0404525 | 12/1990 |
| EP | 0405421 | 1/1991 |
| EP | 0411150 | 2/1991 |
| EP | 0436189 | 7/1991 |
| EP | 0457195 | 11/1991 |
| EP | 0460679 | 12/1991 |
| EP | 0496452 | 7/1992 |
| EP | 0558258 | 9/1993 |
| EP | 0569193 | 11/1993 |
| EP | 0626174 | 11/1994 |
| EP | 0640596 | 3/1995 |
| EP | 0682016 | 11/1995 |
| EP | 0702012 | 3/1996 |
| EP | 0725067 | 8/1996 |
| EP | 0768305 | 4/1997 |
| GB | 0804036 | 11/1958 |
| GB | 1473433 | 5/1977 |
| GB | 2259450 | 3/1993 |
| JP | 60-18808 | 9/1985 |
| JP | 63 238006 | 4/1990 |
| JP | 4134084 | 5/1992 |
| WO | 9115479 | 10/1991 |
| WO | 9308799 | 5/1993 |
| WO | 9427979 | 12/1994 |
| WO | 9524385 | 9/1995 |
| WO | 9604759 | 4/1996 |
| WO | 9631492 | 10/1996 |
| WO | 9725321 | 7/1997 |
| WO | 9735864 | 10/1997 |
| WO | 9739000 | 10/1997 |
| WO | 9813366 | 4/1998 |
| WO | 9849162 | 11/1998 |
| WO | 0149685 | 7/2001 |

OTHER PUBLICATIONS

Anagnostou et al., Erythropoietin has mitogenic and positive chemotactic effects on endothelial cells, *P.N.A.S.* 87:5978–5982 (1990).

Ansel, *Introduction to Pharmaceutical Dosage Forms*, 4th Edition, pp. 126–163 (1985).

Arai et al., Cloning and expression of a cDNA encoding an endothelin receptor, *Nature* 348:730–732 (1990).

Aumelas et al., Determination of the structure of [Nle$^7$]-endothelin by $^1$H NMR, *Int. J. Peptide Protein Res.* 37:315–324 (1991).

Balasubramanian, New type of representation for mapping chain folding in protein molecules, *Nature* 266:856–857 (1977).

Benigni et al., A specific endothelin subtype A receptor antagonist protects against injury in renal disease progression, *Kidney International* 44:440–444 (1993).

Berge et al., Pharmaceutical salts, *J. Pharmaceut. Sci.* 66(1):1–19 (1977).

Bolger et al., Vascular reactivity, tissue levels, and binding sites for endothelin: a comparison in the spontaneously hypertensive and Wistar—Kyoto rats, *Can. J. Physiol. Pharmacol.* 69:406–413 (1991).

Bolger et al., Characterization of binding of the Ca$^{++}$ channel antagonist [$^3$H] nitrendipine, to guinea–pig ileal smooth muscle, *J. Pharmacol. Exptl. Ther.* 225:291–309 (1983).

Borges et al., Tissue selectivity of endothelin, *Eur. J. Pharmacol.* 165:223–230 (1989).

Brint et al., Upperbound procedures for the identification of similar three–dimensional chemical structures, *J. Comput.–Aided Mol. Design* 2:311–310 (1988).

Brooks et al., Effect of nifedipine on cyclosporine A–induced nephrotoxicity, urinary endothelin excretion and renal endothelin receptor number, *Eur. J. of Pharmacology* 194:115–117 (1991).

Buemi et al., Influence of recombinant erythropoietin on the production of endothelin–1 from human umbilical artery, *Nephron* 64(1):165–166 (1993).

Cardell et al., Two functional endothelin receptors in guinea–pig pulmonary arteries, *Neurochem. Int.* 18(4):571–574 (1991).

Carlini et al., Intravenous erythropoietin (rHuEPO) administration increases plasma endothelin and blood pressure in hemodialysis patients, *Am. J. Hyper.* 6:103–107 (1993).

Castiglione et al., Alanine scan of endothelin, Peptides: Chemistry and Biology, Proc. Amer. Rept. Symp. (12th), J.A. Smith and J.E. Rivier, Eds., ESCOM, Leiden, 1992, pp. 402–403.

Certified Translation of French Publication (item EZ) "Synthesis and Structure of N1–Acylated Sulfiodizole and its homologues".

Certified Translation of Japanese Patent 63238006, "Agent protecting against rice blase disease".

Clarke et al., Endothelin is a potent long–lasting vasoconstrictor in men, *Am. J. Physiol.* 257(6 pt 2):H2033–H2035 (1989).

Clozel et al., Pathophysiological role of endothelin revealed by the first orally active endothelin receptor antagonist, *Nature* 365:759–761, (1993).

Cody et al., The rational design of a highly potent combined ET$_A$ and ET$_B$ receptor antagonist (PD145065) and related analogues, *Med. Chem. Res.* 3:154–162 (1993).

Cooper et al., A novel approach to molecular similarity, *J. Comput.–Aided Mol. Design* 3:253–259 (1989).

De Nucci et al., Pressor effects of circulating endothelin are limited by its removal in the pulmonary circulation and by the release of prostacyclin and endothelium–derived relaxing factor, *Proc. Natl. Acad. Sci.* 85:9797 (1988).

DiCarlo et al., $ET_A$–receptor antagonist prevents and reverses chronic hypoxia–induced pulmonary hypertension, *Am. J. Physiol.* 260:L690–L697 (1995).

Doherty, Endothelin: a new challenge, *J. Medicinal Chem.* 35(9):1493–1508 (1992).

Endothelin, Receptor Antagonist (TBC 11251), Research and Development—Compounds Under Development, pp. 3–5 (available at http://www.tbc.com/resrch.htm on Sep. 3, 1997).

Eschbach et al., Recombinant human erythropoietin in anemic patients with end stage renal disease; results of a phase III multicenter clinical trial, *Ann. Intern. Med.* 111:992–1000 (1989).

Filep et al., Endothelin–1 induces prostacyclin release from bovine aortic endothelial cells, *Biochem. and Biophys. Research Comm.* 177(1):171–176 (1991).

Fujimoto and Sakai, "Synthesis and Structure of N1–Acylated Sulfiodizole and its homologues", *Chem. Pharm. Bull.* 14(3):280–284 (1966). Published in French.

Fujimoto et al., A novel non–peptide endothelin antagonist isolated from bayberry, *FEBS* 305(1):41–44 (1992).

Fujimoto et al., Isoxazole derivatives. II. Synthesis and structure of N–acylsufodiazoles and their homologs, *Chemical Abstracts:* 65(2), Abstract No. 2241eq. Jul. 18, 1966.

Furchgott et al., The obligatory role of endothelial cells in the relaxation of arterial smooth muscle by acetylcholine, *Nature* 288:373–376, (1980).

Galantino et al., D–Amino acid scan of endothelin, Peptides: Chemistry & Biology, Proc. Amer. Report. Symp. (12th), J.A. Smith and J.E. Rivier, Eds., ESCOM, Leiden, 1992, pp. 404–405.

Gibaldi, Chapter 8: Bioavailability, *Biopharmaceutics and Pharmacology*, 4th ed., Lea and Sediger, pp. 146–175 (1991).

Gu et al., The inhibitory effect of [D–Arg$^1$, D–Phe, D–Try$^{7,9}$, Leu$^{11}$] substance P on endothelin–1 binding sites in rat cardiac membranes, *Biochem. and Biophys. Research Commun.* 179(1): 130–133 (1991).

Heidenreich et al., Erythropoietin induces contraction of isolated renal small resistance vessels, *Nephrol. Dial. Transplant* 5:739–740 (1990).

Hiley et al., Functional studies on endothelin catch up with molecular biology, *Trends Pharmacol. Sci.* 10:47–49 (1989).

Hirata et al., Receptor binding activity and cytosolic free calcium response by synthetic endothelin analogs in culture rat vascular smooth muscle cells, *Biochem. and Biophys. Research Commun.* 160:228–234 (1989).

Hori et al., Hemodynamics and volume changes by recombinant human erythropoietin (rHuEPO) in the treatment of anemic hemodialysis patients, *Clin. Nephrol.* 33:293–298 (1990).

Ihara et al., An endothelin receptor ($ET_A$) antagonist isolated from *Streptomyces misakiensis*, *Biochem. and Biophys. Research Commun.* 178(1):132–137 (1991).

Ihara et al., Biological profiles of highly potent novel endothelin antagonists selective for the $ET_A$ receptor, *Life Sciences* 50:247–255 (1991).

Inoue et al., The human endothelin family: Three structurally and pharmacologically distinct isopeptides predicted by three separate genes, *Proc. Natl. Acad. Sci. USA*, 86:2863–2867 (1989).

Ishikawa et al., Cyclic pentapeptide endothelin antagonists with high $ET_A$ selectivity. Potency– and solubility–enhancing modifications, *J. Med. Chem.* 35:2139–2142 (1992).

IUPAC–IUB Commission on Biochemical Nomenclature, *Biochem.* 11:942–944, (1972).

Kaltenbronn et al., Renin inhibitors containing isosteric replacements of the amide bond connecting the $P_3$ and $P_2$ sites, *J. Med. Chem.* 33:838–845 (1990).

Kanno et al., Endothelin–1 and Vasculitis, *J. Amer. Med. Assoc.* 264:2868, (1990).

Karplus, Molecular Dynamics: Applications to Proteins, Computer Simulation of Chemical and Biomolecular Systems, (Bevendge and Jorfensen, Eds.) *Ann. New York Acad. Sci.*:482:255–266 (1986).

Kashiwabara et al., Putative precursors of endothelin have less vasoconstrictor activity in vitro but a potent pressor effect in vivo, *FEBS Letters* 247(1):73–76 (1989).

Kemp, Peptidomimetics and the template approach to nucleation of β–sheets and α–helices in peptides, *Trends in Biotech.* 8:249–255 (1990).

Kloog et al., Similarities in mode and sites of action of sarafotoxins and endothelins, *Trends Pharmacol. Sci.* 10:212–214 (1989).

Koyama et al., Plasma endothelin levels in patients with uremia, *Lancet* 1(8645):991–992 (1989).

Kurihara et al., The possible role of endothelin–1 in the pathogenesis of coronary vasospasm, *J. Cardiovas. Pharmacol.* 13:Suppl. 5, S132–S142, (1989).

Lerman et al., Circulating and tissue endothelin immunoreactivity in advanced atherosclerosis, *New Engl. J. Med.* 325:997–1001, (1991).

LexPat Record of U.S. Patent No. 5,464,853.

Maggi et al., Potent contractile effect of endothelin in isolated guinea–pig airways, *Eur. J. Pharmacol.* 160:179–182 (1989).

Martin et al., Identification and characterization of endothelin binding sites in rat renal papillary and glomerular membranes, *Biochem. Biophys. Res. Commun.* 162:130–137 (1989).

Miyata et al., WS–7338, new endothelin receptor antagonists isolated from Streptomyces sp. No. 7338, *J. Antibiotics* 45(1):74–82 (1992).

Miyata et al., WS009 A and B, new endothelin receptor antagonists isolated from Streptomyces sp. No. 89009, *J. Antibiotics* 45(7):1029–1040 (1992).

Miyauchi et al., Increase of the function of intra–cardiac autonomic nerves in isolated atria of swim–trained rats: study by the intra–cardiac nerve stimulation, *Jpn. J. Pharmacol.* 58:279, (1992).

Morel et al., Increased plasma and pulmonary lymph levels of endothelin during endotoxin shock, *Eur. J. Pharm.* 167:427–428 (1989).

Nakajima et al., Synthesis of endothelin–1 analogues, endothelin–3, and sarafotoxin S6b: structure–activity relationships, *J. Cardiovascular Pharm.* 13(Suppl. 5):S8–S12 (1989).

Nakajima et al., Endothelin–binding inhibitors, BE–18257A and BE–18257B II. Structure determination, *J. Antibiotics* 44(12):1348–1356 (1991).

Nirei et al., An endotheline $et_A$ receptor antagonist, FR139317, Amerliorates cerebral vasospasm in dogs, *Life Sciences* 52:1869–1874, (1993).

Nishikibe et al., Antihypertensive effect of a newly synthesized endothelin antagonist, BQ–123, in a genetic hypertensive model, *Life Sci.* 52:717–724 (1993).

Nishikori et al., Receptor binding affinity and biological activity of C–terminal elongated forms of endothelin–1, *Neurochem. Int.* 18(4):535–539 (1991).

Nogrady et al., 4–pro–drugs and soft drugs, *Medicinal Chemistry A Biochemical Approach*:388–392, (1985).

Nonnast–Daniel et al., Atrial natriuretic peptide and central hemodynamics during correction of renal anemia by recombinant human erythropoietin treatment in regular dialysis treatment patients, *Nephrol Dial Transplant* 4:478 (1989).

Official Gazette Notice, Jul. 7, 1998, "Adverse Decisions in Interference", Interference No. 103,876.

Ogawa et al., Molecular cloning of a non–isopeptide–selective human endothelin receptor, *Biochem. and Biophys. Research Comm.* 7, 18(1):248–255 (1991).

Ohashi et al., Asterric acid, a new endothelin binding inhibitor, *J. Antibiotics*, 45(10):1684–1685 (1992).

Ormsbee and Ryan, Production of hypertension with desoxycorticosterone acetate–impregnated silicone rubber implants, *J. of Pharmac Sciences* 62(2):255–257 (1973).

Palmer et al., Nitric oxide release accounts for the biological activity of endothelium–derived relaxing factor, *Nature* 327:524–526 (1987).

Panek et al., Endothelin and structurally related analogs distinguish between endothelin receptor subtypes, *Biochem. and Biophys. Research Commun.* 183(2):566–571 (1992).

Perkins et al., Proposed solution structure of endothelin, *Int. J. Peptide Protein Res.* 36:128–133 (1990).

Press Release, Texas Biotechnology Corporation, Antihypertensive effects of prolonged treatment with oral TBC11251NAa, a novel selective ETa endothelin receptor antagonist, in spontaneoulsy hypertensive hamsters, 10/14/199, located at http://www.tbc.com/.

Press Release, Texas Biotechnology Corporation, Endothelin antagonism inhibits pulmonary vascular remodeling in the hyposic piglet, Oct. 14, 1999, located at http://www.tbc.com/.

Press Release, Texas Biotechnology Corporation, Evaluation of novel, highly selective ETa receptor antagonists in hypoxia–induced pulmonary hypertension, Oct. 14, 1999, located at http://www.tbc.com/.

Press Release, Texas Biotechnology Corporation, Discovery of potent, orally available, ETa selective endothelin antagonists: TBC3214 and TBC3711, Oct. 14, 1999, located at http://www.tbc.com/.

Raine et al., Effect of erythropoietin on blood pressure, *Am. J. Kid. Dis.* 18(*suppl*):76–83 (1991).

Raju et al., Amide bond surrogates: a study in thiophenesulfonamide based endothelin receptor antagonists, *Bioorganic Medicinal Chem. Lett.* 7(7):939–944 (1997).

Raju et al., Search for surrogates: a study of endothelin receptor antagonist structure activity relationships, *Bioorganic Medicinal Chem. Lett.* 7(7): 933–938 (1997).

Raju et al., Thiophenesulfonamides as endothelin receptor antagonists, *Bioorganic Medicinal Chem. Lett.* 6(22):2651–2656 (1996).

Ramachandran et al., Conformation of polypeptides and proteins, *Adv. Prot. Chem.*, 23:283–437 (1968).

Ray et al., Circulating endothelin in acute ischaemic syndromes, *Br. Heart J.* 67:383–386 (1992).

Saeki et al., $[Ala^{1,3,11,15}]$ endothelin–1 analogs with $ET_B$ agonistic activity, *Biochem. Biophys. Research Commun.* 179(1):286–292 (1991).

Saida et al., A novel peptide, vasoactive intestinal contractor, of a new (endothelin) peptide family, *J. Biol. Chem.* 264(25):14613–14616 (1989).

Saito et al., Application of monoclonal antibodies for endothelin to hypertensive research, *Hypertension* 15:734–738 (1990).

Sakurai et al., Cloning of a cDNA encoding a non–isopeptide–selective subtype of the endothelin receptor, *Nature* 348:732–735 (1990).

Samtleben et al., Blood pressure change during treatment with recombinant human erythropoietin, *Contrib. Nephrol.* 66:114–122 (1988).

Sanjay et al., Does PTCA increase circulating endothelin level in Man?, *Circulation* 84:(Suppl. 4):726, (1991).

Saudek et al., Solution conformation of endothelin–1 by $^1$H NMR, CD, and molecular modeling, *Int. J. Peptide Protein Res.* 37:174–179 (1991).

Saudek et al., $^1$H–NMR study of endothelin, sequence–specific assignment of the spectrum and a solution structure, *FEBS Letters* 257(1):145–148 (1989).

Schafer et al., Treatment of renal anemia with recombinant human erythropoietin, *Am. J. Nephrol.* 8:352–362 (1989).

Schvartz et al., Bovine cerebellum endothelin receptor: Solubilization and identification, *Endocrinology* 126(6):3218–3222 (1990).

Shimazaki et al., Piperazine derivatives, *Chem. Abstracts* 106:4558 (abst. No. 33114a) (1987).

Simonson et al., Endothelin–1 stimulates contraction of rat glomerfular mesangial cells and potentiates β–adrenergic–mediated cyclic adenosine monophosphate accumulation, *J. Clin. Invest.* 85:790–797, (1990).

Spinella et al., A proposed structural model of endothelin, *Peptide Research* 2(4):286–291 (1989).

Spinella et al., Design and synthesis of a specific endothelin 1 antagonist: Effects on pulmonary vasoconstriction, *Proc. Natl. Acad. Sci. USA* 88p:7443–7446 (1991).

Spokes et al., Studies with endothelin–3 and endothelin–1 on rat blood pressure and isolated tissues: Evidence for multiple endothelin receptor subtypes, *J. Cardiovasc. Pharmacol.* 13(*Suppl.* 5):S191–S192 (1989).

Stein et al., The Discovery of Sulfonamide Endothelin Antagonists and the Developement of the Orally Active $ET_A$–Antagonist 5–(Dimethylamino)–N–(3, 4–dimethyl–5–isoxazoly)–1–naphthalenesulfonamide, *J. Med. Chem.* 37(3):329–331 (1994).

Stewart et al., Increased plasma endothelin–1 in pulmonary hypertension: marker or mediator of disease? *Annals of Internal Med.* 114:464–469, (1991).

Sundal et al., Correction of anemia of chronic renal failure with recombinant human erythropoietin: safety and efficacy of one year's treatment in a European multicenter study of 150 hemodialysis–dependent patients, *Nephrol. Dial. Transplant* 4:979–987 (1989).

Szelke et al., Novel transition–state analogue inhibitors of renin, *In Peptides: Structure and Function, Proceeding of the Eighth American peptide symposium*, (Hruby and Rich, Eds.), pp. 579–582, Pierce Chemical Co., Rockford, Illinois (1983).

Tahara et al., Circulating immunoreactive endothelin in patients undergoing percutaneous transluminal coronary angioplasty, *Metab. Clin. Exp.* 40:1235–1237, (1991).

Takayanagi et al., Presence of non–selective type of endothelin receptor on vascular endothelium and its linkage to vasodilation, *FEBS Letters*, 282(1):103–106 (1991).

Takayanagi et al., Multiple subtypes of endothelin receptors in porcine tissues: characterization by ligand binding, affinity labeling and regional distribution, *Reg. Pep.* 32:23–37 (1991).

Texas Biotechnology Receives First Patent Issued For New Class of Cardiovascular Drugs, Houston, TX, Dec. 6, 1995, For Immediate Release (avaiable at http://www.tbc.com/PR120695.HTM on Sep. 5, 1997).

Texas Biotechnology Reports Endothelin A Receptor Antagonist and VCAM/VLA–4 Inhibitor Patents, Houston, TX, May 16, 1996, For Immediate Release, (available at http://www.tbc.com/PR051696.HTM on Sep. 5, 1997).

Texas Biotechnology Announces Initiation of Phase 1 Clinical Trial For TBC 11251 To Treat Congestive Heart Failure, Houston, TX, Nov. 13, 1996, For Immediate Release, (available at http://www.tbc.com/PR111396.HTM on Sep. 5, 1997).

Texas Biotechnology Announces Initiation of Phase 1 Clinical Trial For TBC 1269 To Treat Asthma, Houston, TX, Jan. 21, 1997, For Immediate Release, (available at http://www.tbc.com/PR012197.HTM on Sep. 5, 1997).

Texas Biotechnology Announces Initiation of Phase I Clinical Trial for TBC 11251 To Treat Congestive Heart Failure, Houston, TX, Nov. 13, 1996, For Immediate Release (available at http://www.tbc.com/press/pr111396.html on 1.27/99).

Texas Biotechnology Reports Endothelin a Receptor Antagonist and VCAM/VLA–4 Inhibitor Patens, Houston, TX, Mary 16, 1996, For Immediate Release (available at http://www.tbc.com/press/pr051696.html on Jan. 27, 1999).

Texas Biotechnology Receives First Patent Issued For New Class of Cardiovascular Drugs, Houston, TX, Dec. 6, 1995, For Immediate Release, (available at http://www.tbc.com/press/pr120695.html on Jan. 27, 1999).

Texas Biotechnology Annouces Initiation Phase I Clinical Trial For TBC 1269 To Treat Asthma, Houston, TX, Jan. 21, 1997, For Immediate Release, (available at http://www.tbc.com/press/pr012197.html on Jan. 27, 1999).

Texas Biotechnology Presents Clinical Results on its Endothelin A Receptor Antagonist, TBC11251, at HA Sessions, Houston, TX, Nov. 10, 1998, For Immediate Release, (available at http://www.tbc.com/press/pr111098.html on Jan. 28, 1999).

Texas Biotechnology Resubmits Novastan® NDA, Houston, TX, Mar. 22, 1999, For Immediate Release (available at http://www.tbc.com/press/pr032299.html on May 27, 1999).

Texas Biotechnology Announces Positive Data on Initial Phase IIA Asthma Study, Houston, TX, Sep. 9, 1998, For Immediate Release, (available at http://www.tbc.com/press/pr090998.html on Jan. 28, 1999).

Texas Biotechnology Reports Additional Positive Phase IIA Trial Results in Congestive Heart Failure, Houston, TX, Jul. 21, 1998, For Immediate Release, (available at http:www.tbc.com/press/pr072298.html on Jan. 28, 1999).

Texas Biotechnology Reports Additional Positive Phase IIA Trial Results In Congestive Heart Failure, Houston, TX, Jul. 21, 1998, For Immediate Release, (available at http://www.tbc.com/press/pr072298.html on Jan. 28, 1999).

Texas Biotechnology Updates Stockholders at 1998 Annual Meeting, Houston, TX, Jun. 9, 1998, For Immediate Release, (available at http://www.tbc.com/press/pr060998.html on Jan. 28, 1999).

Texas Biotechnology's Submission of Additional Novastan®Data Extends NDA Review by FDA, Houston, TX, Jan. 23, 1998, For Immediate Release (available at http://www.tbc.com/press/pr012398.html on Jan. 27, 1999).

Texas Biotechnology Initiates Phase IIA Trial For Novel Anti–Inflammatory To Treat Asthma, Houston, TX, Oct. 22, 1997, For Immediate Release (available at http://www.tbc-.com/press/pr102297.html on Jan. 28, 1999).

Texas Biotechnology's Novastan®NDA Granted Priority Review Status By The FDA, Houston, TX, Sep. 4, 1997, For Immediate Release (available at http://www.tbc.com/presspr090497.html on Jan. 28, 1999).

Texas Biotechnology and Smithkline Beecham Form Alliance to Market And Develop Novastan®[200] (argatroban) In North American, FDA Filing for New Thrombin Inhibitor to Be Completed This Month, Houston, TX and Philadelphis, PA, Aug. 6, 1997, For Immediate Release, (available at http://www.tbc.com/press/pr080697.thml on Jan. 28, 1999).

Texas Biotechnology Initiates Filing of New Drug Application For Novastan®, Houston, TX, Jul. 2, 1997, For Immediate Release (available at http://www.tbc.com/press/pr070297.html on Jan. 28, 1999).

Texas Biotechnology Announces Promising Clinical Updates on Phase II Trials of Novastan® In Acutte MI, Houston, TX, Mar. 17, 1997, For Immediate Release, (available at http://www.tbc.com/press/pr031797.html on Jan. 28, 1999).

Texas Biotechnology Announces Results of Phase III Novastan® Clinical Study In Patients With Hit and HITTS, Houston, TX, May 22, 1997, For Immediate Release, (available at http://www.tbc.com/press/pr052297.html on Jan. 28, 1999).

Texas Biotechnology Announces Results of Phase III Clinical Study In PTCA Patients With HIT, Houston, TX, For Immediate Release, (available at http://www.tbc.com/press/pr041797.html on Jan. 29, 1999).

Texas Biotechnology Received U.S. Patents For New Class of Cardiovascular Therapeutics, Endothelin A Receptor Antagonists, Houston, TX, Jan. 22, 1997, For Immediate Release, (available at http://www.tcb.com/press/pr0122297.html on Jan. 28, 1999).

Texas Biotechnology Completes Phase I Safety Trial For Oral Endothelin Antagonist, Houston, TX, Dec. 11, 1997, For Immediate Release (available at http://www.tbc.com/press/pr121197.html on Jan. 28, 1999).

Texas Biotechnology And Loyola University Medical Center Sponsor International Symposium On Heparin–Induced Thromobocytopenia And New Thrombin Inhibitors, Houston, TX, Dec. 6, 1996, For Immediate Release, (available at http://www.tbc.com/press/pr120696.html on Jan. 28, 1999).

Texas Biotechnology Announces Clinical Agreements With Synthelabo, Houston, TX, Jan. 22, 1996, For Immediate Release, (available at http://www.tbc.com/press/pr012296.html on Jan. 28, 1999).

Texas Biotechnology Reports Phase II Clinical Trial Results, Houston, TX, Feb. 21, 1996, For Immediate Release, (available at http://www.tbc.com/press/pr022196.html on Jan. 28, 1999).

Texas Biotechnology Initiates Phase III Trial For Novastan® in Coronary Interventional Procedures, Houston, TX, May 9, 1996, For Immediate Release, (available at http://www.tbc.com/press/pr050996.html on Jan. 28, 1999).

Texas Biotechnology Signs Additional Clinical Development Agreement With Synthelabo For Novastan®, Houston, TX, Jun. 25, 1996, For Immediate Release, (available at http://www.tbc.com/press/pr062596.html on Jan. 28, 1999).

Texas Biotechnology Announces Preliminary Phase II Results of Novastan In Acute Myocardial Infarction, Houston, TX, Oct. 21, 1996, For Immediate Release (available at http://www.tbc.com/press/pr102196.html on Jan. 28, 1999).

Texas Biotechnology Reports Partner, Mitsubisi Chemical, Receives Stroke Indication for Novastan® In Japan, Houston, TX Jun. 18, 1996, For Immediate Release, (available at http://www.tbc.com/press/pr061896.html on Jan. 28, 1999).

Texas Biotechnology Presents Clinical Results On Its Endothelin A Receptor Antagonist, TBC11251, at AHA Sessions, Houston, TX, Nov. 10, 1998, For Immediate Release, (available at http://www.tbc.com/press/pr061896.html on May 27, 1999).

Tkayama et al., Effects of recombinant human eryghropoietin on blood coagulation, fibrinolysis and endothelium in hemodialysis patients, *Blood Purif.* 1:53–54 (1991).

Tomita et al., Plasma endothelin levels in patients with acute renal failure, *N. Engl. J. Med.* 321:1127 (1989).

Vanhoutte et al., Modulation of vascular smooth muscle contraction by the endothelium, *Ann. Rev. Physiol.* 48:307–320, (1986).

von Geldern et al., A fluorogenic assay for endothelin–converting enzyme, *Peptide Research* 4(1):32–35 (1991).

Weiner et al., A new force field for molecular mechanical simulation of nucleic acids and proteins, *J. Am. Chem. Soc.* 106(3):765–784 (Eng.) (1984).

Weiner et al., An all atom force field for simulations of proteins and nucleic acids, *J. Comput. Chem.* 7(2):230–252 (1986).

Williams et al., Sarafotoxin S6c: An agonist which distinguishes between endothelin receptor subtypes, *Biochem. and Biophys. Research Commun.* 175(2):556–561 (1991).

Wu et al., Structure–activity relationships of N–2–aryl–3–(isoxazolylsulfamoyl)–2–thiophenecarboxamides as selective endothelin receptor–A antagonists, *J. Medicinal Chem.* 40(11):1682–1689 (1997).

Wu et al., Discovery of TBC11251, a potent, long acting, orally active endothelin receptor–A selective antagonist, *J. Medicinal Chem.* 40(11):1690–1697 (1997).

Yamashita et al., Recombinant human erythropoietin (rHuEPO) induces high plasma endothelin (ET) levels in hemodialysis patients, *J. Am. Soc. Nephrol.* 1:409 (1990).

Yanagisawa et al., A novel potent vasoconstrictor peptide produced by vascular endothelial cells, *Nature* 332:411–415 (1988).

Yasuda et al., Circulating immunoreactive endothelin in ischemic heart disease, *Amer. Heart J.* 119:801–806, (1990).

Zamora et al., Serum endothelin–1 concentrations and cold provocation in primary Raynaud's phenomenon, *Lancet* 336:1144–1147, (1990).

Wu et al., "Endothelin antagonists. Substituted mesitylcarboxamides with high potency and selectivity fo ETA receptors", *J. Med. Chem.* 42:4485–4499 (1999).

SULFONAMIDES FOR TREATMENT OF ENDOTHELIN-MEDIATED DISORDERS

RELATED APPLICATIONS

This application is a 371 of PCT/US98/06680 filed Apr. 2, 1998 and is a CIP of Ser. No. 08/938,444 filed Sep. 26, 1997 now U.S. Pat. No. 6,248,767 B1, which is a CIP of 08/847, 797 filed Apr. 28, 1997 now U.S. Pat. No. 5,783,7059.

This application is related to U.S. application Ser. No. 08/938,325 to Wu et al., filed Sep 27, 1997, entitled "SULFONAMIDES AND DERIVATIVES THEREOF THAT MODULATE THE ACTIVITY OF ENDOTHELIN," and is also related to International application No. PCT/US97/17402 to Wu et al., filed Sep. 27, 1997, entitled "SULFONAMIDES AND DERIVATIVES THEREOF THAT MODULATE THE ACTIVITY OF ENDOTHELIN". This application is related to U.S. application Ser. No. 08/721,183 to Chan et al., filed Sep. 27, 1996, entitled "SULFONAMIDES AND DERIVATIVES THEREOF THAT MODULATE THE ACTIVITY OF ENDOTHELIN"; is also a related to International PCT application No. PCT/US96/04759 to Chan et al., filed Apr. 4, 1996, entitled "THIENYL-, FURYL-, PYRROLYL- AND BIPHENYL-SULFONAMIDES AND DERIVATIVES THEREOF THAT MODULATE THE ACTIVITY OF ENDOTHELIN"; is also related to U.S. application Ser. No. 08/477,223, now U.S. Pat. No. 5,594,021, to Chan et al., filed Jun. 6, 1995, entitled "THIENYL-, FURYL- AND PYRROLYL SULFONAMIDES AND DERIVATIVES THEREOF THAT MODULATE THE ACTIVITY OF ENDOTHELIN"; is also related to U.S. application Ser. No. 08/417,075 to Chan et al., filed Apr. 4, 1995, entitled "THIENYL-, FURYL- AND PYRROLYL SULFONAMIDES AND DERIVATIVES THEREOF THAT MODULATE THE ACTIVITY OF ENDOTHELIN", now abandoned; is also related to U.S. Application Ser. No. 08/247,072, now U.S. Pat. No. 5,571, 821, to Chan et al., filed May 20, 1994, entitled "SULFONAMIDES FONAMIDES AND DERIVATIVES THEREOF THAT MODULATE THE ACTIVITY OF ENDOTHELIN"; is also related to U.S. application Ser. No. 08/222,287, now U.S. Pat. No. 5,591,761, to Chan et al., filed Apr. 5, 1994, entitled "THIOPHENYL-, FURYL- AND PYRROLYL-SULFONAMIDES AND DERIVATIVES THEREOF THAT MODULATE THE ACTIVITY OF ENDOTHELIN"; each of these applications is related to U.S. application Ser. No. 08/142,552, now U.S. Pat. No. 5,514,691, to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN"; U.S. application Ser. No. 08/142,159, now U.S. Pat. No. 5,464,853, to Chan et al., filed Oct. 21, 1993, entitled "N-(5-ISOXAZOLYL) BIPHENYLSULFONAMIDES, N-(3-ISOXAZOLYL) BIPHENYLSULFONAMIDES AND DERIVATIVES THEREOF THAT MODULATE THE ACTIVITY OF ENDOTHELIN"; and U.S. application Ser. No. 08/142,631 to Chan et al., filed Oct. 21, 1993, entitled "N-(5-ISOXAZOLYL)-BENZENESULFONAMIDES, N-(3-ISOXAZOLYL)-BENZENESUL FONAMIDES AND DERIVATIVES THEREOF THAT MODULATE THE ACTIVITY OF ENDOTHELIN", now abandoned.

Where permitted, the subject matter of each of the above-noted applications is herein incorporated in its entirety by reference thereto.

FIELD OF THE INVENTION

The present invention relates to compounds and formulations thereof for administration to mammals that modulate the activity of the endothelin family of peptides. In particular, sulfonamides and formulations of sulfonamide compounds, especially sodium salts of sulfonamide compounds, for administration for treatment of endothelin-mediated disorders are provided. Also provided is a process for preparing alkali metal salts of hydrophobic sulfonamides.

BACKGROUND OF THE INVENTION

The vascular endothelium releases a variety of vasoactive substances, including the endothelium-derived vasoconstrictor peptide, endothelin (ET) (see, e.q., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332:411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$,$Leu^7$) endothelin-1 and endothelin-3 is ($Thr^2$, $Phe^4$, $Thr^5$, $Tyr^6$, $Lys^7$,$Tyr^{14}$) endothelin-1. These peptides are, thus, highly conserved at the C-terminal ends. Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69:406–413). In isolated vascular strips, for example, endothelin-1 is a potent ($EC_{50}=4\times10^{-10}$ M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2-6\times10^{-10}$ M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET^A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states (see, e.g., International PCT Application WO 94/27979, and U.S. Pat. No. 5,382,569, which disclosures are herein incorporated in their entirety by reference). Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Elevated levels of endothelin have also been measured in patients suffering from ischemic heart disease (Yasuda et al. (1990) *Amer. Heart J.* 119:801–806, Ray et al. (1992) *Br. Heart J.* 67:383–386). Circulating and tissue endothelin immunoreactivity is increased more than twofold in patients with advanced atherosclerosis (Lerman et al. (1991) *New Engl. J. Med.* 325:997–1001). Increased endothelin immunoreactivity has also been associated with Buerger's disease (Kanno et al. (1990) *J. Amer. Med. Assoc.* 264:2868) and Raynaud's phenomenon (Zamora et al. (1990) Lancet 336 1144–1147). Increased circulating endothelin levels were observed in patients who underwent percutaneous transluminal coronary angioplasty (PTCA) (Tahara et al. (1991) *Metab. Clin. Exp.* 40:1235–1237; Sanjay et al. (1991) *Circulation* 84(Suppl. 4):726), and in individuals (Miyauchi et al. (1992) *Jpn. J. Pharmacol.*58:279P; Stewart et al. (1991) *Ann. Internal Medicine* 114:464–469) with pulmonary hypertension. Thus, there is clinical human data supporting the correlation between increased endothelin levels and numerous disease states.

Endothelin Agonists and Antagonists

Because endothelin is associated with certain disease states and is implicated in numerous physiological effects, compounds that can interfere with or potentiate endothelin-associated activities, such as endothelin-receptor interaction and vasoconstrictor activity, are of interest. Compounds that exhibit endothelin antagonistic activity have been identified. For example, a fermentation product of *Streptomyces misakiensis*, designated BE-18257B, has been identified as an $ET_A$ receptor antagonist. BE-18257B is a cyclic pentapeptide, cyclo(D-Glu-L-Ala-allo-D-lle-L-Leu-D-Trp), which inhibits $^{125}$I-labelled endothelin-1 binding in cardiovascular tissues in a concentration-dependent manner ($IC_{50}$ 1.4 µM in aortic smooth muscle, 0.8 µM in ventricle membranes and 0.5 μM in cultured aortic smooth muscle cells), but fails to inhibit binding to receptors in tissues in which $ET_B$ receptors predominate at concentrations up to 100 μM. Cyclic pentapeptides related to BE-18257B, such as cyclo(D-Asp-Pro-D-Val-Leu-D-Trp) (BQ-123), have been synthesized and shown to exhibit activity as $ET_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors. Other peptide and non-peptidic $ET_A$ antagonists have been identified (see,e.g., U.S. Pat. Nos. 5,352,800, 5,334,598, 5,352,659, 5,248,807, 5,240,910, 5,198,548, 5,187,195, 5,082,838). These include other cyclic pentapeptides, acyltripeptides, hexapeptide analogs, certain anthraquinone derivatives, indanecarboxylic acids, certain N-pyriminylbenzenesulfonamides, certain benzenesulfonamides, and certain naphthalenesulfonamides (Nakajima et al. (1991) *J. Antibiot.* 44:1348–1356; Miyata et al. (1992) *J. Antibiot.* 45:74–8; Ishikawa et al. (1992) *J.Med. Chem.* 35:2139–2142; U.S. Pat. No. 5,114,918 to Ishikawa et al.; EP A1 0 569 193; EP A1 0 558 258; EP A1 0 436 189 to BANYU PHARMACEUTICAL CO., LTD (Oct. 7, 1991); Canadian Patent Application 2,067,288; Canadian Patent Application 2,071,193; U.S. Pat. No. 5,208,243; U.S. Pat. No. 5,270,313; U.S. Pat. No. 5,612,359, U.S. Pat. No. 5,514,696, U.S. Pat. No. 5,378,715 Cody et al. (1993) *Med. Chem. Res.* 3:154–162; Miyata et al. (1992) *J. Antibiot* 45:1041–1046; Miyata et al. (1992) *J. Antibiot* 45:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO93/08799; Nishikibe et al. (1993) *Life Sci.* 52:717–724; and Benigni et al. (1993) *Kidney Int.* 44:440–444). Numerous sulfonamides that are endothelin peptide antagonists are also described in U.S. Pat. Nos. 5,464,853, 5,594,021, 5,591,761, 5,571,821, 5,514,691, 5,464,853, International PCT application No.96/31492 and International PCT application No. WO 97/27979.

In general, the identified compounds have activities in in vitro assays as $ET_A$ antagonists at concentrations on the order of about 50–100 μM and less. A number of such compounds have also been shown to possess activity in in vivo animal models.

Endothelin Antagonists and Agonists as Therapeutic Agents

In view of the numerous physiological effects of endothelin and its association with certain diseases, endothelin is believed to play a critical role in these pathophysiological conditions (see, e.g., Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(Suppl. 5): S13–S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions. Stable formulations of these compounds in a pharmaceutically acceptable vehicle are needed in order to use the compounds in these ways.

It has been recognized that compounds that exhibit activity at $IC_{50}$ or $EC_{50}$ concentrations on the order of $10^{-4}$ or lower in standard in vitro assays that assess endothelin antagonist or agonist activity have pharmacological utility (see, e.q., U.S. Pat. Nos. 5,352,800, 5,334,598, 5,352,659, 5,248,807, 5,240,910, 5,198,548, 5,187,195, 5,082,838). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated. As noted above, many of the compounds, particularly the sulfonamide compounds, are potent endothelin antagonists, and, thus, are ideal clinical candidates. For clinical use, stable formulations and suitable formulations for various routes of administration are needed.

Existing methods for making such sulfonamides are associated with certain shortcomings. For example, certain steps in the synthetic pathway are known to result in dimerization of intermediates with the resultant decrease in yield and purity. Second, because the compounds are hydrophobic, purification is difficult, typically, requiring the impractical use of preparative HPLC or column chromatography. Finally, the existing methods are limited to the production of the hydrophobic free sulfonamide, which sulfonamide is difficult to formulate into aqueous based pharmaceutical compositions. Attempts to convert the free sulfonamide to useful salts of alkali metals using metal hydroxides or methoxides may lead to decomposition of the compound.

Therefore, it is an object herein to provide formulations of compounds that have the ability to modulate the biological activity of one or more of the endothelin peptides. It is another object to provide formulations of compounds that have use as specific endothelin antagonists. It is also an object to use formulations of compounds that specifically interact with or inhibit the interaction of endothelin peptides with $ET_A$ or $ET_B$ receptors. Such formulations should be useful as therapeutic agents for the treatment of endothelin-mediated diseases and disorders. Furthermore, there continues to be a need in the art for a practical, efficient method for making salts of desired sulfonamides.

SUMMARY OF THE INVENTION

Salts of Sulfonamide Compounds

Sulfonamide derivatives for use in the formulations and methods provided herein, and methods of preparing sulfonamide derivatives are provided. The sulfonamide derivatives are useful as endothelin receptor antagonists. Of interest are pharmaceutically acceptable derivatives, including salts, esters, acids and bases, solvates, hydrates and prodrugs of the sulfonamides. In particular, derivatives of neutral sulfonamide compounds that yield formulations of unexpectedly greater stability than formulations containing the corresponding neutral compounds are provided. Preferred are salts, particularly alkali metal salts, and more preferably sodium salts, including salts prepared from sodium compounds, including, but not limited to, sodium bicarbonate in which the resulting product is a sodium salt and disodium hydrogen phosphate in which the resulting compound is a sodium hydrogen phosphate salt. The sodium salt of each compound is most preferred.

The salt derivatives include, but are not limited to, salts of alkali metals and alkaline earth metals, including but not limited to sodium salts, potassium salts, lithium salts, calcium salts and magnesium salts; transition metal salts, such as zinc salts, copper salts, gold salts and silver salts, and other metal salts, such as aluminum salts; cationic and polycationic counter ion salts, such as but not limited to ammonium and substituted ammonium salts and organic amine salts, such as hydroxyalkylamines and alkylamines; salts of mineral acids, such as but not limited to hydrochlorides and sulfates; salts of organic acids, such as but not limited acetates, lactates, malates, tartrates, citrates, ascorbates, succinates, butyrates, valerates and fumarates. Also contemplated herein are the corresponding esters of any of the acids.

Among the preferred salts are: the salts of acetates, including trifluoroacetate, N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkyl amines, piperazine, tris(hydroxymethyltaminomethane, aluminum, calcium, lithium, magnesium, potassium, sodium hydrogen phosphate, disodium phosphate, sodium, zinc, barium, gold, silver and bismuth. Alkali metal salts, particularly sodium salts, are preferred herein.

The sulfonamides from which the derivatives, particularly the salts, preferably sodium salts, are prepared have formula I:

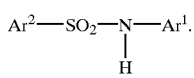

(I)

Such sulfonamides include those described in U.S. Pat. Nos. 5,464,853, 5,594,021, 5,591,761, 5,571,821, 5,514,691, 5,464,853, commonly owned co-pending U.S. application Ser. No. 08/721,183, and commonly owned International PCT application Publication Nos. WO 96/31492 and WO 97/27979.

In certain embodiments, the sulfonamide salts are chosen with the proviso that the salt is not 4-chloro-3-methyl-5-(2-(6-methylbenzold[d][3]dioxol-5-yl)acetyl)-3-thienylsulfonamido)isoxazole, sodium salt; $N^2$-(3-cyanomethyl-2,4,6-trimethylphenyl)-3-(4-chloro-3-methyl-5-isoxazolylsulfamoyl)-2-thiophene carboxamide, sodium salt; $N^2$-(3-acetyloxymethyl-2,4,6-trimethylphenyl)-3-(4-chloro-3-methyl-5-isoxazolylsulfamoyl)-2-thiophenecarboxamide, sodium salt; or $N^2$-(3-hydroxymethyl-2,4,6-trimethylphenyl)-3-(4-chloro-3-methyl-5-isoxazolyl sulfamoyl)-2-thiopenecarboxamide, sodium salt.

In particular, sulfonamides of formula (I) are those in which $Ar^{1'}$ is a substituted or unsubstituted alkyl or is a five or six membered substituted or unsubstituted aromatic or heteroaromatic ring, particularly 3- or 5-isoxazolyl and pyridazinyl, and also including thiazolyl, including 2-thiazolyl, pyrimidinyl, including 2-pyrimidinyl, or substituted benzene groups, including aryloxy substituted benzene groups or is a bicyclic or tricyclic carbon or heterocyclic ring. $Ar^1$ is, in certain embodiments, selected from groups such as:

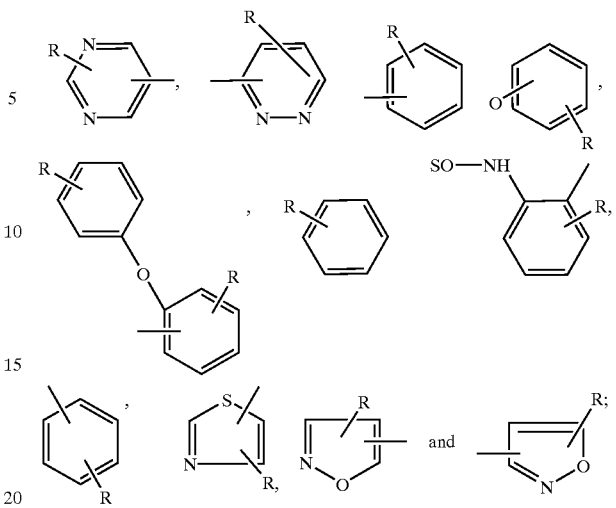

where R is selected from H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and straight or branched chains of from about 1 up to about 10–12 carbons, preferably, 1 to about 5 or 6 carbons. R is preferably H, $NH_2$, halide, $CH_3$, $CH_3O$ or another aromatic group.

$Ar^2$ is any group such that the resulting sulfonamide inhibits binding by 50%, compared to binding in the absence of the sulfonamide, of an endothelin peptide to an endothelin receptor at a concentration of less than about 100 $\mu$M, except that $Ar^2$ is not phenyl or naphthyl when $Ar^1$ is N-(5-isoxazolyl) or N-(3-isoxazolyl) unless the isoxazole is a 4-halo-isoxazole, a 4-higher alkyl ($C_8$ to $C_{15}$)-isoxazole, or the compound is a 4-biphenyl that is unsubstituted at the 2 or 6 position on the sulfonamide-linked phenyl group.

In particular, $Ar^2$ is a substituted or unsubstituted group selected from among groups, subject to the above proviso, including, but not limited to, the following: naphthyl, phenyl, biphenyl, quinolyl, styryl, thienyl, furyl, isoquinolyl, pyrrolyl, benzofuryl, pyridinyl, thianaphthyl, indolyl, alkyl, and alkenyl. It is understood that the positions indicated for substituents, including the sulfonamide groups, may be varied. Thus, for example, compounds herein encompass groups that include thiophene-3-sulfonamides and thiophene-2-sulfonamides.

The sulfonamides are substituted or unsubstituted monocyclic or polycyclic aromatic or heteroaromatic sulfonamides, such as benzene sulfonamides, naphthalene sulfonamides and thiophene sulfonamides. Particularly preferred sulfonamides are N-isoxazolyl sulfonamides. More particularly preferred among such sulfonamides are those in which $Ar^2$ is a heterocycle that contains one ring, multiple rings or fused rings, typically two or three rings and one or two heteroatoms in the ring or rings.

In preferred sulfonamide derivatives, preferably sodium salts, $Ar^2$ is thienyl, furyl, pyrrolyl or a group, such as benzofuryl, thianaphthyl or indolyl, that is a derivative or analog, as described below, of a thienyl, furyl or pyrrolyl group or a 4-biphenyl group, $Ar^1$ is preferably N-(5-isoxazolyl) or N-(3-isoxazolyl). Of most interest herein, are salts, particularly sodium salts, including the sodium salt, of compounds in which $Ar^2$ is a phenylacetyl-substituted thienyl, furyl, pyrrolyl group. Preferred among these as salts, particularly sodium salts, are those in which $Ar^2$ is thienyl, furyl or pyrrolyl, particularly in which $Ar^2$ is substituted with phenylacetyl, and $Ar^1$ is isoxazolyl.

In certain embodiments, preferred salts are selected from among 4-chloro-3-methyl-5-(2-(6-methylbenzo[d][1,3] dioxol-5-yl)acetyl)-3-thienylsulfonamido)isoxazole, sodium salt; $N^2$-(3-cyanomethyl-2,4,6-trimethylphenyl)-3-(4-chloro-3-methyl-5-isoxazolylsulfamoyl)-2-thiophenecarboxamide, sodium salt; $N^2$-(3-acetyloxymethyl-2,4,6-trimethylphenyl)-3-(4-chloro-3-methyl-5-isoxazolylsulfamoyl)-2-thiophenecarboxamide, sodium salt; and $N^2$-(3-hydroxymethyl-2,4,6-trimethylphenyl)-3-(4-chloro-3-methyl-5-isoxazolylsulfamoyl)-2-thiopenecarboxamide, sodium salt.

Among the more preferred sulfonamide salts is the sodium salt of N-(4-chloro-3-methyl-5-isoxazolyl)-2-[2-methyl-4,5-(methylenedioxy)phenylacetyl]thiophene-3-sulfonamide, also referred to herein as 4-chloro-3-methyl-5-(2-(2-(6-methylbenzo[d][1,3]dioxol-5-yl)acetyl)-3-thienylsulfonamido)isoxazole, sodium salt.

Sulfonamides

Also provided are sulfonamide compounds, and derivatives and formulations thereof, as described herein. The sulfonamide compounds are active as endothelin receptor antagonists and provide enhanced tolerability relative to sulfonamides known in the art. Preferred among the sulfonamide compounds are those of formula:

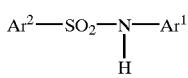

where $Ar^1$ is isoxazolyl and $Ar^2$ has the formula:

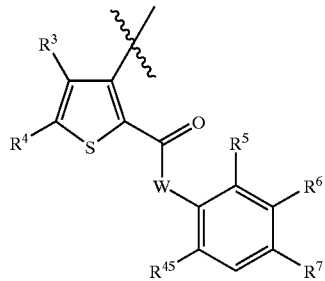

or a pharmaceutically acceptable derivative, including alkali metal salt, particularly sodium salt, thereof, wherein:

$R^3$ and $R^4$ are independently selected from the group consisting of hydrogen, halo, cyano, cyanoalkyl, C(O) $R^{41}$, alkyl, alkenyl, cycloalkyl and aryl, or together form alkylene;

W is O, NH or $CH_2$;

$R^5$, $R^6$ and $R^7$ are each independently selected as in (i) or (ii), with the proviso that at most one of $R^5$, $R^6$ and $R^7$ is hydrogen:

(i) $R^6$ is hydrogen, unsubstituted alkyl, hydroxy, unsubstituted alkoxy, C(O)$R^{41}$, carbamoyloxy or alkoxycarbonyloxy, and $R^5$ and $R^7$ are each independently selected from hydrogen, unsubstituted alkyl, hydroxy, C(O)$R^{41}$, carbamoyloxy and alkoxycarbonyloxy; or (ii) if at least one of $R^3$ and $R^4$ is not hydrogen, then any two may form alkylenedioxy, and the other is selected as in (i);

$R^{45}$ is selected from the group consisting of alkyl, C(O) $R^{41}$, $(CH_2)_xOH$ and $CH(OH)(CH_2)_xCH_3$ in which x is 0–6, $S(O)_nR^{41}$ in which n is 0–2 and $C(=NR^{43})R^{41}$;

$R^{41}$ is alkyl, aryl, heteroaryl, aralkyl, heteroaralkyl, cycloalkyl, alkylamino, dialkylamino, arylamino, diarylamino, alkylsulfonylamino, arylsulfonylamino, alkylsulfonylalkylamino, alkyisulfonylarylamino, arylsulfonylalkylamino or arylsulfonylarylamino; and $R^{43}$ is selected from hydroxy, alkoxy, alkyl and aryl, wherein $R^{41}$ and $R^{43}$ are unsubstituted or substituted with one or more substituents selected from Y, which is alkoxy, halide, pseudohalide, carboxyl, alkoxycarbonyl, aryloxycarbonyl or hydroxy, with the proviso that the compound is not N-(4-chloro-3-methyl-5-isoxazolyl)-2-(2,4,6-trimethylphenylaminocarbonyl)thiophene-3-sulfonamide, N-(4-chloro-3-methyl-5-isoxazolyl)-2-(2,4,6-trimethyl)phenylacetyl-3-thiophenesulfonamide, N-(3,4-dimethyl-5-isoxazolyl)-2-[(2,4,6-trimethylphenoxy)carbonyl]thiophene-3-sulfonamide, N-(4-chloro-3-methyl-5-isoxazolyl)-2-[(2,4,6-trimethylphenoxy)carbonyl]thiophene-3-sulfonamide or N-(4-bromo-3-methyl-5-isoxazolyl)-2-[(2,4,6-trimethylphenoxy)carbonyl]thiophene-3-sulfonamide.

In other embodiments, the sulfonamides are selected with the further proviso that the compound is not N-(4-chloro-3-methyl-5-isoxazolyl)-2-(3-methoxy-2,4,6-trimethylphenylaminocarbonyl)thiophene-3-sulfonamide, N-(4-chloro-3-methyl-5-isoxazolyl)-2-(3-hydroxy-2,4,6-trimethylphenylaminocarbonyl)thiophene-3-sulfonamide, N-(4-chloro-5-methyl-3-isoxazolyl)-2-(3-hydroxy-2,4,6-trimethylphenylaminocarbonyl)thiophene-3-sulfonamide or N-(3,4-dimethyl-5-isoxazolyl)-2-(3-hydroxy-2,4,6-trimethylphenylaminocarbonyl)thiophene-3-sulfonamide.

Thus, the sulfonamides provided herein are 2-acyl-3-thiophenesulfonamides. The corresponding 3-acyl-2-thiophenesulfonamides are also contemplated herein. Formulations and salts as described herein of the above compounds are also provided.

Formulations of Sulfonamides and Sulfonamide Salts

Formulations of sulfonamide compounds, which have activity as endothelin antagonists, for administration to mammals, including humans, are provided. In particular, formulations for parenteral, including intramuscular, intravenous and subcutaneous administration, oral administration, transdermal administration and other suitable routes of administration are provided. The formulations provide a means to consistently deliver effective amounts of the compounds.

Of interest are formulations of pharmaceutically acceptable derivatives, including salts, esters, acids and bases, solvates, hydrates and prodrugs of the sulfonamides. In particular, derivatives of neutral sulfonamide compounds that yield formulations of greater stability than formulations containing the corresponding neutral compounds are provided. Preferred are salts, particularly alkali metal salts, and more preferably sodium salts, including salts prepared from sodium compounds, including, but not limited to, sodium bicarbonate in which the resulting product is a sodium salt and disodium hydrogen phosphate in which the resulting compound is a sodium hydrogen phosphate salt. The sodium salt of each compound is most preferred.

The formulations are compositions suitable for administration by any desired route and include solutions, suspensions, emulsions, tablets, dispersible tablets, pills, capsules, powders, dry powders for inhalers, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Lyophilized powders of the sulfonamide derivatives, methods for preparation thereof, and formulations containing reconstituted forms of the lyophilized powders are also provided. Vials and ampules and syringes and other suitable vessels containing the powders are also provided.

Also among the most preferred formulations for use in methods provided herein, are those that contain compounds that are $ET_A$ selective, i.e., they interact with $ET_A$ receptors at substantially lower concentrations (at an $IC_{50}$ at least about 10-fold lower, preferably 100-fold lower) than they interact with $ET_B$ receptors. In particular, compounds that interact with $ET_A$ with an $IC_{50}$ of less than about 10 $\mu$M, preferably less than 1 $\mu$M, more preferably less than 0.1 $\mu$M, but with $ET_B$ with an $IC_{50}$ of greater than about 10 $\mu$M or compounds that interact with $ET_B$ with an $IC_{50}$ of less than about 10 $\mu$M, preferably less than 1 $\mu$M, more preferably less than 0.1 $\mu$M, but with $ET_A$ with an $IC_{50}$ of greater than about 10 $\mu$M are preferred.

Preferred formulations also include compounds that are $ET_B$ receptor selective or that bind to $ET_B$ receptors with an $IC_{50}$ of less than about 1 $\mu$M. $ET_B$ selective compounds interact with $ET_B$ receptors at $IC_{50}$ concentrations that are at least about 10-fold lower than the concentrations at which they interact with $ET_A$ receptors.

The formulations provided herein are for administration by a selected route and contain effective concentrations of pharmaceutically-acceptable salts of the above-noted compounds. The formulations deliver amounts effective for the treatment of hypertension, stroke, cardiovascular diseases, cardiac diseases including myocardial infarction, pulmonary hypertension, erythropoietin-mediated hypertension, respiratory diseases, inflammatory diseases, including asthma, bronchoconstriction, ophthalmologic diseases including glaucoma and inadequate retinal perfusion, gastroenteric diseases, renal failure, endotoxin shock, menstrual disorders, obstetric conditions, wounds, anaphylactic shock, hemorrhagic shock, and other diseases in which endothelin mediated physiological responses are implicated or that involve vasoconstriction or whose symptoms can be ameliorated by administration of an endothelin antagonist or agonist, are also provided.

In one embodiment, the formulations are capsules and tablets containing the sodium salt of a sulfonamide described herein. Preferred formulations are those that deliver amounts effective for the treatment of hypertension or renal failure. The effective amounts and concentrations are effective for ameliorating any of the symptoms of any of the disorders.

In more preferred embodiments, the formulations are solid dosage forms or gels, preferably capsules or tablets. In a preferred embodiment, the formulations are capsules containing an effective amount, typically about 10–100%, preferably about 50 to 95%, more preferably about 75–85%, most preferably about 80–85%, by weight, of one or more sodium hydrogen phosphate or sodium, preferably sodium, salts of one or more sulfonamide compounds of formula I; about 0 to 25%, preferably 8–15%, of an diluent or a binder, such as lactose or microcrystalline cellulose; about 0 to 10%, preferably about 3–7%, of a disintegrant, such as a modified starch or cellulose polymer, particularly a cross-linked sodium carboxymethyl cellulose, such as crosscarmellose sodium (Crosscarmellose sodium NF is available commercially under the name AC-DI-SOL, FMC Corporation, Philadelphia, Pa.) or sodium starch glycolate; and 0–5%, preferably 0.1–2%, of a lubricant, such a magnesium stearate, talc and calcium stearate. The disintegrant, such as crosscarmellose sodium or sodium starch glycolate, provides for rapid break-up of the cellulosic matrix for immediate release of active agent following dissolution of coating polymer. In all embodiments, the precise amount of active ingredient and auxiliary ingredients can be determined empirically and is a function of the route of administration and the disorder that is treated. Solid forms for administration as tablets are also contemplated herein.

Preferred formulations are prepared from a sterile lyophilized powder containing a sodium salt of a sulfonamide. The lyophilized powders and methods of preparing the powders are also provided herein.

In one embodiment, the compositions are provided in the form of lyophilized solids containing one or more sodium hydrogen phosphate or sodium, preferably sodium, salts of one or more sulfonamide compounds of formula I, and also contain one or more of the following:

a buffer, such as sodium or potassium phosphate, or citrate;

a solubilizing agent, such as LABRASOL (polyethylene glycol-8 caprylic capric glycerides sold by Gattefosse SA, France), dimethylsulfoxide (DMSO), bis (trimethylsilyl)acetamide, ethanol, propyleneglycol (PG), or polyvinylpyrrolidine (PVP); and a sugar or other such carbohydrate, such as sorbitol or dextrose (typically in the range of about 1%–20%, preferably about 5%–15%, more preferably about 5%–10%).

For administration, the lyophilized powder is mixed (typically to yield a single dosage or multiple dosage formulation, about 100–500 mg, preferably 250 mg) with a suitable carrier, such as a phosphate buffered saline.

In other preferred embodiments, in which the formulations are designed for parenteral administration, the compositions contain one or more sodium hydrogen phosphate or sodium, preferably sodium, salts of one or more sulfonamide compounds of formula I; a buffer, such as sodium or potassium phosphate, or citrate; and a sugar, such as sorbitol or dextrose. In a preferred embodiment described in detail herein, the formulations contain one or more sodium salts of the sulfonamide compounds of formula I; a sodium phosphate buffer; and dextrose. Dextrose may be added in the form of a sterile dextrose solution, which is readily available from suppliers known to those of skill in the art.

Methods of Use

Methods using such formulations for modulating the interaction of an endothelin peptide with $ET_A$ and/or $ET_B$ receptors are provided. The methods are effected by contacting the receptors with one or more of the formulated pharmaceutically-acceptable salts of the sulfonamides, preferably formulated sodium salts of the sulfonamides, prior to, simultaneously with, or subsequent to contacting the receptors with an endothelin peptide.

Methods for inhibiting binding of an endothelin peptide to an endothelin receptor are provided. These methods are practiced by contacting the receptor with one or more of the formulations of pharmaceutically-acceptable salts of the compounds provided herein simultaneously, prior to, or subsequent to contacting the receptor with an endothelin peptide.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of formulations of pharmaceutically-acceptable salts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated, by administering effective amounts of one or more of the formulations of pharmaceutically-acceptable salts of the compounds provided herein in pharmaceutically acceptable carriers are provided. Preferred methods of treatment are methods for treatment of hypertension and renal failure.

More preferred methods of treatment are those in which the formulations contain at least one compound that inhibits the interaction of endothelin-1 with $ET_A$ receptors at an $IC_{50}$ of less than about 10 $\mu$M, and preferably less than about 5 $\mu$M, more preferably less than about 1 $\mu$M, even more preferably less than 0.1 $\mu$M, and most preferably less than 0.05 $\mu$M. Other preferred methods are those in which the formulations contain pharmaceutically-acceptable salts of one or more compounds that is (are) $ET_A$ selective or pharmaceutically-acceptable salts of one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of formulations containing therapeutically effective concentrations of pharmaceutically-acceptable salts of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a formulation provided herein, which is effective for ameliorating the symptoms of an endothelin-mediated disorder, antagonizing the effects of endothelin or inhibiting binding of an endothelin peptide to an ET receptor, in which the formulation contained within the packaging material includes a compound that has an $IC_{50}$ of less than about 10 $\mu$M, and a label that indicates that the formulation is used for antagonizing the effects of endothelin, treating an endothelin-mediated disorder, or inhibiting the binding of an endothelin peptide to an ET receptor are provided.

Methods of Preparation

Also provided is a process of making an alkali metal salt of a hydrophobic free sulfonamide is provided. The process includes the steps of dissolving the free sulfonamide in an organic solvent, washing the dissolved free sulfonamide with a saturated solution of a salt of the alkali metal, and recovering the alkali metal salt of the sulfonamide from the organic phase. A preferred organic solvent is ethyl acetate or THF. Preferred alkali metals are sodium, potassium, calcium or magnesium with sodium being most preferred. In accordance with a preferred embodiment, the process uses saturated sodium bicarbonate or sodium carbonate as the alkali metal salt solution. Sodium bicarbonate is most preferred.

Recovery preferably includes the steps of drying the salt solution in organic solvent, concentrating the salt, crystallizing the salt in one or more organic, non-water miscible solvents and collecting the sulfonamide salt by filtration. Preferred organic, non-water miscible solvents are dichloromethane and ether. The process provided herein can further include the step of purifying the sulfonamide salt after recovery.

An embodiment of the process is particularly useful for making 4-chloro-3-methyl-5(2-(6-methylbenzo[d][1,3]dioxol-5-yl)acetyl)-3-thienylsulfonamido)isoxazole, sodium salt; $N^2$-(3-cyanomethyl-2,4,6-trimethylphenyl)-3(4-chloro-3-methyl-5-isoxazolylsulfamoyl)-2-thiophenecarboxamide, sodium salt; $N^2$-(3-acetyloxymethyl-2,4,6-trimethylphenyl)-3-(4-chloro-3-methyl-5-isoxazolylsulfamoyl)-2-thiophenecarboxamide, sodium salt; and $N^2$-(3-hydroxymethyl-2,4,6-trimethylphenyl)-3-(4-chloro-3-methyl-5-isoxazolylsulfamoyl)-2-thiophenecarboxamide, sodium salt.

The, alkali metal salts of sulfonamides, particularly such salts provided by the present process are provided. A preferred such sulfonamide salt is 4-chloro-3-methyl-5-(2-(2-(6-methylbenzo[d][1,3]dioxol-5-yl)acetyl)-3-thienylsulfonamido)isoxazole, sodium salt.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assessed by the ability to interfere with endothelin-induced vasoconstriction. Exemplary assays are set forth in the EXAMPLES. As noted above, the preferred $IC_{50}$ concentration ranges are set forth with reference to assays in which the test compound is incubated with the ET receptor-bearing cells at 4° C. Data presented for assays in which the incubation step is performed at the less preferred 24° C. are identified. It is understood that for purposes of comparison, these concentrations are somewhat higher than the concentrations determined at 4° C.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, eq., Spokes et al. (1989) *J. Cardiovasc. Pharmacol.* 13(Suppl. 5):S191–S192; Spinella et al. (1991) *Proc. Natl. Acad. Sci. USA* 88: 7443–7446; Cardell et al. (1991) *Neurochem. Int.* 18:571–574; and the Examples herein).

As used herein, bioavailability refers to the rate and extent of absorption. Methods for determining bioavailability are well known to those of skill in the art. For example, bioavailability of any of the compounds described herein can be determined empirically by administration of the compound to an animal, followed by taking blood samples over time and measuring the blood concentration of the compound. In vivo half life ($t_{1/2}$) is defined as the time it takes for the concentration of the compound in the blood to be reduced by one-half. Estimations of the area under the curve for intravenous administration can be used to estimate the area under the curve for oral administration, yielding bioavailability data. See, e.g., Milo Gibal (1991) Biopharmaceutics and Pharmacology, 4th edition (Lea and Sediger).

As used herein, efficacy refers to the maximal effect that can be produced by a compound. Efficacy can be determined by methods known to those of skill in the art. For example, it can be determined by the properties of the compound and its receptor-effector system and is reflected in the plateau of the concentration-effect curve. In vivo efficacy refers to efficacy which is determined in an animal model. For example, in vivo efficacy of the compounds described herein can be determined by amelioration of hypoxia-induced pulmonary hypertension in rat. In this context, in vivo efficacy refers to the ability of a compound to restore an elevated pulmonary artery pressure to a normal value. See, eq., DiCarlo et al. (1995) *Am. J. Physiol.* 269:L690–L697.

As used herein, the $IC_{50}$ refers to an amount, concentration or dosage of a particular test compound that achieves a 50% inhibition of a maximal response, such as binding of endothelin to tissue receptors, in an assay that measures such response.

As used herein, EC50 refers to a dosage, concentration or amount of a particular test compound that elicits a dose-dependent response at 50% of maximal expression of a particular response that is induced, provoked or potentiated by the particular test compound.

As used herein a sulfonamide that is $ET_A$ selective refers to sulfonamides that exhibit an $IC_{50}$ that is at least about 10-fold lower with respect to $ET_A$ receptors than $ET_B$ receptors.

As used herein, a sulfonamide that is $ET_B$ selective refers to sulfonamides that exhibit an $IC_{50}$ that is at least about 10-fold lower with respect to $ET_B$ receptors than $ET_A$ receptors.

As used herein, pharmaceutically-acceptable salts, esters, hydrates, solvates or other derivatives of the compounds include any such salts, esters and other derivatives that may be prepared by those of skill in this art using known methods for such derivatization and that produce compounds that may be administered to animals or humans without substantial toxic effects and that either are pharmaceutically active or are prodrugs. Pharmaceutically- acceptable salts include, but are not limited to, salts of alkali metals and alkaline earth metals, including but not limited to sodium salts, potassium salts, lithium salts, calcium salts and magnesium salts; transition metal salts, such as zinc salts, copper salts and aluminum salts; polycationic counter ion salts, such as but not limited ammonium and substituted ammonium salts and organic amine salts, such as hydroxyalkylamines and alkylamines; salts of mineral acids, such as but not limited to hydrochlorides and sulfates, salts of organic acids, such as but not limited acetates, lactates, malates, tartrates, citrates, ascorbates, succinates, butyrate, valerate and fumarates. Also contemplated herein are the corresponding esters.

Preferred pharmaceutically-acceptable salts include, but are not limited to, N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, tris(hydroxymethyl) aminomethane, aluminum, calcium, lithium, magnesium, potassium, sodium hydrogen phosphate, disodium phosphate, sodium, zinc, barium, gold, silver and bismuth salts. Sodium salts, particularly the sodium salt of each of the compound, are most preferred herein.

As used herein, reference to "sodium salts" refers to salts of any sodium compounds in which the counter ion includes $Na^+$ and can include other ions, such as $HPO_4^{2-}$; reference to a "sodium salt" (rather than sodium salts) refers specifically to a salt in which $Na^+$ is the counter ion.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, increased stability of a formulation means that the percent of active component present in the formulation, as determined by assays known to those of skill in the art, such as high performance liquid chromatography, gas chromatography, and the like, at a given period of time following preparation of the formulation is significantly higher than the percent of active component present in another formulation at the same period of time following preparation of the formulation. In this case, the former formulation is said to possess increased stability relative to the latter formulation.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388–392). For example, succinylsulfathiazole is a prodrug of 4-amino-N-(2-thiazoyl) benzenesulfonamide (sulfathiazole) that exhibits altered transport characteristics.

As used herein, acid isostere means a group that is significantly ionized at physiological pH. Examples of suitable acid isosteres include sulfo, phosphono, alkylsulfonylcarbamoyl, tetrazolyl, arylsulfonylcarbamoyl or heteroarylsulfonylcarbamoyl.

As used herein, halo or halide refers to the halogen atoms; F, Cl, Br and I.

As used herein, pseudohalides are compounds that behave substantially similar to halides. Such compounds can be used in the same manner and treated in the same manner as halides (X, in which X is a halogen, such as Cl or Br). Pseudohalides include, but are not limited to cyanide, cyanate, thiocyanate, selenocyanate and azide.

As used herein, haloalkyl refers to a loweralkyl radical in which one or more of the hydrogen atoms are replaced by halogen including, but not limited to, chloromethyl, trifluoromethyl, 1-chloro-2-fluoroethyl and the like.

As used herein, alkyl means an aliphatic hydrocarbon group that is a straight or branched chain preferably having about 1 to 12 carbon atoms in the chain. Preferred alkyl groups are loweralkyl groups which are alkyls containing 1 to about 6 carbon atoms in the chain. Branched means that one or more loweralkyl groups such as methyl, ethyl or propyl are attached to a linear alkyl chain. The alkyl group may be unsubstituted or independently substituted by one or more groups, such as, but not limited to halo, carboxy, formyl, sulfo, sulfino, carbamoyl, amino and imino. Exemplary alkyl groups include methyl, ethyl and propyl.

As used herein the term lower describes alkyl, alkenyl and alkynyl groups containing about 6 carbon atoms or fewer. It is also used to describe aryl groups or heteroaryl groups that contain 6 or fewer atoms in the ring. Loweralkyl, lower alkenyl, and lower alkynyl refer to carbon chains having less than about 6 carbons. In preferred embodiments of the compounds provided herein that include alkyl, alkenyl, or alkynyl portions include loweralkyl, lower alkenyl, and lower alkynyl portions.

As used herein, alkenyl means an aliphatic hydrocarbon group containing a carbon-carbon double bond and which may be straight or branched chained having from about 2 to about 10 carbon atoms in the chain. Preferred alkenyl groups have 2 to about 4 carbon atoms in the chain. Branched means that one or more loweralkyl or lower alkenyl groups are attached to a linear alkenyl chain. The alkenyl group may be unsubstituted or independently substituted by one or more groups, such as, but not limited to: halo, carboxy, formyl, sulfo, sulfino, carbamoyl, amino and imino. Exemplary alkenyl groups include ethenyl, propenyl and butenyl.

As used herein, alkynyl means an aliphatic hydrocarbon group containing a carbon-carbon triple bond and which may be straight or branched having about 2 to 10 carbon atoms in the chain. Branched means that one or more loweralkyl, alkenyl or alkynyl groups are attached to a linear alkynyl chain. An exemplary alkynyl group is ethynyl.

As used herein, aryl means an aromatic monocyclic or multicyclic hydrocarbon ring system containing from 3 to 15 or 16 carbon atoms, preferably from 5 to 10. Aryl groups include, but are not limited to groups, such as phenyl, substituted phenyl, naphthyl, substituted naphthyl, in which the substituent is loweralkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, cycloalkyl refers to saturated cyclic carbon chains; cycloalkenyl and cycloalkynyl refer to cyclic carbon chains that include at least one unsaturated double or triple bond, respectively. The cyclic portions of the carbon chains may include one ring or two or more fused rings.

As used herein, cycloalkenyl means a non-aromatic monocyclic or multicyclic ring system containing a carbon-carbon double bond and having about 3 to about 10 carbon atoms. Exemplary monocyclic cycloalkenyl rings include cyclopentenyl or cyclohexenyl; preferred is cyclohexenyl. An exemplary multicyclic cycloalkenyl ring is norbornylenyl. The cycloalkenyl group may be independently substituted by one or more halo or alkyl.

As used herein, "haloalkyl" refers to a loweralkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "carboxamide" refers to groups of formula $R_pCONH_2$ in which R is selected from alkyl or aryl, preferably loweralkyl or lower aryl and p is 0 or 1.

As used herein, "alkylaminocarbonyl" refers to —C(O)NHR in which R is hydrogen, alkyl, preferably loweralkyl or aryl, preferably lower aryl.

As used herein "dialkylaminocarbonyl" as used herein refers to —C(O)NR'R in which R' and R are independently selected from alkyl or aryl, preferably loweralkyl or loweraryl; "carboxamide" refers to groups of formula NR'COR.

As used herein, "alkoxycarbonyl" as used herein refers to —C(O)OR in which R is alkyl, preferably loweralkyl or aryl, preferably lower aryl.

As used herein, "alkoxy" and "thioalkoxy" refer to RO— and RS—, in which R is alkyl, preferably loweralkyl or aryl, preferably lower aryl.

As used herein, "haloalkoxy" refers to RO—in which R is a haloalkyl group.

As used herein, "aminocarbonyl" refers to —C(O)NH$_2$.

As used herein, cycloalkyl refers to saturated cyclic carbon chains; cycloalkenyl and cycloalkynyl refer to cyclic carbon chains that include at least one unsaturated triple bond. The cyclic portions of the carbon chains may include one ring or two or more fused rings.

As used herein, alkylenedioxy means an —O-alkyl-O— group in which the alkyl group is as previously described. A replacement analog of alkylenedioxy means an alkylenedioxy in which one or both of the oxygen atoms is replaced by a similar behaving atom or group of atoms such as, S, N, NH, Se. An exemplary replacement alkylenedioxy group is ethylenebis(sulfandiyl). Alkylenethioxyoxy is —S-alkyl-O—, —O-alkyl-S— and alkylenedithioxy is —S-alkyl-S—.

As used herein, heteroaryl means an aromatic monocyclic or fused ring system in which one or more of the carbon atoms in the ring system is(are) replaced by an element(s) other than carbon, for example nitrogen, oxygen or sulfur. Preferred cyclic groups contain one or two fused rings and include from about 3 to about 7 members in each ring. Similar to "aryl groups", the heteroaryl groups may be unsubstituted or substituted by one or more substituents. Exemplary heteroaryl groups include pyrazinyl, pyrazolyl, tetrazolyl, furyl, (2- or 3-)thienyl, (2-,3- or 4-)pyridyl, imidazoyl, pyrimidinyl, isoxazolyl, thiazolyl, isothiazolyl, quinolinyl, indolyl, isoquinolinyl, oxazolyl and 1,2,5-oxadiazolyl. Preferred heteroaryl groups include 5 to 6-membered nitrogen-containing rings, such as pyrimidinyl.

As used herein, alkoxycarbonyl means an alkyl-O—CO—group. Exemplary alkoxycarbonyl groups include methoxy- and ethoxycarbonyl.

As used herein, carbamoyl means —CONH$_2$. As with all groups described herein, these groups may be unsubstituted or substituted. Substituted carbamoyl includes groups such as —CONY$^2$Y$^3$ in which Y$^2$ and Y$^3$ are independently hydrogen, alkyl, cyano(loweralkyl), aryalkyl, heteroaralkyl, carboxy(loweralkyl), carboxy(aryl substituted loweralkyl), carboxy(carboxy substituted loweralkyl), carboxy(hydroxy substituted loweralkyl), carboxy(heteroaryl substituted loweralkyl), carbamoyl(loweralkyl), alkoxycarbonyl (loweralkyl) or alkoxycarbonyl(aryl substituted loweralkyl), provided that only one of Y$^2$ and Y$^3$ may be hydrogen and when one of Y$^2$ and Y$^3$ is carboxy(loweralkyl), carboxy(aryl substituted loweralkyl), carbamoyl(loweralkyl), alkoxycarbonyl(loweralkyl) or alkoxycarbonyl(aryl substituted loweralkyl) then the other of Y$^2$ and Y$^3$ is hydrogen or alkyl. Preferred for Y$^2$ and Y$^3$ are independently hydrogen, alkyl, cyano(loweralkyl), aryalkyl, heteroaralkyl, carboxy (loweralkyl), carboxy(aryl substituted loweralkyl) and carbamoyl(loweralkyl).

As used herein, any corresponding N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), N-(4,5-dimethyl-3-isoxazolyl) derivative thereof refers to compounds in which Ar$^2$ is the same as the compound specifically set forth, but Ar$^1$ is N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), or N-(4,5-dimethyl-3-isoxazolyl) in which halo is any halide, preferably Cl or Br.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

A. Salts of Sulfonamide Compounds

In the embodiments described in detail herein, salts, preferably sodium salts, of sulfonamide compounds for use in the formulations and methods provided herein are those in which Ar$^1$ is an isoxazole and the compounds are represented by the formulae II:

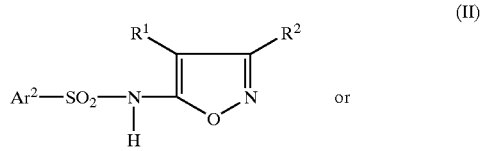

-continued

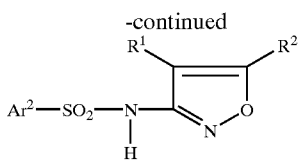

in which
R¹ and R² are either (i), (ii) or (iii) as follows:
(i) R¹ and R² are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that R² is not halide or pseudohalide; or,
(ii) R¹ and R² together form $—(CH_2)_n—$, where n is 3 to 6; or,
(iii) R¹ and R² together form 1,3-butadienyl, and with the above proviso that Ar² is not phenyl or naphthyl when Ar¹ is N-(5-isoxazolyl) or N-(3-isoxazolyl) unless the isoxazole is a 4-halo-isoxazole, a 4-higher alkyl ($C_8$ to $C_{15}$)-isoxazole, or the compound is a 4-biphenylsulfonamide that is unsubstituted at the 2 or 6 position on the sulfonamide-linked phenyl group.

In preferred embodiments herein, R¹ and R² are each selected independently from among alkyl, lower alkenyl, lower alkynyl, lower haloalkyl, halide, pseudohalide or H, except that R² is not halide.

In certain embodiments, the sulfonamides are chosen with the proviso that the compound is not 4-chloro-3-methyl-5 (2-(6-methylbenzo[d][1,3]dioxol-5-yl)acetyl)-3-thienylsulfonamido)isoxazole, sodium salt; $N^2$-(3-cyanomethyl-2,4,6-trimethylphenyl)-3(4-chloro-3-methyl-5-isoxazolylsulfamoyl)-2-thiophenecarboxamide, sodium salt; $N^2$-(3-acetyloxymethyl-2,4,6-trimethylphenyl)-3-(4-chloro-3-methyl-5-isoxazolylsulfamoyl)-2-thiophenecarboxamide, sodium salt; or $N^2$-(3-hydroxymethyl-2,4,6-trimethylphenyl)-3-(4-chloro-3-methyl-5-isoxazolylsulfamoyl)-2-thiopenecarboxamide, sodium salt.

In certain embodiments described in detail herein, Ar² is a 4-biphenyl or is a single ring heterocycle, particularly a 5-membered ring, or is a fused bicyclic or tricyclic heterocycle that contains one or more, particularly one, heteroatom selected from S, O and $NR^{42}$, in the ring, where $R^{42}$ contains up to about 30 carbon atoms, preferably 1 to 10, more preferably 1 to 6 and is selected from hydrogen, alkyl, alkenyl, alkynyl, aryl, alkylaryl, heterocyclyl, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocyclyl, aralkyl, aralkoxy, cycloalkyl, cycloalkenyl, cycloalkynyl; $R^{42}$ and $R^{15}$ are unsubstituted or are substituted with one or more substituents each selected independently from Z, which is hydrogen, halide, pseudohalide, alkyl, alkoxy, alkenyl, alkynyl, aryl, alkynyl, aryl, heterocyclyl, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocyclyl, aralkyl, aralkoxy, cycloalkyl, cycloalkenyl or cycloalkynyl; $R^{12}$, which is selected independently from $R^{42}$ and Z, is selected from hydrogen, alkyl, alkenyl, alkynyl, aryl, alkylaryl, heterocyclyl, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocyclyl, aralkyl, aralkoxy, cycloalkyl, cycloalkenyl or cycloalkynyl; each of $R^{42}$, $R^{12}$, $R^{15}$ and $R^{16}$ may be further substituted with the any of the groups set forth for Z.

In preferred embodiments herein, $R^{42}$ is aryl, such as phenyl or alkyl phenyl, hydrogen or loweralkyl.

Thus, in the compounds provided herein Ar² includes thienyl, furyl and pyrrolyl, benzofuryl, benzopyrrolyl, benzothienyl, benzo[b]furyl, benzo[b]thienyl, and indolyl (benzo[b]pyrrolyl) and 4-biphenyl, and Ar¹ is preferably N-(5-isoxazolyl) or N-(3-isoxazolyl). The sulfonamides are N-isoxazolyl sulfonamides and the compounds have formula III:

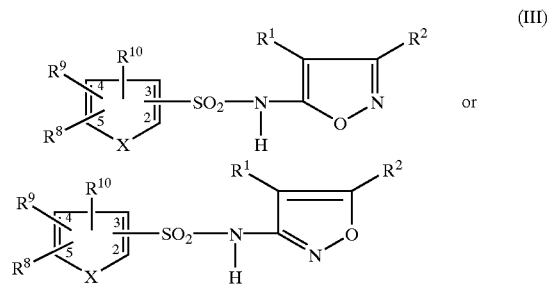

in which X is S, O or $NR^{11}$ in which $R^{11}$ contains up to about 30 carbon atoms, preferably 1 to 10, more preferably 1 to 6 and is selected from hydrogen, alkyl, alkenyl, alkynyl, aryl, alkylaryl, heterocyclyl, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocyclyl, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, heterocyclyl, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$, $R^{16}$ is hydrogen, alkyl, alkenyl, alkynyl, aryl, alkylaryl, heterocyclyl, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocyclyl, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocyclyl, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z, and $R^{11}$ is preferably hydrogen, aryl, such as phenyl or alkyl phenyl, loweralkyl; or the compounds are 4-biphenylsulfonamides in which Ar¹ is preferably N-(5-isoxazolyl) or N-(3-isoxazolyl.

Among the embodiments described in detail herein, Ar² is thienyl, furyl, pyrrolyl or a group that is a derivative or analog, as described below, of a thienyl, furyl or pyrrolyl group, including benzo[b] derivatives such as a benzo[b]

thienyl, $Ar^1$ is N-(5-isoxazolyl) or N-(3-isoxazolyl). $Ar^2$ has the formula IV:

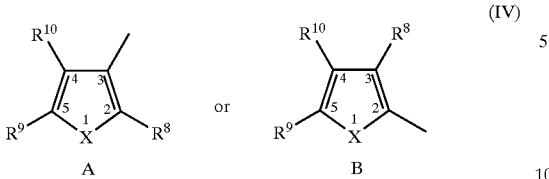

in which X is O, S or $NR^{11}$, where $R^{11}$ is as defined above; that can be substituted at any or all positions or is an analog or derivative of the groups of formula (IV) in which the substituents form fused aromatic, aliphatic or heterocyclic rings; and $R^8$, $R^9$ and $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, $C(O)R^{18}$, $(OAc)CH=CHR^{18}$, $CO_2R^{18}$, SH, $(CH_2)_rC(O)(CH_2)_nR^{18}$, $(CH_2)_r(CH=CH)_s(CH_2)_nR^{18}$, $(CH_2)_rC(O)(CH=CH)_s(CH_2)_nR^{18}$, $(CH_2)_r(CH=CH)_sC(O)(CH_2)_nR^{18}$, $(CH_2)_rNH(CH=CH)_s(CH_2)_nR^{18}$, $C=N(OH)(CH_2)_nR^{18}$, $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$, $(CH_2)_nR^{18}$, $S(O)_mR^{18}$ in which m is 0–2, s, n and r are each independently 0 to 6, preferably 0–3, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocyclyl, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, heteroaryl, alkylaryl, heterocyclyl, alkoxy, aryloxy, aralkyl, aralkoxy, cycloalkyl, cycloalkenyl or cycloalkynyl; and any of the groups set forth for $R^8$, $R^9$ and $R^{10}$ are unsubstituted or substituted with any substituents set forth for Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocyclyl, aralkyl, alkoxy, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocyclyl, aralkyl, aralkoxy, cycloalkyl, cycloalkenyl or cycloalkynyl, with the proviso that if $R^8$ is $NR^{18}R^{19}$, $OR^{18}$, $R^{19}NCOR^{18}$ and $CONR^{19}R^{18}$ $CO_2R^{18}$, $(CH_2)_rNH(CH=CH)_s(CH_2)_nR^{18}$, $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$ or $(CH_2)_rR^{18}$ and $R^{18}$ is an aryl group containing 5 or 6 members, then the aryl group has at least two substituents, and preferably one substituent at the 2-position relative to the linkage to the thienyl, furyl or pyrrolyl;

(ii) any two of $R^8$, $R^9$ and $R^{10}$ with the carbon to which each is attached form an aryl, aromatic ring, heteroaromatic ring, carbocyclic or heterocyclic ring, which is saturated or unsaturated, containing from about 3 to about 16 members, preferably 3 to about 10 members, more preferably 5 to 7 members that is substituted with one or more substituents, each substituent is independently selected from Z; the other of $R^8$, $R^9$ and $R^{10}$ is selected as in (i); and the heteroatoms are $NR^{11}$, O, or S, with the proviso that $Ar^2$ is not 5-halo-3-loweralkylbenzo[b]thienyl, 5-halo-3-loweralkylbenzo[b]furyl, 5-halo-3-loweralkylbenzo[b]pyrrolyl.

In the embodiments provided herein, the alkyl, alkynyl and alkenyl portions of each listed substituent are straight or branched chains, acyclic or cyclic, and preferably have from about 1 up to about 10 carbons; in more preferred embodiments they have from 1–6 carbons. The aryl, alicyclic, aromatic rings and heterocyclic groups can have from 3 to 16, generally, 3–7, more often 5–7 members in the rings, and may be single or fused rings. The ring size and carbon chain length are selected up to an amount that the resulting molecule binds and retains activity as an endothelin antagonist or agonist, such that the resulting compound inhibits binding by 50%, compared to binding in the absence of the sulfonamide, of an endothelin peptide to an endothelin receptor at a concentration of less than about 100 μM.

In preferred embodiments of interest herein, $R^9$ and $R^{10}$ are hydrogen, halide or methyl, more preferably hydrogen or halide, and $R^8$ is selected from $CO_2R^{18}$, $(CH_2)_rC(O)(CH_2)_nR^{18}$, $(CH_2)_r(CH=CH)_s(CH_2)_nR^{18}$, $C=N(OH)(CH_2)_nR^{18}$, $(CH_2)_rC(O)(CH=CH)_s(CH_2)_nR^{18}$, $(CH_2)_r(CH=CH)_sC(O)(CH_2)_nR^{18}$, $(CH_2)_rNH(CH=CH)_s(CH_2)_nR^{18}$, $(CH_2)_r(CH=CH)_sNH(CH_2)_nR^{18}$, $(CH_2)_rC(O)NH(CH_2)_nR^{18}$, $C(O)(CH_2)_rNH(CH_2)_nR^{18}$, $(CH_2)_rNH(CH_2)_nR^{18}$, $(CH_2)_nR^{18}$, with the proviso that if $R^8$ is $CO_2R^{18}$, $(CH_2)_rC(O)NH(CH_2)_nR^{18}$, $C(O)(CH_2)_rNH(CH_2)_nR^{18}$, $(CH_2)_rC(O)NH(CH_2)_nR^{18}$ or $(CH_2)_nR^{18}$ and $R^{18}$ is phenyl, the phenyl group is substituted at least two positions, and preferably, at least one of those positions is ortho.

In the preferred compounds, $R^{18}$ is aryl or heteroaryl, preferably having 5 or 6 members in the ring, more preferably phenyl or pyrimidinyl, most preferably phenyl.

In the most preferred compounds herein, $R^{18}$ is phenyl, which is substituted at more than one position, and most preferably at least one substituent is at the ortho position, $R^9$ and $R^{10}$ are each hydrogen, halide or loweralkyl, preferably hydrogen, and $R^8$ is $C(O)NHR^{18}$, $C(O)CH_2R^{18}$, $(CH_2)R^{18}$, with the proviso that if $R^8$ is $C(O)NHR^{18}$, then the phenyl group must have at least two substituents, preferably one of the substituents is in the ortho position.

In other preferred embodiments, $Ar^2$ is a benzo[b]thienyl, benzo[b]furyl, or indolyl (benzo[b]pyrrolyl), with the proviso that the benzene ring is substituted and the substituents are other than 5 halo, 3-loweralkyl. Preferred substituents on the benzene ring, include, but are not limited to, one or more selected from alkylenedioxy, particularly methylenedioxy, preferably 3,4-methylenedioxy, ethylenedioxy, aryl, particularly phenyl, dimethylamino, diethylamino, benzyl, alkoxy, particularly lower alkoxy, such as methoxy and ethoxy, halide, and alkyl, preferably loweralkyl.

In the preferred compounds herein, $R^2$ is preferably, selected from among alkyl, lower alkenyl, lower alkynyl, lower haloalkyl or H; and $R^1$ is halide or loweralkyl, and more preferably, $R^1$ is bromide or chloride, methyl or ethyl. In the most active compounds provided herein, as evidenced by in vitro binding assays, $R^1$ is bromide or chloride. For use in vivo $R^1$ is preferably chloride.

In most preferred embodiments herein, the formulations contain sodium salts of the above compounds in which $R^8$ is a phenylacetyl. Of the compounds described herein, those that inhibit or increase an endothelin-mediated activity by about 50% at concentrations of less than about 10 μM are preferred. More preferred are those that inhibit or increase an endothelin-mediated activity by about 50% at concentrations of less than about 1 μM, more preferably less than about 0.1 μM, even more preferably less than about 0.01 μM, and most preferably less than about 0.001 μM. It is noted that, as described below, the $IC_{50}$ concentration determined in the in vitro assays is a non-linear function of incubation temperature. The preferred values recited herein refer to the assays that are performed at 4° C. When the assays are performed at 24° C., somewhat higher (see, Table 1) $IC_{50}$ concentrations are observed. Accordingly, the preferred $IC_{50}$ concentrations are about 10-fold higher.

Also among the most preferred compounds for use in methods provided herein, are those that are $ET_A$ selective, i.e., they interact with $ET_A$ receptors at substantially lower concentrations (at an $IC_{50}$ at least about 10-fold lower, preferably 100-fold lower) than they interact with $ET_B$ receptors. In particular, compounds that interact with $ET_A$ with an $IC_{50}$ of less than about 10 μM, preferably less than 1 μM, more preferably less than 0.1 μM, but with $ET_B$ with an $IC_{50}$ of greater than about 10 μM or compounds that interact with $ET_B$ with an $IC_{50}$ of less than about 10 μM, preferably less than 1 μM, more preferably less than 0.1 μM, but with $ET_A$ with an $IC_{50}$ of greater than about 10 μM are preferred.

Preferred compounds also include compounds that are $ET_B$ receptor selective or that bind to $ET_B$ receptors with an $IC_{50}$ of less than about 1 μM. $ET_B$ selective compounds interact with $ET_B$ receptors at $IC_{50}$ concentrations that are at least about 10-fold lower than the concentrations at which they interact with $ET_A$ receptors. In these compounds, $R^2$ is selected from among alkyl, lower alkenyl, lower alkynyl, lower haloalkyl, halide or H; and $R^1$ is halide or loweralkyl, and in preferred embodiments, $R^1$ is bromide or chloride, preferably chloride; $R^9$ and $R^{10}$ are selected independently from hydrogen, loweralkyl, preferably methyl or ethyl, or halide, and $R^8$, which is the substituent at the 5 position (see, e.g., formulae III and IV), is aryl or a heterocycle, particularly phenyl and isoxazolyl, which are unsubstituted or substituted with Z, which is preferably loweralkyl or halide.

1. $Ar^2$ is a thiophene, pyrrole, furan, benzolbithiophene, indolyl (benzo[b]pyrrole), or benzo[b]furan Among the sulfonamide salts provided herein are salts of compounds represented by the formula V:

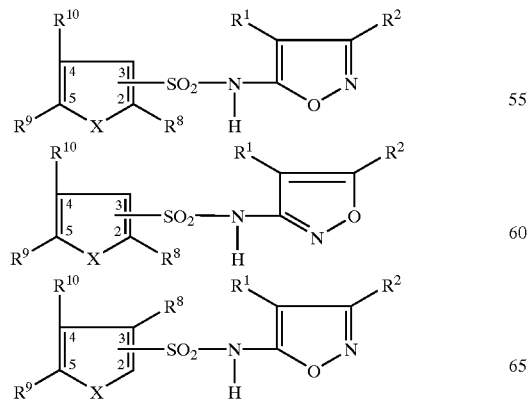

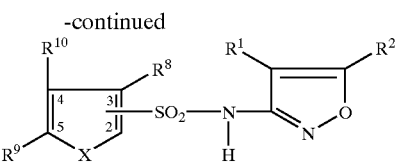

in which $R^1$ and $R^2$ are either (i), (ii) or (iii as follows:
(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, haloalkoxy, haloalkyl, alkylsulfinyl, alkylsulfonyl, aryloxy, arylamino, arylthio, arylsulfinyl, arylsulfonyl, aminocarbonyl, arylaminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons, except the $R^2$ is not halide, pseudohalide or higher alkyl; or,
(ii) $R^1$ and $R^2$ together form —$(CH_2)_n$—, where n is 3 to 6; or,
(iii) $R^1$ and $R^2$ together form 1,3-butadienyl; and X is S, O or $NR^{11}$ in which $R^{11}$ contains up to about 30 carbon atoms, preferably 1 to 10, more preferably 1 to 6 and is selected from hydrogen, alkyl, alkenyl, alkynyl, aryl, alkylaryl, heterocyclyl, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocyclyl, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, heterocyclyl, aralkyl, aralkoxy, cycloalkyl, cycloalkenyl, cycloalkynyl, OH, CN, C(O)$R^{16}$, $CO_2R^{16}$, SH, $S(O)_nR^{16}$ in which n is 0–2, NHOH, $NR^{12}R^{16}$, $N_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocyclyl, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocyclyl, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocyclyl, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z, and $R^{11}$ is preferably hydrogen, aryl, such as phenyl or alkyl phenyl, loweralkyl; and $R^8$, $R^9$ and $R^{10}$, which each contain hydrogen or up to about 50 carbon atoms, generally up to about 30, more generally 20 or fewer, are each independently selected as described above, and more preferably from (i) or (ii) as follows:
(i) $R^9$ and $R^{10}$ are selected from hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, $C(O)R^{18}$, $(OAC)CH=CHR^{18}$, $CO_2R^{18}$, SH, $(CH_2)_rC(O)$ $(CH_2)_nR^{18}$, $(CH_2)_r(CH=CH)_s(CH_2)_nR^{18}$, $(CH_2)_rC$ (O)(CH=CH)$_s$(CH$_2$)$_n$R$^{18}$, (CH$_2$)$_r$(CH=CH)$_s$C(O)(CH$_2$)$_r$R$^{18}$, (CH$_2$)$_r$NH(CH=CH)$_s$(CH$_2$)$_n$R$^{18}$, C=N(OH)(CH$_2$)$_r$R$^{18}$, (CH$_2$)$_r$(CH=CH)$_s$NH(CH$_2$)$_n$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH$_2$)$_n$R$^{18}$, (CH$_2$)$_r$R$^{18}$, S(O)$_m$R$^{18}$ in which m is 0–2, s, n and r are each independently 0 to 6, preferably 0–3, HNOH, NR$^{18}$R$^{19}$, NO$_2$, N$_3$, OR$^{18}$, R$^{19}$NCOR$^{18}$ and CONR$^{19}$R$^{18}$, in which R$^{19}$ is selected from hydrogen, alkyl, alkenyl, alkynyl, aryl, alkylaryl, alkoxy, aryloxy, heterocyclyl, aralkyl, aralkoxy, cycloalkyl, cycloalkenyl, cycloalkynyl, C(O)R$^{20}$, S(O)$_n$R$^{20}$ in which n is 0–2; and R$^{18}$ and R$^{20}$ are independently selected from hydrogen, alkyl, alkenyl, alkynyl, aryl, heteroaryl, alkylaryl, heterocyclyl, alkoxy, aryloxy, aralkyl, aralkoxy, cycloalkyl, cycloalkenyl or cycloalkynyl;

R$^8$ is selected from C(O)R$^{18}$, (OAC)CH=CHR$^{18}$, CO$_2$R$^{18}$, (CH$_2$)$_r$C(O)(CH$_2$)$_n$R$^{18}$, (CH$_2$)$_r$(CH=CH)$_s$(CH$_2$)$_n$R$^{18}$, (CH$_2$)$_r$C(O)(CH=CH)$_s$(CH$_2$)$_n$R$^{18}$, (CH$_2$)$_r$(CH=CH)$_s$C(O)(CH$_2$)$_n$R$^{18}$, (CH$_2$)$_r$NH(CH=CH)$_s$(CH$_2$)$_n$R$^{18}$, C=N(OH)(CH$_2$)$_r$R$^{18}$(CH$_2$)$_r$(CH=CH)$_s$NH(CH$_2$)$_n$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH$_2$)$_n$R$^{18}$, (CH$_2$)$_r$R$^{18}$, in which m is 0–2, s, n and r are each independently 0 to 6, preferably 0–3, in which R$^{18}$ is aryl, preferably phenyl, with the proviso that, if R$^8$ is (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH$_2$)$_n$R$^{18}$, (CH$_2$)$_r$R$^{18}$, particularly if r is 0 and/or n is 0, and R$^{18}$ is aryl, particularly phenyl, then R$^{18}$ must have two or more substituents, with preferably at least one ortho substituent;

where any of the groups set forth for R$^8$, R$^9$ and R$^{10}$ are unsubstituted or substituted with any substituents set forth for Z, which is hydrogen, halide, pseudohalide, alkyl, alkoxy, alkenyl, alkynyl, aryl, aryloxy, heterocyclyl, aralkyl, aralkoxy, cycloalkyl, cycloalkenyl, cycloalkynyl, OH, CN, C(O)R$^{21}$, C$_2$R$^{21}$, SH, S(O)$_n$R$^{21}$ in which n is 0–2, NHOH, NR$^{22}$R$^{21}$, NO$_2$, N$_3$, OR$^{21}$, R$^{22}$NCOR$^{21}$ and CONR$^{22}$R$^{21}$; R$^{22}$ is selected from hydrogen, alkyl, alkenyl, alkynyl, aryl, alkylaryl, heterocyclyl, aralkyl, alkoxy, aralkoxy, cycloalkyl, cycloalkenyl, cycloalkynyl, C(O)R$^{23}$ and S(O)$_n$R$^{23}$ in which n is 0–2; and R$^{21}$ and R$^{23}$ are independently selected from hydrogen, alkyl, alkenyl, alkynyl, aryl, alkylaryl, heterocyclyl, aralkyl, aralkoxy, cycloalkyl, cycloalkenyl or cycloalkynyl; or (ii) any two of R$^8$, R$^9$ and R$^{10}$ form an aryl, aromatic ring, heteroaromatic ring, carbocyclic or heterocyclic ring, which is saturated or unsaturated, containing from about 3 to about 16 members, preferably 3 to about 10 members, more preferably 5 to 7 members that is substituted with one or more substituents, each substituent being independently selected from Z; the other of R$^8$, R$^9$ and R$^{10}$ is selected as from the groups set forth for R$^9$ and R$^{10}$ in (i); and the heteroatoms are NR$^{11}$, O, or S, with the proviso that Ar$^2$ is not 5-halo-3-loweralkylbenzo[b]thienyl, 5-halo-3-loweralkylbenzo[b]furyl, 5-halo-3-loweralkylbenzo[b]pyrrolyl.

In these embodiments, Ar$^2$ is, thus, represented by the formulae (IVA and IVB):

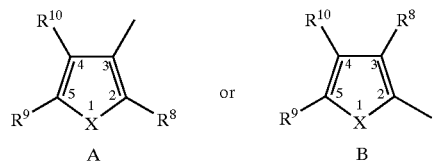

that can be substituted at any or all positions or is an analog of compounds of formula (IV) in which the substituents form fused aromatic, aliphatic or heterocyclic rings; and in which X is NR$^{11}$, O, or S, and R$^{11}$, which is hydrogen or contains up to about 30 carbon atoms, preferably 1 to 10, more preferably 1 to 6, and is selected as defined above. R$^8$, R$^9$, R$^{10}$ are selected as described above.

In the embodiments provided herein, when R$^8$, R$^9$ and R$^{10}$ are selected as in (i), above, R$^8$ is preferably selected from among (CH$_2$)$_r$C(O)(CH$_2$)$_n$R$^{18}$, (CH$_2$)$_r$NH(CH$_2$)$_n$R$^{18}$, (CH$_2$)$_r$NH(CH$_2$)$_n$R$^{18}$, (CH$_2$)$_r$(CH=CH)$_s$(CH$_2$)$_n$R$^{18}$, (CH$_2$)$_r$C(O)(CH=CH)$_s$(CH$_2$)$_n$R$^{18}$, (CH$_2$)$_r$(CH=CH)$_s$C(O)(CH$_2$)$_n$R$^{18}$, (CH$_2$)$_r$(CH=CH)$_s$NH(CH$_2$)$_n$R$^{18}$, C=N(OH)(CH$_2$)$_r$R$^{18}$, (CH$_2$)$_r$C(O)NH(CH$_2$)$_n$R$^{18}$, C(O)(CH$_2$)$_r$NH(CH$_2$)$_n$R$^{18}$, (CH$_2$)$_r$NH(CH=CH)$_s$(CH$_2$)$_n$R$^{18}$, (CH$_2$)$_r$C(O)NH(CH$_2$)$_n$R$^{18}$, (CH$_2$)$_r$NH(CH$_2$)$_n$R$^{18}$, (CH$_2$)$_r$R$^{18}$, with the proviso that if R$^8$ is (CH$_2$)$_r$C(O)NH(CH$_2$)$_n$R$^{18}$, (CH$_2$)$_r$C(O)NH (CH$_2$)$_n$R$^{18}$, or (CH$_2$)$_r$R$^{18}$, and R$^{18}$ is phenyl, the phenyl group is substituted at least two positions, and preferably, at least one of those positions is ortho.

In preferred of these compounds, R$^{18}$ is aryl or heteroaryl, preferably having 5 or 6 members in the ring, more preferably phenyl or pyrimidinyl, most preferably phenyl. R$^9$ and R$^{10}$ are preferably hydrogen, halide, loweralkyl, or halo loweralkyl.

The more preferred compounds provided herein are compounds in which the alkyl, alkynyl and alkenyl portions are straight or branched chains, acyclic or cyclic, and have from about 1 up to about 10 carbons; in certain of the more preferred embodiments they have from 1–6 carbons, and they can have fewer than 6 carbons. The aryl, homocyclic and heterocyclic groups can have from 3 to 16, generally, 3–7, more often 5–7 members in the rings, and may be single or fused rings. The ring size and carbon chain length are selected such that the resulting molecule exhibits activity as an endothelin antagonist or agonist as evidenced by in vitro or in vivo tests, particularly the tests exemplified herein.

In any of the above preferred embodiments: R$^1$ and R$^2$ are preferably selected independently from alkyl, lower alkenyl, lower alkynyl, lower haloalkyl, halide, pseudohalide and H, except that R$^2$ is not halide or pseudohalide, and in preferred embodiments is also not higher alkyl.

In preferred embodiments: X is S, O, NR$^{11}$ in which R$^{11}$ is aryl, hydrogen, or loweralkyl, preferably, a substituted or unsubstituted aryl, particularly phenyl, preferably unsubstituted or substituted with loweralkyl or halogen hydrogen or loweralkyl; R$^1$ is hydrogen, halide, pseudohalide, loweralkyl or lower haloalkyl, most preferably halide; R$^2$ is hydrogen, loweralkyl or lower haloalkyl.

The aryl groups are unsubstituted or is substituted with groups such as alkyl, alkoxy, alkoxyalkyl, halogen, alkylenedioxy, particularly methylenedioxy, amino, nitro and other such groups. The alkyl substituents are preferably loweralkyl, more preferably containing 1–3 carbons.

In more preferred embodiments, two of R$^4$ and R$^{10}$ are hydrogen, halide or loweralkyl and R$^8$ is C(O)NHR$^{18}$ or C(O)CH$_2$R$^{18}$ in which R$^{18}$ is a phenyl group that is substituted at least two positions, most preferably at least one substituent at the ortho position and also 3,4 or 4,5 alkylenedioxy substituents. In more preferred of these embodiments X is S.

In all embodiments, $R^1$ is preferably halide, H, $CH_3$ or $C_2H_5$, and $R_2$ is H; $CH_3$, $C_2H_5$, $C_2F_5$ or $CF_3$. In yet more preferred embodiments, $R^1$ preferably Br, Cl or $CH_3$; $R^2$ is H, $CH_3$, $C_2H_5$, or $CF_3$.

In other embodiments two of $R^8$, $R^9$ and $R^{10}$ form a ring so that $Ar^2$ is benzo[b]thienyl, benzo[b]furyl, or indolyl, with the proviso that there is one or more substituents and they are other than 5-halo and 3-loweralkyl, and the other of $R^8$, $R^9$ and $R^{10}$ is selected from aryl, $(CH_2)_rR^{18}$, $C(O)R^{18}$, $CO_2R^{18}$, $NR^{18}R^{19}$, SH, $S(O)_nR^{18}$ in which n is 0–2, HNOH, $NO_2$, $N_3$, $OR^{18}$, $R^{19}NCOR^{18}$ and $CONR^{19}R^{18}$. $Ar^2$ may be further substituted with any of the groups set forth for $R^8$, $R^9$ and $R^{10}$, and are preferably selected from among alkyl, alkoxy, alkoxyalkyl, aryl, alkylaryl, aminoalkyl, arylamino, aryl-substituted amino, and $NR^{11}$.

In embodiments in which $ET_B$ antagonists are desired, it is preferred that $R^8$ and $R^{10}$ are H or loweralkyl and $R^9$ includes heterocyclic or aromatic ring of preferably from 3 to 14, more preferably, 5 to 7, members in the ring. In particular, if X is S, $R^8$ and $R^{10}$ are H or loweralkyl, and $R^9$, includes an aryl group, particularly a substituted phenyl, such as a 2-loweralkyl substituent. The aryl portion is substituted with groups such as alkyl, alkoxy, alkoxyalkyl, halogen, alkylenedioxy, particularly methylenedioxy, amino, nitro and other such groups. The alkyl substituents are preferably loweralkyl, more preferably containing 1–3 carbons.

If X is $NR^{11}$, then $R^{11}$ is aryl, particularly unsubstituted phenyl or substituted phenyl, such as isopropylphenyl.

Other preferred compounds, which are $ET_B$ active, are those in which $Ar^2$ has formula IVB in which $R^9$ is aryl or Z-substituted aryl, particularly phenyl, and Z is loweralkyl or loweralkoxy.

In all embodiments of all of the compounds herein $R^1$ is preferably halide or loweralkyl, most preferably Br, and the compounds are, with reference to formulae IV, 2- or 3-sulfonamides, particularly thiophene sulfonamides. In certain embodiments provided herein, $Ar^2$ is a benzo[b]thienyl, benzo[b]furyl or indolyl (benzo[b]pyrrolyl) group and the compounds provided herein are preferably benzo[b]thienyl-, benzo[b]furyl- or indolylsulfonamides. Benzo[b]thienyl, benzo[b]furyl and indolyl 2- or 3-sulfonamides are among the compounds preferred herein. The benzo[b]thienyl, benzo[b]furyl and indolyl 2- or 3-sulfonamides provided herein are selected with the proviso that the benzene group has at least one substituent and that substituent is other than 5-halo and 3-loweralkyl.

Compounds of particular interest include salts, particularly sodium salts, of formula III in which $Ar^2$ is a phenyl-, benzothienyl, benzofuryl or indolyl [benzopyrrolyl] group or in which $Ar^2$ is a substituted phenylaminocarbonylthienyl, substituted phenylaminocarbonylfuryl, substituted aminocarbonylpyrrolyl group in which there are at least two substituents or $Ar^2$ is phenylacetylthienyl, phenylacetylfuryl, or phenylacetylpyrrolyl, or is an acetoxystyrylthienyl, acetoxystyrylfuryl or acetoxystyrylpyrrolyl group.

The most preferred compounds provided herein are the salts of the compounds that have an $IC_{50}$ for $ET_A$ receptors in the assays exemplified herein less than 0.1 μM, more preferably less than 0.01 μM, and more preferably less than 0.001 (see, e.g., Table 1 for representative experimental results), when measured at 4° C., as described in the Examples. When measured at 24° C., the $IC_{50}$ concentrations are somewhat higher (2- to 10-fold; see, Table 1 for some comparative values).

Among the preferred compounds of interest herein are the salts of those in which $Ar^2$ has formula VI:

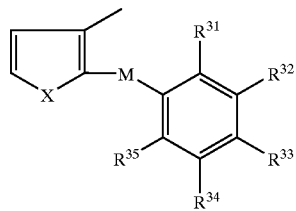

in which

M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH(CH_2)_r$, $(CH_2)_m(CH=CH)(CH_2)_r$, $C=N(OH)(CH_2)_r$, $(CH_2)_mC(O)(CH=CH)_sNH(CH_2)_r$, $CH(OH)(CH_2)_r$, $CH(CH_3)C(O)(CH_2)_r$, $CH(CH_3)C(O)(CH_2)_m$ $(CH=CH)(CH_2)_r$, $(CH_2)_r$, $(CH_2)_rO$, C(O)O, in which m,s and r are each independently 0 to 6, preferably 0 to 3, more preferably M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH(CH_2)_r$, $(CH_2)_m(CH=CH)(CH_2)_r$, $C=N(OH)(CH_2)_r$, $CH(OH)(CH_2)_r$, $(CH_2)_r$, $(CH_2)_rO$, C(O)O;

$R^{31}$, $R^{32}$, $R^{33}$, $R^{34}$ and $R^{35}$ are each independently selected from (i) or (ii) as follows:

(i) $R^{31}$, $R^{32}$, $R^{33}$, $R^{34}$ and $R^{35}$ are each independently selected from among H, OH, $NHR^{38}$, $CONR^{38}R^{39}$, $NO_2$, cyano, halide, pseudohalide, alkyl, alkenyl, alkynyl, aryl, arylalkyl, heteroaryl, alkoxy, alkylamino, alkylthio, haloalkyl, alkylsulfinyl, alkylsulfonyl, alkoxycarbonyl, alkylcarbonyl, alkenylthio, alkenylamino, alkenyloxy, alkenyl sulfinyl, alkenylsulfonyl, alkoxycarbonyl, arylaminocarbonyl, alkylaminocarbonyl, aminocarbonyl, (alkylaminocarbonyl)alkyl, carboxyl, carboxyalkyl, carboxyalkenyl, alkylsulfonylaminoalkyl, cyanoalkyl, acetyl, acetoxyalkyl, hydroxyalkyl, alkyoxyalkoxy, hydroxyalkyl, (acetoxy)alkoxy, (hydroxy)alkoxy and formyl; or (ii) at least two of $R^{31}$, $R^{32}$, $R^{33}$, $R^{34}$ and $R^{35}$, which substitute adjacent carbons on the ring, together form alkylenedioxy, alkylenethioxyoxy or alkylenedithioxy (i.e. —O—$(CH_2)_n$—O—, —S—$(CH_2)_n$—O—, —S—$(CH_2)_n$—S—, where n is 1 to 4, preferably 1 or 2,) which is unsubstituted or substituted by replacing one or more hydrogens with halide, loweralkyl, loweralkoxy or halo loweralkyl, and the others of $R^{31}$, $R^{32}$, $R^{33}$, $R^{34}$ and $R^{35}$ are selected as in (i); and $R^{38}$ and $R^{39}$ are each independently selected from hydrogen, alkyl, alkenyl, alkynyl, aryl, haloalkyl alkylaryl, heterocyclyl, arylalkyl, arylalkoxy, alkoxy, aryloxy, cycloalkyl, cycloalkenyl and cycloalkynyl, and is preferably hydrogen, loweralkyl, loweralkoxy and lowerhaloalkyl, with the proviso that when M is $(CH_2)_mC(O)NH(CH_2)_r$, then at least two of $R^{31}$, $R^{32}$, $R^{33}$, $R^{34}$ and $R^{35}$ are not hydrogen.

M is most preferably selected from

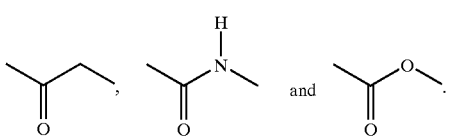

In general, however, in all of these compounds in which Ar² has formula V or VI or in which $R^8$ includes an aryl group, regardless of the selection of M, it is preferred that the aryl substituent have more than one substituent or at least one substituent in the ortho position. Aryl is preferably phenyl that is preferably substituted at the ortho position and, more preferably at least one additional position, particularly 4 and 6, or adjacent positions, such as 3,4 or 4,5 when the substituents are linked to form an alkylenedioxy (or analog thereof in which one or both oxygens is(are) replaced with S.

In all compounds, at least one of $R^{31}$ and $R^{35}$ is other than hydrogen.

In more preferred compounds, M is $C(O)CH_2$, $C(O)NH$, $—CH=CH—$, $CH_2CH_2C(O)(CH)_2$, $CH_2CHC(O)CH_2$, and most preferably has formula VII:

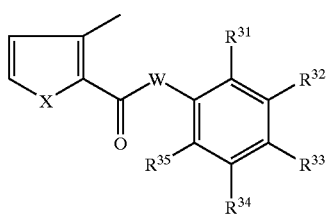

in which W is $CH_2$ or NH.

M is even more preferably selected from among:

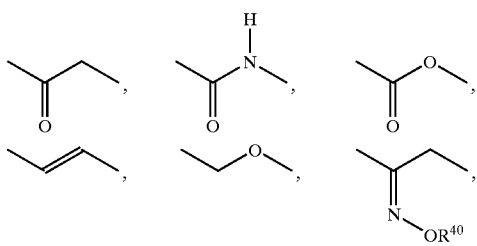

-continued

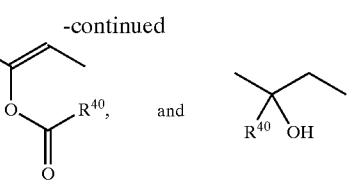

in which $R^{40}$ is preferably hydrogen, alkyl, alkoxy, alkoxyalkyl, haloalkyl, and more preferably loweralkyl, loweralkoxy, or halo loweralkyl, and is more preferably hydrogen or loweralkyl, particularly methy; or ethyl, and is most preferably hydrogen.

M is most preferably:

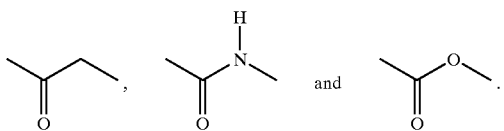

In preferred compounds $R^{31}$, $R^{32}$, $R^{33}$, $R^{34}$ and $R^{35}$ are selected from (i) or (ii):

(i) $R^{31}$, $R^{32}$, $R^{33}$, $R^{34}$ and $R^{35}$ are each independently selected from loweralkyl, haloloweralkyl, phenyl, alkoxy, loweralkylsulfonylaminoloweralkyl, cyanoloweralkyl, acetyl, loweralkoxycarbonyl, cyano, OH, acetoxyloweralkyl, hydroxy loweralkyl, acetoxy loweralkoxy or loweralkoxycarbonyl; or (ii) $R^{32}$ and $R^{33}$ or $R^{33}$ and $R^{34}$ form alkylenedioxy, preferably methylenedioxy, and the others of $R^{31}$, $R^{32}$, $R^{33}$, $R^{34}$ and $R^{35}$ are selected as in (i).

In preferred embodiments, $R^{31}$, $R^{33}$, $R^{35}$ are other then hydrogen and are preferably loweralkyl or lower alkoxy, or $R^{31}$ or $R^{35}$ is other than hydrogen, preferably loweralkyl or lower alkoxy, and $R^{32}$ and $R^{33}$ or $R^{33}$ and $R^{34}$ form methylenedioxy.

In all embodiments, preferred substituents also can be determined by reference to Table 1, which sets forth exemplary compounds. Preferred compounds are those of Table 1 that have the highest activities, and preferred substituents are those on the compounds with the highest activities.

TABLE 1

| COMPOUND | $ET_A$ ($\mu M$)* | $ET_B$ ($\mu M$)* |
|---|---|---|
| N-(4-bromo-3-methyl-5-isoxazolyl)-5-bromothio-phene-2-sulfonamide | 0.314 | 2.26 |
| N-(4-bromo-3-methyl-5-isoxazolyl)-5-(2'-thienyl)thio-phene-2-sulfonamide | 5.1 | 0.363 |
| N-(4-bromo-3-methyl-5-isoxazolyl)-3-phenoxythio-phene-2-sulfonamide | 0.103 | 3.46 |
| N-(3,4-dimethyl-5-isoxazolyl)benzofuran-2-sulfonamide | 5.22 | 38.4 |
| N-(3,4-dimethyl-5-isoxazolyl)furan-2-sulfonamide | 3.13 | — |
| N-(4-bromo-3-methyl-5-isoxazolyl)-5-phenylfuran-2-sulfonamide | 0.857 | 2.43 |
| N-(4-bromo-3-methyl-5-isoxazolyl)furan-2-sulfonamide | 0.75 | 88.1 |
| N-(4-bromo-3-methyl-5-isoxazolyl)-2,5-dimethylfuran-3-sulfonamide | 0.46 | 36.5 |

TABLE 1-continued

| COMPOUND | ET$_A$ ($\mu$M)* | ET$_B$ ($\mu$M)* |
|---|---|---|
| N-(4-bromo-3-methyl-5-isoxazolyl)-5-(phenthio)furan-2-sulfonamide | 5.0 | 7.0 |
| N-(4-Bromo-3-methyl-5-isoxazolyl)-1-(phenyl)pyrrole-2-sulfonamide | 18.1 | 8.7 |
| N-(4-Bromo-3-methyl-5-isoxazolyl)-1-(4'-isopropylphenyl)pyrrole-2-sulfonamide | 11.4 | 0.166 |
| N-(4-Bromo-3-methyl-5-isoxazolyl) 1-(4'-isopropylphenyl)pyrrole-3-sulfonamide | 0.838 | 0.211 |
| (4-bromo-3-methyl-5-isoxazolyl)-1-(4'-biphenyl)pyrrole-2-sulfonamide | 9.17 | 7.84 |
| N-(4-bromo-3-methyl-5-isoxazolyl)2-thiophenesulfonamide | 0.095 ± 0.07 | 27.7 ± 15.0 |
| N-(4-bromo-5-methyl-3-isoxazolyl)thiophene-2-sulfonamide | 0.211 | 27.3 |
| N-(4-bromo-3-methyl-5-isoxazolyl)thiophene-3-sulfonamide | 0.135 | 23.4 |
| 5-(3-isoxazolyl)-N-(3-methyl-5-isoxazolyl)-2-thiophenesulfonamide | 5.6 | 6.7 |
| N-(4-Bromo-3-methyl-5-isoxazolyl)-5-(2-pyridyl)thiophene-2-sulfonamide | 3.84 | 2.70 |
| N-(4-Bromo-3-methyl-5-isoxazolyl)-4,5-dibromothiophene-2-sulfonamide | 0.281 | 2.58 |
| N-(4-Bromo-3-methyl-5-isoxazolyl)-5-chloro-3-methylbenzo[b]thiophene-2-sulfonamide | 0.96 | 1.63 |
| N-(4-Bromo-3-methyl-5-isoxazolyl)-5-(4-chlorobenzamidomethyl)thiophene-2-sulfonamide | 0.311 | 2.57 |
| N-(4-Bromo-3-methyl-5-isoxazolyl)-4-benzenesulfonylthiophene-2-sulfonamide | 0.383 | — |
| 4-bromo-5-chloro-N-(4-Bromo-3-methyl-5-isoxazolyl)-thiophene-2-sulfonamide | 0.359 | 2.67 |
| N-(4-Bromo-3-methyl-5-isoxazolyl)-2,5-dimethylthiophene-3-sulfonamide | 0.0956 | 7.8 |
| N-(4-Bromo-3-methyl-5-isoxazolyl)-4,5-dichlorothiophene-2-sulfonamide | ~0.45 | ~4.9 |
| N-(4-Bromo-3-methyl-5-isoxazolyl)-4-bromo-2,5-dichlorothiophene-3-sulfonamide | ~0.28 | 10.4 |
| N-(4-Bromo-3-methyl-5-isoxazolyl)-2,5-dichlorothiophene-3-sulfonamide | ~0.39 | 2.62 |
| N-(4-Bromo-3-methyl-5-isoxazolyl)-5-{3-[1-methyl-5-(trifluoromethyl)pyrazolyl]}thiophene-2-sulfonamide | ~6.7 | ~0.36 |
| N-(4-Bromo-3-methyl-5-isoxazolyl)-5-benzenesulfonylthiophene-2-sulfonamide | 0.570 | 0.333 |
| N-(4-bromo-3-methy)-5-isoxazolyl)-2-(carbomethoxy)thiophene-3-sulfonamide | 0.0208 | 98.1 |
| N-(3,4-dimethyl-5-isoxazolyl-5-phenylthiophen-2-sulfonamide | 2.55 | 1.29 |
| N-(4-bromo-3-methyl-5-isoxazolyl)-2-(N-phenylaminocarbonyl)thiophene-3-sulfonamide | 0.0054 | 18.8 |
| N-(4-bromo-5-methyl-3-isoxazolyl)-2-(N-phenylaminocarbonyl)thiophene-3-sulfonamide | — | — |
| N-(4-chloro-3-methyl-5-isoxazolyl)-2-(N-phenylaminocarbonyl)thiophene-3-sulfonamide | — | — |
| N-(3,4-dimethyl-5-isoxazolyl)-2-(carboxyl)thiophene-3-sulfonamide | 2.64 | >~100 |
| N-(4-chloro-3-methyl-5-isoxazolyl))-2-(carbomethoxy)thiophene-3-sulfonamide | | |
| N-(3,4-dimethyl-5-isoxazolyl)-2-(N-phenylaminocarbonyl)thiophene-3-sulfonamide | 0.0182 | ~170 |
| N-(3,4-dimethyl-5-isoxazolyl)-2-(carbomethoxy)thiophene-3-sulfonamide | 0.367 | — |
| N-(4-Bromo-3-methyl-5-isoxazolyl)-2-(carboxyl)thiophene-3-sulfonamide | ~0.6 | ~67 |
| N-(4-Bromo-3-methyl-5-isoxazolyl)-2-[N-(4-methoxyphenyl)aminocarbonyl]thiophene-3-sulfonamide | 0.002 | 2.12 |
| N-(4-Bromo-3-methyl-5-isoxazolyl)-2-[N-(3-methoxyphenyl)aminocarbonyl]thiophene-3-sulfonamide | 0.003 | 5.86 |
| N-(4-Bromo-3-methyl-5-isoxazolyl)-2-[N-(2-methoxyphenyl)aminocarbonyl]thiophene-3-sulfonamide | 0.0116 | 13.2 |
| N-(4-Bromo-3-methyl-5-isoxazolyl)-2-(N-benzylaminocarbonyl)thiophene-3-sulfonamide | 0.013 | 12.7 |
| N-(4-Bromo-3-methyl-5-isoxazolyl)-2-[N-(4-ethylphenyl)aminocarbonyl]thiophene-3-sulfonamide | 0.0016 | 0.849 |
| N-(4-Bromo-3-methyl-5-isoxazolyl)-2-[N-(4-biphenyl)aminocarbonyl]thiophene-3-sulfonamide | 0.0376 | 0.912 |
| N-(3,4-dimethyl-5-isoxazolyl)-3-methoxythiophene-2-sulfonamide | 2.5 | 45.5 |

TABLE 1-continued

| COMPOUND | $ET_A$ ($\mu M$)* | $ET_B$ ($\mu M$)* |
|---|---|---|
| N-(4-bromo-3-methyl-5-isoxazolyl)-5-(4-ethylphenyl)thiophene-2-sulfonamide | 3.23 | 0.0855 |
| N-(4-bromo-3-methyl-5-isoxazolyl)-3-phenylthiophene-2-sulfonamide | 0.0547 | 11.1 |
| N-(4-bromo-3-methyl-5-isoxazolyl)-4-phenylthiophene-2-sulfonamide | 0.224 | 1.17 |
| N-(3,4-dimethyl-5-isoxazolyl)benzo[b]thiophene-2-sulfonamide | 7.22 | 11.1 |
| N-(4-bromo-3-methyl-5-isoxazolyl)-2-phenylthiophene-3-sulfonamide | — | — |
| N-(4-chloro-3-methyl-5-isoxazolyl)-2-(N-phenylaminocarbonyl)thiophene-3-sulfonamide | — | — |
| N-(4-bromo-3-methyl-5-isoxazolyl)-5-benzylthiophene-2-sulfonamide | — | — |
| N-(4-chloro-3-methyl-5-isoxazolyl)-2-carboxythiophene-3-sulfonamide | — | — |
| N-(4-bromo-3-methyl-5-isoxazolyl)-5-(4'-isopropylphenyl))thiophene-2-sulfonamide | 1.6 | 0.3 |
| N-(4-bromo-3-methyl-5-isoxazolyl)-4-(4'-isopropylphenyl))thiophene-2-sulfonamide | 5.5 | 1.3 |
| N-(4-bromo-3-methyl-5-isoxazolyl)-5-(4'-propylphenyl))thiophene-2-sulfonamide | 5.6 | 0.51 |
| N-(4-bromo-3-methyl-5-isoxazolyl)-2-[-(4-tolulyl-aminocarbonyl]thiophene-3-sulfonamide | <0.01** | 1.67** |
| N-(4-bromo-3-methyl-5-isoxazolyl)-2-[N-(4-isopropylphenyl)aminocarbonyl]thiophene-3-sulfonamide | <0.01** | 1.13** |
| N-(4-bromo-3-methyl-5-isoxazolyl)-2-(4-t-butylphenyl)aminocarbonylthiophene-3-sulfonamide | 0.011** | 2.82** |
| N-(4-bromo-3-methyl-5-isoxazolyl)-2-(4-butylphenyl)aminocarbonylthiophene-3-sulfonamide | 0.044** | 2.84** |
| N-(4-bromo-3-methyl-5-isoxazolyl)-2-[N-(4-sec-butylphenyl)aminocarbonyl]thiophene-3-sulfonamide | ~0.008** | 1.76** |
| N-(3,4-dimethyl-5-isoxazolyl)-2-methylbenzo[b]thiophene-3-sulfonamide | 0.167 | 16.6 |
| N-(4-bromo-3-methyl-5-isoxazolyl)-2-methylbenzo[b]thiophene-3-sulfonamide | 0.0486 | 3.5 |
| N-(4-bromo-3-methyl-5-isoxazolyl)-2-ethylbenzo[b]thiophene-3-sulfonamide | 0.0067 | 5.13 |
| N-(4-bromo-3-methyl-5-isoxazolyl)-2-n-benzylbenzo[b]thiophene-3-sulfonamide | 0.0182 | ~1 |
| N-(4-bromo-3-methyl-5-isoxazolyl)-2-butylbenzo[b]thiophene-3-sulfonamide | 0.0226 | ~3 |
| N-(4-bromo-3-methyl-5-isoxazolyl)-2-i-propylbenzo[b]thiophene-3-sulfonamide | 0.005<br>0.03† | 5.7<br>10.7† |
| N-(4-bromo-3-methyl-5-isoxazolyl)-2-n-propylbenzo[b]thiophene-3-sulfonamide | 0.024<br>0.074† | 7.95<br>16.6† |
| N-(4-bromo-3-methyl-5-isoxazolyl)-2-(4-ethylbenzyl)benzo[b]thiophene-3-sulfonamide | 0.048† | 1.1† |
| N-(4-bromo-3-methyl-5-isoxazolyl)-2-[3,4-(methylenedioxy)benzyl]benzo[b]thiophene-3-sulfonamide | 0.0015 ± 0.0014<br>0.0074 ± 0.0011† | 0.324 ± 0.78<br>0.939 ± 0.262† |
| N-(4-bromo-3-methyl-5-isoxazolyl)-2-(3,4,5-trimethoxybenzyl)-benzo[b]-thiophene-3-sulfonamide | 0.013† | 1.2† |
| N-(4-bromo-3-methyl-5-isoxazolyl)-2-ethyl-5-methylbenzo[b]thiophene-3-sulfonamide | 1.89 ± 0.431† | 54.3 ± 2.6† |
| N-(4-chloro-3-methyl-5-isoxazolyl)-2-[(3,4-methylenedioxy)benzyl]benzo[b]thiophene-3-sulfonamide | 0.011 ± 0.005† | 0.936 ± 0.095† |
| N-(4-bromo-3-methyl-5-isoxazolyl)-2-(3,4-dimethoxybenzyl)benzo[b]thiophene-3-sulfonamide | 0.021 ± 0.017† | 2.94 ± 1.32† |
| N-(4-bromo-3-methyl-5-isoxazolyl)-5-(benzo[b]thien-2-yl)thiophene-2-sulfonamide | 16† | 0.80† |
| N-(4-bromo-3-methyl-5-isoxazolyl)-2-(4-methoxybenzyl)benzo[b]thiophene-3-sulfonamide | 0.051† | 1.5† |
| N-(4-bromo-3-methyl-5-isoxazolyl)-2-(2-methoxybenzyl)-benzo[b]thiophene-3-sulfonamide | 0.19† | 2.2† |
| N-(3,4-dimethyl-5-isoxazolyl)-2-(4-chlorobenzyl)benzo[b]thiophene-3-sulfonamide | 0.21† | 4.7† |
| N-(4-chloro-3-methyl-5-isoxazolyl)-2-(4-dimethylaminobenzyl)benzo[b]thiophene-3-sulfonamide | 0.041†<br>0.014 | 1.3†<br>0.477 |
| N-(4-chloro-3-methyl-5-isoxazolyl)-2-ethylbenzo[b]furan-3-sulfonamide | 0.15† | 22† |
| N-(4-chloro-3-methyl-5-isoxazolyl)-2-phenylbenzo[b]thiophene sulfonamide | 0.932† | 46.8† |
| N-(4-chloro-3-methyl-5-isoxazolyl)-6-methoxy-2-[3,4-(methylenedioxy)benzyl]benzo[b]thiophene-3-sulfonamide | ~2$^{est†}$ | 2.39† |

TABLE 1-continued

| COMPOUND | ET$_A$ ($\mu$M)* | ET$_B$ ($\mu$M)* |
|---|---|---|
| N-(4-chloro-5-methyl-3-isoxazolyl)-2-[3,4-(methylene-dioxy)benzyl]benzo[b]thiophene-3-sulfonamide | 0.0055† | 0.364† |
| N-(4-chloro-3-methyl-5-isoxazolyl)-2-methoxycarbonylthiophene-3-sulfonamide | 0.631 | 53.2 |
| N-(4-bromo-3-methyl-5-isoxazolyl)-4-(4-propylphenyl(thiophene-2-sulfonamide | 0.962† | 0.435† |
| N-(4-bromo-3-methyl-5-isoxazolyl)-3-(phenylthio)thiophene-2-sulfonamide | 0.0801† | 3.68† |
| N-(3,4-dimethyl-5-isoxazolyl))-3-(phenylaminocarbonyl)thiophene-2-sulfonamide | 0.163 | >100 |
| N-(4-chloro-3-methyl-5-isoxazolyl)-2-[(4-tolyl)amino-carbonyl[thiophene-3-sulfonamide | 0.00116 / 0.0105† | 2.93 / 14† |
| N-(4-bromo-3-methyl-5-isoxazolyl)-5-(4-methoxyphenyl)thiophene-2-sulfonamide | 8.69 / 26.3† | 0.363 / 2.4† |
| N-(4-bromo-3-methyl-5-isoxazolyl)-5-(3-methoxyphenyl)thiophene-2-sulfonamide | 3.26 / 23.4† | 0.776 / 4.7† |
| N-(4-bromo-3-methyl-5-isoxazolyl)-5-(3-thienyl)thio-phene-2-sulfonamide | 4.49 | 0.380 |
| N-(4-bromo-3-methyl-5-isoxazolyl)-3-methylthio-phene-2-sulfonamide | 0.651 | 7.15 |
| N-(4-bromo-3-methyl-5-isoxazolyl)-3-(phenethyl)thio-phene-2-sulfonamide | 0.16 / 0.676† | 10.77 / 37.2† |
| N-(4-bromo-3-methyl-5-isoxazolyl)-4-(phenethyl)thio-phene-2-sulfonamide | 6.64 | 3.97 |
| N-(3,4-dimethyl-5-isoxazolyl)-2-[(4-methylphenyl)-aminocarbonyl]thiophene-3-sulfonamide | 0.00336 | 11.3 |
| N-(4-bromo-3-methyl-5-isoxazolyl)-2,5-dimethyl-4-phenylthiophene-3-sulfonamide | 1.40 | ~100 |
| N-(4-bromo-3-methyl-5-isoxazolyl)-2-[(methyl)phenylaminocarbonyl]thiophene-3-sulfonamide | 0.188 | 16.0 |
| N-(4-bromo-3-methyl-5-isoxazolyl)-2-($\alpha$-hydroxybenzyl)thiophene-3-sulfonamide | 0.337 | 9.37 |
| N-(4-bromo-5-methyl-3-isoxazolyl)-5-(4-methylphenyl)thiophene-2-sulfonamide | 7.10 / 15.8† | 0.3593 / 0.25† |
| N-(4-bromo-3-methyl-5-isoxazolyl)-5-phenylthio-phene-2-sulfonamide | 3.53 / 36.6† | 0.417 / 2.4† |
| N-(4-bromo-3-methyl-5-isoxazolyl)-5-[4-(trifluoromethyl)phenyl]thiophene-2-sulfonamide | 6.39 / 6.31† | 0.0835 / .282† |
| N,N'-bis{3-[(4-bromo-3-methyl-5-isoxazolyl)aminosulfonyl)thien-2-yl} urea | 0.0692 / 0.295† | 0.290 / 1.19† |
| N-(4-bromo-3-methyl-5-isoxazolyl)-2-(hydroxymethyl)thiophene-3-sulfonamide | 0.160 / 1.55† | 44.1 / — |
| N-(4-bromo-3-methyl-5-isoxazolyl)-5-(2-formylphenyl)thiophene-3-sulfonamide | 3.46 / 12.31† | 0.529 / 1.28 ± 0.71† |
| N,N'-bis{3-[3,4-dimethyl-5-isoxazolyl)aminosulfonyl]thien-2-yl}urea | 1.01 ± 1.03 / 2.7† | 3.7 ± 2.7 / 5.9† |
| N-(3,4-dimethyl-5-isoxazolyl))-2-[(3-methylanilino)methyl]thiophene-3-sulfonamide | 0.214 / 0.933† | 5.34 / 7.7† |
| N-(4-bromo-3-methyl-5-isoxazolyl)-5-(3-aminophenyl)thiophene-2-sulfonamide | 0.537 / 1.44† | 1.07 / 2.63† |
| N-(4-bromo-3-methyl-5-isoxazolyl)-5-[3,5-bis(triflouromethyl)phenyl]thiophene-2-sulfonamide | 0.794 / 5.9† | 12.0 / 15.5† |
| N-(4-bromo-3-methyl-5-isoxazolyl)-5-(3,3-dimethylbutyn-1-yl)thiophene-2-sulfonamide | 1.12 / 7.24† | 24.0 / 35.5† |
| N-(4-bromo-3-methyl-5-isoxazolyl)-5-(2-methoxyphenyl)thiophene-2-sulfonamide | 0.381 | 1.097 |
| N-(4-bromo-3-methyl-5-isoxazolyl)-5-(2-tolyl)thio-phene-2-sulfonamide | 0.432 | 0.313 |
| N-(4-bromo-3-methyl-5-isoxazolyl)-2-[(3-carboxyphenyl)aminocarbonyl]thiophene-3-sulfonamide | 0.062† | >100† |
| N-(4-bromo-3-methyl-5-isoxazolyl)-2-[2-carboyxylphenyl)aminocarbonyl]-thiophene-3-sulfonamide | 0.21† | 20† |
| N-(4-bromo-3-methyl-5-isoxazolyl)-2-(aminocarbonyl)thiophene-3-sulfonamide | 0.84† | >100† |
| N-(4-bromo-3-methyl-5-isoxazolyl)-2-[(5-dimethylamino-1-naphthyl)sulfonyl-aminocarbonyl]thiophene-3-sulfonamide | 0.97† | 3.9† |
| N-(4-bromo-3-methyl-5-isoxazolyl)-5-(5-methyl-2-thienyl)thiophene-2-sulfonamide | 17† | 0.21† |
| N-(4-bromo-3-methyl-5-isoxazolyl)-2-[(3,4-methylenedioxyphenyl)aminocarbonyl]thiophene-3-sulfonamide | 0.017† | 9.8† |
| N-(4-bromo-3-methyl-5-isoxazolyl)-2-[(3,4-methylenedioxy)phenoxycarbonyl]thiophene-3-sulfonamide | 0.0073† | 6.0† |
| N-(4-bromo-3-methyl-5-isoxazolyl)-3-[(3,4-methylenedioxy)phenyl]thiophene-2-sulfonamide | 0.50† | 79† |

TABLE 1-continued

| COMPOUND | $ET_A$ ($\mu M$)* | $ET_B$ ($\mu M$)* |
|---|---|---|
| N-(4-bromo-3-methyl-5-isoxazolyl)-3-[(3,4-methylenedioxy)benzyl]thiophene-2-sulfonamide | 8.1[†] | 3.2[†] |
| N-(4-bromo-3-methyl-5-isoxazolyl)-3-benzylthiophene-2-sulfonamide | 1.6[†] | 39[†] |
| N-(4-bromo-3-methyl-5-isoxazolyl)-5-(3-tolyl)thiophene-2-sulfonamide | 15[†] | 4.2[†] |
| N-(4-bromo-3-methyl-5-isoxazolyl)-2-[(3,4-methylenedioxy)benzyl]thiophene-3-sulfonamide | 0.27[†] | 7.7[†] |
| N-(4-bromo-3-methyl-5-isoxazolyl)-2-[(3,4-methylenedioxy)benzoyl]thiophene-3-sulfonamide | 2.0[†] | 15[†] |
| N-(4-bromo-3-methyl-5-isoxazolyl)-2-[(2-hydroxyphenyl)aminocarbonyl]thiophene-3-sulfonamide | 0.013[†] | 38[†] |
| N-(3,4-dimethyl-5-isoxazolyl)-2-[3,4-(methylenedioxy)phenoxycarbonyl]thiophene-3-sulfonamide | 6.1[†] | >~50[†] |
| N-(4-bromo-3-methyl-5-isoxazolyl)-5-(5-ethylthien-2-yl)thiophene-2-sulfonamide | 24[†] | 7.7[†] |
| N-(4-bromo-3-methyl-5-isoxazolyl)-2-[(3,4-methylenedioxy)benzoyl]aminocarbonyl]thiophene-3-sulfonamide | 0.089[†] | 37[†] |
| N-(4-chloro-3-methyl-5-isoxazolyl)-2-[3,4-(methylenedioxy)phenoxycarbonyl]thiophene-3-sulfonamide | 0.0065[†] | 7.4[†] |
| N-(4-bromo-3-methyl-5-isoxazolyl)-5-(1-pentynyl)thiophene-2-sulfonamide | 29[†] | 5.6[†] |
| N-(4-chloro-3-methyl-5-isoxazolyl)-5-(5-ethylthien-2-yl)thiophene-2-sulfonamide | 12[†] | 0.71[†] |
| N-(4-bromo-3-methyl-5-isoxazolyl)-2-[(3,4-methylenedioxy)phenylacetyl]thiophene-3-sulfonamide | 0.0091[†] | 5.5[†] |
| N-(4-bromo-3-methyl-5-isoxazolyl)-2-[3,4-(methylenedioxy)phenoxycarbonylamino]thiophene-3-sulfonamide | 0.087[†] | 5.9[†] |
| N-(4-bromo-3-methyl-5-isoxazolyl)-2-[(2-chloro-3,4-methylenedioxy)phenoxymethyl]thiophene-3-sulfonamide | 13[†] | 0.76[†] |
| N-(4-bromo-3-methyl-5-isoxazolyl)-2-[trans-(3,4-methylenedioxy)cinnamyl]thiophene-3-sulfonamide | 0.14[†] | 1.4[†] |
| N-(4-bromo-3-methyl-5-isoxazolyl)-5-(1-naphthyl)-thiophene-2-sulfonamide | 14[†] | 1.4[†] |
| N-(4-bromo-3-methyl-5-isoxazolyl)-5-(3-nitrophenyl)thiophene-2-sulfonamide | 26[†] | 4.5[†] |
| N-(4-bromo-3-methyl-5-isoxazolyl)-2-[(3,4-methylenedioxy)phenylureido]thiophene-3-sulfonamide | 0.57[†] | 1.3[†] |
| N-(4-chloro-3-methyl-5-isoxazolyl)-2-[(3,4-(methylenedioxy)phenylacetyl]thiophene-3-sulfonamide | 0.021[†] | 6.5[†] |
| N-(4-bromo-3-methyl-5-isoxazolyl)-5-(4-methyoxycarbonylphenyl)thiophene-2-sulfonamide | >100[†] | 17[†] |
| N-(4-bromo-3-methyl-5-isoxazolyl)-5-(4-carboxyphenyl)thiophene-2-sulfonamide | >100[†] | 31[†] |
| N-(4-bromo-3-methyl-5-isoxazolyl)-5-(4-tolyl)aminocarbonyl)thiophene-2-sulfonamide | 28[†] | 8.6[†] |
| N-(4-bromo-3-methyl-5-isoxazolyl)-5-(2-methyfuranyl)thiophene-2-sulfonamide | 32[†] | 7.5[†] |
| N-(4-chloro-3-methyl-5-isoxazolyl)-2-[3,4-(methylenedioxy)benzyloxycarbonyl]thiophene-3-sulfonamide | .42[†] | 12[†] |
| N-(4-chloro-3-methyl-5-isoxazolyl)-2-[2-(3,4-methylenedioxyphenyl)ethoxycarbonyl-3-sulfonamide | .23[†] | 6.2[†] |
| N-(4-chloro-3-methyl-5-isoxazolyl)-2-{[4-(3,4-methylenedioxybenzyl)piperazin-1-yl]carbonyl}thiophene-3-sulfonamide | 20[†] | >~100[†] |
| N-(4-chloro-3-methyl-5-isoxazolyl)-2-aminothiophene-3-sulfonamide | 14[†] | 6.2[†] |
| N-(4-bromo-3-methyl-5-isoxazolyl)-5-(benzyloxymethyl)thiophene-2-sulfonamide | 12[†] | 9.0[†] |
| N-(4-chloro-3-methyl-5-isoxazolyl)-2-{1-cyano-1-[(3,4-methylenedioxy)phenyl]acetyl}thiophene-3-sulfonamide | 2.1[†] | 27[†] |
| N-(4-bromo-3-methyl-5-isoxazolyl)-2-[(3,4-methylenedioxy)phenethyl]thiophene-3-sulfonamide | 0.21[†] | 9.2[†] |
| N-(4-chloro-3-methyl-5-isoxazolyl)-2-[(3-dimethylamino)phenoxycarbonyl]thiophene-3-sulfonamide | 1.4[†] | 60[†] |
| N-(4-bromo-3-methyl-5-isoxazolyl)-1-methylindole-2-sulfonamide | 77[†] | ~100[†] |
| N-(4-chloro-3-methyl-5-isoxazolyl-2-(cyclohexyloxycarbonyl)thiophene-3-sulfonamide | 0.44[†] | 34[†] |
| N-(4-chloro-3-methyl-5-isoxazolyl)-2-[β-hydroxy(3,4-methylenedioxy)phenylethyl]thiophene-3-sulfonamide | 0.053[†] | 16[†] |
| N-(4-bromo-3-methyl-5-isoxazolyl)-2-carboxyl-1-methylidole-3-sulfonamide | 0.59[†] | 104[†] |

TABLE 1-continued

| COMPOUND | $ET_A$ ($\mu M$)* | $ET_B$ ($\mu M$)* |
|---|---|---|
| N-(4-chloro-3-methyl-5-isoxazolyl)-2-[(4-oxacyclohexyl)oxycarbonyl]thiophene-3-sulfonamide | 1.37† | — |
| N-2-[3,4-(methylenedioxy)phenylacetyl]thiophene-3-sulfonamide | 1.8† | 32.5† |
| N-(4-chloro-3-methyl-5-isoxazolyl)-{2-[3,4-(methylenedioxy)phenyl]acetyl}thiophene-3-sulfonamide oxime | — | — |
| N-(4-chloro-3-methyl-5-isoxazolyl)-2-[(4-tolyl)aminocarbonyl]-1-methylindole-3-sulfonamide | 31.3† | 14.7† |
| N-(4-chloro-3-methyl-5-isoxazolyl)-2-[(4-methoxyphenoxy)carbonyl]thiophene-3-sulfonamide | 0.023† | 15† |
| N-(4-bromo-3-methyl 5-isoxazolyl)-1-[3,4-(methylenedioxy)benzyl]indole-2-sulfonamide | 5.29† | 18.6† |
| N-(4-bromo-3-methyl-5-isoxazolyl)-2-[(4-methylphenoxy)carbonyl]thiophene-3-sulfonamide | 122† | 9.7† |
| N-(4-chloro-3-methyl-5-isoxazolyl)-2-[(4-methoxyphenyl)acetyl]thiophene-3-sulfonamide | 0.043† | 10.1† |
| N-(4-bromo-3-methyl-5-isoxazolyl)-3-[(4-methylphenoxy)methyl]thiophene-2-sulfonamide | 1.64† | 22.8† |
| N-(4-bromo-3-methyl-5-isoxazolyl)-2-[(4-methylphenoxy)methyl]thiophene-3-sulfonamide | 1.2† | 15† |
| N-(4-bromo-3-methyl-5-isoxazolyl)-3-(4-methyl-trans-styryl)thiophene-2-sulfonamide | 0.94† | 0.66† |
| N-(4-bromo-3-methyl-5-isoxazolyl)-3-(4-methyl-phenethyl)thiophene-2-sulfonamide | 0.347† | 9.4† |
| N-(4-bromo-3-methyl-5-isoxazolyl)-2-[(4-methyl-phenyl)acetyl]thiophene-3-sulfonamide | 0.198† | 9.13† |
| N-(4-bromo-3-methyl-5-isoxazolyl)-2-[(3-methoxyphenyl)acetyl]thiophene-3-sulfonamide | 0.030† | 19.1† |
| N-(4-bromo-3-methyl-5-isoxazolyl)-3-(4-methyl-phenethyl)-5-(4-tolyl)thiophene-2-sulfonamide | 6.1† | 2.09† |
| N-(4-bromo-3-methyl-5-isoxazolyl)-3-(4-methylbenzyl)-5-(4-tolyl)thiophene-2-sulfonamide | 4.69† | 1.56† |
| N-(4-bromo-3-methyl-5-isoxazolyl)-3-(4-methyl-trans-styryl)-5-(4-tolyl)thiophene-2-sulfonamide | 6.9† | 1.58† |
| N-(4-chloro-3-methyl-5-isoxazolyl)-2-[β,β-(ethylenedioxy)-3,4-(methylenedioxy)phenethyl]thiophene-3-sulfonamide | 0.128† | 2.09† |
| N-(4-chloro-3-methyl-5-isoxazolyl)-2-[β-(dimethylamino)-3,4-(methylenedioxy)phenethyl]thiophene-3-sulfonamide | 20.9† | ~100† |
| N-(4-chloro-3-methyl-5-isoxazolyl)-2-{α-hydroxy-[3,4-(methylenedioxy)phenyl]acetyl}thiophene-3-sulfonamide | 2.5† | 30† |
| N-(4-chloro-3-methyl-5-isoxazolyl)-2-[(5-methyl-3-isoxazolyl)aminocarbonyl]thiophene-3-sulfonamide | 0.056† | 92† |
| N-(4-bromo-3-methyl-5-isoxazolyl)-2-[(3-hydroxyl-6-pyridazinyl)aminocarbonyl]thiophene-3-sulfonamide | 0.066† | 81.3† |
| N-(4-chloro-3-methy)-5-isoxazolyl)2-{[2-acetyl-4,5-(methylenedioxy)phenyl]aminocarbonyl}thiophene-3-sulfonamide | 0.010† | 31.6† |
| N-(4-bromo-3-methy)-5-isoxazolyl)-3-{[3,4-(methylenedioxy)phenoxy]methyl}thiophene-2-sulfonamide | 0.513† | 9.6† |
| N-(4-bromo-3-methyl-5-isoxazolyl)-2-[(4-methyl)(cinnamyl)]thiophene-3-sulfonamide | 0.26† | 0.413† |
| N-(4-chloro-3-methyl-5-isoxazolyl)-2-[(4,5-dimethoxy-2-methoxycarbonylphenyl)aminocarbonyl]thiophene-3-sulfonamide | 0.55† | — |
| N-(4-chloro-3-methyl-5-isoxazolyl)-2-[(2-methyl-1,3,4-thiadiazol-5-yl)aminocarbonyl]thiophene-3-sulfonamide | 0.13† | — |
| N-(4-chloro-3-methyl-5-isoxazolyl)2-{[4,5-dimethoxy-2,4,5-dimethoxy-2-methoxycarbonyl)phenyl]phenylaminocarbonyl}thiophene-3-sulfonamide | 3.80† | — |
| N-(4-chloro-3-methyl-5-isoxazolyl)2-{(2-carboxyl-4,5-(methylenedioxy)phenyl]aminocarbonyl}thiophene-3-sulfonamide | 1.43† | — |
| N-(4-bromo-3-methyl-5-isoxazolyl)-3-[3,4-(methylenedioxy)phenethyl]thiophene-2-sulfonamide | 0.236† | 18† |
| N-(4-bromo-3-methy)-5-isoxazolyl)-3-[3,4-(methylenedioxy)-trans-styryl]thiophene-2-sulfonamide | 0.218† | 10† |
| N-(4-bromo-3-methy)-5-isoxazolyl)-2-[(4-methyl)-phenethyl]thiophene-3-sulfonamide | 0.106† | 40.1† |
| N-(3,4-dimethyl-5-isoxazolyl)-2-{[2-acetyl-4,5-(methylenedioxy)phenyl]aminocarbonyl}thiophene-3-sulfonamide | 0.032† | — |

TABLE 1-continued

| COMPOUND | ET$_A$ ($\mu$M)* | ET$_B$ ($\mu$M)* |
|---|---|---|
| N-(4-chloro-3-methy)-5-isoxazolyl)-2-[4-methoxy-2-methylphenyl)aminocarbonyl]thiophene-3-sulfonamide | 0.027† | 0.14† |
| N-(4-chloro-3-methyl-5-isoxazolyl)-2-[{2-cyano-4,5-dimethoxyphenyl)aminocarbonyl]thiophene-3-sulfonamide | 0.0039† | 12.2† |
| N-(3,4-dimethyl-5-isoxazolyl)-2-(4-tolylacetylphenyl)-thiophene-3-sulfonamide | 0.0027† | 29.2† |
| N-(3,4-dimethyl-5-isoxazolyl)-2-[3,4-(methylene-dioxy)phenylacetyl]thiophene-3-sulfonamide | 0.0273† | 12.2† |
| N-(4-chloro-3-methyl-5-isoxazolyl)-2-[(2,4-dimethoxyphenyl)aminocarbonyl]thiophene-3-sulfonamide | 0.158† | 63.1† |
| N-(4-chloro-3-methyl-5-isoxazolyl)-2-[(3-methyl-6-pyridyl)aminocarbonyl]thiophene-3-sulfonamide | 0.023† | 43.7† |
| N-(4-chloro-3-methyl-5-isoxazolyl)-2-[2-hydroxy-4-methylphenyl)aminocarbonyl]thiophene-3-sulfonamide | .006† | — |
| N-(4-chloro-3-methyl-5-isoxazolyl)-2-{[2-cyano-4,5-(methylenediXoxy)phenyl]aminocarbonyl}thiophene-3-sulfonamide | 0.0034† | 40.4† |
| N-(4-chloro-3-methyl-5-isoxazolyl)-2-(2-methyl-4,5-(methylenedioxy)phenylaminocarbonyl]thiophene-3-sulfonamide | 0.0030† | 355† |
| N-(4-chloro-3-methyl-5-isoxazolyl)-2-(2-carboxamido-4,5-dimethoxyphenylamino-carbonyl)thiophene-3-sulfonamide | 0.011† | 61† |
| N-(3,4-dimethyl-5-isoxazolyl)-2-(2,4-dimethylphenylacetyl)thiophene-3-sulfonamide | 0.0027† | 17.4† |
| N-(4-chloro-3-methyl-5-isoxazolyl)-2-(2,4-dimethyl-phenylacetyl)thiophene-3-sulfonamide | 0.0004† | 4.8† |
| N-(4-bromo-3-methyl-5-isoxazolyl)-2-(2,4-dimethylphenylacetyl)thiophene-3-sulfonamide | 0.0008†** | 3.6† |
| N-(4-chloro-3-methyl-5-isoxazolyl)-2-[3,4-(methylenedioxy)phenylaminocarbonyl-3-thio-phenesulfonamide | 0.0073† | 9.2† |
| N-(4-chloro-3-methyl-5-isoxazolyl)-2-[2-methyl-4,5-(methylenedioxy)phenylacetyl]thiophene-3-sulfonamide | 0.0032† | 9† |
| N-(4-chloro-3-methyl-5-isoxazolyl)-2-[3,4-(methylenedioxy)-6-(2-acetoxyethyl)phenylamino-carbonyl]thiophene-3-sulfonamide | 0.0045† | 25.7† |
| N-(4-chloro-3-methyl-5-isoxazolyl)-2-(3,4-(methylenedioxy)-6-(2-hydroxyethyl)phenyl-aminocarbonyl]thiophene-3-sulfonamide | 0.0056† | 16.8† |
| N-(4-chloro-3-methyl-5-isoxazolyl)-2-(3,5-dimethyl-phenylacetyl)thiophene-3-sulfonamide | 0.045† | 17.7† |
| N-(4-chloro-3-methyl-5-isoxazolyl)-2-(2,5-dimethylphenylacetyl)thiophene-3-sulfonamide | 0.007† | 18† |
| N-(4-chloro-3-methyl-5-isoxazolyl)-2-[2-methanesulfonylaminomethyl)-4,5-(methylenedioxylphenylaminocarbonyl)thiophene-3-sulfonamide | 0.0068† | 19.8† |
| N-(4-chloro-3-methyl-5-isoxazolyl)-2-[2-cyanomethyl-4,5-(methylenedioxy)-6-cyanomethyl]-phenylaminocarbonyl-3-thiophenesulfonamide | 0.0038† | 25† |
| N-(4-chloro-3-methyl-5-isoxazolyl)-2-[2-hydroxypropyl-4,5-(methylenedioxy)phenylaminocarbonyl]thiophene-3-sulfonamide | 0.0073† | 8.3† |
| N (4-bromo-3-methyl-5-isoxazolyl)-3-[2-methyl-4,5-(methylenedioxy)cinnamyl]thiophene-2-sulfonamide | ~0.1†** | ~6†** |
| N-(4-bromo-3-methyl-5-isoxazolyl)-3-[2-methyl-4,5-(methylenedioxy)phenethyl]thiophene-2-sulfonamide | ~0.1†** | ~5†** |
| N-(4-bromo-3-methyl-5-isoxazolyl)-3-{[2-propyl-4,5-(methylenedioxy)phenoxy]methyl}thiophene-2-sulfonamide | ~0.2†** | ~1.5†** |
| N-(4-chloro-3-methyl-5-isoxazolyl)-2-[3,4-(methylenedioxy)-6-(2-acetoxyethoxy)]phenylaminocarbonyl]thiophene-3-sulfonamide | ~0.02†** | ~18† |
| N-(4-chloro-3-methyl-5-isoxazolyl)-2-(3,4-(methylenedioxyl-6-(2-hydroxyethoxylphenyl-aminocarbonyl]thiophene-3-sulfonamide | ~0.01†** | ~18† |
| N-(4-chloro-3-methyl-5-isoxazolyl)-2-[2-cyano-4,5-(methylenedioxy)phenylacetyl]thiophene-3-sulfonamide | ~0.3†** | ~0.7† |
| N-(4-chloro-3-methyl-5-isoxazolyl)-2-{2-[(dimethylamino)carbonylmethyl]-4,5-(methylene-dioxylphenylaminocarbonyl}thiophene-3-sulfonamide | 0.009† | 13.8† |
| N-(4-chloro-3-methyl-5-isoxazolyl)-2-[2-methyl-4,5-(methylenedioxy)phenylhydroxylmino]thiophene-3-sulfonamide | 0.794† | 6.49† |
| N-(4-bromo-3-methyl-5-isoxazolyl)-2-[2-methyl-4,5-(methylenedioxy)phenethyl]thiophene-3-sulfonamide | 0.0619† | 8.90† |

TABLE 1-continued

| COMPOUND | ET$_A$ ($\mu$M)* | ET$_B$ ($\mu$M)* |
|---|---|---|
| N-(4-bromo-3-methyl-5-isoxazolyl)-3-[2-(hydroxymethyl)-4,5-(methylenedioxy)cinnamyl]thiophene-2-sulfonamide | 0.0795† | 3.24† |
| N-(4-bromo-3-methyl-5-isoxazolyl)-3-{2-[(tetrahydro-4H-pyran-2-ylxoy)methyl]-4,5-(methylenedioxy)cinnamyl}thiophene-2-sulfonamide | 0.0967† | 4.14 |
| N-(4-bromo-3-methy)-5-isoxazolyl)-3-(2,4-dimethylphenethyl)thiophene-2-sulfonamide | 0.1006† | 4.30† |
| N-(4-bromo-3-methyl-5-isoxazolyl)-3-(2,4-dimethylcinnamyl)thiophene-2-sulfonamide | 0.180† | 2.97† |
| N-(4-bromo-3-methyl-5-isoxazolyl)-2-(2,4-dimethylcinnamyl)thiophene-3-sulfonamide | 0.166† | 2.97† |
| N-(4-bromo-3-methyl-5-isoxazolyl)-3-[(2,4-dimethylphenoxy)methyl]thiophene-2-sulfonamide | 0.346† | 7.45† |
| N-(4-bromo-3-methyl-5-isoxazolyl)-2-[(2,4-dimethylphenoxy)methyl]thiophene-3-sulfonamide | 0.308† | 4.48† |
| N-(4-chloro-3-methyl-5-isoxazolyl)-5-(phenylaminocarbonyl)thiophene-2-sulfonamide | 28.1† | 60.6† |
| N-(4-chloro-3-methyl-5-isoxazolyl)-2-[β-acetoxy-2-methyl-4,5-(methylenedioxy)styryl]thiophene-3-sulfonamide | 0.00544 | 3.74† |
| N-(4-chloro-3-methyl-5-isoxazolyl)-2-[(2,3,4-trimethoxy-6-cyano)phenylaminocarbonyl]thiophene-3-sulfonamide | 0.000169† | 12.5† |
| N-(4-chloro-3-methyl-5-isoxazolyl)-2-[2-(cyano)phenyl]benzo[b]thiophene-3-sulfonamide | 6.33† | 8.82† |
| N-(4-chloro-3-methyl-5-isoxazolyl)-2-[3,4-(methylenedioxy)phenyl]benzo[b]thiophene-3-sulfonamide | 0.550† | 52.6† |
| N-(4-bromo-3-methy)-5-isoxazolyl)-3-(2-tolyl)thiophene-2-sulfonamide | 0.324† | 55.1† |
| N-(4-bromo-3-methyl-5-isoxazolyl)-3-(3-tolyl)thiophene-2-sulfonamide | 0.832† | 21.2† |
| N-(4-bromo-3-methyl-5-isoxazolyl)-3-(2-tolyl)thiophene-2-sulfonamide | 0.302† | 31% @ 100† |
| N-(4-bromo-3-methyl-5-isoxazolyl)-3-(3-methoxyphenyl)thiophene-2-sulfonamide | 0.334† | ** |
| N-(4-bromo-3-methyl-5-isoxazolyl)-3-(3-methoxyphenyl)thiophene-2-sulfonamide | 1.32† | 56.3† |
| N-(4-bromo-3-methyl-5-isoxazolyl)-3-(2-methoxyphenyl)thiophene-2-sulfonamide | 1.71† | 59.1† |
| N-(4-bromo-3-methyl-5-isoxazolyl)-3-(4-ethylphenyl)thiophene-2-sulfonamide | 0.184 | 43.9† |
| N-(4-bromo-3-methyl-5-isoxazolyl)-3-(4-propylphenyl)thiophene-2-sulfonamide | 0.0873 | 8.48† |
| N-(4-bromo-3-methyl-5-isoxazolyl)-3-(4-iso-propylphenyl)thiophene-2-sulfonamide | 0.218 | 28.3† |
| N-(4-bromo-3-methyl-5-isoxazolyl)-3-(4-butylphenyl)thiophene-2-sulfonamide | 0.160 | 6.11† |
| N-(3,4-dimethyl-5-isoxazolyl)-2-[2-methyl-4,5-(methylenedioxy)phenylacetyl]thiophene-3-sulfonamide | 0.00328† | 34.3† |
| N-(4-chloro-3-methyl-5-isoxazolyl)-2-(2,4,6-trimethylphenylaminocarbonyl)thiophene-3-sulfonamide | 0.000626† | 8.27† |
| N-(4-chloro-3-methyl-5-isoxazolyl)-2-(2,4,6-tri-methylphenylacetyl)thiophene-3-sulfonamide | 0.000238† | 3.82† |
| N-(4-chloro-5-methyl-3-isoxazolyl)-2-[2-methyl-4,5-(methylenedioxy)phenylacetyl]thiophene-3-sulfonamide | 0.000625† | 3.69† |
| N-(4-bromo-3-methyl-5-isoxazolyl)-2-[2-methyl-4,5-(methylenedioxy)cinnamyl]thiophene-3-sulfonamide | 0.0804† | 3.28† |
| N-(4-bromo-3-methyl-5-isoxazolyl)-2-(2,4-dimethylphenethyl)thiophene-3-sulfonamide | 0.0555† | 3.48† |
| N-(4-chloro-3-methyl-5-isoxazolyl)-2-[(4-methoxycarbonyl-2,6-dimethyl)-phenylaminocarbonyl]thiophene-3-sulfonamide | 0.000266† | 9.78† |
| N-(4-chloro-3-methyl-5-isoxazolyl)-2-(phenoxycarbonyl)thiophene-3-sulfonamide | 4.41† | 31% @ 100† |
| N-(4-bromo-3-methyl-5-isoxazolyl)-2-(phenoxycarbonyl)thiophene-3-sulfonamide | 2.71† | 20% @ 100† |
| N-(3,4-dimethyl-5-isoxazolyl)-2-{[3,4-(methylenedioxy)phenoxy]carbonyl}thiophene-3-sulfonamide | 3.61† | 30% @ 100† |
| N-(4-bromo-3-methyl-5-isoxazolyl)-2-[(2-methylphenoxy)carbonyl]thiophene-3-sulfonamide | 0.684† | 105† |
| N-(4-bromo-3-methyl-5-isoxazolyl)-2-[(3-methylphenoxy)carbonyl]thiophene-3-sulfonamide | 1.20† | 111† |
| N-(4-bromo-3-methyl-5-isoxazolyl)-2-[(2,4-dimethylphenoxy)carbonyl]thiophene-3-sulfonamide | 0.291† | 43.2† |
| N-(4-bromo-3-methyl-5-isoxazolyl)-2-[(2-methoxylphenoxy)carbonyl]thiophene-3-sulfonamide | 0.761† | 29% @ 100† |

TABLE 1-continued

| COMPOUND | ET$_A$ ($\mu$M)* | ET$_B$ ($\mu$M)* |
|---|---|---|
| N-(4-bromo-3-methyl-5-isoxazolyl)-2-[(3-methoxylphenoxy)carbonyl]thiophene-3-sulfonamide | 0.79† | 90† |
| N-(4-bromo-3-methyl-5-isoxazolyl)-2-[(4-methoxylphenoxy)carbonyl]thiophene-3-sulfonamide | 1.73† | 111† |
| N-(3,4-dimethyl-5-isoxazolyl)-2-[(4-methoxylphenoxy)carbonyl]thiophene-3-sulfonamide | 5.88† | 13% @ 100† |
| N-(3,4-dimethyl-5-isoxazolyl)-2-[(4-methoxylphenoxy)carbonyl]thiophene-3-snamide | 2.5† | 33% @ 100† |
| N-(4-chloro-3-methyl-5-isoxazolyl)-2-[(4-methylphenoxy)carbonyl]thiophene-3-sulfonamide | 3.2† | 43% @ 100† |
| N-(4-chloro-3-methyl-5-isoxazolyl)-2-[(2,4-dimethylphenoxy)carbonyl]thiophene-3-sulfonamide | 0.648† | 68.5† |
| N-(3,4-dimethyl-5-isoxazolyl)-2-[(2,4-dimethylphenoxy)carbonyl]thiophene-3-sulfonamide | 0.274† | 21% @ 100† |
| N-(4-bromo-3-methyl-5-isoxazolyl)-2-{[2-propyl-4,5-(methylenedioxy)phenoxy]carbonyl}thiophene-3-sulfonamide | 0.138† | 11.9† |
| N-(4-chloro-3-methyl-5-isoxazolyl)-2-(3-methoxycarbonyl-2,4,6-trimethylphenylaminocarbonyl)thiophene-3-sulfonamide | 0.000321† 0.00092† | 16.5† — |
| N-(4-bromo-3-methyl-5-isoxazolyl)-3-(2,4-dimethylphenyl)thiophene-2-sulfonamide | 0.100† | 60.3† |
| N-(3,4-dimethyl-5-isoxazolyl)-2-(phenoxycarbonyl)thiophene-3-sulfonamide | 2.85† | 31%† |
| N-(4-bromo-3-methyl-5-isoxazolyl)-3-(4-iso-butylphenyl)thiophene-2-sulfonamide | 0.0823† | 2.76† |
| N-(4-bromo-3-methyl-5-isoxazolyl)-3-(4-iso-pentylphenyl)thiophene-2-sulfonamide | 0.155† | 3.31† |
| N-(4-bromo-3-methyl-5-isoxazolyl)-3-[(2,4,6-trimethylphenoxy)methyl]thiophene-2-sulfonamide | 0.0457† | 4.68† |
| N-(4-bromo-3-methyl-5-isoxazolyl)-2-[(2,4,6-trimethylphenoxy)methyl]thiophene-3-sulfonamide | 0.0562† | 3.39† |
| N-(4-bromo-3-methyl-5-isoxazolyl)-3-(2,4,6-trimethylcinnamyl)thiophene-2-sulfonamide | 0.0490† | 1.86† |
| N-(4-bromo-3-methyl-5-isoxazolyl)-3-(2-methyl-4-propylphenyl)thiophene-2-sulfonamide | 0.0468† | 3.63† |
| N-(4-bromo-3-methyl-5-isoxazolyl)-3-(4-iso-butyl-2-methylphenyl)thiophene-2-sulfonamide | 0.0468† | 1.66† |
| N-(4-bromo-3-methyl-5-isoxazolyl)-3-(4-iso-pentyl-2-methylphenyl)thiophene-2-sulfonamide | 0.107† | 2.40† |
| N-(4-bromo-3-methyl-5-isoxazolyl)-2-{[3,4-(methylenedioxy)phenoxy]methyl}thiophene-3-sulfonamide | 0.302† | 6.61† |
| N-(4-bromo-3-methyl-5-isoxazolyl)-2-{[4,5-(methylenedioxy)-2-propylphenoxy]methyl}thiophene-3-sulfonamide | 0.107† | 0.407† |
| N-(4-bromo-3-methyl-5-isoxazolyl)-2-(2,4,6-trimethylphenethyl)thiophene-3-sulfonamide | 0.0417† | 1.23† |
| N-(4-bromo-3-methyl-5-isoxazolyl)-3-(2,4,6-trimethylphenethyl)thiophene-2-sulfonamide | 0.055† | 1.62† |
| N-(3,4-dimethyl-5-isoxazolyl)-2-[(2,4,6-trimethylphenoxy)carbonyl]thiophene-3-sulfonamide | 0.537† | 8% @ 100† |
| N-(4-chloro-3-methyl-5-isoxazolyl)-2-[(2,4,6-trimethylphenoxy)carbonyl]thiophene-3-sulfonamide | 0.0776† | 30.2† |
| N-(4-bromo-3-methyl-5-isoxazolyl)-2-[(2,4,6-trimethylphenoxy)carbonyl]thiophene-3-sulfonamide | 0.479† | 24.5† |
| N-(4-chloro-3-methyl-5-isoxazolyl)-2-(3-cyanomethyl-2,4,6-trimethylphenylaminocarbonyl)thiophene-3-sulfonamide | 0.0006† | ~45† |
| N-(4-chloro-3-methyl-5-isoxazolyl)-2-(3-carboxymethyl-2,4,6-trimethylphenylaminocarbonyl)thiophene-3-sulfonamide | 0.0015† | ~>100† |
| N-(4-chloro-3-methyl-5-isoxazolyl)-2-(3-acetoxymethyl-2,4,6-trimethylphenylaminocarbonyl)thiophene-3-sulfonamide | 0.0006† | >>100† |
| N-(4-chloro-3-methyl-5-isoxazolyl)-2-(3-hydroxymethyl-2,4,6-trimethylphenylaminocarbonyl)thiophene-3-sulfonamide | 0.0004† | ~80† |

*results are generally the average of 2 to 5 experiments
**preliminary results or results in which one or more data points were only determined approximately
†assay performed with incubation at 24° C. As described in the Examples, incubation at the higher temperature reduces the activity by a factor of 2- to about 10-compared to the activity at 4° C.
— data not available or measured as % inhibition @ 100 $\mu$M
% % inhibition @ 100 $\mu$M It is understood that 4-bromo or 4-chloro groups can be replaced by other 4-halo substituents or other suitable substituents for $R^1$, such as alkyl, particularly alkyl with between about 1 and 15 carbons in the chain.

2. $Ar^2$ is a substituted 4-biphenyl group

Compounds of formulae I in which $Ar^1$ is N-(5-isoxazolyl) or N-(3-isoxazolyl) in which $Ar^2$ is selected from biphenyl derivatives are provided. These compounds can be represented by the following formulae (VII):

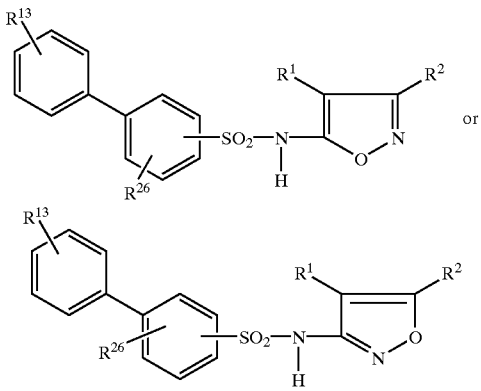

in which $R^{26}$ and $R^{13}$ are each independently selected from H, OH, HONH, $NH_2$, $NO_2$, halide, pseudohalide, alkyl, alkenyl, alkynyl, aryl, arylalkyl, heteroaryl, alkoxy, alkylamino, dialkylamino, alkylthio, haloalkoxy, haloalkyl, alkylsulfinyl, alkylsulfonyl, aryloxy, arylamino, arylthio, arylsulfinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, preferably from 1 to 6 atoms, and are either straight or branched chains or cyclic, and the aryl portions contain from about 4 to about 16 carbons, preferably 4 to 10 carbons. $R^{13}$ and $R^{26}$ are preferably each selected from H, loweralkyl, haloalkyl and halide. Again, it is understood that $Ar^2$ may be substituted with more than one substituent, each of which is selected independently from the selections set forth for $R^{26}$ and $R^{13}$, and $R^2$ and $R^1$ are as defined above.

In the embodiments herein, the biphenylsulfonamides are substituted 4-biphenylsulfonamides, $R^{13}$ is preferably at the para position and $R^{26}$, if it is not hydrogen, is at any position except the 2-position.

In more preferred embodiments, $R^1$ is halide or methyl or higher ($C_9$–$C_{13}$) alkyl. $R^1$ is selected from halide, $CH_3$, $C_2H_5$, $CF_3$, $C_2F_5$, n-$C_3H_7$ and cyclo-$C_3H_7$, preferably halide or $CH_3$, and $R^2$ is selected from H, $CH_3$, $C_2H_5$, $CF_3$, $C_2F_5$, n-$C_3H_7$ and cyclo-$C_3H_7$, more preferably $R^1$ is halide or $CH_3$, and $R^2$ are selected from H, $CH_3$, $C_2H_5$, or $CF_3$.

In more preferred embodiments, $R^1$ is Cl or Br, or if greater $ET_B$ activity is preferred a higher alkyl ($C_9H_{19}$ to $C_{13}H_{27}$; $R^2$ is selected from H, $CH_3$, $C_2H_5$, $CF_3$, $C_2F_5$, n-$C_3H_7$, cyclo-$C_3H_7$, n$C_{13}H_{27}$ and n$C_9H_{19}$. In yet more preferred embodiments, $R^1$ is Br, Cl or $C_9H_{19}$ to $C_{13}H_{27}$; $R^2$ is H, $CH_3$, $C_2H_5$, or $CF_3$.

The biphenyl compounds provided herein are generally $ET_B$ active or $ET_B$ selective (see, e.g., Table 2); i.e. the compounds provided herein inhibit binding of endothelin to $ET_B$ receptors at concentrations about 10- to about 30-fold less than they inhibit binding of endothelin to $ET_A$ receptors. In particular the 4-biphenylsulfonamides are $ET_B$ selective.

In general in all embodiments herein, 4-haloisoxazolyl sulfonamides exhibit substantially enhanced activity with respect to at least one of the ET receptors (about two-fold to twenty-fold greater activity), as assessed by assays, such as those provided herein, that measure binding to $ET_A$ and/or $ET_B$ receptors, compared to corresponding sulfonamides in which the substituent at the 4 position in the isoxazolyl is other than halo, such as alkyl. For example: the $IC_{50}$ of N-(3,4-dimethyl-5-isoxazolyl)-2-biphenylsulfonamide for $ET_A$ receptors is about 0.008 $\mu$M, whereas, the $IC_{50}$ of N-(4-bromo-3-methyl-5-isoxazolyl)-2-biphenylsulfonamide is about 0.0016 $\mu$M (see, Table 2 below); and (3) the $IC_{50}$ of N-(3,4-dimethyl-5-isoxazolyl)-3-biphenylsulfonamide for $ET_B$ receptors is about 3.48 $\mu$M; whereas, the $IC_{50}$ of N-(4-bromo-3-methyl-5-isoxazolyl)-3-biphenylsulfonamide for $ET_B$ receptors is about 0.76 $\mu$M and the $IC_{50}$ of N-(4-chloro-3-methyl-5-isoxazolyl)-3-biphenylsulfonamide for $ET_B$ receptors is about 0.793 $\mu$M (see, Table 2 below).

Exemplary biphenyl sulfonamides are the following and those set forth in Table 2, and include, but are not limited to: N-(3-methyl-5-isoxazolyl)-4'-methylphenyl-4-biphenylsulfonamide, N-(4-bromo-3-methyl-5-isoxazolyl)-4'-methylphenyl-4-biphenylsulfonamide, N-(4-chloro-3-methyl-5-isoxazolyl)-4'-methylphenyl-4-biphenylsulfonamide, (3-methyl-5-isoxazolyl)-4'-trifluorophenyl-4-biphenylsulfonamide, (4-bromo-3-methyl-5-isoxazolyl)-4'-trifluorophenyl-4-biphenylsulfonamide, (3-methyl-5-isoxazolyl)-4'-methyoxyphenyl-4-biphenylsulfonamide, (4-bromo-3-methyl-5-isoxazolyl)-4'-methoxyphenyl-4-biphenylsulfonamide, (4-bromo-3-methyl-5-isoxazolyl)-3'-methoxyphenyl-4-biphenylsulfonamide, (4-bromo-3-methyl-5-isoxazolyl)-2'-methoxyphenyl-4-biphenylsulfonamide, N-(4-bromo-3-methyl-5-isoxazolyl)-3',4'-methylenedioxyphenyl-4-biphenylsulfonamide and (4-bromo-3-methyl-5-isoxazolyl)-3'-methylphenyl-4-biphenylsulfonamide. Corresponding 4-chloro and 4-fluoro isoxazolyl compounds are also encompassed herein.

Exemplary biphenyl compounds were tested using the exemplified assays (see, EXAMPLES) and the results, which are intended to be exemplary or provided for comparison with compounds provided herein, and are not limiting, are as set forth in the following table (Table 2):

TABLE 2

| COMPOUND | $ET_A$($\mu$M)* | $ET_B$($\mu$M)* |
|---|---|---|
| N-(4-bromo-3-methyl-5-isoxazolyl)-4-biphenylsulfonamide | 3.3<br>49↑ | ~0.17<br>1.23↑ |
| N-(4-bromo-5-methyl-3-isoxazolyl)-4-biphenylnamide | 6.4 ± 2<br>49↑ | 0.29 ± 0.02<br>1.78↑ |
| N-(4-chloro-3-methyl-5-isoxazolyl)-4-biphenylsulfonamide | 4.93 ± 3 | 0.29 ± 0.1 |
| N-(3,4-dimethyl-5-isoxazolyl)-4-biphenylsulfonamide | 9.9 ± 1.4<br>6.3 | 0.77 ± 0.32<br>0.15↑ |
| N-(4-chloro-5-methyl-3-isoxazolyl)-4-biphenylsulfonamide | 3.7<br>18.6↑ | 0.23 ± 0.01<br>1.29↑ |
| N-(4-Methyl-3-trifluoromethyl-5-isoxazolyl)-4-biphenylsulfonamide | 19.0<br>— | 1.7<br>5.62↑ |
| N-(4-Tridecyl-3-trifluoromethyl-5-isoxazolyl)-4-biphenylsulfonamide | 34.0 ± 9<br>33.0↑ | 0.99 ± 0.2<br>0.95↑ |
| N-(3,4-dimethyl-5-isoxazolyl)-2-biphenylsulfonamide | 0.0083 ± 0.0014 | 12.8 |
| N-(4-bromo-3-methyl-5-isoxazolyl)-2-biphenylsulfonamide | 0.00127" | 8.54" |
| N-(4-chloro-3-methyl-5-isoxazolyl)-2-biphenylsulfonamide | 0.00123" | ~14" |
| N-(3,4-dimethyl-5-isoxazolyl)-3-biphenylsulfonylsulfonamide | >0.03" | 3.48" |
| N-(4-bromo-3-methyl-5-isoxazolyl)-3-biphenylsulfonamide | ~0.03" | 0.76" |

TABLE 2-continued

| COMPOUND | $ET_A(\mu M)^*$ | $ET_B(\mu M)^*$ |
|---|---|---|
| N-(4-chloro-3-methyl-5-isoxazolyl)-3-biphenylsulfonamide | >0.03" | 0.793" |
| N-(4-bromo-3-methyl-5-isoxazolyl)-4'-methylphenyl-4-biphenylsulfonamide | 14.53 ± 9.6<br>22.17 ± 3.77* | 0.046 ±<br>0.044<br>0.168 ±<br>0.0032' |
| N-(4-bromo-3-methyl-5-isoxazolyl)-4'-trifluorophenyl-4-biphenylsulfonamide | 5.4 ± 0.3<br>25.9 ± 3.7† | 0.083 ± 0.02<br>0.71 ± 0.43† |
| N-(4-bromo-3-methyl-5-isoxazolyl)-4'-methoxyphenyl-4-biphenylsulfonamide | 14.7 ± 5.6<br>121.5 ± 2.12* | 1.15 ± 0.44<br>3.94 ± 0.89† |
| N-(4-bromo-3-methyl-5-isoxazolyl)-3'-methoxyphenyl-4-biphenylsulfonamide | 4.97 ± 3.4<br>162.6 ± 7.14† | 0.66 ± 0.25<br>2.08 ± 0.23† |
| N-(4-bromo-3-methyl-5-isoxazolyl)-2'-methoxyphenyl-4-biphenylsulfonamide | 3.3 ± 3.5 | 0.41 ± 0.14 |
| N-(4-bromo-3-methyl-5-isoxazolyl)-3'-4'-methylenedioxyphenyl-4-biphenylsulfonamide | 38.2 ± 4.95† | 3.0 ± 0.78† |
| N-(4-bromo-3-methyl-5-isoxazolyl)-3'-methylphenyl-4-biphenylsulfonamide | — | — |

*results generally from 1, 2 or 3 experiments with the same preparation
**preliminary results Preferred compounds are those in which $Ar^2$ is a 4-biphenyl in which, referring to formula VII and at least one substituent $R^{13}$ is at the para position. Preferred substituents are loweralkyl, halo loweralkyl and lower alkoxy. Such compounds are $ET_B$ active.

The preparation of the above and other compounds that possess the requisite activities are set forth in the Examples.

B. Sulfonamides and Sulfonamide Derivatives

Sulfonamides and sulfonamide derivatives are also provided. These compounds are active in assays which measure endothelin antagonist activity. The sulfonamides are of formula:

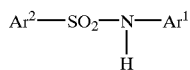

where $Ar^1$ is isoxazolyl and $Ar^2$ has the formula:

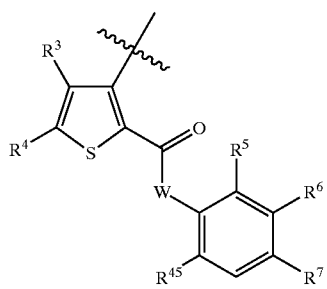

where
  $R^3$ and $R^4$ are hydrogen, or are substituents which are believed to provide enhanced tolerability of the compounds (i.e., by altering the pharmacokinetic profile of the compound). Such substituents are preferably independently selected from halo, cyano, cyanoalkyl, C(O)$R^{41}$, alkyl, alkenyl, cycloalkyl and aryl, or $R^3$ and $R^4$ together form alkylene; W is O, NH or $CH_2$;
  $R^5$, $R^6$ and $R^7$ are each independently selected as in (i) or (ii):
    (i) $R^6$ is hydrogen, unsubstituted alkyl, hydroxy, unsubstituted alkoxy, C(O)$R^{41}$, carbamoyloxy or alkoxycarbonyloxy, and
    $R^5$ and $R^7$ are each independently selected from hydrogen, unsubstituted alkyl, hydroxy, C(O)$R^{41}$, carbamoyloxy and alkoxycarbonyloxy; or
    (ii) if at least one of $R^3$ and $R^4$ is not hydrogen, then any two may form alkylenedioxy, and the other is selected as in (i); and
  $R^{45}$ is selected from among alkyl, C(O)$R^{41}$, $(CH_2)_xOH$ and $CH(OH)(CH_2)_xCH_3$ in which x is 0–6, S(O)$_nR^{41}$ in which n is 0–2 and C(=$NR^{43}$)$R^{41}$; $R^{41}$ is alkyl, aryl, heteroaryl, aralkyl, heteroaralkyl, cycloalkyl, alkylamino, dialkylamino, arylamino, diarylamino, (aryl)(alkyl)amino, alkylsulfonylamino, arylsulfonylamino, (alkylsulfonyl)(alkyl or aryl)amino or (arylsulfonyl)(alkyl or aryl)amino; and $R^{43}$ is selected from hydroxy, alkoxy, alkyl and aryl. $R^{41}$ and $R^{43}$ are unsubstituted or substituted with one or more substituents selected from Y, which is defined as alkoxy, halide, pseudohalide, alkylcarbonyl, arylcarbonyl, amino, alkylamino, dialkylamino, carboxyl, alkoxycarbonyl, aryloxycarbonyl or hydroxy. Also of interest are the corresponding 3-acyl-2-thiophenesulfonamides.

These compounds appear to exhibit superior potency, efficacy, bioavailability, in vivo half-life and/or stability compared with compounds where the aryl group has more than two hydrogen substituents, while avoiding toxicological effects associated with hydrophobicity (see, Table 4). In addition, these compounds appear to exhibit good profiles in standard in vitro toxicity tests.

It has been found that for in vivo administration, it is desirable to achieve the proper degree of hydrophilicity, which reduces potential hemolytic properties of the compounds. It has been found herein, for example, that this is achieved if the aryl group is tetra-, penta- or hexasubstituted, preferably pentasubstituted. If the aryl group is tetrasubstituted, will preferably be substituted at the 2, 4 and 6 positions, and one of these substituents will be a polar group, such as hydroxyl, acetoxy, carboxyl and carboxamide. Such substitution enhances the endothelin antagonist activity and the hydrophilicity of the compounds. If the aryl group is substituted at the 2, 4 and 6 positions with nonpolar groups, such as alkyl groups, more specifically methyl groups, then the aryl group will preferably be penta- or hexasubstituted. In pentasubstituted aryl groups, the fifth substituent will be at the 3 position and will preferably be a polar group, such as hydroxyl, acetoxy, carboxyl and carboxamide. Such substitution is preferred to achieve highest levels of activity for therapeutic use.

Such substitution provides compounds with good bioavailability, long in vivo half-life, and/or good in vivo efficacy. In view of the disclosure herein, other such optimal substituent patterns and substituents can be determined empirically using suitable animal models.

As noted above, the compounds of this embodiment provide enhanced tolerability as compared to similar compounds known in the art. Such enhanced tolerability is manifested through alteration of the pharmacokinetic profile of the compounds. The pharmacokinetic profile is based on a number of factors, including, but not limited to, bioavailability, in vivo half-life, in vivo efficacy, potency, stability, receptor-selectivity, and the like.

In certain embodiments, the compounds are selected with the proviso that at most one of $R^5$, $R^6$ and $R^7$ is hydrogen and that the compound is not N-(4-chloro-3-methyl-5-isoxazolyl)-2-(2,4,6-trimethylphenylaminocarbonyl)thiophene-3-sulfonamide, N-(4-chloro-3-methyl-5-isoxazolyl)-2-(2,4,6-trimethyl)phenylacetyl-3- thiophenesulfonamide, N-(3,4-dimethyl-5-isoxazolyl)-2-[(2,4,6-trimethylphenoxy)carbonyl]thiophene-3-sulfonamide, N-(4-chloro-3-methyl-5-isoxazolyl)-2-[(2,4,6-trimethylphenoxy)carbonyl]thiophene-3-sulfonamide or N-(4-bromo-3-methyl-5-isoxazolyl)-2-[(2,4,6-trimethylphenoxy)carbonyl]thiophene-3-sulfonamide.

In other embodiments, the sulfonamides are selected with the further proviso that the compound is not N-(4-chloro-3-methyl-5-isoxazolyl)-2-(3-methoxy-2,4,6-trimethylphenylaminocarbonyl)thiophene-3-sulfonamide, N-(4-chloro-3-methyl-5-isoxazolyl)-2-(3-hydroxy-2,4,6-trimethylphenylaminocarbonyl)thiophene-3-sulfonamide, N-(4-chloro-5-methyl-3-isoxazolyl)-2-(3-hydroxy-2,4,6-trimethylphenylaminocarbonyl)thiophene-3-sulfonamide or N-(3,4-dimethyl-5-isoxazolyl)-2-(3-hydroxy-2,4,6-trimethylphenylaminocarbonyl)thiophene-3-sulfonamide.

Preferred compounds include those in which $R^3$ and $R^4$ are each independently hydrogen, alkyl, halo, cyano, cyanomethyl, acetyl or cycloalkyl, or together form alkylene;

$R^5$, $R^6$ and $R^7$ are each independently selected as in (i) or (ii), with the proviso that at most one of $R^5$, $R^6$ and $R^7$ are hydrogen:
  (i) $R^6$ is hydrogen, unsubstituted alkyl, hydroxy, unsubstituted alkoxy, $C(O)R^{41}$, carbamoyloxy or alkoxycarbonyloxy, and
  $R^5$ and $R^7$ are each independently selected from hydrogen, unsubstituted alkyl, hydroxy, $C(O)R^{41}$, carbamoyloxy or alkoxycarbonyloxy; or
  (ii) if at least one of $R^3$ and $R^4$ is not hydrogen, then any two may form methylenedioxy, and the other is selected as in (i);

x is 0 or 1; n is 2; $R^{41}$ is alkyl, cycloalkyl, alkylamino, dialkylamino, arylamino, diarylamino, alkylsulfonylamino or arylsulfonylamino; and $R^{43}$ is hydroxy or alkoxy, with the proviso that the compound is not N-(4-chloro-3-methyl-5-isoxazolyl)-2-(2,4,6-trimethylphenylaminocarbonyl)-thiophene-3-sulfonamide, N-(4-chloro-3-methyl-5-isoxazolyl)-2-(2,4,6-trimethyl)phenylacetyl-3-thiophenesulfonamide, N-(3,4-dimethyl-5-isoxazolyl)-2-[(2,4,6-trimethylphenoxy)carbonyl]thiophene-3-sulfonamide, N-(4-chloro-3-methyl-5-isoxazolyl)-2-[(2,4,6-trimethylphenoxy)carbonyl]thiophene-3-sulfonamide or N-(4-bromo-3-methyl-5-isoxazolyl)-2-[(2,4,6-trimethylphenoxy)-carbonyl]thiophene-3-sulfonamide.

In particular, compounds. which are preferred are those in which $Ar^1$ is 4-chloro-3-methyl-5-isoxazolyl; $R^3$ and $R^4$ are each independently hydrogen, methyl, cyclopropyl, fluoro, chloro, cyano, cyanomethyl or acetyl, or together form butylene;

$R^5$, $R^6$ and $R^7$ are each independently selected from (i) or (ii), with the proviso that at most one of $R^5$, $R^6$ and $R^7$ is hydrogen:
  (i) $R^6$ is selected from hydrogen, methyl, hydroxy, methoxy, acetyl, carbamoyloxy and methoxycarbonyloxy, and
  $R^5$ and $R^7$ are each independently hydrogen, methyl, hydroxy, acetyl, carbamoyloxy and methoxycarbonyloxy; or
  (ii) if at least one of $R^3$ and $R^4$ is not hydrogen, then $R^6$ and $R^7$ may form methylenedioxy and $R^5$ is selected as in (i); and $R^{45}$ is acetyl, propanoyl, 2-methylpropanoyl, cyclopropylcarbonyl, benzoyl, cyclohexylcarbonyl, methyl, 1-hydroxy-1-ethyl, hydroxymethyl, methoxyacetyl, fluoroacetyl, carboxyacetyl, hydroxyacetyl, oximinoacetyl or $SO_2R^{41}$, with the proviso that the compound is not N-(4-chloro-3-methyl-5-isoxazolyl)-2-(2,4,6-trimethylphenylaminocarbonyl)-thiophene-3-sulfonamide, N-(4-chloro-3-methyl-5-isoxazolyl)-2-(2,4,6-trimethyl)phenylacetyl-3-thiophenesulfonamide, N-(3,4-dimethyl-5-isoxazolyl)-2-[(2,4,6-trimethylphenoxy)carbonyl]thiophene-3-sulfonamide, N-(4-chloro-3-methyl-5-isoxazolyl)-2-[(2,4,6-trimethylphenoxy)carbonyl]thiophene-3-sulfonamide or N-(4-bromo-3-methyl-5-isoxazolyl)-2-[(2,4,6-trimethylphenoxy)-carbonyl]thiophene-3-sulfonamide.

Particularly preferred compounds are selected from the following:

N-(2-acetyl-4,6-dimethylphenyl)-3-(((4-chloro-3-methyl-5-isoxazolyl)amino)sulfonyl)-2-thiophenecarboxamide, N-(2-benzoyl-4,6-dimethylphenyl)-3-(((4-chloro-3-methyl-5-isoxazolyl)amino)sulfonyl)-2-thiophenecarboxamide, 3-(((4-chloro-3-methyl-5-isoxazolyl)amino)sulfonyl)-N-(2-hydroxyethanimidoyl)-4,6-dimethylphenyl)-2-thiophenecarboxamide, 3-(((4-chloro-3-methyl-5-isoxazolyl)amino)sulfonyl)-N-(2,4-dimethyl-6-propionylphenyl)-2-thiophenecarboxamide, 3-(((4-chloro-3-methyl-5-isoxazolyl)amino)sulfonyl)-N-(2-isobutyryl-4,6-dimethylphenyl)-2-thiophenecarboxamide, 3-(((4-chloro-3-methyl-5-isoxazolyl)amino)sulfonyl)-N-(2-(cyclohexylcarbonyl)-4,6-dimethylphenyl)-2-thiophenecarboxamide, 3-(((4-chloro-3-methyl-5-isoxazolyl)amino)sulfonyl)-N-(2-(cyclopropylcarbonyl)-4,6-dimethylphenyl)-2-thiophenecarboxamide, 3-(((3-(((4-chloro-3-methyl-5-isoxazolyl)amino)sulfonyl)-2-thienyl)carbonyl)amino)-2,4,6-trimethylphenyl carbamate, 3-(((3-(((4-chloro-3-methyl-5-isoxazolyl)amino)sulfonyl)-2-thienyl)carbonyl)amino)-2,4,6-trimethylphenyl methyl carbonate, N-(4-chloro-3-methyl-5-isoxazolyl)-2-(2-(3-methoxy-2,4,6-trimethylphenyl)acetyl)-3-thiophenesulfonamide, N-(4-chloro-3-methyl-5-isoxazolyl)-2-(2-(3-hydroxy-2,4,6-trimethylphenyl)acetyl)-3-thiophenesulfonamide, 3-(((4-chloro-3-methyl-5-isoxazolyl)amino)sulfonyl)-N-(2-(2-hydroxy-1-methylethyl)-4,6-dimethylphenyl)-2-thiophenecarboxamide, 3-(((4-chloro-3-methyl-5-isoxazolyl)amino)sulfonyl)-N-(2-(2-hydroxyethyl)-4,6-dimethylphenyl)-2-thiophenecarboxamide, 3-(((4-chloro-3-methyl-5-isoxazolyl)amino)sulfonyl)-N-(2,6-diacetyl)-4-methylphenyl)-2-thiophenecarboxamide, 3-(((4-chloro-3-methyl-5-isoxazolyl)amino)sulfonyl)-N-(2-(2-methoxyacetyl)-4,6-dimethylphenyl)-2-thiophenecarboxamide, 3-(2-(((4-chloro-3-methyl-5-isoxazolyl)amino)sulfonyl)-2-thienyl)carbonyl)amino)-3,5-dimethylphenyl)-3-oxopropanoic acid, 3-(((4-chloro-3-methyl-5-isoxazolyl)amino)sulfonyl)-N-(2-glycolyl-4,6-dimethylphenyl)-2-thiophenecarboxamide, 3-(((4-chloro-3-methyl-5-isoxazolyl)amino)sulfonyl)-N-(2,4-dimethyl-6-methylsulfonyl)phenyl)-2-thiophenecarboxamide, 3-(((4-chloro-3-methyl-5-isoxazolyl)amino)sulfonyl)-N-(2,4-dimethyl-6-((methylamino)sulfonyl)phenyl)-2thiophenecarboxamide, 3-(((4-chloro-3-methyl-5-isoxazolyl)amino)sulfonyl)-N-(2,4-dimethyl-6-((dimethylamino)sulfonyl)phenyl)-2-thiophenecarboxamide, 3-(((4-chloro-3-methyl-5-isoxazolyl)amino)sulfonyl)-N-(2,4-dimethyl-6-(((methylsulfonyl)amino)carbonyl)phenyl)-2-thiophenecarboxamide, 3-(((4-chloro-3-methyl-5-isoxazolyl)amino)sulfonyl)-N-(2-(2-fluoroacetyl)-4,6-dimethylphenyl)-2-thiophenecarboxamide, N-(2-acetyl-4,6-dimethylphenyl)-3-(((4-chloro-3-methyl-5-isoxazolyl)amino)sulfonyl)-5-methyl-2-thiophenecarboxamide, N-(2-benzoyl-4,6-dimethylphenyl)-3-(((4-chloro-3-methyl-5-isoxazolyl)amino)sulfonyl)-5-methyl-2-thiophenecarboxamide, 3-(((4-chloro-3-methyl-5-isoxazolyl)amino)sulfonyl)-N-(2-hydroxyethanimidoyl)-4,6-dimethylphenyl)-5-methyl-2-thiophenecarboxamide, 3-(((4-chloro-3-methyl-5-isoxazolyl)amino)sulfonyl)-N-(2,4-dimethyl-6-propionylphenyl)-5-methyl-2-thiophenecarboxamide, 3-(((4-chloro-3-methyl-5-isoxazolyl)amino)sulfonyl)-N-(2-isobutyryl-4,6-dimethylphenyl)-5-methyl-2-thiophenecarboxamide, 3-(((4-chloro-3-methyl-5-isoxazolyl)amino)sulfonyl)-N-(2-(cyclohexylcarbonyl)-4,6-dimethylphenyl)-5-methyl-2-thiophenecarboxamide, 3-(((4-chloro-3-methyl-5-isoxazolyl)amino)sulfonyl)-N-(2-(cyclopropylcarbonyl)-4,6-dimethylphenyl)-5-methyl-2-thiophenecarboxamide, 3-(((3-(((4-chloro-3-methyl-5-isoxazolyl)amino)sulfonyl)-2-(5-methylthienyl))carbonyl)amino)-2,4,6-trimethylphenyl carbamate, 3-(((3-(((4-chloro-3-methyl-5-isoxazolyl)amino)sulfonyl)-2-(5-methylthienyl))carbonyl)amino)-2,4,6-trimethylphenyl methyl carbonate, N-(4-chloro-3-methyl-5-isoxazolyl)-2-(2-(3-methoxy-2,4,6-trimethylphenyl)acetyl)-5-methyl-3-thiophenesulfonamide, N-(4-chloro-3-methyl-5-isoxazolyl)-2-(2-(3-hydroxy-2,4,6-trimethylphenyl)acetyl)-5-methyl-3-thiophenesulfonamide, 3-(((4-chloro-3-methyl-5-isoxazolyl)amino)sulfonyl)-N-(2-(2-hydroxy-1-methylethyl)-4,6-dimethylphenyl)-5-methyl-2-thiophenecarboxamide, 3-(((4-chloro-3-methyl-5-isoxazolyl)amino)sulfonyl)-N-(2-(2-hydroxyethyl)-4,6-dimethylphenyl)-5-methyl-2-thiophenecarboxamide, 3-(((4-chloro-3-methyl-5-isoxazolyl)amino)sulfonyl)-N-(2-(2,6-diacetyl)-4-methylphenyl)-5-methyl-2-thiophenecarboxamide, 3-(((4-chloro-3-methyl-5-isoxazolyl)amino)sulfonyl)-N-(2-(2-methoxyacetyl)-4,6-dimethylphenyl)-5-methyl-2-thiophenecarboxamide, 3-(2-(((4-chloro-3-methyl-5-isoxazolyl)amino)sulfonyl)-2-(5-methylthienyl))carbonyl)amino)-3,5-dimethylphenyl)-3-oxopropanoic acid, 3-(((4-chloro-3-methyl-5-isoxazolyl)amino)sulfonyl)-N-(2-glycolyl-4,6-dimethylphenyl)-5-methyl-2-thiophenecarboxamide, 3-(((4-chloro-3-methyl-5-isoxazolyl)amino)sulfonyl)-N-(2,4-dimethyl-6-methylsulfonyl)phenyl)-5-methyl-2-thiophenecarboxamide, 3-(((4-chloro-3-methyl-5-isoxazolyl)amino)sulfonyl)-N-(2,4-dimethyl-6-((methylamino)sulfonyl)phenyl)-5-methyl-2-thiophenecarboxamide, 3-(((4-chloro-3-methyl-5-isoxazolyl)amino)sulfonyl)-N-(2,4-dimethyl-6-((dimethylamino)sulfonyl)phenyl)-5-methyl-2-thiophenecarboxamide, 3-(((4-chloro-3-methyl-5-isoxazolyl)amino)sulfonyl)-N-(2,4-dimethyl-6-(((methylsulfonyl)amino)carbonyl)phenyl)-5-methyl-2-thiophenecarboxamide, 3-(((4-chloro-3-methyl-5-isoxazolyl)amino)sulfonyl)-N-(2-(2-fluoroacetyl)-4,6-dimethylphenyl)-5-methyl-2-thiophenecarboxamide, N-(6-acetyl-4-methyl-1,3-benzodioxol-5-yl)-3-(((4-chloro-3-methyl-5-isoxazolyl)amino)sulfonyl)-5-methyl-2-thiophenecarboxamide, N-(4-acetyl-6-methyl-1,3-benzodioxol-5-yl)-3-(((4-chloro-3-methyl-5-isoxazolyl)amino)sulfonyl)-5-methyl-2-thiophenecarboxamide, N-(2-acetyl-4,6-dimethylphenyl)-3-(((4-chloro-3-methyl-5-isoxazolyl)amino)sulfonyl)-4-methyl-2-thiophenecarboxamide, N-(2-benzoyl-4,6-dimethylphenyl)-3-(((4-chloro-3-methyl-5-isoxazolyl)amino)sulfonyl)-4-methyl-2-thiophenecarboxamide, 3-(((4-chloro-3-methyl-5-isoxazolyl)amino)sulfonyl)-N-(2-hydroxyethanimidoyl)-4,6-dimethylphenyl)-4-methyl-2-thiophenecarboxamide, 3-(((4-chloro-3-methyl-5-isoxazolyl)amino)sulfonyl)-N-(2,4-dimethyl-6-propionylphenyl)-4-methyl-2-thiophenecarboxamide, 3-(((4-chloro-3-methyl-5-isoxazolyl)amino)sulfonyl)-N-(2-isobutyryl-4,6-dimethylphenyl)-4-methyl-2-thiophenecarboxamide, 3-(((4-chloro-3-methyl-5-isoxazolyl)amino)sulfonyl)-N-(2-(cyclohexylcarbonyl)-4,6-dimethylphenyl)-4-methyl-2-thiophenecarboxamide, 3-(((4-chloro-3-methyl-5-isoxazolyl)amino)sulfonyl)-N-(2-(cyclopropylcarbonyl)-4,6-dimethylphenyl)-4-methyl-2-thiophenecarboxamide, 3-(((3-(((4-chloro-3-methyl-5-isoxazolyl)amino)sulfonyl)-2-(4-methylthienyl))carbonyl)amino)-2,4,6-trimethylphenyl carbamate, 3-(((3-(((4-chloro-3-methyl-5-isoxazolyl)amino)sulfonyl)-2-(4-methylthienyl))carbonyl)amino)-2,4,6-trimethylphenyl methyl carbonate, N-(4-chloro-3-methyl-5-isoxazolyl)-2-(2-(3-methoxy-2,4,6-trimethylphenyl)acetyl)-4-methyl-3-thiophenesulfonamide, N-(4-chloro-3-methyl-5-isoxazolyl)-2-(2-(3-hydroxy-2,4,6-trimethylphenyl)acetyl)-4-methyl-3-thiophenesulfonamide, 3-(((4-chloro-3-methyl-5-isoxazolyl)amino)sulfonyl)-N-(2-(2-hydroxy-1-methylethyl)-4,6-dimethylphenyl)-4-methyl-2-thiophenecarboxamide, 3-(((4-chloro-3-methyl-5-isoxazolyl)amino)sulfonyl)-N-(2-(2-hydroxyethyl)-4,6-dimethylphenyl)-4-methyl-2-thiophenecarboxamide, 3-(((4-chloro-3-methyl-5-isoxazolyl)amino)sulfonyl)-N-(2-(2,6-diacetyl)-4-methylphenyl)-4-methyl-2-thiophenecarboxamide, 3-(((4-chloro-3-methyl-5-isoxazolyl)amino)sulfonyl)-N-(2-(2-methoxyacetyl)-4,6-dimethylphenyl)-4-methyl-2-thiophenecarboxamide, 3-(2-(((4-chloro-3-methyl-5-isoxazolyl)amino)sulfonyl)-2-(4-methylthienyl))carbonyl)amino)-3,5-dimethylphenyl)-3-oxopropanoic acid, 3-(((4-chloro-3-methyl-5-isoxazolyl)amino)sulfonyl)-N-(2-glycolyl-4,6-dimethylphenyl)-4-methyl-2-thiophenecarboxamide, 3-(((4-chloro-3-methyl-5-isoxazolyl)amino)sulfonyl)-N-(2,4-dimethyl-6-methylsulfonyl)phenyl)-4-methyl-2-thiophenecarboxamide, 3-(((4-chloro-3-methyl-5-isoxazolyl)amino)sulfonyl)-N-(2,4-dimethyl-6-((methylamino)sulfonyl)phenyl)-4-methyl-2-thiophenecarboxamide, 3-(((4-chloro-3-methyl-5-isoxazolyl)amino)sulfonyl)-N-(2,4-dimethyl-6-((dimethylamino)sulfonyl)phenyl)-4-methyl-2-thiophenecarboxamide, 3-(((4-chloro-3-methyl-5-isoxazolyl)amino)sulfonyl)-N-(2, 4-dimethyl-6-(((methylsulfonyl)amino)carbonyl)phenyl)-4-methyl-2-thiophenecarboxamide,
3-(((4-chloro-3-methyl-5-isoxazolyl)amino)sulfonyl)-N-(2-(2-fluoroacetyl)-4,6-dimethylphenyl)-4-methyl-2-thiophenecarboxamide,
N-(6-acetyl-4-methyl-1,3-benzodioxol-5-yl)-3-(((4 -chloro-3-methyl-5-isoxazolyl)amino)sulfonyl)-4-methyl-2-thiophenecarboxamide,
N-(4-acetyl-6-methyl-1,3-benzodioxol-5-yl)-3-(((4-chloro-3-methyl-5-isoxazolyl)amino)sulfonyl)-4-methyl-2-thiophenecarboxamide,
N-(2-acetyl-4,6-dimethylphenyl )-3-(((4-chloro-3-methyl-5-isoxazolyl)amino)sulfonyl)-4,5-dimethyl-2-thiophenecarboxamide,
N-(2-benzoyl-4,6-dimethylphenyl)-3-(((4-chloro-3-methyl-5-isoxazolyl)amino)sulfonyl)-4,5-dimethyl-2-thiophenecarboxamide,
3-(((4-chloro-3-methyl-5-isoxazolyl)amino)sulfonyl)-N-(2-hydroxyethanimidoyl)-4,6-dimethylphenyl)-4,5-dimethyl-2-thiophenecarboxamide,
3-(((4-chloro-3-methyl-5-isoxazolyl)amino)sulfonyl)-N-(2,4-dimethyl-6-propionylphenyl)-4,5-dimethyl-2-thiophenecarboxamide,
3-(((4-chloro-3-methyl-5-isoxazolyl)amino)sulfonyl)-N-(2-isobutyryl-4,6-dimethylphenyl)-4,5-dimethyl-2-thiophenecarboxamide,
3-(((4-chloro-3-methyl-5-isoxazolyl)amino)sultonyl)-N-(2-(cyclohexylcarbonyl)-4,6-dimethylphenyl)-4,5-dimethyl-2-thiophenecarboxamide,
3-(((4-chloro-3-methyl-5-isoxazolyl)amino)sulfonyl)-N-(2-(cyclopropylcarbonyl)-4,6-dimethylphenyl)-4,5-dimethyl-2-thiophenecarboxamide,
3-(((3-(((4-chloro-3-methyl-5-isoxazolyl)amino)sulfonyl)-2-(4,5-dimethylthienyl))carbonyl)amino)-2,4,6-trimethylphenyl carbamate,
3-(((3-(((4-chloro-3-methyl-5-isoxazolyl)amino)sulfonyl)-2-(4,5-dimethylthienyl))carbonyl)amino)-2,4,6-trimethylphenyl methyl carbonate,
N-(4-chloro-3-methyl-5-isoxazolyl)-2-(2-(3-methoxy-2,4,6-trimethylphenyl)acetyl)-4,5-dimethyl-3-thiophenesulfonamide,
N-(4-chloro-3-methyl-5-isoxazolyl)-2-(2-(3-hydroxy-2,4,6-trimethylphenyl)acetyl)-4,5-dimethyl-3-thiophenesulfonamide,
3-(((4-chloro-3-methyl-5-isoxazolyl)amino)sulfonyl)-N-(2-(2-hydroxy-1-methylethyl)-4,6-dimethylphenyl)-4,5-dimethyl-2-thiophenecarboxamide,
3-(((4-chloro-3-methyl-5-isoxazolyl)amino)sulfonyl)-N-(2-(2-hydroxyethyl)-4,6-dimethylphenyl)-4,5-dimethyl-2-thiophenecarboxamide,
3-(((4-chloro-3-methyl-5-isoxazolyl)amino)sulfonyl)-N-(2-(2,6-diacetyl)-4-methylphenyl)-4,5-dimethyl-2-thiophenecarboxamide,
3-(((4-chloro-3-methyl-5-isoxazolyl)amino)sulfonyl)-N-(2-(2-methoxyacetyl)-4,6-dimethylphenyl)-4,5-dimethyl-2-thiophenecarboxamide,
3-(2-(((4-chloro-3-methyl-5-isoxazolyl)amino)sulfonyl)-2-(4,5-dimethylthienyl))carbonyl)amino)-3,5-dimethylphenyl)-3-oxopropanoic acid,
3-(((4-chloro-3-methyl-5-isoxazolyl)amino)sulfonyl)-N-(2-glycolyl-4,6-dimethylphenyl)-4,5-dimethyl-2-thiophenecarboxamide,
3-(((4-chloro-3-methyl-5-isoxazolyl)amino)sulfonyl)-N-(2,4-dimethyl-6-methylsulfonyl)phenyl)-4,5-dimethyl-2-thiophenecarboxamide,
3-(((4-chloro-3-methyl-5-isoxazolyl)amino)sulfonyl)-N-(2,4-dimethyl-6-((methylamino)sulfonyl)phenyl)-4,5-dimethyl-2-thiophenecarboxamide,
3-(((4-chloro-3-methyl-5-isoxazolyl)amino)sulfonyl)-N-(2,4-dimethyl-6-((dimethylamino)sulfonyl)phenyl)-4,5-dimethyl-2-thiophenecarboxamide,
3-(((4-chloro-3-methyl-5-isoxazolyl)amino)sulfonyl)-N-(2,4-dimethyl-6-(((methylsulfonyl)amino)carbonyl)phenyl)-4,5-dimethyl-2-thiophenecarboxamide,
3-(((4-chloro-3-methyl-5-isoxazolyl)amino)sulfonyl)-N-(2-(2-fluoroacetyl)-4,6-dimethylphenyl)-4,5-dimethyl-2-thiophenecarboxamide,
N-(6-acetyl-4-methyl-1,3-benzodioxol-5-yl)-3-(((4-chloro-3-methyl-5-isoxazolyl)amino)sulfonyl)-4,5-dimethyl-2-thiophenecarboxamide, and
N-(4-acetyl-6-methyl-1,3-benzodioxol-5-yl)-3-(((4-chloro-3-methyl-5-isoxazolyl)amino)sulfonyl)-4,5-dimethyl-2-thiophenecarboxamide.

Also among the preferred compounds are those selected from the following:
N-(2-acetyl-4,6-dimethylphenyl)-3-(((4-chloro-3-methyl-5-isoxazolyl)amino)sulfonyl)-5-cyclopropyl-2-thiophenecarboxamide,
5-acetyl-(N-(2-acetyl-4,6-dimethylphenyl)-3-(((4-chloro-3-methyl-5-isoxazolyl)amino)sulfonyl)-2-thiophenecarboxamide,
N-(2-acetyl-4,6-dimethylphenyl)-3-(((4-chloro-3-methyl-5-isoxazolyl)amino)sulfonyl)-5-cyano-2-thiophenecarboxamide,
N-(2-acetyl-4,6-dimethylphenyl)-3-(((4-chloro-3-methyl-5-isoxazolyl)amino)sulfonyl)-5-(cyanomethyl)-2-thiophenecarboxamide,
N-(2-acetyl-4, 6-dimethylphenyl)-3-(((4-chloro-3-methyl-5-isoxazolyl)amino)sulfonyl)-5-fluoro-2-thiophenecarboxamide,
N-(2-acetyl-4,6-dimethylphenyl)-3-(((4-chloro-3-methyl-5-isoxazolyl)amino)sulfonyl)-5-chloro-2-thiophenecarboxamide, and
N-2-acetyl-4,6-dimethylphenyl)-5-chloro-3-(((4-chloro-3-methyl-5-isoxazolyl)amino)sulfonyl)-4,5,6,7-tetrahydro-1-benzothiophene-2-carboxamide.

Preferred compounds are also those where W is O or $CH_2$. The sulfonamides are thus 2-phenoxycarbonyl-3-sulfonamide, 3-phenoxycarbonyl-2-sulfonamide, 2-phenylacetyl-3-sulfonamide and 3-phenylacetyl-2-sulfonamide derivatives of the above compounds.

Table 3 sets forth exemplary compounds of this embodiment and demonstrates that the compounds have activity as endothelin receptor antagonists. More preferred compounds of Table 3 are those that have the highest activities, and preferred substituents are those on the compounds with the highest activities. The data in Table 3 is intended for exemplary and comparison purposes only and is not intended to limit the scope of this embodiment in any way.

TABLE 3

| COMPOUND | $ET_A(\mu M)$* | $ET_A/ET_B$ |
|---|---|---|
| N-(2-acetyl-4,6-dimethylphenyl)-3-(((4-chloro-3-methyl-5-isoxazolyl)amino)sulfonyl)-2-thiophenecarboxamide | 0.00055[†] | 34000[‖] |
| 3-(((4-chloro-3-methyl-5-isoxazolyl)amino)sulfonyl)-N-(2-isobutyryl-4,6-dimethylphenyl)-2-thiophenecarboxamide | 0.00111[†] | 14000[‖] |
| N-(2-benzoyl-4,6-dimethylphenyl)-3-(((4-chloro-3-methyl-5-isoxazolyl)amino)sulfonyl)-2-thiophenecarboxamide | 0.00426[†] | 6000[‖] |
| N-(2-acetyl-4,6-dimethylphenyl)-3-(((4-chloro-3-methyl-5-isoxazolyl)amino)sulfonyl)-5-methyl-2-thiophenecarboxamide | 0.00294[†] | 9000[‖] |

TABLE 3-continued

| COMPOUND | $ET_A(\mu M)$* | $ET_A/ET_B$ |
|---|---|---|
| 3-(((4-chloro-3-methyl-5-isoxazolyl)amino)sulfonyl)-N-(2,4-dimethyl-6-propionylphenyl)-2-thiophenecarboxamide | 0.00061† | 21000‖ |
| 3-(((4-chloro-3-methyl-5-isoxazolyl)amino)sulfonyl)-N-(2-(cyclopropylcarbonyl)-4,6-dimethylphenyl)-2-thiophenecarboxamide | 0.00036† | 45000‖ |
| 3-(((4-chloro-3-methyl-5-isoxazolyl)amimo)sulfonyl)-N-(2-(cyclohexylcarbonyl)-4,6-dimethylphenyl)-2-thiophenecarboxamide | 0.0149† | 1300‖ |
| 3-(((3-(((4-chloro-3-methyl-5-isoxazolyl)amino)sulfonyl)-2-thienyl)carbonyl)amino)-2,4,6-trimethylphenyl methyl carbonate | 0.00075† | — |
| 3-(((3-(((4-chloro-3-methyl-5-isoxazolyl)amino)sulfonyl)-2-thienyl)carbony))amino)-2,4,6-trimethylphenyl carbamate | 0.00545† | — |

*results are generally the average of 2 to 5 experiments
†assay performed with incubation at 24° C. As described in the Examples, incubation at the higher temperature reduces the activity by a factor of 2- to about 10-compared to the activity at 4° C.
— data not available or measured as % inhibition @ 100 $\mu$M
‖$ET_A/ET_B$ selectivity Table 4 lists oral half-life, bioavailability, and in vivo activity of selected exemplary compounds. The in vivo activity was measured in a pulmonary hypertension model and is a measure of the activity of the compounds at selected dosages. As Table 4 indicates, the compounds claimed herein exhibit improved oral half-life, bioavailability, and/or in vivo activity over those disclosed previously (see, e.g., PCT International Publication No. WO 96/31492).

TABLE 4

| COMPOUND | $P_{app}$[a] | $POt_{1,2}$ in Rat[b] | Peak Plasma Levels[c] | in vivo Efficacy[d] |
|---|---|---|---|---|
| N-(4-chloro-3-methyl-5-isoxazolyl)-2-(2-methyl-4,5-(methylenedioxy)phenyl-acetyl)thiophene-3-sulfonamide | 2.32 | 4.1 | 173 | + + |
| N-(4-chloro-3-methyl-5-isoxazolyl)-2-[(2,3,4-trimethoxy-6-cyano)phenyl-aminocarbonyl]thiophene-3-sulfonamide | 0.58 | | | |
| N-(4-chloro-3-methyl-5-isoxazolyl)-2-(3-cyanomethyl-2,4,6-trimethylphenyl-aminocarhonyl)thiophene-3-sulfonamide | 1.78 | 3.4 | 40.2 | + + |
| N-(4-chloro-3-methyl-5-isoxazolyl)-2-(3-carboxymethyl-2,4,6-trimethyl-phenylaminocarbonyl)thiophene-3-sulfonamide | 1.10 | | | |
| N-(4-chloro-3-methyl-5-isoxazolyl)-2-(3-hydroxymethyl-2,4,6-trimethyl-phenylaminocarbonyl)thiophene-3-sulfonamide | 1.56 | 1.5 | 3 | -/+ |
| N-(4-chloro-3-methyl-5-isoxazolyl)-2-(3-methanesulfonylamino-2,4,6-trimethylphenylaminocarbonyl)thiophene-3-sulfonamide | | 5.9 | 2.6 | |
| N-(4-chloro-3-methyl-5-isoxazolyl)-2-(3-cyano-2,4,6-trimethylphenylamino-carbonyl)thiophene-3-sulfonamide | | 3.9 | 20 | + + |
| N-(2-acetyl-4,6-dimethylphenyl)-3-(((4-chloro-3-methyl-5-isoxazolyl)amino)sulfonyl)-2-thiophenecarboxamide | 40% | 8.6 | 57 | + +[e] |
| 3-(((4-chloro-3-methyl-6-isoxazolyl)amino)sulfonyl)-N-(2-isobutyryl-4,6-dimethylphenyl)-2-thiophenecarboxamide | | 5.4 | 59 | |
| 3-(((4-chloro-3-methyl-5-isoxazolyl)amino)sulfonyl)-N-(2-(cyclopropylcarbonyl)-4,6-dimethylphenyl)-2-thiophenecarboxamide | | 5.5 | 53 | |

[a]× $10^{-6}$ cm/sec
[b]in hours
[c]in $\mu$g/mL
[d]Pulmonary Hypertension model: + + effective at 5 mg/kg
  − no effect at 5 mg/kg
  + effective at 15 mg/kg
[e]effective at 0.3 mg/kg in vivo

C. Preparation of the Compounds

The preparation of the neutral (i.e., free) sulfonamide compounds that possess the requisite activities are set forth in U.S. Pat. Nos. 5,464,853, 5,594,021, 5,591,761, 5,571,821, 5,514,691, 5,464,853, commonly owned co-pending U.S. application Ser. Nos. 08/721,183 and 08/847,797, and commonly owned published International PCT application Nos. WO 96/31492 and WO 97/27979. Representative syntheses are set forth the Examples. Compounds whose synthesis is not explicitly exemplified herein or in the above-listed patents and published International PCT applications can be synthesized by routine modification of one or more methods described in detail in the Examples by substituting appropriate readily available reagents.

Salts, acids and other derivatives thereof can be synthesized as outlined and exemplified herein, or by other methods known to those of skill in the art.

1. Neutral Compounds

In general, most of the syntheses involve the condensation of a sulfonyl chloride with an aminoisoxazole in dry pyridine or in tetrahydrofuran (THF) and sodium hydride. The sulfonyl chlorides and aminoisoxazoles either can be obtained commercially or synthesized according to methods described in the Examples or using other methods available to those of skill in this art (see, e.g., U.S. Pat. Nos. 4,659,369, 4,861,366 and 4,753,672).

The N-(alkylisoxazolyl)sulfonamides can be prepared by condensing an aminoisoxazole with a sulfonyl chloride in dry pyridine with or without the catalyst 4-(dimethylamino) pyridine. The N-(3,4-dimethyl-5-isoxazolyl)sulfonamides and N-(4,5-dimethyl-3-isoxazolyl)sulfonamides can be prepared from the corresponding aminodimethylisoxazole, such as 5-amino-3,4-dimethylisoxazole. For example, N-(3, 4-dimethyl-5-isoxazolyl)-2-(carbomethoxy)thiophene-3-sulfonamide was prepared from 2-methoxycarbonylthiophene-3-sulfonyl chloride and 5-amino-3,4-dimethylisoxazole in dry pyridine.

The N-(4-haloisoxazolyl)sulfonamides can be prepared by condensation of amino-4-haloisoxazole with a sulfonyl chloride in THF with sodium hydride as a base. For example, N-(4-bromo-3-methyl-5-isoxazolyl)thiophene-2-sulfonamide was prepared from 5-amino-4-bromo-3-methylisoxazole and thiophene-2-sulfonyl chloride in THF and sodium hydride. N-(4-bromo-3-methyl-5-isoxazolyl)-5-(3-isoxazolyl)thiophene-2-sulfonamide was prepared from 5-amino-4-bromo-3-methylisoxazole and 5-(3-isoxazolyl) thiophene-2-sulfonyl chloride.

Alternatively, compounds, such as those in which $Ar^2$ is thienyl, furyl and pyrrolyl herein, may be prepared by reacting an appropriate sulfonyl chloride with a 5-aminoisoxazole substituted at the 3 and 4 positions, such as 5-amino-4-bromo-3-methylisoxazole, in tetrahydrofuran (THF) solution containing a base, such as sodium hydride. Following the reaction, the THF is removed under reduced pressure, the residue dissolved in water, acidified and extracted with methylene chloride. The organic layer is washed and then dried over anhydrous magnesium sulfate, the solvents are evaporated and the residue is purified by recrystallization using hexanes/ethyl acetate to yield pure product.

These sulfonamides also can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

Other examples include:
(a) N-(4-bromo-3-methyl-5-isoxazolyl)-2-(N-phenylaminocarbonyl)thiophene-3-sulfonamide was prepared from N-(4-bromo-3-methyl-5-isoxazolyl)-2-carboxylthiophene-3-sulfonamide, aniline and 1-ethyl-3'-[3-dimethylaminopropyl]carbodiimide (EDCI). N-(4-bromo-3-methyl-5-isoxazolyl)-2-[(4-methoxyphenyl)aminocarbonyl]thiophene-3-sulfonamide was prepared from 4-methoxyaniline, N,N'-diisopropylethylamine and N-(4-bromo-3-methyl-5-isoxazolyl)-2-carboxylthiophene-3-sulfonamide. N-(4-bromo-3-methyl-5-isoxazolyl)-2-(benzylaminocarbonyl)thiophene-3-sulfonamide was prepared from N-(4-bromo-3-methyl-5-isoxazolyl)-2-carboxylthiophene-3-sulfonamide and benzylamine as described above.

N-(4-bromo-3-methyl-5-isoxazolyl)-2-carboxylthiophene-3-sulfonamide was prepared from N-(4-bromo-3-methyl-5-isoxazolyl)-2-(carbomethoxy)thiophene-3-sulfonamide, which was prepared from the condensation of 5-amino-4-bromo-3-methylisoxazole and 2-(carbomethoxy)thiophene-3-sulfonyl chloride.

(b) N-(4-bromo-3-methyl-5-isoxazolyl)-1-(4'-isopropylphenyl)pyrrole-2-sulfonamide and N-(4-bromo-3-methyl-5-isoxazolyl)-1-(4'-isopropylphenyl)pyrrole-3-sulfonamide were prepared from 5-amino-4-bromo-3-methylisoxazole and a mixture of 1-(4'-isopropylphenyl)pyrrole-2-sulfonyl chloride and 1-(4'-isopropylphenyl)pyrrole-3-sulfonyl chloride. These sulfonyl chlorides were prepared from 1-(4'-isopropylphenyl)pyrrole-2-sulfonic acid, phosphorus oxychloride and phosphorus pentachloride. 1-(4'-isopropylphenyl)pyrrole-2-sulfonic acid was prepared from 1-(4'-isopropylphenyl)pyrrole and chlorosulfonic acid. 1-(4'-isopropylphenyl)pyrrole was prepared from 4-isopropylaniline and 2,5-dimethoxytetrahydrofuran.

2. Salts of the Neutral Compounds

Pharmaceutically-acceptable salts of the compounds may be prepared by the exemplified method or any other method known to those of skill in the art. As exemplified herein, in the case of organic salts, the organic base, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, or tris(hydroxymethyl) aminomethane, may be mixed with an equimolar amount of the sulfonamide. Subsequent recovery of the salt by crystallization, precipitation, concentration of the solution, lyophilization, spray-drying, chromatography, including, but not limited to, normal- and reverse-phase chromatography or resin chromatography, or any other method known to those of skill in the art would provide the desired salts. The pharmaceutically acceptable cationic salts can be prepared by reacting the acid forms with an appropriate base.

3. Salts of Hydrophobic Sulfonamides

A process of making an alkali metal salt of hydrophobic sulfonamide modulators of endothelin activity is provided. More particularly, processes for making sodium salts of such sulfonamides are provided. Each process includes the steps of dissolving the free sulfonamide in an organic solvent in the presence of a saturated aqueous solution of an alkali metal salt and recovering and purifying the sulfonamide salt.

The sulfonamide to be converted to an alkali metal salt can be made by any process well known in the art (see, e.g, U.S. Pat. Nos. 5,591,761 and 5,594,021). By way of example, $N^2$-methoxy-$N^2$-methyl-3-(4-chloro-3-methyl-5-isoxazolylsulfamoyl)-2-thiophenecarboxamide is reacted with 6-methylbenzo[d][1,3]dioxolyl-5-methyl magnesium chloride in an organic solvent to provide 4-chloro-3-methyl-5-(2-(2-(6-methylbenzo[d][1,3]dioxol-5-yl)acetyl)-3-thienylsulfonamido)isoxazole as a crude product that is purified be preparative HPLC.

A Process for Preparation of Alkali Metal Salts

An alternative process for preparing the salts is provided herein and exemplified below (see, Example 7). Briefly, the process includes the steps of (a) admixing 5-chloromethyl-6-methylbenzo[d][1,3]dioxole and activated magnesium in tetrahydrofuran to form a Grignard reagent; (b) adding $N_2$-methoxy-$N^2$-methyl-3-(4-chloro-3-methyl-5-isoxazolylsulfamoyl)-2-thiophenecarboxamide to the reaction mixture; (c) diluting the mixture from step (b) sequentially with a concentrated inorganic acid and an organic solvent to form an aqueous layer and an organic layer; and (d) drying the organic layer and evaporating the solvent to form a residue.

The salt-forming process of begins with dissolution of the free sulfonamide in an organic solvent. Suitable organic solvents suitable for use in these processes are well known in the art. Exemplary and preferred organic solvents are ethyl acetate, methyl t-butyl ether, methylene chloride, THF, ether, acetonitrile, dioxane and chloroform. Ethyl acetate is the most preferred organic solvent.

Formation of the alkali metal salt proceeds by exposing the organic solvent containing the free sulfonamide to a saturated solution of an alkali metal salt. The particular salt used with depend on the desired sulfonamide salt to be formed. Alkali metals suitable for use in the present process are well known in the art and include sodium, potassium, calcium, magnesium and the like. For preparation of a sulfonamide salt useful for a pharmaceutical composition, sodium and calcium are the preferred alkali metals. Sodium is most preferred. Anionic components of the salt are well known in the art and include carbonate, phosphate, bicarbonate, nitrate, hydroxide and the like and combinations thereof. Carbonate, bicarbonate and hydroxide anions are preferred. Bicarbonate is more preferred. The alkali metal salt used to form the sulfonamide salt is in the form of a highly concentrated aqueous solution. It is preferred that saturated solutions be used. Means for making saturated alkali metal salt solutions are well known in the art. The biphasic mixture is agitated by any number of methods including shaking, stirring, sonication, etc. After allowing the layers to separate, the aqueous phase is removed.

Recovery of the product from the organic solvent is accomplished using any means well known in the art, such as crystallization and filtration. In one embodiment, the organic solvent containing the sulfonamide salt is washed with a concentrated salt solution, wherein the alkali metal is the same as used for salt formation. Where the alkali metal salt is sodium, exemplary wash solutions are concentrated solutions of sodium chloride (e.g., brine) or sodium bicarbonate. Once the protonated form of the sulfonamide has been converted to the salt form, it is important to use concentrated (>than about 3 percent by weight) salt wash solutions. Surprisingly, the alkali metal sulfonamide salt is more soluble in organic solvents than in saturated alkali metal solutions. Use of a diluted solution of salt (e.g., half-strength brine) or water for washing the organic solvent may cause disproportionation of the product between water and the organic layer, and subsequent loss of material. After washing, the product solution can be dried concentrated to provide crude product as, for example, a residue. In a preferred embodiment, drying occurs over $Na_2SO_4$ or $MgSO_4$ and concentration occurs in vacuo.

The residue is further recovered and purified using recrystallization. In accordance with this embodiment, the product is dissolved in a organic, non-water miscible solvent. Such solvents are well known in the art. Exemplary and preferred such solvents are ether and halomethanes such as dichloromethane and chloroform. A combination of such solvents can also be used. The crystalline product can be isolated from the organic solvent via filtration. The recovered product can be washed one or more times with the organic, non-water miscible solvent. A detailed description of the making of 4-chloro-3-methyl-5-(2-(2-(6-methylbenzo[d][1,3]dioxol-5-yl)acetyl)-3-thienylsulfonamido)isoxazole, sodium salt in accordance with the disclosed process can be found hereinafter in the Examples.

The sulfonamide salts provided herein can be converted back to the free sulfonamide form and further purified by this process. The sulfonamide salt is dissolved in an aqueous solvent (e.g., water) and filtered. Preferably, filtration occurs through more than one layer of filter paper. Negative pressure or suction may not be needed to complete filtration. In some cases, the large amount of impurities that are not soluble in water (10% or higher) slows down the filtration process. This problem can be avoided by using a larger size of filter during the filtration. Usually there is no problem with filtration if the purity of the crude salt is 90% or higher.

The isolation salt, typically in the form of a turbid solution, is converted to an acid by exposing the salt to a concentrated inorganic acid. Suitable acids include hydrochloric acid (HCl), sulfuric acid ($H_2SO_4$), nitric acid ($H_2NO_3$) and the like. Acidification continues until the pH of the product solution is about 1.5 to about 2.5. Acidification preferably takes place at temperatures below about 10° C. The product can precipitate as a milky, non-filtrable material during acidification. The slow, dropwise addition of some extra amount of acid causes the product to form a fine, easy filterable precipitate. The precipitate is filtered off, washed with water until neutral and pressed on the filter to get rid of excess water. The obtained free acid is typically >95% pure as determined by HPLC. The purified sulfonamide can then be converted to the alkali metal salt by the previously described procedure.

Practice the process provided herein permits shortened reaction times, and results in a more pure product than is possible with other methods. Direct isolation of the sulfonamide salt may be achieved by mixing the product with concentrated alkali salt solutions and organic solvents. A surprising key observation is that the sulfonamide salt stays in the organic layer, so long as the aqueous layer is heavily salted rather than the aqueous layer as expected. This permits direct isolation of the salt, which can be further purified by conversion to the free sulfonamide and back to the salt, as well as recrystallization. This discovery is key to synthesizing sulfonamide salts with high purity at large scale.

4. Other Derivatives

Prodrugs and other derivatives of the compounds suitable for administration to humans may also be designed and prepared by methods known to those of skill in the art (see, e.g., Nogrady (1985) *Medicinal Chemistry A Biochemical Approach,* Oxford University Press, New York, pages 388–392).

Compounds described herein have been synthesized and tested for activity in in vitro assays and, in some cases, in in vivo animal models. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All of the compounds exemplified or described herein exhibited activity as endothelin antagonists.

D. Formulation of Sulfonamides and Sulfonamide Salts

Formulations of the sulfonamides and sulfonamide salts described above are provided herein. The formulations prepared as described below are compositions designed for administration of the pharmaceutically acceptable derivatives, particularly salts of the sulfonamide compounds provided herein. Because of the observed superior stability characteristics of the salts, compared to the neutral forms, such salts, particularly the sodium salts are particularly suitable for oral and parenteral administration. Such compositions include solutions, suspensions, tablets, dispersible tablets, pills, capsules, powders, dry powders for inhalers, sustained release formulations and any other suitable formulation. Preferably the compositions will take the form of a pill or tablet. Methods for manufacture of tablets, capsules and other such formulations are known to those of skill in the art (see, e.g., Ansel, H. C (1985) *Introduction to Pharmaceutical Dosage Forms,* 4th Edition, pp. 126–163).

It is understood that for the formulations herein, derivatives, including pharmaceutically acceptable acids, esters, salts and prodrugs of these compounds are preferred. Preferred for use herein for preparing the formulations are sodium salts, particularly the sodium salt in which $Na^+$ is the counter ion.

In the formulations, effective concentrations of one or more pharmaceutically acceptable derivatives is (are) mixed with a suitable pharmaceutical carrier or vehicle. Preferably, the sulfonamide compounds are derivatized as the corresponding salts, preferably sodium salts, prior to formulation, as described above. The concentrations of the salts of the compounds in the formulations are effective for delivery of an amount, upon administration, that ameliorates the symptoms of the endothelin-mediated disease. Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound as salt, preferably as a sodium salt, is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound sodium salt in the drug composition will depend on absorption, inactivation and excretion rates of the active compound, the physicochemical properties of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 ng/ml to about 50–100 $\mu$g/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred derivatives include acids, salts, esters and prodrug forms. The derivative is selected to be a more stable form than the corresponding neutral compound. Preferred are pharmaceutically-acceptable salts, including, but not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, tris(hydroxymethyl) aminomethane, alkali metal salts, such as but not limited to lithium, potassium and sodium, alkali earth metal salts, such as but not limited to barium, calcium and magnesium, transition metal salts, such as but not limited to iron, zinc, gold and silver, and other metal salts, such as but not limited to aluminum, sodium hydrogen phosphate, disodium phosphate, or bismuth salts, preferably sodium salts, more preferably the sodium salt, and also including, but not limited to, salts of mineral acids, such as but not limited to hydrochlorides and sulfates, salts of organic acids, such as but not limited to acetates, lactates, malates, tartrates, citrates, ascorbates, succinates, butyrates, valerates and fumarates of the sulfonamide compounds or pharmaceutically acceptable esters or other derivatives thereof. More preferred salts include sodium salts, such as, but not limited to, a sodium hydrogen phosphate salt and a sodium salt, most preferably the sodium salt.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the endothelin-mediated disorder for which treatment is contemplated. The concentration of active compound in the composition will depend on absorption, inactivation, excretion rates of the active compound, the dosage schedule, amount administered, particular formulation as well as other factors known to those of skill in the art.

The compositions are intended to be administered by an suitable route, which includes orally, parenterally, rectally and topically and locally depending upon the disorder being treated. For example, for treatment of ophthalmic disorders, such as glaucoma, formulation for intraocular and also intravitreal injection is contemplated. For oral administration, capsules and tablets are presently preferred. For parenteral administration reconstitution of a lyophilized powder, prepared as described herein, is preferred. The compounds in liquid, semi-liquid or solid form and are formulated in a manner suitable for each route of administration. Preferred modes of administration include parenteral and oral modes of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as prodrugs of the compounds may also be used in formulating effective pharmaceutical compositions.

Upon mixing or addition of the sodium salt of the sulfonamide compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The formulations are provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these formulations are known to those skilled in the art and the like. The contemplated compositions may contain 0.01–100% active ingredient, preferably 0.1–95%, typically 75–95%.

The salts, preferably sodium salts, of the active compounds may be prepared with carriers that protect the compound against rapid elimination from the body, such as time release formulations or coatings. The formulations may be include other active compounds to obtain desired combinations of properties. The compounds of formula I, or a pharmaceutically acceptable salts and derivatives thereof as described herein, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, asteroid, a beta-agonist, an anti-coagulant, or a thrombolytic agent. It is to be understood that such combination therapy constitutes a further aspect of the compositions and methods of treatment provided herein.

1. Formulations for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; an diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the salt of the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively. The active ingredient is a compound or salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with polymers or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic adds and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

In one embodiment, the formulations are solid dosage forms, preferably capsules or tablets. In a preferred embodiment, the formulations are solid dosage forms, preferably capsules or tablets, containing 10–100%, preferably 50–95%, more preferably 75–85%, most preferably 80–85%, by weight, of one or more sulfonamides or sulfonamide salts, preferably sodium hydrogen phosphate or sodium salts, more preferably the sodium salts, of one or more sulfonamide compounds of formula I; about 0–25%, preferably 8–15%, of a diluent or a binder, such as lactose or microcrystalline cellulose; about 0 to 10%, preferably about 3–7%, of a disintegrant, such as a modified starch or cellulose polymer, particularly a cross-linked sodium carboxymethyl cellulose, such as crosscarmellose sodium (Crosscarmellose sodium NF is available commercially under the name AC-DI-SOL, FMC Corporation, Philadelphia, Pa.) or sodium starch glycolate; and 0–2% of a lubricant, such a magnesium stearate, talc and calcium stearate. The disintegrant, such as crosscarmellose sodium or sodium starch glycolate, provides for rapid break-up of the cellulosic matrix for immediate release of active agent following dissolution of coating polymer. In all embodiments, the precise amount of active ingredient and auxiliary ingredients can be determined empirically and is a function of the route of administration and the disorder that is treated.

In an exemplary embodiment, the formulations are capsules containing about 80–90%, preferably about 83% of one or more sodium salts of one or more sulfonamide compounds of formula I; about 10–15%, preferably about 11% of a diluent or a binder, such as lactose or microcrystalline cellulose; about 1–10%, preferably about 5% of a disintegrant, such as crosscarmellose sodium or sodium starch glycolate; and about 0.1 to 5%, preferably about 1% of a lubricant, such as magnesium stearate. Solid forms for administration as tablets are also contemplated herein.

In an exemplary preferred embodiment, the formulations are capsules containing 83% of one or more sodium salts of one or more sulfonamide compounds; 11% of microcrystalline cellulose; 5% of a disintegrant, such as Crosscarmellose sodium or sodium starch glycolate; and 1% of magnesium stearate.

The above embodiments may also be formulated in the form of a tablet, which may optionally be coated. Tablets will contain the compositions described herein.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is know and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

It has been found that formulations containing certain sodium salts of the sulfonamides provided herein, particularly those in which $R^8$ is phenylacetyl exhibit an increase in stability as compared to formulations containing the neutral compound. The data in Table 5 reflects the increased stability of solutions of the sodium hydrogen phosphate and sodium salts of 4-chloro-3-methyl-5-(2-(2-(6-methylbenzo[d][1,3]dioxol-5-yl)acetyl)-3-thienylsulfonamido)isoxazole as compared to the neutral compound. These salts also exhibit improved solubility over the neutral compound in aqueous media. As can be seen from Table 5, the sodium hydrogen phosphate salt is more stable than the neutral compound in a LABRASOL solution. The sodium salt was found, in certain aqueous formulations, to be as stable as the sodium hydrogen phosphate salt.

TABLE 5

| SALT | mg/mL | VEHICLE | h[a] | (%)[b] |
|---|---|---|---|---|
| none | 150 | LABRASOL | 24 | 90.1 |
| sodium hydrogen phosphate | 100 | LABRASOL | 22.5 50.5 | 98.2 97.1 |
| sodium hydrogen phosphate | 50 | 10% LABRASOL/water | 6 | 87.0 |
| sodium hydrogen phosphate | 25 | 10% LABRASOL/water | 6 | 89.4 |
| sodium hydrogen phosphate | 100 | DMSO | 25 | 98.6 |
| sodium hydrogen phosphate | 10 | 0.01 M NaPO$_4$:PEG:EtOH (6:3:1) (pH 7.7) | 24.5 48 | 98.6 100 |
| sodium hydrogen phosphate | 2.4 | water | 17.5 | 96.5 |
| sodium hydrogen phosphate | 25 | 0.1% BSA in water | 92 | 46.6 |
| sodium hydrogen phosphate | 25 | water | 6 | 94.5 |
| sodium hydrogen phosphate | 10 | water:PEG 400:EtOH (6:3:1) | 6 | 100 |
| sodium hydrogen phosphate | 10 | 0.01 M NaPO$_4$:PEG 400:EtOH (6:3:1) (pH 7.5) | 67.5 7 days 19 days | 100 98.8 95.6 |
| sodium hydrogen phosphate | 5 | deionized water | 24 48 72 | 93 85 77 |
| sodium hydrogen phosphate | 5 | tap water | 24 38 72 | 91 84 76 |
| sodium | 0.51 | normal saline | 24 | 96.9 |
| sodium | 0.51 | 5% dextrose | 24 | 99.4 |

TABLE 5-continued

| SALT | mg/mL | VEHICLE | h[a] | (%)[b] |
|---|---|---|---|---|
| sodium | 0.57 | 0.75% PVP + 1.5% PG | 24 | 74.4 |
| sodium | 0.49 | 1.5% PVP ± 3.0% PG | 24 | 90.0 |
| sodium | 100 | 5% dextrose | 6 | 93.0 |
| sodium | 100 | 30% sorbitol | 24 | 93.2 |
| sodium | 30 | 5% dextrose | 24 | 92.2 |
| sodium | 30 | 20% sorbitol | 24 | 93.2 |
| sodium | 20 | 5% dextrose | 24 | 92.4 |
| sodium | 20 | 10% dextrose | 24 | 93.4 |
| sodium | 20 | 10% dextrose + 10% PG | 24 | 95.6 |
| sodium | 20 | 5% dextrose | 24 (13° C.) | 93.7 |
| sodium | 20 | 5% dextrose | 24 | 90.1 |
| sodium | 20 | 5% dextrose + K-phosphate buffer, 2.5% w/v (pH 7) | 20 | 92.6 |
| sodium | 20 | 5% dextrose + K-phosphate buffer, 2.5% w/v (pH 6.5) | 24 | 89.4 |
| sodium | 20 | 5% dextrose + K-phosphate buffer, 2.5% w/v (pH 6) | 24 | 84.6 |
| sodium | 20 | 5% dextrose + K-phosphate buffer, 2.5% w/v (pH 7.5) | 24 | 93.4 |
| sodium | 20 | 5% dextrose + citrate buffer, 0.3% w/v (pH 8) | 21 | 92.9 |
| sodium | 20 | 10% dextrose + 10% PG + Na-phosphate buffer, 0.3% w/v (pH 7.5) | 24 | 90.7 |
| sodium | 20 | 10% dextrose + 10% PG + Na-phosphate buffer, 0.3% w/v (pH 7.5) | 24 (4° C.) | 97.4 |
| sodium | 20 | 10% dextrose + 10% PG + Na-phosphate buffer, 0.3% w/v (pH 8) | 24 (4° C.) | 96.4 |
| sodium | 20 | 10% dextrose + 10% PG + citrate buffer, 0.3% w/v (pH 7.4) | 24 (4° C.) | 97.6 |
| sodium | 20 | 10% dextrose + 10% PG | 24 (4° C.) | 97.6 |
| sodium | 30 | 10% dextrose + 10% PG + citrate buffer, 0.3% w/v (pH 7.5) | 24 (4° C.) | 98.0 |
| sodium | 20 | 5% dextrose + 5% PG + citrate buffer, 0.3% w/v (pH 7.5) | 26 (4° C.) | 97.2 |
| sodium | 100 | 10% dextrose + 10% PG + citrate buffer, 0.3% w/v (pH 7.5) | 24 (4° C.) | 94.2 |
| sodium | 20 | 5% dextrose + citrate buffer, 0.3% w/v (pH 7.5) | 27 (4° C.) | 96.6 |
| sodium | 100 | 30% sorbitol | 24 | 93.2 |
| sodium | 30 | 5% dextrose | 24 | 92.2 |
| sodium | 30 | 20% sorbitol | 24 | 93.2 |
| sodium | 20 | 5% dextrose | 24 | 92.4 |
| sodium | 20 | 10% dextrose | 24 | 93.4 |
| sodium | 20 | 10% dextrose + 10% PG | 24 | 95.6 |
| sodium | 20 | 5% dextrose | 24 | 9Q 2 |
| sodium | 20 | 5% dextrose | 25 (10° C.) | 93.7 |
| sodium | 20 | 5% dextrose + 5% buffer (pH 7.0) | 24 | 92.6 |

[a]hours following preparation of the formulation
[b]percent 4-chloro-3-methyl-5-(2-(2-(6-methylbenzo[d][1,3]dioxol-5-yl)acetyl)-3-thienylsulfonamido)isoxazole remaining as determined by high performance liquid chromatographic analysis.

In many instances, the solutions of sodium salts, including the sodium salt and sodium hydrogen phosphate salts exhibit improved stability as compared to the neutral compound. These salts also exhibit improved solubility over the neutral compound in aqueous media.

3. Lyophilized Powders

Of particular interest herein, are lyophilized powders, which can be reconstituted for administration as solutions, emulsions and other mixtures. They may also be formulated as solids or gels.

In particular embodiments, formulations of sodium hydrogen phosphate or sodium, preferably sodium, salts of the sulfonamide compounds, which possess increased stability relative to formulations of the neutral sulfonamides are provided. Specifically, formulation of sulfonamide sodium salts as a sterile, lyophilized powder are provided. These powders were found to have increased stability relative to formulations of the neutral sulfonamides.

The sterile, lyophilized powder is prepared by dissolving the sodium salt in a sodium phosphate buffer solution containing dextrose or other suitable excipient. Subsequent sterile filtration of the solution followed by lyophilization under standard conditions known to those of skill in the art provides the desired formulation. Briefly, the lyophilized powder is prepared by dissolving dextrose, sorbitol, fructose, corn syrup, xylitol, glycerin, glucose, sucrose or other suitable agent, about 1–20%, preferably about 5 to 15%, in a suitable buffer, such as citrate, sodium or potassium phosphate or other such buffer known to those of skill in the art at, typically, about neutral pH. Then, a selected salt, preferably the sodium salt of the sulfonamide (about 1 g of the salt per 10–100 g. of the buffer solution, typically about 1 g/30 g), is added to the resulting mixture, preferably above room temperature, more preferably at about 30–35° C., and stirred until it dissolves. The resulting mixture is diluted by adding more buffer (so that the resulting concentration of the salt decreases by about 10–50%, typically about 15–25%). The resulting mixture is sterile filtered or treated to remove particulates and to insure sterility, and apportioned into vials for lyophilization. Each vial will contain a single dosage (100–500 mg, preferably 250 mg) or multiple dosages of the sulfonamide salt. The lyophilized powder can be stored under appropriate conditions, such as at about 4° C. to room temperature. Details of an exemplary procedure are set forth in the Examples.

Reconstitution of this lyophilized powder with water for injection provides a formulation for use in parenteral administration of sodium salts of the sulfonamides. For reconstitution about 1–50 mg, preferably 5–35, more preferably about 9–30 is added per ml of sterile water or other suitable carrier. The precise amount depends upon the indication treated and selected compound. Such amount can be empirically determined.

In one embodiment, the formulations contain lyophilized solids containing one or more sodium hydrogen phosphate or sodium, preferably sodium, salts of one or more sulfonamide compounds of formula I, and also contain one or more of the following:
- a buffer, such as sodium or potassium phosphate, or citrate;
- a solubilizing agent, such as LABRASOL, DMSO, bis(trimethylsilyl)acetamide, ethanol, propyleneglycol (PG), or polyvinylpyrrolidine (PVP); and
- a sugar or carbohydrate, such as sorbitol or dextrose.

In more preferred embodiments, the formulations contain one or more sodium hydrogen phosphate or sodium, preferably sodium, salts of one or more sulfonamide compounds of formula I; a buffer, such as sodium or potassium phosphate, or citrate; and a sugar or carbohydrate, such as sorbitol or dextrose.

In the most preferred embodiments, the formulations contain one or more sodium salts of the sulfonamide compounds; a sodium phosphate buffer; and dextrose. The preparation of these formulations is exemplified in the EXAMPLES.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The sodium salts and other derivatives of the compounds may be formulated as aerosols for topical application, such as by inhalation (see, eq., U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically diameters of less than 50 microns, preferably less than 10 microns.

The sodium salts of the compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%–10% isotonic solutions, pH about 5–7, with appropriate salts.

5. Articles of Manufacture

The derivatives, particularly the salts, acids, esters and preferably the sodium salts of the compounds may be packaged as articles of manufacture containing packaging material, a sodium salt of a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 $\mu$M, within the packaging material, and a label that indicates that the compound or salt thereof is used for antagonizing the effects of endothelin, treating endothelin-mediated disorders or inhibiting the binding of an endothelin peptide to an ET receptor.

6. Formulations for Other Routes of Administration

Depending upon the condition treated other routes of administration, such as topical application, transdermal patches, an rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

E. Evaluation of the Bioactivity of the Compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those specifically identified herein, that are endothelin antagonists or agonists may be identified using such screening assays.

1. Identifying Compounds that Modulate the Activity of an Endothelin Peptide

The compounds are tested for the ability to modulate the activity of endothelin-1. Numerous assays are known to those of skill in the art for evaluating the ability of compounds to modulate the activity of endothelin (see, e.q., U.S. Pat. No. 5,114,918 to Ishikawa et al.; EP A 1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., U.S. Pat. No. 5,114,918 to Ishikawa et al.; EP A 1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., "Tissue selectivity of endothelin," *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A 1 0 436 189 to BANYU PHARMACEUTICAL CO., LTD (Oct. 7, 1991); see, also Bolger et al. (1983) *J. Pharmacol. Exp. Ther.* 225291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.q., Filep et al. (1991) *Biochem. and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. Nos. 5,248,807; 5,240,910; 5,198,548; 5,187,195; 5,082,838; 5,230,999; published Canadian Application Nos. 2,067,288 and 2071193; published Great Britain Application No. 2,259, 450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of Endothelin Receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptor subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

The following examples are included for illustrative purposes only and are not intended to limit the scope of the invention.

EXAMPLE 1

N-(4-bromo-3-methyl-5-isoxazolyl)-2-(aminocarbonyl)thiophene-3-sulfonamide

Carbonydiimidazole (485 mg, 2.99 mmol) was added to a solution of N-(4-bromo-3-methyl-5-isoxazolyl)-2-carboxylthiophene-3-sulfonamide (1 g, 2.72 mmol) in THF (10 ml) at room temperature. The mixture was stirred for 15 minutes. Aqueous $NH_3$ (5 ml) was then added, and the mixture was stirred at room temperature for 30 minutes. The solvent was evaporated and the residue was partitioned between EtOAc and 1 N HCl. The organic layer was dried ($MgSO_4$). The solid was filtered and the filtrate concentrated. The oily residue was recrystallized from EtOAc to give N-(4-bromo-3-methyl-5-isoxazolyl)-2-(aminocarbonyl)thiophene-3-sulfonamide (946 mg, 95% yield) as a white solid, m.p. 168–170° C.

EXAMPLE 2

N-(4-Bromo-3-methyl-5-isoxazolyl)-2-[(3,4-methylenedioxy)benzoyl]thiophene-3-sulfonamide A. N-(4-bromo-3-methyl-5-isoxazolyl)-2-[(N-methoxy-N-methyl)aminocarbonyl]thiophene-3-sulfonamide N-(4-bromo-3-methyl-5-isoxazolyl)-2-[(N-methoxy-N-methyl)carboxamide]thiophene-3-sulfonamide was prepared by the same method as described in Example 1 with the exception that N,O-dimethylhydroxylamine was used in place of ammonium hydroxide. The yield was 90%.

B. N-(4-Bromo-3-methyl-5-isoxazolyl)-2-[(3,4-methylenedioxy)benzoyl]thiophene-3-sulfonamide Freshly prepared (3,4-methylenedioxy)phenyl magnesium bromide (1.28 g of (3,4-methylenedioxy) bromobenzene and 172 mg Mg turnings) was added to a solution of N-(4-bromo-3-methyl-5-isoxazolyl)-2-[(N-methoxy-N-methyl)aminocarbonyl]thiophene-3-sulfonamide (A) (652 mg, 1.59 mmol) in THF (10 ml) at room temperature. The resulting mixture was refluxed for 30 minutes. To workup, the mixture was allowed to cool to room temperature and was quenched with 1N HCl (10 ml). THF was then evaporated. The aqueous residue was partitioned between 1 N HCl and EtOAc. The organic layer was concentrated and the residue was purified by HPLC to give N-(4-bromo-3-methyl-5-isoxazolyl)-2-[(3,4-methylenedioxy)benzoyl]thiophene-3-sulfonamide (90 mg, 12% yield) as a dark yellow powder, m.p. 47–49° C.

EXAMPLE 3

N-(4-Bromo-3-methyl-5-isoxazolyl)-2-[(2-hydroxyphenyl)aminocarbonyl]thiophene-3-sulfonamide N-(4-bromo-3-methyl-5-isoxazolyl)-2-[(2-hydroxyphenyl)aminocarbonyl]-thiophene-3-sulfonamide was prepared by the same method as described in Example 1 with the exception that 3-aminophenol was used in place of ammonium hydroxide. The product was purified by HPLC to give N-(4-bromo-3-methyl-5-isoxazolyl)-2-[(2-hydroxyphenyl)aminocarbonyl]thiophene-3-sulfonamide (50 mg, 18% yield) as a dull yellow solid, m.p. 42–44° C.

EXAMPLE 4

N-(4-Bromo-3-methyl-5-isoxazolyl)-2-[(3,4-methylenedioxy)phenylacetyl]thiophene-3-sulfonamide N-(4-bromo-3-methyl-5-isoxazolyl)-2-[(3,4-methylenedioxy)phenylacetyl]thiophene-3-sulfonamide was prepared by the same method as described in Example 2 with the exception that piperonylmagnesium chloride was used instead of (3,4-methylenedioxy)phenylmagnesium bromide and the reaction mixture was stirred overnight at room temperature instead of refluxing for 30 minutes. The crude mixture was purified by HPLC to give N-(4-bromo-3-methyl-5-isoxazolyl)-2-[3,4-(methylenedioxy)phenylacetyl]thiophene-3-sulfonamide (20 mg, 40% yield) as a yellow oil.

EXAMPLE 5

N-(4-chloro-3-methyl-5-isoxazolyl)-2-[(3,4-methylenedioxy)phenylacetyl]thiophene-3-sulfonamide N-(4-chloro-3-methyl-5-isoxazolyl)-2-[(3,4-methylenedioxy)phenylacetyl]-thiophene-3-sulfonamide was prepared by the same method as described in Example 4 with the exception that N-(4-chloro-3-methyl-5-isoxazolyl)-2-carboxylthiophene-3-sulfonamide was used instead of N-(4-bromo-3-methyl-5-isoxazolyl)-2-carboxylthiophene-3-sulfonamide. N-(4-chloro-3-methyl-5-isoxazolyl)-2-[(3,4-methylenedioxy)phenylacetyl]thiophene-3-sulfonamide (3 g, 50% yield) was obtained via HPLC purification as a yellow solid, m.p. 35–38° C.

EXAMPLE 6

N-(4-chloro-3-methyl-5-isoxazolyl)-2-[3,4-(methylenedioxy)-6-methyl]phenylacetyl-3-thiophenesulfonamide also designated 4-chloro-3-methyl-5-(2-(2-(6-methylbenzo[d][1,3dioxol-5-yl)acetyl)-3-thienylsulfonamido)isoxazole and N-(4-chloro-3-methyl-5-isoxazolyl)-2-[2-methyl-4,5-(methylenedioxy)phenylacetyl]thiophene-3-sulfonamide A. (3,4-methylenedioxy)-6-methylbenzyl chloride To a 1:1 mixture of ethyl ether (100 ml) and conc. HCl (100 ml) at 0° C. was added (3,4-methylenedioxy)toluene (10 ml). Formaldehyde (20 ml, 37% in water) was then added dropwise. The reaction was stirred at 0° C. for 2 hours and at room temperature for an additional 10 hours. The reaction mixture was then diluted with ethyl ether (100 ml) and the two layers were separated. The organic layer was dried (MgSO$_4$), the solid was filtered and the filtrate was concentrated. The residue was then heated with hexane (200 ml) and the insolubles were filtered off the hot solution. The filtrate was concentrated to give a mixture of (3,4-methylenedioxy)-6-methylbenzyl chloride (9.4 g, 63% yield) and bis[(3,4-methylenedioxy)-6-methyl] phenylmethane (3.6 g) as a white solid. This mixture was carried on to the next step without further purification.

B. N-(4-chloro-3-methyl-5-isoxazolyl)-2-[3,4-(methylenedioxy)-6-methyl]phenylacetyl-3-thiophenesulfonamide N-(4-chloro-3-methyl-5-isoxazolyl)-2-[3,4-(methylenedioxy)-6-methyl]phenylacetyl-3-thiophenesulfonamide was synthesized in the same manner as for Example 5 using (3,4-methylenedioxy)-6-methylbenzyl chloride instead of (3,4-methylenedioxy) benzyl chloride. The crude product was purified by preparative HPLC to give N-(4-chloro-3-methyl-5-isoxazolyl)-2-[3,4-(methylenedioxy)-6-methyl]phenylacetyl-3-thiophenesulfonamide as a yellow powder (71% yield, m.p. 42–45° C.).

EXAMPLE 7

4-Chloro-3-methyl-5-(2-(2-(6-methylbenzo[d][1,3] dioxol-5-yl)acetyl)-3-thienylsulfonamido)isoxazole, sodium salt A. Preparation of (4-chloro-3-methyl-5-(2-(2-(6-methylbenzo[d][1,3]dioxol-5-yl)acetyl)-3-thienylsulfonamido)isoxazole 1. Preparation of 5-chloromethyl-6-methylbenzo[d][1,3] dioxole To a mixture of methylene chloride (130 L), concentrated HCl (130 L), and tetrabutylammonium bromide (1.61 Kg) was added 5-methylbenzo[d][1,3]dioxole (10 Kg) followed by the slow addition of formaldehyde (14 L, 37 wt % in water). The mixture was stirred overnight. The organic layer was separated, dried with magnesium sulfate and concentrated to an oil. Hexane (180 L) was added and the mixture heated to boiling. The hot hexane solution was decanted from a heavy oily residue and evaporated to give almost pure 5-chloromethyl-6-methylbenzo[d][1,3]dioxole as a white solid. Recrystallization from hexane (50 L) gave 5-chloromethyl-6-methylbenzo[d][1,3]dioxole (80% recovery after recrystallization).

2. Formation of (4-chloro-3-methyl-5-(2-(2-(2-methylbenzo[d][1,3]dioxol-5-yl)acetyl)-3-thienylsulfonamido)isoxazole A portion of a solution of 5-chloromethyl-6-methylbenzo[d][1,3]dioxole (16.8 g, 0.09 mol) in tetrahydrofuran (THF) (120 mL) was added to a well stirred slurry of magnesium powder, (3.3 g, 0.136 g-atom, Alfa, or Johnson-Matthey, −20+100 mesh) in THF (120 mL) at room temperature. The resulting reaction admixture was warmed up to about 40–45° C. for about 2–3 min, causing the reaction to start. Once the magnesium was activated by the heating, and the reaction begun, the mixture was cooled and maintained at a temperature below about 8° C. The magnesium can be activated with dibromoethane in place of heat.

A flask containing the reaction mixture was cooled and the remaining solution of 5-chloromethlybenzo[d][1,3] dioxole added dropwise during 1.5 hours while maintaining an internal temperature below 8° C. Temperature control is important: if the Grignard is generated and kept below 8° C., no Wurtz coupling takes place. Longer times at higher temperatures promote the Wurtz coupling pathway. Wurtz coupling can be avoided by using high quality Mg and by keeping the temperature of the Grignard below about 8° C. and stirring vigorously. The reaction works fine at −20° C., so any temperature below 8° C. is acceptable at which the Grignard will form. The color of the reaction mixture turns greenish.

The reaction mixture was stirred for an additional 5 min at 0° C., while N$^2$-methoxy-N$^2$-methyl-3-(4-chloro-3-methyl-5-isoxazolylsulfamoyl)-2-thio-phenecarboxamide (6.6 g, 0.018 mol) in anhydrous THF (90 mL) was charged into the addition funnel. The reaction mixture was degassed two times then the solution of N$^2$-methoxy-N$^2$-methyl-3-(4-chloro-3-methyl-5-isoxazolylsulfamoyl)-2-thiophenecarboxamide was added at 0° C. over 5 min. TLC of the reaction mixture (Silica, 12% MeOH/CH$_2$Cl$_2$) taken immediately after the addition shows no N$^2$-methoxy-N$^2$methyl-3-(4-chloro-3-methyl-5-isoxazolysulfamoyl)-2-thiophenecarboxamide.

The reaction mixture was transferred into a flask containing 1 N HCl (400 mL, 0.4 mol HCl, ice-bath stirred), and the mixture stirred for 2 to 4 min, transferred into a separatory funnel and diluted with ethyl acetate (300 mL). The layers were separated after shaking. The water layer was extracted with additional ethyl acetate (150 mL) and the combined organics washed with half-brine. Following separation, THF was removed by drying the organic layer over sodium sulfate and concentrating under reduced pressure at about 39° C.

B. Preparation of 4-chloro-3-methyl-5-(2-(2-(6-methylbenzo[d][1,3]dioxol-5-yl)acetyl)-3-thienylsulfonamido)isoxazole, sodium salt The product from part A was then re-dissolved in ethyl acetate and washed with saturated NaHCO$_3$ (5×50 mL) until the washings became colorless. The solution was washed with brine, dried over Na$_2$SO$_4$ and concentrated in vacuo to give a semicrystalline yellow residue. 100 mL of CH$_2$Cl$_2$ was added to the solution and the mixture stirred under nitrogen for from 5 to 10 minutes until a fine crystalline product was formed. Ether (150 mL) was added and the mixture stirred from an appropriate time (e.g., 10 min). The product was isolated by filtration, washed with a mixture of CH$_2$Cl$_2$/ether (1:2) (30 mL) then with ether (30 mL) and dried under reduced pressure. When prepared in accordance with the specific embodiments set forth above, the title product was produced in quantity of 7.3 g with a purity of around 85% (HPLC, RP, 40% acetonitrile/water, 0.1% TFA neutralized with ammonia to pH 2.5, isocratic conditions, 1 mL/min).

The salt product from above was dissolved in water (600 mL) at 10° C., the solution stirred for a short period of time (e.g., 3 min) and then filtered through a layer of paper filters (e.g., 3 filters) with suction. In some cases, the large amount of impurities that are not soluble in water (10% or higher) slows down the filtration process extremely. This problem can be avoided by using a larger size filter during the filtration. Usually there is no problem with filtration if the purity of the crude salt is 90% or higher.

The greenish slightly turbid solution obtained from filtration was cooled in an ice bath and acidified to a pH of 2 using an acid such as 4 N HCl. When the pH of the solution was 2, the product precipitates as a milky, non-filterable material. Slow dropwise addition of extra 4 N HCl causes the product to form a fine, easily filterable precipitate. The pale yellow precipitate was filtered off, washed with water until neutral and pressed on the filter to get rid of excess of water). The obtained free acid was typically 95% pure as determined by HPLC.

The free acid form of the product was dissolved in ethyl acetate (about 100 mL), washed with brine (30 mL) to remove water. The dehydrated solution was shaken with cold saturated NaHCO$_3$ solution (2×30 mL), then with brine again, dried over Na$_2$SO$_4$ and concentrated in vacuo (bath temperature lower than 40° C.) to give a very bright yellow foam. After complete removal of the ethyl acetate from this product, CH$_2$Cl$_2$ (100 mL) was added and the mixture stirred for 5 to 10 min until the product became crystalline. Ether (150 mL) was added and stirring continued for 10 min longer. The formed solid was isolated by filtration, washed with a mixture of CH$_2$Cl$_2$/ether (1:2)(30 mL) then with ether (30 mL) and dried under reduced pressure. When purified in this manner, 4-chloro-3-methyl-5-(2-(2-(6-methylbenzo[d][1,3]dioxol-5-yl)acetyl)-3-thienylsufonamido)isoxazole, sodium salt was obtained in high yield (5.7 g, 68%) with good purity (98.2% pure by HPLC). The product can also be further purified by recrystallization from EtOH/methyl t-butylether (MTBE) after the above procedure if the initial purity is sufficiently high.

C. N-(4-Chloro-3-methyl-5-isoxazolyl)-2-[3,4-(methylenedioxy)-6-methyl]-phenylacetyl-3-thiophenesulfonamide,sodium hydrogen phosphate salt also designated 4-Chloro-3-methyl-5-(2-(2-(6-methylbenzo[d][1,3]dioxol-5-yl)acetyl)-3-thienylsulfonamido)isoxazole, sodium hydrogen phosphate salt To a solid mixture of N-(4-chloro-3-methyl-5-isoxazolyl)-2-[3,4-(methylenedioxy)-6-methyl] phenylacetyl-3-thiophenesulfonamide (1.1492 g, 2.5263 mmol) and sodium phosphate dibasic (0.3486 g, 2.5263 mmol) was added de-ionized water (25 mL) and acetonitrile (25 mL). The resulting mixture was well shaken and warmed at 50° C. to obtain a clear solution, which was filtered. The filtrate was frozen at −78° C. and lyophilized to give the salt as a yellow powder (≈1.50 g).

EXAMPLE 8

Formulations of sulfonamide sodium salts as lyophilized powder Formulation of 4-chloro-3-methyl-5-(2-(2-(6-methylbenzo[d][1,3]dioxol-5-yl) acetyl)-3-thienylsulfonamido)isoxazole, sodium salt for parenteral administration Phosphate buffer was prepared by adding 3200 mL of sterile water for injection, USP, to a 4 L graduated cylinder. Sodium phosphate dibasic heptahydrate, USP (21.44 g) was added to the sterile water and the mixture was stirred for 5 minutes or until the solid had dissolved. Sodium phosphate monobasic, USP (11.04 g) was added and the mixture was stirred until the solids had dissolved. The solution was diluted to 4.0 L and stirred. 3000 g of the sodium phosphate buffer was added to an eight liter beaker. Dextrose, USP (200.0 g) was added, and the mixture was heated to 30–35° C. in a water bath and stirred until a complete solution formed. 4-chloro-3-methyl-5-(2-(2-(6-methylbenzo[d][1,3] dioxol-5-yl)acetyl)-3-thienylsulfonamido)isoxazole, sodium salt (100.0 g) was added with efficient mixing. This mixture was stirred for a minimum of ten minutes or until a solution formed.

The solution was removed from the water bath after the sodium salt dissolved, diluted to 4000 g with sodium phosphate buffer and stirred for five minutes. This solution was sterile filtered using a sterile 0.22 micron pre-size Durapore Millipak 200 filter. The filtered solution was filled into sterile vials and lyophilized under standard conditions. The vials were stoppered. The lyophilized product was then reconstituted with either 9.4 mL or 19.4 mL of water for injection, to give a final concentration of 25 mg/mL or 12.5 mg/mL, respectively.

EXAMPLE 9

N-(4-Bromo-3-methyl-5-isoxazolyl)thiophene-2-sulfonamide

A solution of 5-amino-4-bromo-3-methylisoxazole (177 mg, 1.0 mmol) in dry tetrahydrofuran (THF, 2 ml) was added to a suspension of sodium hydride (60% dispersion in mineral oil, 90 mg, 2.2 mmol) in dry THF (1 ml) at 0–5° C. After stirring at 0–5° C. for 5 min., the reaction was stirred at room temperature for 10 min to complete the reaction. The reaction mixture was re-cooled to 0° C. and thiophene-2-sulfonyl chloride (200 mg, 1.1 mmol) dissolved in dry THF (2 ml) was added dropwise. Stirring was continued for 1 h; during this period the reaction mixture slowly attained ambient temperature. THF was removed under reduced pressure. The residue was dissolved in water (10 ml), the pH was adjusted to 10–11 by adding 5 N sodium hydroxide solution, and was extracted with ethyl acetate (3×10 ml) to remove the neutral impurities. The aqueous layer was acidified with concentrated HCl (pH 2–3) and extracted with methylene chloride (3×10 ml). The combined organic layers was dried over anhydrous magnesium sulfate and concentrated under reduced pressure to give N-(4-bromo-3-methyl-5-isoxazolyl)thiophene-2-sulfonamide. The pure material was obtained by recrystallization using hexanes/ethyl acetate (110 mg, 34% yield), m.p. 125–127° C.

EXAMPLE 10

N-(4-Bromo-3-methyl-5-isoxazolyl)-5-(3-isoxazolyl)thiophene-2-sulfonamide

A solution of 5-amino-4-bromo-3-methylisoxazole (1 77 mg, 1.0 mmol) in dry THF (2 ml) was added to a suspension of sodium hydride (60% dispersion in mineral oil, 90 mg, 2.2 mmol) in dry THF (1 ml) at 0–5° C. After stirring at 0–5° C. for 5 min, the reaction was warmed to room temperature for 10 min to complete the reaction. The reaction mixture was re-cooled to 0° C., and 5-(3-isoxazolyl)thiophene-2-sulfonyl chloride (273 mg, 1.1 mmol), which had been dissolved in dry THF (2 ml), was added slowly. Stirring was continued for 1 h; during this period the reaction mixture slowly attained ambient temperature. THF was removed under reduced pressure. The residue was dissolved in water (10 ml), the pH was adjusted to 2–3 by adding concentrated HCl, and was extracted with methylene chloride (3×10 ml). The combined organic layers was dried over anhydrous magnesium sulfate and concentrated under reduced pressure to give N-(4-bromo-3-methyl-5-isoxazolyl)-5-(3-isoxazolyl)thiophene-2-sulfonamide. The pure material was obtained by recrystallization using hexanes/ethyl acetate (160 mg, 41% yield), m.p. 120–123° C.

EXAMPLE 11

N-(4-Bromo-3-methyl-5-isoxazolyl)-2-(carbomethoxy)thiophene-3-sulfonamide

N-(4-Bromo-3-methyl-5-isoxazolyl)-2-(carbomethoxy) thiophene-3-sulfonamide was prepared in the same manner as described in Example 10 from 5-amino-4-bromo-3-methylisoxazole and 2-(carbomethoxy)thiophene-3-sulfonyl chloride in 73% yield. Purification was achieved by recrystallization from ethyl acetate/hexanes to give a crystalline solid, m.p. 198–200° C.

EXAMPLE 12

N-(4-Bromo-3-methyl-5-isoxazolyl)-2-(carboxyl)thiophene-3-sulfonamide

N-(4-Bromo-3-methyl-5-isoxazolyl)-2-(carbomethoxy)thiophene-3-sulfonamide (Example 11) (1.5 g, 3.95 mmol) was dissolved in methanol (10 ml). Sodium hydroxide pellets (1 g, 25 mmol) and a few drops of water were then added. The resultant solution was stirred for 16 h at ambient temperature. Methanol was removed under reduced pressure. The residue was diluted with water and was extracted with ethyl acetate (2×10 ml). The aqueous layer was acidified (pH=2) with concentrated hydrochloric acid and was extracted with ethyl acetate (2×60 ml). The combined organic layers was dried over anhydrous magnesium sulfate and filtered. Removal of the solvent gave N-(4-bromo-3-methyl-5-isoxazolyl)-2-(carbomethoxy)thiophene-3-sulfonamide (1.2 g, 82% yield), which was purified by silica gel column chromatography using ethyl acetate as eluent, m.p. 188–194° C.

EXAMPLE 13

N-(3,4-dimethyl-5-isoxazolyl)-5-phenylthiophene-2-sulfonamide

A. N-(3,4-dimethyl-5-isoxazolyl)-5-bromothiophene-2-sulfonamide

A solution of 5-bromothiophene-2-sulfonyl chloride (2.75 g, 10 mmol) and 5-amino-3,4-dimethylisoxazole (1.07 g, 9.57 mmol) in pyridine containing a catalytic amount of 4-dimethylaminopyridine (DMAP, 10 mg) was stirred at room temperature for a period of 3 h. The solution was heated at 50° C. for an additional 1.5 h to drive the reaction to completion as judged by TLC. The pyridine was removed under reduced pressure and the residue, after extraction into ethyl acetate, was washed with 1 N HCl (2×25 ml), water (1×25), brine solution, (1×25 ml) and dried over magnesium sulfate. Evaporation of solvent left a viscous brown gum, which was subjected to flash chromatography. Elution with 3% methanol hexanes gave 246 mg (10%) of pure sulfonamide.

B. N-(methoxyethoxymethyl)-N-(3,4-dimethyl-5-isoxazolyl)-5-bromothiophene-2-sulfonamide N-(3,4-dimethyl-5-isoxazolyl)-5-bromothiophene-2-sulfonamide (680 mg, 2 mmol) in dry THF (2 ml) was added to sodium hydride (121 mg of a 60% oil dispersion, 3 mmol) in dry THF (1 ml). The resulting suspension was cooled to 0° C. and methoxyethoxymethyl chloride (334 mg, 2.68 mmol) was added dropwise via syringe. The solution was warmed to room temperature, and stirring continued overnight. Evaporation of solvent left an oil that was extracted into ethyl acetate, washed with brine, dried over magnesium sulfate and evaporated. Flash chromatography of the residue on silica gel using 10–15% ethyl acetate/hexanes yielded 480 mg (56%) of a colorless oil.

C. N-(methoxyethoxymethyl)-N-(3,4-dimethyl-5-isoxazolyl)-5-phenylthiophene-2-sulfonamide Sodium carbonate (2 ml of a 2 M aqueous solution) followed by phenyl boronic acid (86 mg, 0.71 mmol) in 2 ml of 95% ethanol were added to a solution of N-(methoxyethoxymethyl)-N-(3,4-dimethyl-5-isoxazolyl)-5-bromothiophene-2-sulfonamide (200 mg, 0.47 mmol) and tetrakis (triphenylphosphine) palladium (0) (23 mg, 0.02 mmol) in dry benzene (4 ml) under argon. The mixture was refluxed for 12 h, diluted with 5 ml of water and extracted into ethyl acetate (3×25 ml). The combined organic extracts was washed with brine (1×25 ml), dried and evaporated. The residue was flash chromatographed on silica gel using 25% ethyl acetate/hexanes to afford 123 mg (62%) of the sulfonamide as a colorless gum.

D. N-(3,4-dimethyl-5-isoxazolyl)-5-phenylthiophene-2-sulfonamide

HCl (3 ml of a 3 N aqueous solution) was added to a solution of N-(methoxyethoxymethyl)-N-(3,4-dimethyl-5-isoxazolyl)-5-phenylthiophene-2-sulfonamide (100 mg, 0.24 mmol) in 3 ml of 95% ethanol and the resulting mixture was refluxed for 6 h. The mixture was then concentrated, diluted with 5 ml of water, neutralized with saturated aqueous sodium bicarbonate solution and acidified to pH 4 using glacial acetic acid. The mixture was extracted with ethyl acetate (2×25 ml) and the combined organic extract was washed with brine (1×5 ml), dried and evaporated. Flash chromatography of the residue on silica gel using 2% MeOH/CHCl$_3$ and further purification by reverse phase HPLC yielded 33.4 mg (42%) of the pure sulfonamide as a white powder, m.p. 176–178° C.

EXAMPLE 14

N-(4-Bromo-3-methyl-5-isoxazolyl)-5-(4-ethylphenyl)thiophene-2-sulfonamide

A. N-(5-bromothiophene-2-sulfonyl)-pyrrole

Sodium hydride (60% oil dispersion, 191 m.g., 4.78 mmol) was suspended in dry tetrahydrofuran (2 ml) and the resulting cloudy suspension was cooled to 0° C. in an ice bath. Pyrrole (385 mg, 5.75 mmol) in dry tetrahydrofuran (2 ml) was added dropwise over a period of 10 min. The ice bath was removed and the solution was stirred at room temperature until gas evolution ceased (15 minutes), whereupon 5-bromothiophene-2-sulfonyl chloride (1.0 g, 3.82 mmol) previously dissolved in tetrahydrofuran (4.0 ml) was added dropwise through a steel cannula. After stirring for 1 h at room temperature, the mixture was filtered through Celite. The filter pad was rinsed with tetrahydrofuran, and the filtrate was evaporated, which left a light brown solid that was recrystallized from methanol to produce the sulfonamide (821 mg, 74% yield) as a white powder.

B. 4-Ethylphenylboronic acid

A solution of 1-bromo-4-ethyl benzene (2.0 g, 11 mmol) in dry ether (5 ml) was added to magnesium turnings (311 mg, 13 mmol), which had been suspended in dry ether, by dropwise addition. After addition was complete, the suspension was refluxed for a period of 15 min, by which time nearly all of the magnesium had reacted. The solution was then added to trimethyl borate (1.12 g, 11 mmol), previously dissolved in ether (5 ml) at −78° C., warmed to room temperature and stirred for 90 min. The reaction was quenched by the addition of 10% aqueous HCl (2 ml) and the solution was extracted with ether. The combined ether extract was extracted with 1 M NaOH (2×20 ml), the aqueous extracts were acidified with dilute HCl to pH 2 and extracted with ether (2×25 ml). The resulting combined ether extract was washed once with water (10 ml), dried and evaporated to produce a white solid (676 mg, 38% yield), m.p. 138–140° C.

C. N-[5-(4-ethylphenyl)thiophene-2-sulfonyl]pyrrole

N-[5-(4-ethylphenyl)thiophene-2-sulfonyl]pyrrole was prepared, in the same manner as described in Example 13C, from 4-ethylphenylboronic acid and N-(5-bromothiophenesulfonyl)pyrrole. Purification by column chromatography using 10% ethyl acetate/hexanes gave the pure sulfonamide as a tan solid in 81% yield.

D. 5-Chlorosulfonyl-2-(4-ethylphenyl)thiophene

A solution of N-[5-(4-ethylphenyl)thiophene-2-sulfonyl] pyrrole (100 mg, 0.32 mmol) and 6 N sodium hydroxide (1 ml) in methanol (1.5 ml) was refluxed for approximately 6 h. Evaporation of solvents and drying in vacuo resulted in an oil. Phosphorus oxychloride (258 ml, 2.52 mmol) and phosphorus pentachloride (131 mg, 0.63 mmol) were added to the oil and the resulting brown suspension was heated at 50° C. for 3 h. The resulting clear brown solution was carefully added to about 20 ml of crushed ice and then extracted with ethyl acetate (3×25 ml). The combined organic layers was washed with brine (2×5 ml), dried ($MgSO_4$) and evaporated to leave an oily residue. Flash chromatography over silica gel using 2% ethyl acetate/hexanes yielded (53 mg, 59%) of the pure sulfonyl chloride as a pale yellow oil.

E. N-(4-bromo-3-methyl-5-isoxazolyl )-5-(4-ethylphenyl) thiophene-2-sulfonamide

N-(4-bromo-3-methyl-5-isoxazolyl)-5-(4-ethylphenyl) thiophene-2-sulfonamide was prepared in the same manner as described in Example 10. Reaction of 5-chlorosulfonyl-2-(4-ethylphenyl)thiophene (47.1 mg, 11.16 mmol) with 5-amino-4-bromo-3-methyl isoxazole (29 mg, 0.16 mmol) yielded, after flash chromatography using 10% MeOH/ $CHCl_3$, a pale brown solid (46 mg, 66% yield), m.p. 172–175° C.

EXAMPLE 15

N-(4-Bromo-3-methyl-5-isoxazolyl)-4-phenethylthiophene-2-sulfonamide

N-(4-bromo-3-methyl-5-isoxazolyl)-4-phenethylthiophene-2-sulfonamide was prepared in the same manner as described in Example 10 from 5-amino-4-bromo-3-methylisoxazole and 4-phenethyl-2-thiophenesulfonyl chloride in 32% yield. This was purified by HPLC (5% $CH_3CN$ to 100% $CH_3CN$ over 30 min.) to give a gum.

EXAMPLE 16

N-(4-bromo-3-methyl-5-isoxazolyl)-2-[N-(3-carboxyphenylaminocarbonyl]thiophene-3-sulfonamide $Et_3N$ (2.27 ml. 16. mmol), ethyl 3-aminobenzoate (836 ml, 5.44 mmol) and phosphonitrilic chloride trimer (1.89 g, 5.44 mmol) were sequentially added to a solution of N-(4-bromo-3-methyl-5-isoxazolyl)-2-(carbonyl)thiophene-3-sulfonamide (Example 12) (1 g, 2.27 mmol) in dry THF (20 ml). The reaction was stirred at room temperature for 1 hour and cooled. Water (5 ml) was added to quench the reaction. The resulting solution was concentrated on a rotavap. The residue was diluted with EtOAc and washed with 2 N HCl (2×150 ml). The organic layer was dried ($MgSO_4$). The solid was filtered off and the filtrate was concentrated. The residue was treated with 1 N NaOH (200 ml) and stirred at 0° C. for 15 minutes. The mixture was then acidified with conc. HCl to pH ~1. The resulting yellow precipitate was filtered off and recrystallized from $CH_3CN/H_2O$ to give N-(4-bromo-3-methyl-5-isoxazolyl)-2-[N-(3-carboxyphenyl) aminocarbonyl]thiophene-3-sulfonamide (153 mg., 11.6%) as a yellowish powder, m.p. 183–185° C.

EXAMPLE 17

N-(4-Bromo-5-methyl-3-isoxazolyl)-5-(4-methylphenyl)thiophene-2-sulfonamide

A. N-[5-(4-methylphenyl)thiophene-2-sulfonyl]pyrrole

N-[5-(4-methylphenyl)thiophene-2-sulfonyl]pyrrole was prepared in the same manner as described in Example 13C using 4-methyl-phenylboronic acid and N-(5-bromothiophenesulfonyl)pyrrole. Purification by column chromatography using 2% ethyl acetate/hexanes gave N-[5-(4-methylphenyl)-thiophene-2-sulfonyl]pyrrole as a pale yellow solid in 77% yield.

B. 2-chlorosulfonyl-5-(4-methylphenyl)thiophene 2-chlorosulfonyl-5-(4-methylphenyl)thiophene was prepared in the same manner as described in Example 14D using N-[5-(4-methylphenyl)thiophene-2-sulfonyl]pyrrole. Purification by column chromatography using 2% ethyl acetate/hexanes gave 2-chlorosulfonyl-5-(4-methylphenyl) thiophene as a pale yellow powder (61% yield).

C. N-(4-bromo-3-methyl-5-isoxazolyl)-5-(4-methylphenyl) thiophene-2-sulfonamide

N-(4-bromo-3-methyl-5-isoxazolyl)-5-(4-methylphenyl) thiophene-2-sulfonamide was prepared in the same manner as described in Example 10. Reaction of 2-chlorosulfonyl-5-(4-methylphenyl)thiophene (100 mg, 0.37 mmol) with 5-amino-4-bromo-3-methylisoxazole (65 mg, 0.37 mmol) yielded, after column chromatography using 10% MeOH/ $CHCl_3$, 96 mg final product as a pale yellow solid, (63% yield, m.p. 175° C.).

EXAMPLE 18

N-(4-Bromo-3-methyl-5-isoxazolyl)-5-(benzyloxymethylthiophene-2-sulfonamide

A. 2-(benzyloxymethyl)thiophene

Sodium hydride (0.41 mg, 20 mmol) was added to a solution of 2-thiophene methanol (2.0 g, 0.18 mmol) in THF (20 ml) at −40° C. The reaction was stirred at −40° C. for 25 min., then neat benzylbromide (3.6 g, 20 mmol) was added by syringe. The solution was stirred at −40° C. for 0.5 hr, then at room temperature for 1 hr. The THF was evaporated off and the remaining residue was taken up in ether (~50 ml). The organic solution was washed with water (1×10 ml), brine (1×10 ml) and dried over $MgSO_4$. Evaporation of solvents left an oil which was purified by column chromatography using 1% ether-hexanes to give 2.6 g of the thiophene as a pale yellow oil (78% yield).

B. 2-chlorosulfonyl-5-(benzyloxymethyl)thiophene 2-chlorosulfonyl-5-(benzyloxymethyl)thiophene was prepared in the same manner as described in Example 17A from 2-(benzyloxymethyl)thiophene (1.0 g, 5.25 mmol). Purification by column chromatography using 2.5% ethyl acetate/ hexanes gave 520 mg of the pure thiophene as a brown oil (32% yield).

C. N-(4-bromo-3-methyl-5-isoxazolyl)-5-(benzyloxymethyl)thiophene-2-sulfonamide

N-(4-bromo-3-methyl-5-isoxazolyl)-5-(benzyloxymethyl)thiophene-2-sulfonamide was prepared as described in Example 10 from 2-chlorosulfonyl-5-(benzyloxymethyl)thiophene (520 mg, 1.72 mmol) and 5-amino-4-bromo-3-methyl isoxazole (319 mg, 1.8 mmol). Purification by column chromatography using 10% MeOH/ $CHCl_3$) gave 238 mg of pure N-(4-bromo-3-methyl-5-isoxazolyl)-5-(benzyloxymethyl)thiophene-2-sulfonamide as brown semisolid (31% yield, m.p. 92° C.).

EXAMPLE 19

N-(4-Bromo-3-methyl-5-isoxazolyl)-3-[3,4-(methylenedioxy)phenyl]thiophene-2-sulfonamide A. 3-bromothiophene-2-sulfonyl chloride Chlorosulfonic acid (20 ml, 300 mmol) was added to a solution of 3-bromothiophene (8.15 g, 50 mmol) in methylene chloride (50 ml) at −78° C. over a 20 min. period. After the completion of addition, the cold bath was removed and stirring continued at ambient temperature for 1 hr. The reaction mixture was carefully added, dropwise, to crushed ice (100 g). The mixture was extracted with methylene chloride (2×100 ml). The combined organic layers was dried over MgSO$_4$ and evaporated. The crude product was purified by flash chromatography on silica gel using hexane as the eluent resulting in 3-bromothiophene-2-sulfonyl chloride (4 g, 30% yield) and 4-bromothiophene-2-sulfonyl chloride (200 mg, ≦1%).

B. N-(3-bromothiophene-2-sulfonyl)pyrrole

N-(3-bromothiophene-2-sulfonyl)pyrrole was prepared in the same manner as described in Example 14A by reacting 3-bromothiophene-2-sulfonylchloride with pyrrole (for 16 hr.). N-(3-bromothiophene-2-sulfonyl)pyrrole was obtained in 54% yield.

C. N-{[3-(3,4-methylenedioxy)phenyl]thiophene-2-sulfonyl}pyrrole

N-{[3-(3,4-methylenedioxy)phenyl]thiophene-2-sulfonyl}pyrrole was prepared in the same manner as described in Example 13C using 3,4-methylenedioxyphenylboronic acid and N-(3-bromothiophene-2-sulfonyl)pyrrole. The crude product was purified by flash column chromatography on silica gel using 2% EtOAc in hexane as the eluent resulting in N-{[3-(3,4-methylenedioxy)phenyl]thiophene-2-sulfonyl}pyrrole in a 90% yield.

D. 2-chlorosulfonyl-3-[3,4-(methylenedioxy)phenyl]thiophene 2-chlorosulfonyl-3-[3,4-(methylenedioxy)phenyl]thiophene was prepared in the same manner as described in Example 18B using N-{[3-(3,4-methylenedioxy)phenyl]thiophene-2-sulfonyl}pyrrole by basic hydrolysis of the sulfonamide to the sodium sulfonate (100% yield) followed by conversion of the salt to the corresponding sulfonyl chloride resulting in a 34% yield of the final product.

E. N-(4-bromo-3-methyl-5-isoxazolyl)-3-[3,4-(methylenedioxy)phenyl]thiophene-2-sulfonamide N-(4-bromo-3-methyl-5-isoxazolyl)-3-[3,4-(methylenedioxy)phenyl]thiophene-2-sulfonamide was prepared in the same manner as described in Example 9 by reaction of 2-chlorosulfonyl-3-[3,4-(methylenedioxy)phenyl]thiophene with 5-amino-4-bromo-3-methylisoxazole resulting in a 60% yield, m.p. 183–186° C.

EXAMPLE 20

N-(4-Bromo-3-methyl-5-isoxazolyl)-2-[(2-chloro-3, 4-methylenedioxy)phenoxymethyl]thiophene-3-sulfonamide A. N-{2-[(3,4-methylenedioxy)phenoxymethyl]thiophene-3-sulfonyl}pyrrole Sodium hydride (100 mg, 5 mmol) was added to a stirred solution of 3,4-methylenedioxyphenol (0.607 g, 4.5 mmol) in DMF (dry, 5 ml) at 0° C. under a nitrogen atmosphere with stirring. The reaction mixture was permitted to attain room temp and stirring continued for 1 hr. The reaction mixture was cooled to 0° C. and N-[(2-bromomethyl)thiophene-3-sulfonyl]pyrrole was added. Stirring was continued at ambient temperature for 16 hr. The reaction mixture was diluted with water (100 ml), extracted with ethyl acetate (2×50 ml) and washed with 1N NaOH (2×25 ml) to remove phenol derivative. The mixture was dried over MgSO$_4$ and concentrated resulting in N-{2-[(3, 4-methylenedioxy)phenoxymethyl]thiophene-3-sulfonyl}pyrrole, which was recrystallized using hexane/EtOAc (1.0 g, 92% yield).

B. 3-chlorosulfonyl-2-[(2-chloro-3,4-methylenedioxy) phenoxymethyl]thiophene 3-chlorosulfonyl-2-[(2-chloro-3,4-methylenedioxy) phenoxymethyl]thiophene was prepared in the same manner as described in Example 15E using N-{2-[(3,4-methylenedioxy)phenoxymethyl]thiophene-3-sulfonyl}pyrrole by conducting a basic hydrolysis (using potassium hydroxide in iso-propanol) to the potassium sulfonate followed by conversion of the salt to the corresponding sulfonyl chloride in an overall yield of 50%.

C. N-(4-bromo-3-methyl-5-isoxazolyl)-2-[(2-chloro-3,4-methylenedioxy)-phenoxymethyl]thiophene-3-sulfonamide N-(4-bromo-3-methyl-5-isoxazolyl)-2-[(2-chloro-3,4-methylenedioxyphenoxy)methyl]thiophene-3-sulfonamide was prepared in the same manner as described in Example 9 by reaction of 3-chlorosulfonyl-2-[(2-chloro-3,4-methylenedioxyphenoxy)methyl]thiophene with 5-amino-4-bromo-3-methylisoxazole, 47% yield, m.p. 152–154° C.

EXAMPLE 21

N-(4-Bromo-3-methyl-5-isoxazolyl)-2-[trans-3,4-(methylenedioxy)cinnamyl]thiophene-3-sulfonamide A. Diethyl 2-{3-[(N-pyrrolyl)sulfonyl]thienylmethyl}phosphonate N-[2-bromomethyl)thiophene-3-sulfonyl]pyrrole (0.915 g, 3 mmol) was suspended in triethyl phosphite (5 ml) and was heated to 140° C. for 1 hr. with stirring under nitrogen atmosphere. Excess triethyl phosphate was removed under reduced pressure and the residue was dried under vacuum resulting in 0.9 g, 83% yield of diethyl 2-{3-[(N-pyrrolyl)sulfonyl]thienylmethyl}phosphonate.

B. N-{2-[trans-3,4-(methylenedioxy)cinnamyl]thiophene-3-sulfonyl}pyrrole

Sodium hydride (200 mg, 60% dispersion) was added in two lots to the stirred solution of diethyl 2-{3-[(N-pyrrolyl)sulfonyl]thienylmethyl}phosphonate (900 mg, 2.48 mmol) in dry THF (10 ml) at 0° C. The mixture was stirred at room temperature for 1 hr. then piperonal (600 mg) was added. Stirring was continued for 12 hours. The mixture was diluted with water (100 ml) and extracted with methylene chloride (2×50 ml). The combined organic layers was dried over MgSO$_4$, evaporated, and the residue was flash chromatographed on silica gel using 0.5% ethyl acetate in hexane to give N-{2-[trans-(3,4-methylenedioxy)cinnamyl]thiophene-3-sulfonyl}pyrrole (750 mg, 84% yield).

C. 3-chlorosulfonyl-2-[trans-3,4-(methylenedioxy) cinnamyl]thiophene 3-chlorosulfonyl-2-[trans-3,4-(methylenedioxy) cinnamyl]thiophene was prepared in the same manner as described in Example 15E from N-{2-[trans-3,4-(methylenedioxy)cinnamyl]thiophene-3-sulfonyl}pyrrole by basic hydrolysis (using isopropanol and potassium hydroxide) to the corresponding potassium sulfonate (100%) followed by conversion of the salt to the corresponding sulfonyl chloride in a 31% overall yield.

D. N-(4-bromo-3-methyl-5-isoxazolyl)-2-[trans-3,4-(methylenedioxy)cinnamyl]thiophene-3-sulfonamide N-(4-bromo-3-methyl-5-isoxazolyl)-2-[trans-3,4-(methylenedioxy)cinnamyl]thiophene-3-sulfonamide was prepared in the same manner as described in Example 9 by reaction of 3-chlorosulfonyl-2-[trans-3,4-(methylenedioxy)-cinnamyl]thiophene with 5-amino-4-bromo-3-methylisoxazole. The crude product was purified by HPLC resulting in a 33% yield, m.p. 147–149° C.

EXAMPLE 22

N-(4-Bromo-3-methyl-5-isoxazolyl)-2-[3,4-(methylenedioxy)phenethyl]thiophene-3-sulfonamide A. N-{2-[3,4-(methylenedioxy)phenethyl]thiophene-3-sulfonyl}pyrrole An ethyl acetate (15 ml) solution of N-{2-[trans-3,4-(methylenedioxy)-cinnamyl]thiophene-3-sulfonyl}pyrrole (Example 21B, 0.6 g, 1.67 mmol) was subjected to catalytic hydrogenation using 10% Pd—C (100 mg) at 55 psi for 14 hr. The catalyst was filtered and the filtrate concentrated to resulting in N-{2-[3,4-(methylenedioxy)phenethyl]thiophene-3-sulfonyl}pyrrole (0.55 g, 91% yield).

B. 3-chlorosulfonyl-2-[3,4-(methylenedioxy)phenethyl]thiophene 3-chlorosulfonyl-2-[3,4-(methylenedioxy)phenethyl]thiophene was prepared in the same manner as described in the Example 15E using N-{2-[3,4-(methylenedioxy)phenethyl]thiophene-3-sulfonyl}pyrrole by conducting basic hydrolysis (iso-propanol and potassium hydroxide) of the sulfonamide to the potassium salt of sulfonic acid (93%) followed by conversion of the salt to the corresponding sulfonyl chloride in a 42% yield.

C. N-(4-bromo-3-methyl-5-isoxazolyl)-2-[3,4-(methylenedioxy)phenethyl]-thiophene-3-sulfonamide N-(4-bromo-3-methyl-5-isoxazolyl)-2-[3,4-(methylenedioxy)phenethyl]-thiophene-3-sulfonamide was prepared in the same manner as described in Example 10. By reacting 3-chlorosulfonyl-2-[3,4-(methylenedioxy)phenethyl]thiophene with 5-amino-4-bromo-3-methylisoxazole and purifying the crude product by HPLC, N-(4-bromo-3-methyl-5-isoxazolyl)-2-[3,4-(methylenedioxy)phenethyl]thiophene-3-sulfonamide was obtained in a 30% yield, m.p. 180° (dec.).

EXAMPLE 23

N-(4-bromo-3-methyl-5-isoxazolyl)-2-[(4-methyl)(cinnamyl)]thiophene-3-sulfonamide A. N-[2-(4-methyl-trans-styryl)-3-sulfonyl}pyrrole N-[2-(4-methyl-trans-styryl)-3-sulfonyl}pyrrole was prepared in the same manner as described in Example 21B using diethyl{3-[(N-pyrrolylsulfonyl)thien-2[yl]methyphosphonate and 4-methylbenzaldehyde in 30% yield.

B. 2-(4-methyl-trans-styryl)thiophene-3-sulfonyl chloride 2-(4-methyl-trans-styryl)thiophene-3-sulfonyl chloride was prepared in the same manner as described in Example 15E from N-[2-(4-methyl-trans-styryl)-3-sulfonyl}pyrrole by basic hydrolysis (using ethanol and sodium hydroxide) to the corresponding sodium sulfonate followed by conversion to the corresponding sulfonyl chloride in 13% yield.

C. N-(4-bromo-3-methyl-5-isoxazolyl)-2-(4-methyl-trans-styryl)thiophene-3-sulfonamide N-(4-bromo-3-methyl-5-isoxazolyl)-2-(4-methyl-trans-styryl)thiophene-3-sulfonamide was prepared in the same manner as described in Example 10 by reaction of 2-(4-methyl-trans-styryl)thiophene-3-sulfonyl chloride with 5-amino-4-bromo-3-methylisoxazole. The crude product was purified by HPLC followed by crystallization resulting in a 34% yield, m.p. 101–105° C.

EXAMPLE 24

N-(4-bromo-3-methyl-5-isoxazolyl)-2-[(4-methyl)phenethyl]thiophene-3-sulfonamide A. N-{2-[(4-methyl)phenethyl]thiophene-3-sulfonyl}pyrrole N-{2-[(4-methyl)phenethyl]thiophene-3-sulfonyl}pyrrole was prepared as described in Example 22A by the catalytic hydrogenation of N-[2-(4-methyl-trans-styryl)-3-sulfonyl}pyrrole in 80% yield.

B. 2-[(4-methyl)phenethyl]thiophene-3-sulfonylchloride

2-[(4-methyl)phenethyl]thiophene-3-sulfonylchloride was prepared, as described in Example 15E, using N-{2-[(4-methyl)phenethyl]thiophene-3-sulfonyl}pyrrole by basic hydrolysis (KOH/ethanol) of the sulfonamide to this potassium salt followed by conversion of salt to the corresponding sulfonyl chloride in 51% yield.

C. N-(4-bromo-3-methyl-5-isoxazolyl)-2-[(4-methyl)phenethyl]thiophene-3-sulfonamide N-(4-bromo-3-methyl-5-isoxazolyl)-2-[(4-methyl)phenethyl]thiophene-3-sulfonamide was prepared, as described in Example 10, using 2-[(4-methyl)-phenethyl]thiophene-3-sulfonylchloride and 5-amino-4-bromo-3-methylisoxazole in 52% yield.

EXAMPLE 25

N-(4-bromo-3-methyl-5-isoxazolyl)-2-[(4-methylphenoxy)methyl]thiophene-3-sulfonamide A. N-{2-[(4-methylphenoxy)methyl]thiophene-3-sulfonyl}pyrrole N-{2-[(4-methylphenoxy)methyl]thiophene-3-sulfonyl}pyrrole was prepared, as described in Example 20A, by reacting N-[2-bromomethyl)thiophene-3-sulfonyl]pyrrole with 4-methylphenol, in 81% yield.

B. 2-[(4-methylphenoxy)methyl]thiophene-3-sulfonyl chloride

2-[(4-methylphenoxy)methyl]thiophene-3-sulfonyl chloride was prepared, as described in Example 15E, using N-{2-[(4-methylphenoxymethyl]thiophene-3-sulfonyl}pyrrole by basic hydrolysis (NaOH/EtOH) followed by conversion to the corresponding sulfonyl chloride, in 46% yield.

C. N-(4-bromo-3-methyl-5-isoxazolyl)-2-[(4-methylphenoxy)methyl]thiophene-3-sulfonamide N-(4-bromo-3-methyl-5-isoxazolyl)-2-[(4-methylphenoxy)methyl]thiophene-3-sulfonamide was prepared, as described in Example 10, by reacting 3-chlorosulfonyl-2-[(4-methylphenoxy)methyl]thiophene with 5-amino-4-bromo-3-methylisoxazole,resulting in a 64% yield, m.p. 128–130° C.

EXAMPLE 26

N-(4-chloro-3-methyl-5-isoxazolyl)-2-[3,4-(methylenedioxy)-6-methyl]phenylaminocarbonyl-3-thiophenesulfonamide A. (3,4-methylenedioxy)-6-methylaniline To a solution of (3,4-methylenedioxy)toluene (5 ml) in acetic acid (20 ml) cooled with a cold water bath was added, dropwise, nitric acid (70%, 5 ml). The mixture was stirred for 45 min. To work up, water (100 ml) was added and the resulting yellow precipitate was filtered and washed with water until the aqueous filtrate was colorless. The yellow solid was dissolved in EtOAc (250 ml) and dried (MgSO$_4$), and the solid was filtered off. The filtrate was subjected to catalytic hydrogenation (10% Pd/C, 1 atm) for 12 hours. The reaction mixture was then filtered off the catalyst and the filtrate was concentrated on a rotavap to give (3,4-methylenedioxy)-6-methylaniline as a brownish grey solid (5.49 g, 87% yield).

B. N-(4-chloro-3-methyl-5-isoxazolyl)-2-[3,4-(methylenedioxy)-6-methyl]phenylaminocarbonyl-3-thiophenesulfonamide N-(4-chloro-3-methyl-5-isoxazolyl)-2-[3,4-(methylenedioxy)-6-methyl]phenylaminocarbonyl-3-thiophenesulfonamide was synthesized in the same manner as Example 3 using (3,4-methylenedioxy)-6-methylaniline. The crude product was purified by preparative HPLC to give N-(4-chloro-3-methyl-5-isoxazolyl)-2-[3,4-(methylenedioxy)-6-methyl]phenylaminocarbonyl-3-thiophenesulfonamide as a yellow solid (45% yield, m.p. 60–62° C.).

EXAMPLE 27

N-(4-chloro-3-methyl-5-isoxazolyl)-2-(3-methoxycarbonyl-2,4,6-trimethyl)phenylaminocarbonyl-3-thiophenesulfonamide A. Methyl 3-amino-2,4,6-trimethylbenzoate Methyl 3-amino-2,4,6-trimethylbenzoate was synthesized in the same manner as (3,4-methylenedioxy)-6-methylaniline (see Example 26).

B. N-(4-chloro-3-methyl-5-isoxazolyl)-2-(3-methoxycarbonyl-2,4,6-trimethyl)phenylaminocarbonyl-3-thiophenesulfonamide N-(4-chloro-3-methyl-5-isoxazolyl)-2-(3-methoxycarbonyl-2,4,6-trimethyl)phenylaminocarbonyl-3-thiophenesulfonamide was synthesized in the same manner as for Example 3 except that DMF was used instead of THF and the reaction was heated at 80° C. for 5 hours. The crude product was purified via preparative HPLC to give N-(4-chloro-3-methyl-5-isoxazolyl)-2-(3-methoxycarbonyl-2,4,6-trimethyl)phenylaminocarbonyl-3-thiophenesulfonamide as an off-white powder (48 mg, 1% yield, m.p. 66–70° C.).

EXAMPLE 28

N-(4-chloro-3-methyl-5-isoxazolyl)-2-(2,4,6-trimethyl)phenylacetyl-3-thiophenesulfonamide N-(4-chloro-3-methyl-5-isoxazolyl)-2-(2,4,6-trimethyl)phenylacetyl-3-thiophenesulfonamide was synthesized in the same manner as for Example 5 using 2,4,6-trimethylbenzyl chloride and N-(4-chloro-3-methyl-5-isoxazolyl)-2-(N-methyl-N'-methoxy)aminocarbonyl-3-thiophenesulfonamide. The crude product was purified by flash column chromatography (eluent 1% methanol in $CH_2Cl_2$) to give N-(4-chloro-3-methyl-5-isoxazolyl)-2-(2,4,6-trimethyl)phenylacetyl-3-thiophenesulfonamide as a solid (31% yield, m.p. 42–46° C.).

EXAMPLE 29

N-(4-chloro-3-methyl-5-isoxazolyl)-2-(2,4,6-trimethyl)phenylaminocarbonyl-3-thiophenesulfonamide N-(4-chloro-3-methyl-5-isoxazolyl)-2-(2,4,6-trimethyl)phenylaminocarbonyl-3-thiophenesulfonamide was synthesized in the same manner as Example 3. The crude product was purified via preparative HPLC to give N-(4-chloro-3-methyl-5-isoxazolyl)-2-(2,4,6-trimethyl)phenylaminocarbonyl-3 -thiophenesulfonamide as a yellowish-brownish powder (410 mg, 30% yield, m.p. 45–48° C.).

EXAMPLE 30

N-(3,4-dimethyl-5-isoxazolyl)-2-(2,4-dimethyl)phenylacetyl-3-thiophenesulfonamide N-(3,4-dimethyl-5-isoxazolyl)-2-(2,4-dimethyl)phenylacetyl-3-thiophenesulfonamide was synthesized by the same method as described for Example 5 using 2,4-dimethylbenzyl chloride and N-(3,4-dimethyl5-isoxazolyl)-2-(N-methyl-N'-methoxy)aminocarbonyl-3-thiophenesulfonamide. The crude product was purified by flash column chromatography (eluent 1% methanol in $CH_2Cl_2$) and further by preparative HPLC to give N-(3,4-dimethyl-5-isoxazolyl)-2-(2,4-dimethyl)phenylacetyl-3-thiophenesulfonamide as a semi-solid (34% yield).

EXAMPLE 31

N-(4-chloro-3-methyl-5-isoxazolyl)-2-(2,4-dimethyl)phenylacetyl-3-thiophenesulfonamide N-(4-chloro-3-methyl-5-isoxazolyl)-2-(2,4-dimethylophenylacetyl-3-thiophenesulfonamide was synthesized in the same manner as for Example 5 using 2,4-dimethylbenzyl chloride and N-(4-chloro-3-methyl-5-isoxazolyl)-2-(N-methyl-N'-methoxy)aminocarbonyl-3-thiophenesulfonamide. The crude product was purified by flash column chromatography (eluent 1% methanol in $CH_2Cl_2$) to give N-(4-chloro-3-methyl-5-isoxazolyl)-2-(2,4-dimethyl)phenylacetyl-3-thiophenesulfonamide as a solid (52% yield, m.p. 48–54° C.).

EXAMPLE 32

N-(4-bromo-3-methyl-5-isoxazolyl)-2-(2,4-dimethyl)phenylacetyl-3-thiophenesulfonamide N-(4-bromo-3-methyl-5-isoxazolyl)-2-(2,4-dimethyl)phenylacetyl-3-thiophenesulfonamide was synthesized in the same manner as for Example 5 using 2,4-dimethylbenzyl chloride and N-(4-bromo-3-methyl-5-isoxazolyl)-2-(N-methyl-N'-methoxy)aminocarbonyl-3-thiophenesulfonamide. The crude product was purified by flash column chromatography (eluent 1% methanol in $CH_2Cl_2$) and further by preparative HPLC to give N-(4-bromo-3-methyl-5-isoxazolyl)-2-(2,4-dimethyl)phenylacetyl-3-thiophenesulfonamide as a solid (28% yield, m.p. 58–63° C.).

EXAMPLE 33

N-(4-chloro-3-methyl-5-isoxazolyl)-2-(3,5-dimethyl)phenylacetyl-3-thiophenesulfonamide N-(4-chloro-3-methyl-5-isoxazolyl)-2-(3,5-dimethyl)phenylacetyl-3-thiophenesulfonamide was synthesized in the same manner as for Example 5 using 3,5-dimethylbenzyl bromide and N-(4-chloro-3-methyl-5-isoxazolyl)-2-(N-methyl-N'-methoxy)aminocarbonyl-3-thiophenesulfonamide. The crude product was purified by flash column chromatography (eluent 2% methanol in $CH_2Cl_2$) to give N-(4-chloro-3-methyl-5-isoxazolyl)-2-(3,5-dimethyl)phenylacetyl-3-thiophenesulfonamide as a solid (57% yield, m.p. 45–50° C.).

EXAMPLE 34

N-(4-chloro-3-methyl-5-isoxazolyl)-2-(2,5-dimethyl)phenylacetyl-3-thiophenesulfonamide N-(4-chloro-3-methyl-5-isoxazolyl)-2-(2,5-dimethyl)phenylacetyl-3-thiophenesulfonamide was synthesized in the same manner as for Example 5 using 2,5-dimethylbenzyl chloride and N-(4-chloro-3-methyl-5-isoxazolyl)-2-(N-methyl-N'-methoxy)aminocarbonyl-3-thiophenesulfonamide. The crude product was purified by flash column chromatography (eluent 2% methanol in $CH_2Cl_2$) to give N-(4-chloro-3-methyl-5-isoxazoly)-2-(2,5-dimethyl)phenylacetyl-3-thiophenesufonamide as a solid (33% yield, m.p. 72–76° C.).

EXAMPLE 35

N-(4-chloro-3-methyl-5-isoxazolyl)-2-[3,4-(methylenedioxy)-6-(2-acetoxyethyl)]phenylaminocarbonyl-3-thiophenesulfonamide A. 2-(3,4-methylenedioxy)phenyl-1-ethanol To a solution of 2-(3,4-methylenedioxy)phenylacetic acid (5 g, 25.75 mmol) in anhydrous THF (20 ml) at 0° C. was added $BH_3$.THF (40 ml, 1.0 M in THF). The mixture was stirred at room temperature for 1 h. To work up, THF was evaporated on a rotavap. The residue was treated with water (100 ml) Acidified and extracted with ether (2×100 ml). Removal of the solvent under reduced pressure gave 2-(3,4-methylenedioxy)phenyl-1-ethanol as an oil (4.7 g, 98% yield).

B. 1-acetoxy-2-[(3,4-methylenedioxy)phenyl]ethane

To a stirred solution of 2-(3,4-methylenedioxy)phenyl-1-ethanol (1.68 g, 10 mmol) in dry pyridine was added acetic anhydride and the resultant reaction mixture was stirred at 80° C. for 1 h. The reaction mixture was poured into ice-water and was extracted with ether (2×75 ml). The combined ether extract was washed with water (2×50 ml), 5% HCl (2×50 ml) and then with 5% $NaHCO_3$ (2×50 ml). The organic layer was dried over magnesium sulfate and the solvent was removed under reduced pressure to give 1-acetoxy-2-[(3,4-methylenedioxy)phenyl]ethane as a solid (1.7 g, 81% yield).

C. 1-acetoxy-2-[(3,4-methylenedioxy)-6-nitrophenyl]ethane

To a stirred solution of 1-acetoxy-2-[(3,4-methylenedioxy)-phenyl]ethane (1.7 g, 8.09 mmol) in acetic acid (10 ml) was added, dropwise, concentrated $HNO_3$ (4.5 ml). This was stirred at room temperature for 30 min. The reaction mixture was poured into water (100 ml). The precipitated solid was filtered, washed with water and dried under high vacuum to get 1-acetoxy-2-[(3,4-methylenedioxy)-6-nitrophenyl]ethane (1.8 g, 88% yield).

D. 1-acetoxy-2-[(3,4-methylenedioxy)-6-aminophenyl]ethane

The solution of 1-acetoxy-2-[(3,4-methylenedioxy)-6-nitrophenyl]ethane (0.8 g, 3.13 mmol) in ethyl acetate (25 ml) was subjected to catalytic hydrogenation using 10% palladium on carbon (100 mg) at 50 psi for 30 min. The catalyst was filtered and the solvent was removed under reduced pressure to give 1-acetoxy-2-[(3,4-methylenedioxy)-6-aminophenyl]ethane as a solid (0.69 g, 98% yield).

E. N-(4-chloro-3-methyl-5-isoxazolyl)-2-[3,4-(methylenedioxy)-6-(2-acetoxyethyl)]phenylaminocarbonyl-3-thiophenesulfonamide N-(4-chloro-3-methyl-5-isoxazolyl)-2-[3,4-(methylenedioxy)-6-(2-acetoxyethyl)]phenylaminocarbonyl-3-thiophenesulfonamide was synthesized in the same manner as Example 16. The crude product was purified by preparative HPLC to give N-(4-chloro-3-methyl-5-isoxazolyl)-2-[3,4-(methylenedioxy)-6-(2-acetoxyethyl)]phenylaminocarbonyl-3-thiophenesulfonamide as a dull yellow powder (12% yield, m.p. 78–82° C.).

EXAMPLE 36

Other compounds that have been prepared by the above methods or routine modifications thereof, include, but are not limited to:

N-(4-chloro-3-methyl-5-isoxazolyl)-2-[(4-methoxyphenoxy)carbonyl]thiophene-3-sulfonamide, N-(4-bromo-3-methyl-5-isoxazolyl)-2-[(4-methylphenoxy)carbonyl]thiophene-3-sulfonamide, N-(4-bromo-3-methyl-5-isoxazolyl)-3-[(4-methylphenoxy)methyl]thiophene-2-sulfonamide, N-(4-bromo-3-methyl-5-isoxazolyl)-2-[(4-methylphenoxy)methyl]thiophene-3-sulfonamide, N-(4-bromo-3-methyl-5-isoxazolyl)-3-(4-methyl-trans-styryl)thiophene-2-sulfonamide, N-(4-bromo-3-methyl-5-isoxazolyl)-3-(4-methylphenethyl)thiophene-2-sulfonamide, N-(4-bromo-3-methyl-5-isoxazoly)-2-[(4-methylphenyl)acetyl]thiophene-3-sulfonamide, N-(4-bromo-3-methyl-5-isoxazolyl)-2-[(3-methoxyphenyl)acetyl]thiophene-3-sulfonamide, N-(4-bromo-3-methyl-5-isoxazolyl)-3-(4-methylphenethyl)-5-(4-tolyl)thiophene-2-sulfonamide, N-(4-bromo-3-methyl-5-isoxazolyl)-3-(4-methylbenzyl)-5-(4-tolyl)thiophene-2-sulfonamide, N-(4-bromo-3-methyl-5-isoxazolyl)-3-(4-methyl-trans-styryl)-5-(4-tolyl)thiophene-2-sulfonamide, N-(4-chloro-3-methyl-5-isoxazolyl)-2-[3,4-(methylenedioxy)benzyl]thiophene-3-sulfonamide, N-(4-chloro-3-methyl-5-isoxazolyl)-2-[(5-methyl-3-isoxazolyl)aminocarbonyl]thiophene-3-sulfonamide, N-(4-bromo-3-methyl-5-isoxazolyl)-2-[(3-hydroxyl-6-pyridazinyl)aminocarbonyl]thiophene-3-sulfonamide, N-(4-bromo-3-methyl-5-isoxazolyl)-3-{[3,4-(methylenedioxy)phenoxy]methyl}thiophene-2-sulfonamide, N-(4-bromo-3-methyl-5-isoxazolyl)-2-[(4-methyl)(cinnamyl)]thiophene-3-sulfonamide, N-(4-bromo-3-methyl-5-isoxazolyl)-3-[3,4-(methylenedioxy)phenethyl]thiophene-2-sulfonamide, N-(4-bromo-3-methyl-5-isoxazolyl)-3-[3,4-(methylenedioxy)-trans-styryl]thiophene-2-sulfonamide, N-(4-bromo-3-methyl-5-isoxazolyl)-2-[(4-methyl)phenethyl]thiophene-3-sulfonamide, N-(3,4-dimethyl-5-isoxazolyl)-2-(4-tolylacetylphenyl)thiophene-3-sulfonamide, N-(3,4-dimethyl-5-isoxazolyl)-2-[3,4-(methylenedioxy)phenylacetyl]thiophene-3-sulfonamide, N-(4-chloro-3-methyl-5-isoxazolyl)-2-[2-hydroxy-4-methylphenyl)aminocarbonyl]thiophene-3-sulfonamide and others, including those set forth in TABLE 1 that are not specifically exemplified herein.

For example, N-(4-bromo-3-methyl-5-isoxazolyl)-3-[2-methyl-4,5-(methylenedioxy)cinnamyl]thiophene-2-sulfonamide, N-(4-bromo-3-methyl-5-isoxazolyl)-3-[2-(hydroxymethyl)-4,5-(methylenedioxy)cinnamyl]thiophene-2-sulfonamide, N-(4-bromo-3-methyl-5-isoxazolyl)-3-{2-[(tetrahydro-4H-pyran-2-ylxoy)methyl]-4,5-(methylenedioxy)cinnamyl}thiophene-2-sulfonamide and N-(4-bromo-3-methyl-5-isoxazolyl)-3-(2,4-dimethylcinnamyl)thiophene-2-sulfonamide have been prepared in the same manner as N-(4-bromo-3-methyl-5-isoxazolyl)-3-[3,4-(methylenedioxy)-trans-styryl]thiophene-2-sulfonamide. N-(4-bromo-3-methyl-5-isoxazolyl)-3-[2-methyl-4,5-(methylenedioxy)phenethyl]thiophene-2-sulfonamide and N-(4-bromo-3-methyl-5-isoxazolyl)-2-(2,4,6-trimethylphenethyl)thiophene-3-sulfonamide have been prepared in the same manner as N-(4-bromo-3-methyl-5-isoxazolyl)-2-[(4-methyl)phenethyl]thiophene-3-sulfonamide (see, Example 24). N-(4-bromo-3-methyl-5-isoxazolyl)-3-{[2-propyl-4,5-(methylenedioxy)phenoxy]methyl}thiophene-2-sulfonamide has been prepared in the same manner as N-(4-bromo-3-methyl-5-isoxazolyl)-3-[(4-methylphenoxy)methyl]thiophene-2-sulfonamide and N-(4-bromo-3-methyl-5-isoxazolyl)-3-{[3,4-(methylenedioxy)phenoxy]methyl}thiophene-2-sulfonamide. N-(4-bromo-3-methyl-5-isoxazolyl)-2-[2-methyl-4,5-(methylenedioxy)phenethyl]-thiophene-3-sulfonamide has been prepared in the same manner as N-(4-bromo-3-methyl-5-isoxazolyl)-2-[(3,4-methylenedioxy)phenethyl]thiophene-3-sulfonamide. Compounds, such as N-(4-bromo-3-methyl-5-isoxazolyl)-3-(2-tolyl)thiophene-2-sulfonamide, N-(4-bromo-3-methyl-5-isoxazolyl)-3-(3-tolyl)thiophene-2-sulfonamide, N-(4-bromo-3-methyl-5-isoxazolyl)-3-(2-tolyl)thiophene-2-sulfonamide, N-(4-bromo-3-methyl-5-isoxazolyl)-3-(3-methoxyphenyl)thiophene-2-sulfonamide, N-(4-bromo-3-methyl-5-isoxazolyl)-3-(3-methoxyphenyl)thiophene-2-sulfonamide, N-(4-bromo-3-methyl-5-isoxazolyl)-3-(2-methoxyphenyl)thiophene-2-sulfonamide, N-(4-bromo-3-methyl-5-isoxazolyl)-3-(4-ethylphenyl)thiophene-2-sulfonamide, N-(4-bromo-3-methyl-5-isoxazolyl)-3-(4-propylphenyl)thiophene-2-sulfonamide, N-(4-bromo-3-methyl-5-isoxazolyl)-3-(4-iso-propylphenyl)thiophene-2-sulfonamide, N-(4-bromo-3-methyl-5-isoxazolyl)-3-(4-butylphenyl)thiophene-2-sulfonamide, N-(4-bromo-3-methyl-5-isoxazolyl)-3-(2,4-dimethylphenyl)thiophene-2-sulfonamide, N-(4-bromo-3-methyl-5-isoxazolyl)-3-(4-iso-butylphenyl)thiophene-2-sulfonamide, N-(4-bromo-3-methyl-5-isoxazolyl)-3-(4-iso-pentylphenyl)thiophene-2-sulfonamide, N-(4-bromo-3-methyl-5-isoxazolyl)-3-(2-methyl-4-propylphenyl)thiophene-2-sulfonamide, N-(4-bromo-3-methyl-5-isoxazolyl)-3-(4-iso-butyl-2-methylphenyl)thiophene-2-sulfonamide and N-(4-bromo-3-methyl-5-isoxazolyl)-3-(4-iso-pentyl-2-methylphenyl)thiophene-2-sulfonamide have been prepared in the same manner as N-(4-bromo-3-methyl-5-isoxazolyl)-3-[(3,4-methylenedioxy)phenyl]thiophene-2-sulfonamide (see, Example 125 of International Patent Application Publication No. WO 96/31492).

N-(4-bromo-3-methyl-5-isoxazolyl)-2-[2-methyl-4,5-(methylene-dioxy)phenethy]thiophene-3-sulfonamide has been prepared in the same manner as N-(4-Bromo-3-methyl-5-isoxazolyl)-2-[3,4-(methylenedioxy)phenethyl]thiophene-3-sulfonamide (Example 22). N-(4-bromo-3-methyl-5-isoxazolyl)-2-[2-methyl-4,5-(methylenedioxy)cinnamyl]thiophene-3-sulfonamide has been prepared in the same manner as N-(4-bromo-3-methyl-5-isoxazolyl)-2-[(4-methyl)(cinnamyl)]thiophene-3-sulfonamide (Example 23).

N-(4-bromo-3-methyl-5-isoxazolyl)-2-{[3,4-(methylenedioxy)-phenoxy]methyl}thiophene-3-sulfonamide, N-(4-bromo-3-methyl-5-isoxazolyl)-2-[(2,4,6-trimethylphenoxy)methyl]thiophene-3-sulfonamide, N-(4-bromo-3-methyl-5-isoxazolyl)-2-{[4,5-(methylenedioxy)-2-propylphenoxy]methyl}thiophene-3-sulfonamide have been prepared in the same manner as N-(4-bromo-3-methyl-5-isoxazolyl)-2-[(4-methylphenoxy)methyl]thiophene-3-sulfonamide (Example 25).

Any corresponding N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), N-(4,5-dimethyl-3-isoxazolyl) derivative of any of these compounds or any compound disclosed herein may also be prepared and used as described herein. The pharmaceutically acceptable derivatives, including the salts, particularly sodium salts are intended for formulation as described herein.

EXAMPLE 37

Other compounds that can be prepared by the above methods or routine modifications thereof, include, but are not limited to:

N-(4-chloro-3-methyl-5-isoxazolyl)-2-(2,3,4-trimethoxy-6-methylphenylaminocarbonyl)thiophene-3-sulfonamide,
N-(4-chloro-3-methyl-5-isoxazolyl)-2-(2,3,4-trimethoxy-6-acetylphenylaminocarbonyl)thiophene-3-sulfonamide,
N-(4-chloro-3-methyl-5-isoxazolyl)-2-(2,3,4-trimethoxy-6-methoxycarbonylphenylaminocarbonyl)thiophene-3-sulfonamide,
N-(4-chloro-3-methyl-5-isoxazolyl)-2-(2,3,4-trimethoxy-6-carboxylphenylaminocarbonyl)thiophene-3-sulfonamide,
N-(4-chloro-3-methyl-5-isoxazolyl)-2-(2,3,4-trimethoxy-6-methanesulfonylphenylaminocarbonyl)thiophene-3-sulfonamide,
N-(4-chloro-3-methyl-5-isoxazolyl)-2-[2,3,4-trimethoxy-6-(cyanomethyl)phenylaminocarbonyl]thiophene-3-sulfonamide,
N-(4-chloro-3-methyl-5-isoxazolyl)-2-[2,3,4-trimethoxy-6-(2-hydroxyethyl)phenylaminocarbonyl]thiophene-3-sulfonamide,
N-(4-chloro-3-methyl-5-isoxazolyl)-2-[3,4-(methylenedioxy)-2-methoxy-6-methylphenylaminocarbonyl]thiophene-3-sulfonamide,
N-(4-chloro-3-methyl-5-isoxazolyl)-2-[3,4-(methylenedioxy)-2-methoxy-6-acetylphenylaminocarbonyl]thiophene-3-sulfonamide,
N-(4-chloro-3-methyl-5-isoxazolyl)-2-[3,4-(methylenedioxy)-2-methoxy-6-methoxycarbonylphenylaminocarbonyl]thiophene-3-sulfonamide,
N-(4-chloro-3-methyl-5-isoxazolyl)-2-[3,4-(methylenedioxy)-2-methoxy-6-carboxylphenylaminocarbonyl]thiophene-3-sulfonamide,
N-(4-chloro-3-methyl-5-isoxazolyl)-2-[3,4-(methylenedioxy)-2-methoxy-6-methanesulfonylphenylaminocarbonyl]thiophene-3-sulfonamide,
N-(4-chloro-3-methyl-5-isoxazolyl)-2-[3,4-(methylenedioxy)-2-methoxy-6-cyanophenylaminocarbonyl]thiophene-3-sulfonamide,
N-(4-chloro-3-methyl-5-isoxazolyl)-2-[3,4-(methylenedioxy)-2-methoxy-6-cyanomethylphenylaminocarbonyl]thiophene-3-sulfonamide,
N-(4-chloro-3-methyl-5-isoxazolyl)-2-[3,4-(methylenedioxy-2-methoxy-6-(2-hydroxyethyl)phenylaminocarbonyl]thiophene-3-sulfonamide,
N-(4-chloro-3-methyl-5-isoxazolyl)-2-[3,4-(methylenedioxy)-2,6-dimethylphenylaminocarbonyl]thiophene-3-sulfonamide,
N-(4-chloro-3-methyl-5-isoxazolyl)-2-[3,4-(methylenedioxy)-6-acetyl-2-methylphenylaminocarbonyl]thiophene-3-sulfonamide,
N-(4-chloro-3-methyl-5-isoxazolyl)-2-[3,4-(methylenedioxy)-6-methoxycarbonyl-2-methylphenylaminocarbonyl]thiophene-3-sulfonamide,
N-(4-chloro-3-methyl-5-isoxazolyl)-2-[3,4-(methylenedioxy)-6-carboxyl-2-methylphenylaminocarbonyl]thiophene-3-sulfonamide,
N-(4-chloro-3-methyl-5-isoxazolyl)-2-[3,4-(methylenedioxy)-6-methoxy-2-methylphenylaminocarbonyl]thiophene-3-sulfonamide,
N-(4-chloro-3-methyl-5-isoxazolyl)-2-[3,4-(methylenedioxy)-6-methanesulfonyl-2-methylphenylaminocarbonyl]thiophene-3-sulfonamide,
N-(4-chloro-3-methyl-5-isoxazolyl)-2-[3,4-(methylenedioxy)-6-cyano-2-methylphenylaminocarbonyl]thiophene-3-sulfonamide,
N-(4-chloro-3-methyl-5-isoxazolyl)-2-[3,4-(methylenedioxy)-6-(cyanomethyl)-2-methylphenylaminocarbonyl[thiophene-3-sulfonamide,
N-(4-chloro-3-methyl-5-isoxazolyl)-2-[3,4-methylenedioxy)-6-(2-hydroxyethyl)-2-methylphenylaminocarbonyl]thiophene-3-sulfonamide, N-(4-chloro-3-methyl-5-isoxazolyl)-2-[3,4-(methylenedioxy)-2-cyano-6-methylphenylaminocarbonyl]thiophene-3-sulfonamide,
N-(4-chloro-3-methyl-5-isoxazolyl)-2-[3,4-(methylenedioxy)-6-methoxy-2-cyanophenylaminocarbonyl]thiophene-3-sulfonamide,
N-(4-chloro-3-methyl-5-isoxazolyl)-2-[3,4-(methylenedioxy)-2-acetyl-6-methylphenylaminocarbonyl]thiophene-3-sulfonamide,
N-(4-chloro-3-methyl-5-isoxazolyl)-2-[3,4-(methylenedioxy)-6-methoxy-2-acetylphenylaminocarbonyl]thiophene-3-sulfonamide,
N-(4-chloro-3-methyl-5-isoxazolyl)-2-(3-cyano-2,4,6-trimethylphenylaminocarbonyl]thiophene-3-sulfonamide,
N-(4-chloro-3-methyl-5-isoxazolyl)-2-(3-carboxyl-2,4,6-trimethylphenylaminocarbonyl]thiophene-3-sulfonamide,
N-(4-chloro-3-methyl-5-isoxazolyl)-2-(3-hydroxymethyl-2,4,6-trimethylphenylaminocarbonyl]thiophene-3-sulfonamide,
N-(4-chloro-3-methyl-5-isoxazolyl)-2-(3-methanesulfonyl-2,4,6-trimethylphenylaminocarbonyl]thiophene-3-sulfonamide,
N-(4-chloro-3-methyl-5-isoxazolyl)-2-(3-cyanomethyl-2,4,6-trimethylphenylaminocarbonyl]thiophene-3-sulfonamide,
N-(4-chloro-3-methyl-5-isoxazolyl)-2-[3-(2-hydroxyethyl)-2,4,6-trimethylphenylaminocarbonyl]thiophene-3-sulfonamide,
N-(4-chloro-3-methyl-5-isoxazolyl)-2-[3-(carboxylmethyl)-2,4,6-trimethylphenylaminocarbonyl]thiophene-3-sulfonamide,
N-(4-chloro-3-methyl-5-isoxazolyl)-2-(4-cyano-2,6-dimethylphenylaminocarbonyl)thiophene-3-sulfonamide,
N-(4-chloro-3-methyl-5-isoxazolyl)-2-(4-carboxyl-2,6-dimethylphenylaminocarbonyl)thiophene-3-sulfonamide,
N-(4-chloro-3-methyl-5-isoxazolyl)-2-[4-(hydroxymethyl)-2,6-dimethylphenylaminocarbonyl)thiophene-3-sulfonamide,
N-(4-chloro-3-methyl-5-isoxazolyl)-2-[4-(2-hydroxyethyl)-2,6-dimethylphenylaminocarbonyl]thiophene-3-sulfonamide,
N-(4-chloro-3-methyl-5-isoxazolyl)-2-[4-(cyanomethyl)-2,6-dimethylphenylaminocarbonyl]thiophene-3-sulfonamide,
N-(4-chloro-3-methyl-5-isoxazolyl)-2-[4-(carboxylmethyl)-2,6-dimethylphenylaminocarbonyl]thiophene-3-sulfonamide,
N-(4-chloro-3-methyl-5-isoxazolyl)-2-(4-methanesulfonyl-2,6-dimethylphenylaminocarbonyl)thiophene-3-sulfonamide,
N-(4-chloro-3-methyl-5-isoxazolyl)-2-(2,3,4-trimethoxy-6-methylphenylacetyl)thiophene-3-sulfonamide,
N-(4-chloro-3-methyl-5-isoxazolyl)-2-(2,3,4-trimethoxy-6-acetylphenylacetyl)thiophene-3-sulfonamide,
N-(4-chloro-3-methyl-5-isoxazolyl)-2-(2,3,4-trimethoxy-6-methoxycarbonylphenylacetyl)thiophene-3-sulfonamide,
N-(4-chloro-3-methyl-5-isoxazolyl)-2-(2,3,4-trimethoxy-6-carboxylphenylacetyl)thiophene-3-sulfonamide,
N-(4-chloro-3-methyl-5-isoxazolyl)-2-(2,3,4-trimethoxy-6-methanesulfonytphenylacetyl)thiophene-3-sulfonamide,
N-(4-chloro-3-methyl-5-isoxazolyl)-2-[2,3,4-trimethoxy-6-(cyanomethyl)phenylacetyl]thiophene-3-sulfonamide,
N-(4-chloro-3-methyl-5-isoxazolyl)-2-[2,3,4-trimethoxy-6-(2-hydroxyethyl)phenylacetyl]thiophene-3-sulfonamide,
N-(4-chloro-3-methyl-5-isoxazolyl)-2-[3,4-(methylenedioxy)-2-methoxy-6-methylphenylacetyl]thiophene-3-sulfonamide,
N-(4-chloro-3-methyl-5-isoxazolyl)-2-[3,4-(methylenedioxy)-2-methoxy-6-acetylphenylacetyl]thiophene-3-sulfonamide,
N-(4-chloro-3-methyl-5-isoxazolyl)-2-[3,4-(methylenedioxy)-2-methoxy-6-methoxycarbonylphenylacetyl]thiophene-3-sulfonamide,
N-(4-chloro-3-methyl-5-isoxazoyl)-2-[3,4-(methylenedioxy)-2-methoxy-6-carboxylphenylacetyl]thiophene-3-sulfonamide,
N-(4-chloro-3-methyl-5-isoxazolyl)-2-[3,4-(methylenedioxy-2-methoxy-6-methanesulfonyl)phenylacetyl]thiophene-3-sulfonamide,
N-(4-chloro-3-methyl-5-isoxazolyl)-2-[3,4-(methylenedioxy)-2-methoxy-6-(cyano)phenylacetyl]thiophene-3-sulfonamide,
N-(4-chloro-3-methyl-5-isoxazolyl)-2-[3,4-(methylenedioxy)-2-methoxy-6--(cyanomethylphenylacetyl]thiophene-3-sulfonamide,
N-(4-chloro-3-methyl-5-isoxazolyl)-2-[3,4-(methylenedioxy)-2-methoxy-6-(2-hydroxyethyl)phenylacetyl]thiophene-3-sulfonamide,
N-(4-chloro-3-methyl-5-isoxazolyl)-2-[3,4-(methylenedioxy)-2,6-dimethylphenylacetyl]thiophene-3-sulfonamide,
N-(4-chloro-3-methyl-5-isoxazolyl)-2-[3,4-(methylenedioxy)-6-acetyl-2-methylphenylacetyl]thiophene-3-sulfonamide,
N-(4-chloro-3-methyl-5-isoxazolyl)-2-[3,4-(methylenedioxy)-6-methoxycarbonyl-2-methylphenylacetyl]thiophene-3-sulfonamide,
N-(4-chloro-3-methyl-5-isoxazolyl)-2-[3,4-(methylenedioxy)-6-carboxyl-2-methylphenylacetyl]thiophene-3-sulfonamide,
N-(4-chloro-3-methyl-5-isoxazolyl)-2-[3,4-(methylenedioxy)-6-methoxy-2-methylphenylacetyl]thiophene-3-sulfonamide,
N-(4-chloro-3-methyl-5-isoxazolyl)-2-[3,4-(methylenedioxy)-6-methanesulfonyl-2-methylphenylacetyl]thiophene-3-sulfonamide,
N-(4-chloro-3-methyl-5-isoxazolyl)-2-[3,4-(methylenedioxy)-6-cyano-2-methylphenylacetyl]thiophene-3-sulfonamide,
N-(4-chloro-3-methyl-5-isoxazolyl)-2-[3,4-(methylenedioxy)-6-(cyanomethyl)-2-methylphenylacetyl]thiophene-3-sulfonamide,
N-(4-chloro-3-methyl-5-isoxazolyl)-2-[3,4-(methylenedioxy)-6-(2-hydroxyethyl)-2-methylphenylacetyl]thiophene-3-sulfonamide,
N-(4-chloro-3-methyl-5-isoxazolyl)-2-[3,4-(methylenedioxy)-2-cyano-6-methylphenylacetyl]thiophene-3-sulfonamide,
N-(4-chloro-3-methyl-5-isoxazolyl)-2-[3,4-(methylenedioxy)-6-methoxy-2-cyanophenylacetyl]thiophene-3-sulfonamide,
N-(4-chloro-3-methyl-5-isoxazolyl)-2-[3,4-(methylenedioxy)-2-acetyl-6-methylphenylacetyl]thiophene-3-sulfonamide,
N-(4-chloro-3-methyl-5-isoxazolyl)-2-[3,4-(methylenedioxy)-6-methoxy-2-acetylphenylacetyl]thiophene-3-sulfonamide,
N-(4-chloro-3-methyl-5-isoxazolyl)-2-(3-cyano-2,4,6-trimethylphenylacetyl)thiophene-3-sulfonamide,
N-(4-chloro-3-methyl-5-isoxazolyl)-2-[3,4-(methylenedioxy)-2methoxy-6-(2-hydroxyethyl)phenylacetyl]thiophene-3-sulfonamide,
N-(4-chloro-3-methyl-5-isoxazolyl)-2-(3-hydroxymethyl-2,4,6-trimethylphenylacetyl)thiophene-3-sulfonamide, N-(4-chloro-3-methyl-5-isoxazolyl)-2-(3-methanesulfonyl-2,4,6-trimethylphenylacetyl)thiophene-3-sulfonamide,
N-(4-chloro-3-methyl-5-isoxazolyl)-2-(3-(cyanomethyl)-2,4,6-trimethylphenylacetyl]thiophene-3-sulfonamide,
N-(4-chloro-3-methyl-5-isoxazolyl)-2-[3-(2-hydroxyethyl)-2,4,6-trimethylphenylacetyl)thiophene-3-sulfonamide,
N-(4-chloro-3-methyl-5-isoxazolyl)-2-[3-(carboxylmethyl)-2,4,6-trimethylphenylacetyl]thiophene-3-sulfonamide,
N-(4-chloro-3-methyl-5-isoxazolyl)-2-(4-cyano-2,6-dimethylphenylacetyl)thiophene-3-sulfonamide,
N-(4-chloro-3-methyl-5-isoxazolyl)-2-(4-carboxyl-2,6-dimethylphenylacetyl)thiophene-3-sulfonamide,
N-(4-chloro-3-methyl-5-isoxazolyl)-2-(4-hydroxymethyl-2,6-dimethylphenylacetyl)thiophene-3-sulfonamide,
N-(4-chloro-3-methyl-5-isoxazolyl)-2-[4-(2-hydroxyethyl)-2,6-(dimethyl)phenylacetyl]thiophene-3-sulfonamide,
N-(4-chloro-3-methyl-5-isoxazolyl)-2-[4-cyanomethyl-2,6-(dimethyl)phenylacetyl]thiophene-3-sulfonamide,
N-(4-chloro-3-methyl-5-isoxazolyl)-2-[4-(carboxylmethyl)-2,6-dimethylphenylacetyl]thiophene-3-sulfonamide, and
N-(4-chloro-3-methyl-5-isoxazolyl)-2-(4-methanesulfonyl-2,6-dimethylphenylacetyl)thiophene-3-sulfonamide. The pharmaceutically acceptable derivatives, including the salts, particularly sodium salts are intended for formulation as described herein.

EXAMPLE 38

Other compounds, having activity generally at $IC_{50}$ concentrations of 10 μM or substantially less for $ET_A$ or $ET_B$ receptors, in which $Ar^2$ contains a heterocyclic ring, such as thienyl-, furyl- and pyrrole-sulfonamides of interest herein, can be or have been prepared (see, e.q., TABLE 1) by methods analogous to those set forth in the above Examples. Such compounds include, but are not limited to the following compounds: N-(4-bromo-3-methyl-5-isoxazolyl)-2-carboxyl-1-methylindole-3-sulfonamide, N-(4-chloro-3-methyl-5-isoxazolyl)-2-[(4-oxacyclohexyl)oxycarbonyl]thiophene-3-sulfonamide, 2-[3,4-(methylenedioxy)phenylacetyl]thiophene-3-sulfonamide, N-(4-chloro-3-methyl-5-isoxazolyl)-{2-[3,4-(methylenedioxy)phenyl]acetyl}thiophene-3-sulfonamide oxime, N-(4-chloro-3-methyl-5-isoxazolyl)-2-phenylbenzo[b]thiophene sulfonamide, N-(4-chloro-3-methyl-5-isoxazolyl)-2-[(4-tolyl)aminocarbonyl]-1-methylindole-3-sulfonamide, N-(4-chloro-3-methyl-5-isoxazolyl)-2-[(4-methoxyphenoxy)carbonyl]thiophene-3-sulfonamide, N-(4-bromo-3-methyl-5-isoxazolyl)-1-[3,4-(methylenedioxy)benzyl]indole-2-sulfonamide, N-(4-bromo-3-methyl-5-isoxazolyl)-2-[(4-methylphenoxy)carbonyl]thiophene-3-sulfonamide, N-(4-chloro-3-methyl-5-isoxazolyl)-2-[(4-methoxyphenyl)acetyl]thiophene-3-sulfonamide, N-(4-chloro-3-methyl-5-isoxazolyl)-6-methoxy-2-[3,4-(methylenedioxy)benzyl]benzo[b]thiophene-3-sulfonamide, N-(4-bromo-3-methyl-5-isoxazolyl)-3-[(4-methylphenoxy)-methyl]thiophene-2-sulfonamide, N-(4-bromo-3-methyl-5-isoxazolyl)-2-[(4-methylphenoxy)methyl]thiophene-3-sulfonamide, N-(4-bromo-3-methyl-5-isoxazolyl)-3-(4-methyl-trans-styryl)thiophene-2-sulfonamide, N-(4-bromo-3-methyl-5-isoxazolyl)-3-(4-methylphenethyl)thiophene-2-sulfonamide, N-(4-bromo-3-methyl-5-isoxazolyl)-2-[(4-methylphenyl)acetyl]thiophene-3-sulfonamide, N-(4-chloro-3-methyl-5-isoxazolyl)-2-[(3-methoxyphenyl)acetyl]thiophene-3-sulfonamide, N-(4-chloro-3-methyl-5-isoxazolyl)-2-{1-hydroxy-1-[3,4-(methylenedioxy)-benzyl]ethyl}thiophene-3-sulfonamide, N-4-(bromo-3-methyl-5-isoxazolyl)-3-(4-methylphenethyl)(4-tolyl)thiophene-2-sulfonamide, N-(4-bromo-3-methyl-5-isoxazolyl)-3-(4-methylbenzyl)-5-(4-tolyl)thiophene-2-sulfonamide, N-(4-bromo-3-methyl-5-isoxazolyl)-3-(4-methyl-trans-styryl)-5-(4-tolyl)thiophene-2-sulfonamide, N-(4-chloro-3-methyl-5-isoxazolyl)-2-[β,β-(ethylenedioxy)3,4-(methylenedioxy)-phenethyl]thiophene-3-sulfonamide, N-(4-chloro-3-methyl-5-isoxazolyl)-2-[β-(dimethylamino)-3,4-(methylenedioxy)phenethy]thiophene-3-sulfonamide, N-(4-chloro-3-methyl-5-isoxazolyl)-2-{α-hydroxy-[3,4-(methylenedioxy)phenyl]acetyl}-thiophene-3-sulfonamide; N-(4-chloro-5-methyl-3-isoxazolyl)-2-[3,4-(methylenedioxy)benzyl]benzo[b]thiophene-3-sulfonamide; N-(4-bromo-3-methyl-5-isoxazolyl)-3-styrylthiophene-2-sulfonamide; N-(4-bromo-3-methyl-5-isoxazolyl)-2-styrylthiophene-3-sulfonamide; N-(4-bromo-3-methyl-5-isoxazolyl)-2-(benzoylamino)thiophene-3-sulfonamide; N-(4-bromo-3-methyl-5-isoxazolyl)-2-[(phenyl)-methylaminocarbonyl]thiophene-3-sulfonamide; N-(4-bromo-3-methyl-5-isoxazolyl)-5-(phenylthio)furan-2-sulfonamide; N-(4-bromo-3-methyl-5-isoxazolyl)-5-(hydroxymethyl)furan-2-sulfonamide; N-(4-bromo-3-methyl-5-isoxazolyl)-5-(carbomethoxy)furan-2-sulfonamide; N-(4-bromo-3-methyl-5-isoxazolyl)-2,5-dimethylfuran-3-sulfonamide; N-(4-bromo-3-methyl-5-isoxazolyl)-2-(diisopropylaminocarbonyl)thiophene-3-sulfonamide; N-(4-bromo-3-methyl-5-isoxazolyl)-2-(diethylaminocarbonyl)thiophene-3-sulfonamide; N-(4-bromo-3-methyl-5-isoxazolyl)-5-styrylfuran-2-sulfonamide; N-(4-bromo-3-methyl-5-isoxazolyl)-5-styrylthiophene-2-sulfonamide; N-(4-chloro-3-methyl-5-isoxazolyl)-2-[3,4-(methylenedioxy)benzyl]-5-(dimethylamino)benzo[b]thiophene-3-sulfonamide; N-(4-chloro-3-methyl-5-isoxazolyl)-2-[3,4-(methylenedioxy)benzyl]-7-methoxybenzo[b]thiophene-3-sulfonamide; N-(4-chloro-3-methyl-5-isoxazolyl)-2-[3,4-(methylenedioxy)benzyl]-7-phenoxybenzo[b]thiophene-3-sulfonamide; N-(4-chloro-3-methyl-5-isoxazolyl)-2-[3,4-(methylenedioxy)benzyl]-5-methoxybenzo[b]thiophene-3-sulfonamide; N-(4-chloro-3-methyl-5-isoxazolyl)-2-[3,4-(methylenedioxy)benzyl]-5-isobutylaminobenzo[b]thiophene-3-sulfonamide; N-(4-chloro-3-methyl-5-isoxazolyl)-2-[3,4-(methylenedioxy)benzyl]-5-benzylaminobenzo[b]thiophene-3-sulfonamide; N-(4-chloro-3-methyl-5-isoxazolyl)-2-[3,4-(methylenedioxy)phenoxy]benzo[b]thiophene-3-sulfonamide; N-(4-chloro-3-methyl-5-isoxazolyl)-2-[3,4-(methylenedioxy)phenoxy]-5-dimethylamino-benzo[b]thiophene-3-sulfonamide; N-(4-chloro-3-methyl-5-isoxazolyl)-2-[(3,4-methylenedioxy)phenyl]acetyl-5-dimethylaminobenzo[b]thiophene-3-sulfonamide; N-(4-chloro-3-methyl-5-isoxazolyl)-2-[3,4-(methylenedioxy)benzylcarbonyl]-N-methylindole-3-sulfonamide; N-(4-chloro-3-methyl-5-isoxazolyl)-2-[3,4-(methylenedioxy)phenoxycarbonyl]indole-3-sulfonamide; N-(4-chloro-3-methyl-5-ioxazolyl)-2-[3,4-(methylenedioxy)phenoxycarbonyl]-N-methylindole-3-sulfonamide; N-(4-chloro-3-methyl-5-isoxazolyl)-2-[3,4-(methylenedioxy)phenoxycarbonyl]indole-3-sulfonamide; N-(4-chloro-3-methyl-5-isoxazolyl)-2-[3,4-(methylenedioxy)benzyl]-N-methylindole-3-sulfonamide; N-(4-chloro-3-methyl-5-isoxazolyl)-2-[3,4-(methylenedioxy)benzyl]indole-3-sulfonamide; N-(4-chloro-3-methyl-5-isoxazolyl)-2-[3,4-(methylenedioxy)benzyloxycarbonyl]-7-(N,N-dimethylamino)benzo[b]thiophene-3-sulfonamide; N-(4-chloro-3-methyl-5-isoxazolyl)-2-[3,4-(methylenedioxy)benzyl]-7-(N,N-dimethylamino)benzo[b]thiophene-3-sulfonamide; N-(4-chloro-3-methyl-5-isoxazolyl)-2-[3,4-(methylenedioxy)benzoyl]-7-(N,N-dimethyl)amino)benzo[b]thiophene-3-sulfonamide; N-(4-chloro-3-methyl-5-isoxazolyl)-7-(N,N- dimethylamino)benzo[b]thiophene-3-sulfonamide; N-(4-chloro-3-methyl-5-isoxazolyl)-7-(methoxycarbonyl)benzo[b]thiophene-3-sulfonamide; N-(4-chloro-3-methyl-5-isoxazolyl)-2-[3,4-(methylenedioxy)benzyl]-7-(methoxy)benzo[b]thiophene-3-sulfonamide; N-(4-chloro-3-methyl-5-isoxazolyl)-7-(methoxy)benzo[b]thiophene-3-sulfonamide; N-(4-bromo-3-methyl-5-isoxazolyl)-2-(4-methylphenethyl)thiophene-3-sulfonamide; N-(4-bromo-3-methyl-5-isoxazolyl)-2-(trans-4-methylcinnamyl)thiophene-3-sulfonamide; N-(4-bromo-3-methyl-5-isoxazolyl)-3-(4-methylphenethyl)thiophene-2-sulfonamide; N-(4-bromo-3-methyl-5-isoxazolyl)-3-(3-methylphenethyl)thiophene-2-sulfonamide; N-4-bromo-3-methyl-5-isoxazolyl)-3-(2-methylphenethyl)thiophene-2-sulfonamide; N-(4-bromo-3-methyl-5-isoxazolyl)-3-(trans-4-methylcinnamyl)thiophene-2-sulfonamide; N-(4-bromo-3-methyl-5-isoxazolyl)-3-(trans-3-methylcinnamyl)thiophene-2-sulfonamide; N-(4-bromo-3-methyl-5-isoxazolyl)-3-(trans-2-methylcinnamyl)-thiophene-2-sulfonamide; N-(4-bromo-3-methyl-5-isoxazolyl)-3-[(4-methylphenoxy)methyl]thiophene-2-sulfonamide; N-(4-bromo-3-methyl-5-isoxazolyl)-3-[3,4-(methylenedioxy)phenethyl]thiophene-2-sulfonamide; N-(4-chloro-3-methyl-5-isoxazolyl)-2-{(3,4-(dimethoxy)phenyl]acetyl)}thiophene-3-sulfonamide; N-(4-chloro-3-methyl-5-isoxazolyl)-2-[(3,5-dimethoxyphenyl)acetyl]thiophene-3-sulfonamide; N-(4-chloro-3-methyl-5-isoxazolyl)-2-[(3,4,5-trimethoxyphenyl)acetyl]thiophene-3-sulfonamide; N-(4-chloro-3-methyl-5-isoxazolyl)-2-[3,4-(methylenedioxy)benzylsulfonyl]thiophene-3-sulfonamide; N-(4-chloro-3-methyl-5-isoxazolyl)-2-[3,4-(methylenedioxy)benzylsulfinyl]thiophene-3-sulfonamide; N-(4-chloro-3-methyl-5-isoxazolyl)-2-[3,4-(methylenedioxy)benzylsulfonyl]thiophene-3-sulfonamide; N-(4-chloro-3-methyl-5-isoxazolyl)-2-{1-(dimethylamino)-2-[3,4-(methylenedioxy)phenyl]ethyl}thiophene-3-sulfonamide; N-(4-chloro-3-methyl-5-isoxazolyl)-2-{1-methylamino)-2-[3,4-(methylenedioxy)phenyl]ethyl}thiophene-3-sulfonamide; N-(4-chloro-3-methyl-5-isoxazolyl)-2-{1-(methoxylimino)-2-[3,4-(methylenedioxy)phenyl]ethyl}thiophene-3-sulfonamide; N-(4-chloro-3-methyl-5-isoxazolyl)-2-{1-(carboxyl)-2-[3,4-(methylenedioxy)phenyl]ethyl}thiophene-3-sulfonamide; N-(4-chloro-3-methyl-5-isoxazolyl)-2-{2-(carboxyl)-1-[3,4-(methylenedioxy)benzyl]vinyl}thiophene-3-sulfonamide; N-(4-chloro-3-methyl-5-isoxazolyl)-2-{3-[3,4-(methylenedioxy)phenyl]-1,2,4-oxadiazol-5-lyl}thiophene-3-sulfonamide; and N-(4-chloro-3-methyl-5-isoxazol-2-{3-[3,4-(methylenedioxy)benzyl]-1,2,4-oxadiazol-5-lyl}thiophene-3-sulfonamide.

Additional compounds include, but are not limited to: N-(4-chloro-3-methyl-5-isoxazolyl)-2-{[2-(methanesulfonyl)4,5-(methylenedioxy)phenyl]aminocarbonyl}thiophene-3-sulfonamide; N-(4-chloro-3-methyl-5-isoxazolyl)-2-{[3,4-(methylenedioxy)-6-carboxylphenyl]aminocarbonyl}thiophene-3-sulfonamide; N-(4-chloro-3-methyl-5-isoxazolyl)-2-{[4,5-(methylenedioxy)-2-(methoxycarbonyl)phenyl]aminocarbonyl}thiophene-3-sulfonamide; N-(4-chloro-3-methyl-5-isoxazolyl)-2-{[2-cyano-4,5-(methylenedioxy)phenyl]aminocarbonyl}thiophene-3-sulfonamide; N-(4-chloro-3-methyl-5-isoxazolyl)-2-[4,5-(methylenedioxy)-2-hydroxymethyl)phenyl]aminocarbonylthiophene-3-sulfonamide; N-(4-chloro-3-methyl-5-isoxazolyl)-2-[(2-acetyl-4-methylphenyl)aminocarbonyl]thiophene-3-sulfonamide; N-(4-chloro-3-methyl-5-isoxazolyl)-2-{[2-(methanesulfonyl)-4-methylphenyl]aminocarbonyl}thiophene-3-sulfonamide; N-(4-chloro-3-methyl-5-isoxazolyl)-2-[(2-carboxyl-4-methylphenyl)aminocarbonyl]thiophene-3-sulfonamide; N-(4-chloro-3-methyl-5-isoxazolyl)-2-[(2-methoxycarbonyl-4-methylphenyl)aminocarbonyl]thiophene-3-sulfonamide; N-(4-chloro-3-methyl-5-isoxazolyl)-2-[(2-cyano-4-methylphenyl)aminocarbonyl]thiophene-3-sulfonamide; N-(4-chloro-3-methyl-5-isoxazolyl)-2-{[2-(hydroxymethyl)-4-methylphenyl]aminocarbonyl}thiophene-3-sulfonamide; N-(4-chloro-3-methyl-5-isoxazolyl)-2-[(3,4-dimethoxy-6-acetylphenyl)aminocarbonyl]thiophene-3-sulfonamide; N-(4-chloro-3-methyl-5-isoxazolyl)-2-{[2-(methanesulfonyl)-4,5-dimethoxyphenyl]aminocarbonyl}thiophene-3-sulfonamide; N-(4-chloro-3-methyl-5-isoxazolyl)-2-[(4,5-dimethoxy-2-carboxylphenyl)aminocarbonyl]thiophene-3-sulfonamide; N-(4-chloro-3-methyl-5-isoxazolyl)-2-[(4,5-dimethoxy-2-methoxycarboxyl)phenyl)aminocarbonyl]thiophene-3-sulfonamide; N-(4-chloro-3-methyl-5-isoxazolyl)-2-[2-cyano(4,5-dimethoxyphenyl)aminocarbonyl]thiophene-3-sulfonamide; N-(4-chloro-3-methyl-5-isoxazolyl)-2-(4,5-dimethoxy-2-hydroxymethyl)phenylaminocarbonylthiophene-3-sulfonamide; N-(4-chloro-3-methyl-5-isoxazolyl)-2-{[2-acetyl-4,5-(methylenedioxy)phenyl]acetyl}thiophene-3-sulfonamide; N-(4-chloro-3-methyl-5-isoxazolyl)-2-{[2-(methanesulfonyl)-4,5-(methylenedioxy)phenyl]acetyl}thiophene-3-sulfonamide; N-(4-chloro-3-methyl-5-isoxazolyl)-2-{[carboxyl4,5-(methylenedioxy)-2-phenylacetylthiophene-3-sulfonamide; N-(4-chloro-3-methyl-5-isoxazolyl)-2-{[4,5-(methylenedioxy)-2-methoxycarbonylphenyl]acetylthiophene-3-sulfonamide; N-(4-chloro-3-methyl-5-isoxazolyl)-2-{2-cyano[4,5-(methylenedioxy)-phenyl]acetyl}thiophene-3-sulfonamide; N-(4-chloro-3-methyl-5-isoxazolyl)-2-{2-hydroxymethyl[4,5-(methylenedioxy)-phenyl]-acetyl}thiophene-3-sulfonamide; N-(4-chloro-3-methyl-5-isoxazolyl)-2-[(2,4-dimethoxy)phenyl)aminocarbonyl]thiophene-3-sulfonamide; N-(4-chloro-3-methyl-5-isoxazolyl)-2-[(4-methoxy-2-methylphenyl)aminocarbonyl]thiophene-3-sulfonamide; N-(4-chloro-3-methyl-5-isoxazolyl)-2-[(2,3-dimethylphenyl)aminocarbonyl]thiophene-3-sulfonamide; N-(4-chloro-3-methyl-5-isoxazolyl)-2-[(2,4-dimethylphenyl)aminocarbonyl]thiophene-3-sulfonamide; N-(4-chloro-3-methyl-5-isoxazolyl)-2-[(2,5-dimethylphenyl)aminocarbonyl]thiophene-3-sulfonamide; N-(4-chloro-3-methyl-5-isoxazolyl)-2-[(2,6-dimethylphenyl)aminocarbonyl]thiophene-3-sulfonamide; N-(4-chloro-3-methyl-5-isoxazolyl)-2-[(3,4-dimethylphenyl)aminocarbonyl]thiophene-3-sulfonamide; N-(4-chloro-3-methyl-5-isoxazolyl)-2-[(2,5-dimethylphenyl)aminocarbonyl]thiophene-3-sulfonamide; N-(4-chloro-3-methyl-5-isoxazolyl)-2-(3,5-dimethyl)phenylaminocarbonylthiophene-3-sulfonamide; N-(4-chloro-3-methyl-5-isoxazolyl)-2-[(2-methoxy-6-methylphenyl)aminocarbonyl]thiophene-3-sulfonamide; N-(4-chloro-3-methyl-5-isoxazolyl)-2-[(2,4,6-trimethylphenyl)aminocarbonyl]-thiophene-3-sulfonamide; N-(4-chloro-3-methyl-5-isoxazolyl)-2-[(4-methoxy-2-methylphenyl)aminocarbonyl]-thiophene-3-sulfonamide; N-(4-chloro-3-methyl-5-isoxazolyl)-2-[2-ethyl(4-methoxy-)phenyl)aminocarbonyl]thiophene-3-sulfonamide; N-(4-chloro-3-methyl-5-isoxazolyl)-2-[(2-isopropyl-4-methoxy-phenyl)aminocarbonyl]thiophene-3-sulfonamide; N-(4-chloro-3-methyl-5-isoxazolyl)-2-[(2-propyl-4-methoxyphenyl)aminocarbonyl]-thiophene-3-sulfonamide; N-(4-chloro-3-methyl-5-isoxazolyl)-2-[(4-methoxy-2-biphenylaminocarbonyl]-thiophene-3-sulfonamide; N-(4- chloro-3-methyl-5-isoxazolyl)-2-{[3,4-(methylenedioxy)-6-methylphenyl)acetyl]-thiophene-3-sulfonamide; N-(4-chloro-3-methyl-5-isoxazolyl)-2-{[3,4-(methylenedioxy)-6-ethylphenyl)acetyl}thiophene-3-sulfonamide; N-(4-chloro-3-methyl-5-isoxazolyl)-2-{[3,4-(methylenedioxy)-6-methoxyphenyl]acetyl}thiophene-3-sulfonamide.

The pharmaceutically acceptable derivatives, including the salts, particularly sodium salts are intended for formulation as described herein.

EXAMPLE 39

N-(2-Acetyl-4,6-dimethylphenyl)-3-(((4-chloro-3-methyl-5-isoxazolyl)amino)sulfonyl)-2-thiophenecarboxamide A. 2'-Amino-3',5'-dimethylacetophenone To a solution of BCl₃ in dichloromethane (1.0 M, 25 mL) at 0° C. was slowly added 2,4-dimethylaniline (3.03 g, 25 mmol) in 1,2-dichloroethane (25 mL). Acetonitrile (25 mL) was then added dropwise at 0° C. The mixture was then heated with a bath temperature of 100° C. for 2 days with a slow and steady flow of nitrogen to remove the low boiling dichloromethane. The reaction was cooled to 0° C. and quenched with 2 N HCl (~25 mL) and the mixture was heated at 80° C. until a homogenous solution formed (~20 min). This was allowed to cool to room temperature and the two layers were separated. The aqueous layer was basified with sodium bicarbonate until no more gas evolution was seen and much precipitate formed. The mixture was then extracted with chloroform (~30 mL) and the organic layers were combined and concentrated. The residue was dissolved in ethyl acetate (50 mL) and washed with 1 N NaOH (40 mL). The organic layer was then dried (MgSO₄), the solids were filtered, and the filtrate was concentrated. The oily residue was dissolved in ethyl ether (~5 mL) and let stand at room temperature for 24 h. The resulting yellow precipitate was filtered to give 2'-amino-3',5'-dimethylacetophenone (1.3 g, 30%).

B. N-(2-Acetyl-4,6-dimethylphenyl)-3-(((4-chloro-3-methyl-5-isoxazolyl)amino)sulfonyl)-2-thiophenecarboxamide To a solution of 2'-amino-3',5'-dimethylacetophenone (1.9 g, 11.66 mmol) in dichloromethane (20 mL) at room temperature was added N-(4-chloro-3-methyl-5-isoxazolyl)-N-methoxymethyl-3-sulfamoyl-2-thiophenecarbonyl chloride (Example 51) (1 g, 2.86 mmol). The mixture was stirred for 10 h during which much yellow precipitate formed. The reaction was then concentrated and the residue was diluted with ethyl acetate (50 mL) and washed with 1 N HCl (50 mL). The organic layer was concentrated and the residue was dissolved in methanol (30 mL) followed by the addition of concentrated HCl (15 mL). The mixture was then heated under reflux for 2 h before it was cooled to room temperature, diluted with ethyl acetate (200 mL) and washed with water (2×200 mL). The organic layer was separated, dried (MgSO₄), the solids filtered and the filtrate concentrated. The residue was then purified by reverse phase HPLC to give N-(2-acetyl-4,6-dimethylphenyl)-3-(((4-chloro-3-methyl-5-isoxazolyl)amino)sulfonyl)-2-thiophenecarboxamide (580 mg, 43%).

EXAMPLE 40

3-(((4-Chloro-3-methyl-5-isoxazolyl)amino)sulfonyl)-N-(2,4-dimethyl-6-propionylphenyl)-2-thiophenecarboxamide A. 2'-Amino-3',5'-dimethylpropiophenone 2'-Amino-3',5'-dimethylpropiophenone was synthesized in the same fashion as for 2'-amino-3',5'-dimethylacetophenone (Example 39) except that propionitrile was used instead of acetonitrile.

B. 3-(((4-Chloro-3-methyl-5-isoxazolyl )amino)sulfonyl)-N-(2,4-dimethyl-6-propionylphenyl)-2-thiophenecarboxamide 3-(((4-Chloro-3-methyl-5-isoxazolyl)amino)sulfonyl)-N-(2,4-dimethyl-6-propionylphenyl)-2-thiophenecarboxamide was synthesized in the same fashion as for N-(2-acetyl-4,6-dimethylphenyl)-3-(((4-chloro-3-methyl-5-isoxazolyl)amino)sulfonyl)-2-thiophenecarboxamide (Example 39) except that 2'-amino-3',5'-dimethylpropiophenone was used instead of 2-amino-3',5'-dimethylacetophenone.

EXAMPLE 41

3-(((4-Chloro-3-methyl-5-isoxazolyl)amino)sulfonyl)-N-(2-isobutyryl-4,6-dimethylphenyl)-2-thiophenecarboxamide A. 2'-Amino-3',5'-dimethyl-2-methylpropiophenone 2'-Amino-3',5'-dimethyl-2-methylpropiophenone was synthesized in the same fashion as for 2'-amino-3',5'-dimethylacetophenone (Example 39) except that isobutyronitrile was used instead of acetonitrile.

B. 3-(((4-Chloro-3-methyl-5-isoxazolyl)amino)sulfonyl)-N-(2-isobutyryl-4,6-dimethylphenyl)-2-thiophenecarboxamide 3-(((4-Chloro-3-methyl-5-isoxazolyl)amino)sulfonyl)-N-(2-isobutyryl-4,6-dimethylphenyl)-2-thiophenecarboxamide was synthesized in the same fashion as for N-(2-acetyl-4,6-dimethylphenyl)-3-(((4-chloro-3-methyl-5-isoxazolyl)amino)sulfonyl)-2-thiophenecarboxamide (Example 39) except that 2'-amino-3',5'-dimethyl-2-methylpropiophenone was used instead of 2'-amino-3',5'-dimethylacetophenone.

EXAMPLE 42

3-(((4-Chloro-3-methyl-5-isoxazolyl)amino)sulfonyl)-N-(2-(cyclohexylcarbonyl)-4,6-dimethylphenyl)-2-thiophenecarboxamide A. Cyclohexyl 2-amino-3,5-dimethylphenyl ketone Cyclohexyl 2-amino-3,5-dimethylacetophenone was synthesized in the same fashion as for 2'-amino-3',5'-dimethylacetophenone (Example 39) except that cyclohexyl cyanide was used instead of acetonitrile.

B. 3-(((4-Chloro-3-methyl-5-isoxazolyl)amino)sulfonyl)-N-(2-(cyclohexylcarbonyl)-4,6-dimethylphenyl)-2-thiophenecarboxamide 3-(((4-Chloro-3-methyl-5-isoxazolyl)amino)sulfonyl)-N-(2-(cyclohexylcarbonyl)-4,6-dimethylphenyl)-2-thiophenecarboxamide was synthesized in the same fashion as for N-(2-acetyl-4,6-dimethylphenyl)-3-(((4-chloro-3-methyl-5-isoxazolyl)amino)sulfonyl)-2-thiophenecarboxamide (Example 39) except that cyclohexyl 2-amino-3,5-dimethylphenyl ketone was used instead of 2'-amino-3',5'-dimethylacetophenone.

EXAMPLE 43

3-(((4-Chloro-3-methyl-5-isoxazolyl)amino)sulfonyl)-N-(2-(cyclopropylcarbonyl)-4,6-dimethylphenyl)-2-thiophenecarboxamide A. Cyclopropyl 2-amino-3,5-dimethylphenyl ketone Cyclopropyl 2-amino-3,5-dimethylphenyl ketone was synthesized in the same fashion as for 2'-amino-3',5'-dimethylacetophenone (Example 39) except that cyclopropyl cyanide was used instead of acetonitrile.

B. 3-(((4-Chloro-3-methyl-5-isoxazolyl)amino)sulfonyl)-N-(2-(cyclopropylcarbonyl)-4,6-dimethylphenyl)-2-thiophenecarboxamide 3-(((4-Chloro-3-methyl-5-isoxazolyl)amino)sulfonyl)-N-(2-(cyclopropylcarbonyl)-4,6-dimethylphenyl)-2-thiophenecarboxamide was synthesized in the same fashion as for N-(2-acetyl-4,6-dimethylphenyl)-3-(((4-chloro-3-methyl-5-isoxazolyl)amino)sulfonyl)-2-thiophenecarboxamide (Example 39) except that cyclopropyl 2-amino-3,5-dimethylphenyl ketone was used instead of 2'-amino-3',5'-dimethylacetophenone.

EXAMPLE 44

N-(2-Benzoyl-4,6-dimethylphenyl)-3-(((4-chloro-3-methyl-5-isoxazolyl)amino)sulfonyl)-2-thiophenecarboxamide A. 2-Amino-3,5-dimethylphenyl phenyl ketone 2-Amino-3,5-dimethylphenyl phenyl ketone was synthesized in the same fashion as for 2'-amino-3',5'-dimethylacetophenone (Example 39) except that benzonitrile was used instead of acetonitrile.

B. N-(2-Benzoyl-4,6-dimethylphenyl)-3-(((4-chloro-3-methyl-5-isoxazolyl)amino)sulfonyl)-2-thiophenecarboxamide N-(2-Benzoyl-4,6-dimethylphenyl)-3-(((4-chloro-3-methyl-5-isoxazolyl)amino)sulfonyl)-2-thiophenecarboxamide was synthesized in the same fashion as for N-(2-acetyl-4,6-dimethylphenyl)-3-(((4-chloro-3-methyl-5-isoxazolyl)amino)sulfonyl)-2-thiophenecarboxamide (Example 39) except that 2-amino-3,5-dimethylphenyl phenyl ketone was used instead of 2'-amino-3',5'-dimethylacetophenone.

EXAMPLE 45

N-(2-Acetyl-4,6-dimethylphenyl)-3-(((4-chloro-3-methyl-5-isoxazolyl)amino)sulfonyl)-5-methyl-2-thiophenecarboxamide A. N-(4-Chloro-3-methyl-5-isoxazolyl)-3-sulfamoyl-5-methyl-2-thiophenecarboxylic acid To a solution of N-(4-chloro-3-methyl-5-isoxazolyl)-3-sulfamoyl-2-thiophenecarboxylic acid (6 g, 18.60 mmol) in anhydrous tetrahydrofuran (240 mL) at −78° C. and under nitrogen was added nBuLi (2.5 M in hexane, 30 mL, 74.4 mmol). The mixture was stirred at this temperature for 2 h before the addition of iodomethane (6.6 g, 74.4 mmol). The mixture was then poured into crushed ice and then allowed to warm to room temperature. After acidification with concentrated HCl to pH ~1, the mixture was extracted with ethyl acetate (2×200 mL). The organic layers were combined, dried (MgSO$_4$), the solids were filtered and the filtrate was concentrated to give N-(4-chloro-3-methyl-5-isoxazolyl)-3-sulfamoyl-5-methyl-2-thiophenecarboxylic acid and the starting material in about a 2:1 ratio (8.5 g combined weight).

B. N-(4-Chloro-3-methyl-5-isoxazolyl)-3-sulfamoyl-5-methyl-2-thiophenecarboxylic acid To a solution of the product mixture of Example 45A (8.5 g) in THF (150 mL) were sequentially added diisopropylethylamine (9.62 g, 74.4 mmol) and bromomethyl methyl ether (90%, 7.75 g, 55.80 mmol). The mixture was stirred for 10 h before the addition of morpholine (4.6 g, 55.80 mmol) to scavenge the excess bromomethyl methyl ether. The reaction was stirred for another 30 min before it was diluted with ethyl acetate (150 mL) and washed with 1 N HCl (200 mL). The organic layer was dried (MgSO$_4$), the solids were filtered and the filtrate was concentrated. The residue was chromatographed (10% ethyl acetate in hexanes) to give methoxymethyl N-(4-chloro-3-methyl-5-isoxazolyl)-3-sulfamoyl-5-methyl-2-thiophenecarboxylate. The carboxylate was then hydrolyzed with 1 N NaOH to give the corresponding carboxylic acid (3.5 g).

C. N-(4-Chloro-3-methyl-5-isoxazolyl)-N-methoxymethyl-3-sulfamoyl-5-methyl-2-thiophenecarboxylic acid chloride N-(4-Chloro-3-methyl-5-isoxazolyl)-N-methoxymethyl-3-sulfamoyl-5-methyl-2-thiophenecarboxylic acid chloride was synthesized in the same fashion as for N-(4-chloro-3-methyl-5-isoxazolyl)-N-methoxymethyl-3-sulfamoyl-2-thiophenecarbonyl chloride (Example 51) except that N-(4-chloro-3-methyl-5-isoxazolyl)-N-methoxymethyl-3-sulfamoyl-5-methyl-2-thiophenecarboxylic acid was used instead of N-(4-chloro-3-methyl-5-isoxazolyl)-N-methoxymethyl-3-sulfamoyl-2-thiophenecarboxylic acid.

D. N-(2-Acetyl-4,6-dimethylphenyl)-3-(((4-chloro-3-methyl-5-isoxazolyl)amino)sulfonyl)-5-methyl-2-thiophenecarboxamide N-(2-Acetyl-4,6-dimethylphenyl)-3-(((4-chloro-3-methyl-5-isoxazolyl)amino)sulfonyl)-5-methyl-2-thiophenecarboxamide was synthesized in the same fashion as for N-(2-acetyl-4,6-dimethylphenyl)-3-(((4-chloro-3-methyl-5-isoxazolyl)amino)sulfonyl)-2-thiophenecarboxamide (Example 39) except that N-(4-chloro-3-methyl-5-isoxazolyl)-N-methoxymethyl-3-sulfamoyl-5-methyl-2-thiophenecarboxylic acid chloride was used instead of N-(4-chloro-3-methyl-5-isoxazolyl)-N-methoxymethyl-3-sulfamoyl-2-thiophenecarboxylic acid chloride.

EXAMPLE 46

3-(((4-Chloro-3-methyl-5-isoxazolyl amino)sulfonyl)-N-(2-hydroxyethanimidoyl)-4,6-dimethylphenyl)-2-thiophenecarboxamide To a solution of N-(2-acetyl-4,6-dimethylphenyl)-3-(((4-chloro-3-methyl-5-isoxazolyl)amino)sulfonyl)-2-thiophenecarboxamide (Example 39) (50 mg, 0.11 mmol) in 2 N NaOH (40 mL) and methanol (4 mL) was added hydroxylamine hydrochloride (4 g, 57.6 mmol). The mixture was heated at 60° C. for 3 h before it was cooled to 0° C. and acidified with concentrated HCl to pH 1–2. The resulting white precipitate was filtered, washed with dilute acid and dried by lyophilization to give 3-(((4-chloro-3-methyl-5-isoxazolyl)amino)sulfonyl)-N-(2-hydroxyethanimidoyl)-4,6-dimethylphenyl)-2-thiophenecarboxamide (45 mg, 87%).

EXAMPLE 47

3-(((3-(((4-Chloro-3-methyl-5-isoxazolyl)amino)sulfonyl)-2-thienyl)carbonyl)amino)-2,4,6-trimethylphenyl methyl carbonate To a solution of N$^2$-(4-chloro-3-methyl-5-isoxazolyl)-N-(3-hydroxy-2,4,6-trimethylphenyl)-3-sulfamoyl-2-thiophenecarboxamide (Example 52) (238 mg, 0.524 mmol) in anhydrous DMF at 0° C. was added potassium tert-butoxide (177 mg, 1.57 mmol). After the mixture was stirred for 30 min at this temperature, methyl chloroformate (99.2 mg, 1.05 mmol) was added. The reaction was poured into iced diluted acid and the resulting precipitate was collected and purified by HPLC to give 3-(((3-(((4-chloro-3-methyl-5-isoxazolyl)amino)sulfonyl)-2-thienyl)carbonyl)amino)-2,4,6-trimethylphenyl methyl carbonate (186 mg, 70%).

EXAMPLE 48

3-(((3-(((4-Chloro-3-methyl-5-isoxazolyl)amino)sulfonyl)-2-thienyl)carbonyl)amino)-2,4,6-trimethylphenyl carbamate To a solution of N$^2$-(4-chloro-3-methyl-5-isoxazolyl)-N-(3-hydroxy-2,4,6-trimethylphenyl)-3-sulfamoyl-2- thiophenecarboxamide (Example 52) (500 mg, 1.05 mmol) in anhydrous DMF at 0° C. was added potassium tert-butoxide (295 mg, 2.61 mmol). After the mixture was stirred for 10 min at this temperature, p-nitrophenyl chloroformate (317 mg, 1.57 mmol) was added. After about 1 min stirring, the mixture was treated with ammonium hydroxide (8 mL) and stirring was continued at room temperature for 2 h. The reaction was poured into iced dilute acid and the resulting precipitate was collected and purified by HPLC to give 3-(((3-(((4-chloro-3-methyl-5-isoxazolyl)amino)sulfonyl)-2-thienyl)carbonyl)amino)-2,4,6-trimethylphenyl carbamate (213 mg, 42%).

EXAMPLE 49

N-(4-Chloro-3-methyl-5-isoxazolyl)-2-(2-(3-methoxy-2,4,6-trimethylphenyl)acetyl)-3-thiophenesulfonamide A . N-(4-Chloro-3-methyl-5-isoxazolyl)-3-sulfamoyl-2-thiophenecarbonitrile A solution of N-(4-chloro-3-methyl-5-isoxazolyl)-3-sulfamoyl-2-thiophenecarboxamide (5 g, 15.6 mmol) in $POCl_3$ (50 mL) was heated at 60° C. for 3 h. The reaction was cooled to room temperature and poured to crushed ice (~250 g), and the icy mixture was shaken, stirred until all the ice melted (~2 h). The mixture was extracted with ethyl acetate and the organic layer was dried ($MgSO_4$), the solids were filtered and the filtrate was concentrated and dried under vacuum to give N-(4-chloro-3-methyl-5-isoxazolyl)-3-sulfamoyl-2-thiophenecarbonitrile (4.8 g ~100%).

B. 3-Methoxy-2,4,6-trimethylbenzyl chloride

3-Methoxy-2,4,6-trimethylbenzyl chloride was synthesized in the same fashion as for 5-chloromethyl-6-methylbenzo[d][1,3]dioxole (Example 7) except that 1-methoxy-2,4,6-trimethylbenzene was used instead of 5-methylbenzo[d][1,3]dioxole.

C. N-(4-Chloro-3-methyl-5-isoxazolyl)-2-(2-(3-methoxy-2,4,6-trimethylphenyl)acetyl)-3-thiophenesulfonamide N-(4-Chloro-3-methyl-5-isoxazolyl)-2-(2-(3-methoxy-2,4,6-trimethylphenyl)acetyl)-3-thiophenesulfonamide was synthesized in the same fashion as for 4-chloro-3-methyl-5-(2-(2-(6-methylbenzo[d][1,3]dioxol-5-yl)acetyl)-3-thienylsulfonamido)isoxazole (Example 7) except that N-(4-chloro-3-methyl-5-isoxazolyl)-3-sulfamoyl-2-thiophenecarbonitrile (Example 49A) was used instead of $N^2$-methoxy-$N^2$-methyl-3-(4-chloro-3-methyl-5-isoxazolylsulfamoyl)-2-thiophenecarboxamide.

EXAMPLE 50

N-(4-Chloro-3-methyl-5-isoxazolyl)-2-(2-(3-hydroxy-2,4,6-trimethylphenyl)acetyl)-3-thiophenesulfonamide To a solution of N-(4-chloro-3-methyl-5-isoxazolyl)-2-(2-(3-methoxy-2,4,6-trimethylphenyl)acetyl)-3-thiophenesulfonamide (Example 49) (50 mg, 0.107 mmol) in dichloromethane (20 mL) at 0° C. was added $BBr_3$ (1 M in dichloromethane, 3 mL, 3.0 mmol). The resulting mixture was stirred at 0° C. for 1 h and at room temperature for 8 h before it was poured into crushed ice (~100 g). The aqueous mixture was stirred until all ice melted and extracted with dichloromethane (2×100 mL). The organic layers were combined and concentrated, and the residue was purified by HPLC to give N-(4-chloro-3-methyl-5-isoxazolyl)-2-(2-(3-hydroxy-2,4,6-trimethylphenyl)acetyl)-3-thiophenesulfonamide (47 mg, 85%).

EXAMPLE 51

N-(4-chloro-3-methyl-5-isoxazolyl)-N-methoxymethyl-3-sulfamoyl-2-thiophenecarbonyl chloride A. 5-Amino-4-chloro-3-methylisoxazole To a solution of 5-amino-3-methylisoxazole (9.8 g, 100 mmol) in methylene chloride (200 mL) was added N-chlorosuccinimide (14.7 g, 110 mmol) at 0° C. over the period of 20 min. The reaction mixture was stirred for 2 h at RT. To work up the reaction mixture was concentrated and partitioned between 1N NaOH (150 mL)/ethyl acetate (400 mL). The organic layer was washed with 1N NaOH, water, brine, dried over $MgSO_4$ then concentrated to a brown solid. For purification the product was reprecipitated from chloroform/hexane then recrystallized from ethyl acetate/hexane to give 5-amino-4-chloro-3-methylisoxazole as a brownish solid (5.5 g, 41%).

B. 2-Carbomethoxy-3-[N-(4-chloro-3-methylisoxazol-5-yl)]thiophenesulfonamide

To a slurry of 60% mineral oil suspension of NaH (8.5 g, 0.21 mol) in THF (100 mL) at −20° C. was added a solution of 5-amino-4-chloro-3-methylisoxazole (12.4 g, 92.4 mmol) in anhydrous THF (65 mL) under nitrogen over a period of 20 min. After 10 min stirring was added a solution of 2-carbomethoxy-3-thiophenesulfonyl chloride (22.2 g, 92.4 mmol) in THF (65 mL) at −20° C. over 15 min. The reaction mixture was stirred for 10 min then quenched with $H_2O$ (5 mL) at the same temperature. To work up the reaction mixture was poured into 4 N HCl and the product was extracted with ethyl acetate. The combined organics were washed with water then the compound was extracted with half-saturated $NaHCO_3$. The combined basic solutions were decolorized with activated charcoal, cooled to 0° C. and acidified with 4 N HCl. The product was isolated by filtration, washed with water, dried to give 2-carbomethoxy-3-[N-(4-chloro-3-methylisoxazol-5-yl)]thiophenesulfonamide as a white powder (23.4 g, 75%).

C. 2-Carbomethoxy-3-[N-(4-chloro-3-methylisoxazol-5-yl)-N-methoxymethyl]thiophenesulfonamide To a solution of 2-carbomethoxy-3-[N-(4-chloro-3-methylisoxazol-5-yl)]thiophenesulfonamide (3.3 g, 10.0 mmol) in THF (50 mL) diisopropylethylamine (1.9 g, 15.0 mmol) was added at 0° C. followed by addition of bromomethyl methyl ether (1.5 g, 12.0 mmol). The reaction mixture was stirred overnight at RT. To work up the reaction mixture was concentrated and partitioned between water and ethyl acetate. The organic layer was washed with water, brine, dried over $MgSO_4$, concentrated to give 2-carbomethoxy-3-[N-(4-chloro-3-methylisoxazol-5-yl)-N-methoxymethyl] thiophenesulfonamide as a greenish oil (3.5 g, 90%).

D. 2-Carboxy-3-[N-(4-chloro-3-methylisoxazol-5-yl)-N-methoxymethyl]thiophenesulfonamide 2-Carbomethoxy-3-[N-(4-chloro-3-methylisoxazol-5-yl)-N-methoxymethyl]thiophenesulfonamide (3.0 g, 7.8 mmol) in a mixture of THF (30 mL) and 1N NaOH (30 mL) was stirred for 3 h at RT. The reaction mixture was diluted with water (20 mL) and extracted with ethyl acetate (5 mL). The water solution was acidified with 1 N HCl then extracted with ethyl acetate. The organics were washed with water, brine, dried over $MgSO_4$ and concentrated to give 2-carboxy-3-[N-(4-chloro-3-methylisoxazol-5-yl)-N-methoxymethyl]thiophenesulfonamide as an oil (quantitative yield).

E. N-(4-chloro-3-methyl-5-isoxazolyl)-N-methoxymethyl-3-sulfamoyl-2-thiophenecarbonyl chloride To a solution of 2-carboxy-3-[N-(4-chloro-3-methylisoxazol-5-yl)-N-methoxymethyl]

thiophenesulfonamide (1.5 g, 4.1 mmol) in a mixture of THF (10 mL) and chloroform (5 mL), pyridine (1 drop) was added at 0° C. followed by addition of 2 M solution of oxalyl chloride (4.5 mL, 9.0 mmol). The reaction mixture was stirred overnight at RT. To work up the reaction mixture was concentrated under reduced pressure to remove all volatiles. The desired product was obtained as a sticky oil which solidifies upon standing.

EXAMPLE 52

$N^2$-(4-Chloro-3-methyl-5-isoxazolyl)-N-(3-hydroxy-2,4,6-trimethylphenyl)-3-sulfamoyl-2-thiophenecarboxamide A. 3-Acetoxy-2,4,6-trimethylaniline To a solution of 2,4,6-trimethylphenol (10 g, 73.5 mmol) and triethylamine (11.1 g, 110.3 mmol) in ethyl acetate (200 mL) was added acetyl chloride (7.5 g, 95.6 mmol) dropwise at 0° C. The mixture was stirred overnight. The reaction was quenched with water and the organic layer was washed with 1 N HCl. The organic layer was dried and concentrated as usual. The residue was nitrated at RT with 70% $HNO_3$ and conc. $H_2SO_4$. The brown reaction mixture was stirred for 1 h, poured into ice-water. The product was extracted into ethyl acetate, the extract was washed with water, dried over $MgSO_4$ and concentrated to give the desired nitro compound. This compound was reduced in methanol by sequential addition of ammonium chloride and zinc powder. The exothermic reaction was vigorously stirred until it was back to RT (2 h). To work up the crude mixture was filtered off and the cake was washed with methanol. The methanolic solutions were concentrated and the residue partitioned between ethyl acetate and 1 N NaOH. The organic layer was dried over $MgSO_4$ and concentrated to give 3-acetoxy-2,4,6-trimethylaniline.

B. $N^2$-(4-Chloro-3-methyl-5-isoxazolyl)-N-(3-hydroxy-2,4,6-trimethylphenyl)-3-sulfamoyl-2-thiophenecarboxamide $N^2$-(4-Chloro-3-methyl-5-isoxazolyl)-N-(3-hydroxy-2,4,6-trimethylphenyl)-3-sulfamoyl-2-thiophenecarboxamide was synthesized by reaction of the above amine (Example 52A) with the product of Example 51 in THF at 0° C. The reaction mixture was allowed to warm up to RT and stirred for 2 h. To work up the reaction mixture was poured into 0.05 N HCl and the product was extracted with ethyl acetate. The organics were washed with 0.05 N HCl, water, half-saturated $NaHCO_3$, water, brine, dried over MgSO, and concentrated. Purification via column chromatography (silica, 40% ethyl acetate/hexane) gave $N^2$-(4-chloro-3-methyl-5-isoxazolyl)-N-(3-hydroxy-2,4,6-trimethylphenyl)-N-methoxymethyl-3-sulfamoyl-2-thiophenecarboxamide. A solution of this carboxamide in THF and conc. HCl was stirred at 65–72° C. for 3.5 h. To work up the reaction mixture was cooled and poured into water. The product was taken into ethyl acetate. The extract was washed with water, brine saturated $NaHCO_3$, brine, dried over $MgSO_4$ and concentrated as an oil. The acetoxy group was hydrolyzed to the corresponding hydroxyl during deprotection of the MOM group. $N^2$-(4-chloro-3-methyl-5-isoxazolyl)-N-(3-hydroxy-2,4,6-trimethylphenyl)-3-sulfamoyl-2-thiophenecarboxamide was obtained as a solid (mp 75–78°0 C., 54%).

EXAMPLE 53

Assays for Identifying Compounds that Exhibit Endothelin Antagonistic and/or Agonist Activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin Binding Inhibition—Binding Test #1: Inhibition of Binding to $ET_A$ Receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5 mM $MgCl_2$, 0.5% Bacitracin) to a concentration of 8 μg/50 μl. $^{125}$I-endothelin-1 (3,000 cpm, 50 mL) was added to 50 μL of either: (A) endothelin-1 (for non specific binding) to give a final concentration 80 nM); (B) binding buffer (for total binding); or (C) a test compound (final concentration 1 nM to 100 μM). The membrane suspension (50 μL), containing up to 8 μg of membrane protein, was added to each of (A), (B), or (C). Mixtures were shaken, and incubated at 4° C. for 16–18 hours, and then centrifuged at 4° C. for 25 min at 2,500×g. Alternatively, the incubation was conducted at 24° C. When incubated at 24° C., the $IC_{50}$ concentrations are 2- to 10-fold higher than when the incubation is conducted at 4° C. This, must be kept in mind when comparing $IC_{50}$ concentrations among compounds provided herein.

The supernatant, containing unbound radioactivity, was decanted and the pellet counted on a Genesys multiwell gamma counter. The degree of inhibition of binding (D) was calculated according to the following equation:

$$\% \ D = 100 - \frac{(C)-(A)}{(B)-(A)} \times 100$$

Each test was generally performed in triplicate.

B. Endothelin Binding Inhibition—Binding Test #2: Inhibition of Binding to $ET_B$ Receptors COS7 cells were transfected with DNA encoding the $ET_B$ receptor. The resulting cells, which express the human $ET_B$ receptor, were grown to confluence in T-150 flasks. Membrane was prepared as described above. The binding assay was performed as described above using the membrane preparation diluted with binding buffer to a concentration of 1 μg/50 μl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. 57,800×g for 15 min, the pellet was resuspended in 5 ml of buffer A (5 mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 $\mu$g/50 $\mu$l of binding buffer.

C. Test for Activity Against Endothelin-induced Contraction of Isolated Rat Thoracic Aortic Rings The effectiveness of the test compound as an antagonist or agonist of the biological tissue response of endothelin also is assessed by measuring the effect on endothelin induced contraction of isolated rat thoracic aortic rings (see, e.g., Borges et al. (1989) *Eur. J. Pharmacol.* 165:223–230) or by measuring the ability to contract the tissue when added alone.

Compounds to be tested are prepared as 100 $\mu$M stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'-Henseleit solution saturated with a gas mixture of 95% $O_2$ and 5% $CO_2$ (118 mM NaCl, 4.7 mM KCl, 1.2 mM $MgSO_4$, 1.2 mM $KH_2PO_4$, 25 mM $NaHCO_3$, 2.5 mM $CaCl_2$, 10 mM D-glucose).

There is a correlation between activity as an antagonist of endothelin-induced thoracic aortic ring contraction and activity as an inhibitor of binding of endothelin to endothelin receptors. The $pA_2$ is a linear function of the log of the $IC_{50}$.

D. Assay for Identifying Compounds that have Agonist and/or Antagonistic Activity Against $ET_B$ Receptors 1. Stimulation of Prostacyclin Release Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and sub-cultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of Sarafotoxin 6c Induced Contraction

Sarafotoxin 6c is a specific $ET_B$ antagonist that contracts rat fundal stomach strips. The effectiveness of tests compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs'-Henseleit solution containing 10 $\mu$M cyclo(D-Asp-Pro-D-Val-Leu-D-Trp) (BQ-123; see, U.S. Pat. No. 5,114, 918 to Ishikawa et al.), 5 $\mu$M indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preincubated for 15 min with a test compound prior to addition of cumulative doses of sarafotoxin 6c. The effects of the test compounds on the concentration-response curve for sarafotoxin 6c are examined.

E. Deoxycorticosterone Acetate (DOCA)-salt Hypertensive Rat Model for Assessing in Vivo Activity of Selected Compounds Selected compounds disclosed herein have been tested for activity in the deoxycorticosterone acetate (DOCA)-salt hypertensive rat model. To perform these tests, silastic MDX4-4210 elastomer implants containing 47 mg (DOCA) were prepared according to the method of Ornmsbee et al. ((1973) the *J. Pharm. Sci.* 62:255–257). Briefly, DOCA is incorporated into silicon rubber implants for sustained release. To prepare the implants the DOCA is incorporated into unpolymerized silicone rubber, catalyst is added and the mixture is cast in a hemicylindrical shape.

Sprague Dawley rats (7–8 weeks old) were unilaterally nephrectomized under ketamine anesthesia and a DOCA-implant was placed on the left lateral dorsal abdomen of the animal. The rats were allowed to recover for three weeks. During recovery they were permitted free access to normal rat chow and 0.9% NaCl drinking solution in place of drinking water. The rats develop hypertension within 3 weeks.

All animals were used in the tests between 21 and 30 days post surgery. The mean arterial blood pressure in these animals ranged from 165–200 mm Hg.

On the day of experimentation, catheters were inserted under brevital anesthesia into the right femoral artery for measurement of blood pressure, and into the right femoral vein for administration of a selected compound. The animals were placed in a restrainer and allowed to recover for a minimum of 60 min or until a steady mean arterial blood pressure was recorded. At that time, the selected compound or control vehicle was administered either intravenously, as a 60 minute infusion, or orally by oral gavage. Blood pressure was recorded continuously for a further 10 hrs.

F. Effect of Intravenous Administration on ET-1-induced Pressor Responses in Conscious, Autonomically Blocked Rats; a Model for Assessing in vivo Activity of Selected Compounds Male Sprague Dawley rats (250–450 g) were anesthetized (Brevital 50 mg/kg, IP) and cannulae were placed in the femoral artery to measure mean arterial pressure (MAP) and in the femoral vein for intravenous drug administration. Animals were placed in a restrainer and allowed to regain consciousness. Thirty minutes later autonomic blockade was administered (atropine methyl nitrate, 3 mg/kg, IV, followed by propranalol, 2 mg/kg, IV). An hour later animals received a bolus injection of vehicle (0.5 ml) followed thirty minutes later by intravenous bolus administration of ET-1 (Control, 1 µg/kg). Following recovery from this challenge, test-compounds were administered by intravenous bolus administration (0.5 ml) and then re-challenged with ET-1 thirty minutes later. Results are expressed as the percent inhibition of the ET-1-induced pressor response after administration of the test compound compared to the pressor response induced by the control ET-1 challenge. In some cases a third ET-1 challenge was administered ninety minutes after administration of the test compound.

G. Results

1. In vitro

The $IC_{50}$ for each of the compounds of the preceding Examples for $ET_A$ and $ET_B$ receptors has been measured. Almost all of the compounds have an $IC_{50}$ of less than 10 µM for either or both of the $ET_A$ and $ET_B$ receptors. Many of the compounds have an $IC_{50}$ less than about 10 µM, others have an $IC_{50}$ less than about 1 µM and some of the compounds have an $IC_{50}$ less than about 0.1 µM. A number of the compounds have an $IC_{50}$ for $ET_A$ receptors that is substantially less (10 to 100-fold or more) than for $ET_B$ receptors, and, thus are selective for $ET_A$ receptors. Others of the compounds are $ET_B$ selective.

2. In vivo a. Selected compounds, such as N-(4-chloro-3-methyl-5-isoxazolyl)-2-(N-(4-methyl-phenyl)aminocarbonyl) thiophene-3-sulfonamide, N-(4-bromo-3-methyl-5-isoxazolyl)-2-[3,4-(methylenedioxy)benzyl]benzo[b] thiophene-3-sulfonamide, N-(4-chloro-3-methyl-5-isoxazolyl)-2-(3,4,-methylenedioxy)benzyl)benzo[b] thiophene-3-sulfonamide, N-(4-chloro-3-methyl-5-isoxazolyl)-2-[β-hydroxy(3,4-methylenedioxy)phenylethyl] thiophene-3-sulfonamide, and N-(4-chloro-3-methyl-5-isoxazolyl)-2-(3,4-methylenedioxybenzylcarbonyl) thiophene-3-sulfonamide, have been tested in the hypertensive rat model, and were effective in decreasing blood pressure.

b. Selected compounds, such as N-(4-chloro-3-methyl-5-isoxazolyl)-2-{[3,4-(methylenedioxy)phenyl] acetyl}thiophene-3-sulfonamide, N-(4-chloro-3-methyl-5-isoxazolyl)2-{[2-acetyl-4,5-(methylenedioxy)-phenyl] aminocarbonyl}thiophene-3-sulfonamide, N-(4-chloro-3-methyl-5-isoxazolyl)-2-[(4-methoxy-2-methylphenyl) aminocarbonyl]thiophene-3-sulfonamide, N-(4-chloro-3-methyl-5-isoxazolyl)-2-[2-cyano-4,5-dimethoxyphenyl) aminocarbonyl]thiophene-3-sulfonamide, and N-(4-chloro-3-methyl-5-isoxazolyl)-2-[2-methyl-4,5-(methylenedioxy) phenylacetyl]thiophene-3-sulfonamide have been tested in the autonomically blocked, normotensive rat model and shown to have substantial activity, reducing pressure about 30% in 30 min at dosages as low as 30 mg/kg, and more than 50% at dosages of 60 mg/kg. On the average dosages of 30–60 mg/kg of the test compound resulted in a 40–60% inhibition of pressor response.

Since modifications will be apparent to those of skill in this art, it is intended that this invention be limited only by the scope of the appended claims.

What is claimed is:

1. A compound that is N-(2-acetyl-4,6-dimethylphenyl)-3-(((4-chloro-3-methyl-5-isoxazolyl)amino)sulfonyl)-2-thiophenecarboxamide or any corresponding N-(4-halo-3-methyl-5-isoxazolyl), N-(4-halo-5-methyl-3-isoxazolyl), N-(3,4-dimethyl-5-isoxazolyl), or N-(4,5-dimethyl-3-isoxazolyl) derivative thereof, or a pharmaceutically acceptable derivative thereof.

2. A compound that is N-(2-acetyl-4,6-dimethylphenyl)-3-(((3,4-dimethyl-5-isoxazolyl)amino)sulfonyl)-2-thiophenecarboxamide or a pharmaceutically acceptable derivative thereof.

3. A pharmaceutical composition, comprising the compound of claim 1 or a pharmaceutically acceptable derivative thereof, in a pharmaceutically acceptable carrier.

4. A method for the treatment of endothelin-mediated diseases, comprising administering an effective amount of the compound of claim 1, wherein the effective amount is sufficient to ameliorate one or more symptoms of the disease.

5. The method of claim 4, wherein the compound is a sodium salt.

6. The method of claim 4, wherein the disease is selected from the group consisting of glaucoma, hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction, endotoxin shock, anaphylactic shock and hemorrhagic shock.

7. An article of manufacture, comprising packaging material and a salt of the compound of claim 1, within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM, and the packaging material includes a label that indicates that the compound salt is used for antagonizing the effects of endothelin, inhibiting the binding of endothelin to an endothelin receptor or treating an endothelin-mediated disorder.

8. The pharmaceutical composition of claim 3 that is formulated for single dosage administration.

9. A pharmaceutical composition, comprising the compound of claim 2, or a pharmaceutically acceptable derivative thereof, in a pharmaceutically acceptable carrier.

10. A method for the treatment of endothelin-mediated diseases, comprising administering an effective amount of the compound of claim 2, wherein the effective amount is sufficient to ameliorate one or more symptoms of the disease.

11. The method of claim 10, wherein the compound is a sodium salt.

12. The method of claim 10, wherein the disease is selected from the group consisting of glaucoma, hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasocon-striction, erythropoietin-mediated vasoconstriction, endotoxin shock, anaphylactic shock and hemorrhagic shock.

13. An article of manufacture, comprising packaging material and a salt of the compound of claim 2 within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM, and the packaging material includes a label that indicates that the compound salt is used for antagonizing the effects of endothelin, inhibiting the binding of endothelin to an endothelin receptor or treating an endothelin-mediated disorder.

14. The pharmaceutical composition of claim 9 that is formulated for single dosage administration.

15. A method for inhibiting the binding of an endothelin peptide to endothelin$_A$ (ET$_A$) or endothelin$_B$ (ET$_B$) receptors, comprising contacting the receptors with an endothelin peptide and with one or more compounds of claim 1, wherein:
  the contacting is effected prior to, simultaneously with or subsequent to contacting the receptors with the endothelin peptide.

16. A method for altering endothelin receptor-mediated activity, comprising contacting endothelin receptors with one or more compounds of claim 1.

17. A method for inhibiting the binding of an endothelin peptide to endothelin$_A$ (ET$_A$) or endothelin$_B$ (ET$_B$) receptors, comprising contacting the receptors with an endothelin:peptide and with a compound of claim 2, wherein:
  the contacting is effected prior to, simultaneously with or subsequent to contacting the receptors with the endothelin peptide.

18. A method for altering endothelin receptor-mediated activity, comprising contacting endothelin receptors with a compound of claim 2.

\* \* \* \* \*

UNITED STATES PATENT AND TRADEMARK OFFICE
CERTIFICATE OF CORRECTION

PATENT NO.    : 6,432,994 B1
DATED         : August 13, 2002
INVENTOR(S)   : Wu et al.

It is certified that error appears in the above-identified patent and that said Letters Patent is hereby corrected as shown below:

<u>Title page,</u>
Item [75], delete "Karin Keller, Houston, TX (US); Patricia Woodard, Escondido, CA (US)"

Signed and Sealed this

Fourth Day of January, 2003

JAMES E. ROGAN
*Director of the United States Patent and Trademark Office*